(12) United States Patent
Choi et al.

(10) Patent No.: US 9,373,798 B2
(45) Date of Patent: Jun. 21, 2016

(54) ORGANOMETALLIC COMPOUND AND ORGANIC LIGHT-EMITTING DEVICE INCLUDING THE SAME

(71) Applicants: Jong-Won Choi, Yongin (KR);
Yoon-Hyun Kwak, Yongin (KR);
Bum-Woo Park, Yongin (KR);
Sun-Young Lee, Yongin (KR); Wha-Il Choi, Yongin (KR); So-Yeon Kim, Yongin (KR); Ji-Youn Lee, Yongin (KR)

(72) Inventors: Jong-Won Choi, Yongin (KR);
Yoon-Hyun Kwak, Yongin (KR);
Bum-Woo Park, Yongin (KR);
Sun-Young Lee, Yongin (KR); Wha-Il Choi, Yongin (KR); So-Yeon Kim, Yongin (KR); Ji-Youn Lee, Yongin (KR)

(73) Assignee: SAMSUNG DISPLAY CO., LTD., Yongin, Gyunggi-do (KR)

( * ) Notice: Subject to any disclaimer, the term of this patent is extended or adjusted under 35 U.S.C. 154(b) by 449 days.

(21) Appl. No.: 13/803,650

(22) Filed: Mar. 14, 2013

(65) Prior Publication Data
US 2014/0070180 A1    Mar. 13, 2014

(30) Foreign Application Priority Data
Sep. 7, 2012  (KR) .................. 10-2012-0099543

(51) Int. Cl.
*B32B 19/00*    (2006.01)
*H01L 51/00*    (2006.01)
(Continued)

(52) U.S. Cl.
CPC .......... *H01L 51/0085* (2013.01); *C07F 15/004* (2013.01); *C07F 15/0026* (2013.01);
(Continued)

(58) Field of Classification Search
CPC ............ H01L 51/0085; H01L 51/0087; H01L 51/0088; H01L 51/5012; H01L 51/5016; C07F 15/0026; C07F 15/0033; C07F 15/004; C07F 15/0084; C07F 15/0093; C07D 401/14; C07D 403/14

USPC ............. 428/689, 690, 917; 257/40; 544/225; 252/301.16, 301.18; 313/504
See application file for complete search history.

(56) References Cited

U.S. PATENT DOCUMENTS 6,465,115 B2    10/2002  Shi et al.
6,596,415 B2    7/2003   Shi et al.
(Continued)

FOREIGN PATENT DOCUMENTS

JP    2000-003782    1/2000
JP    2005-068110    3/2005
(Continued)

OTHER PUBLICATIONS

Baldo et al., Very High Efficiency Green Organic Light-Emitting Devices Based on Electrophosphorescence, Applied Physics Letters, Jul. 5, 1999, vol. 75, No. 1, pp. 3-6.
(Continued)

*Primary Examiner* — Ruiyun Zhang
(74) *Attorney, Agent, or Firm* — Lee & Morse, P.C.

(57) ABSTRACT

An organometallic compound may be represented by Formula 1:

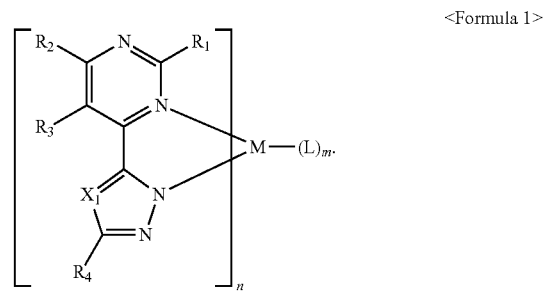

<Formula 1>

32 Claims, 1 Drawing Sheet

(51) Int. Cl.
*C07F 15/00* (2006.01)
*H01L 51/50* (2006.01)

(52) U.S. Cl.
CPC ......... *C07F15/0033* (2013.01); *C07F 15/0086* (2013.01); *C07F 15/0093* (2013.01); *H01L 51/0087* (2013.01); *H01L 51/0088* (2013.01); *H01L 51/0081* (2013.01); *H01L 51/5016* (2013.01)

(56) References Cited

U.S. PATENT DOCUMENTS

| | | |
|---|---|---|
| 7,002,013 B1 | 2/2006 | Chi et al. |
| 7,759,490 B2 | 7/2010 | Tao et al. |
| 7,868,170 B2 | 1/2011 | Chi et al. |
| 8,216,698 B2 | 7/2012 | Murakami et al. |
| 2001/0019782 A1 | 9/2001 | Igarashi et al. |
| 2011/0282059 A1 | 11/2011 | Baranoff et al. |
| 2012/0025177 A1 | 2/2012 | Yoon et al. |

FOREIGN PATENT DOCUMENTS

| | | |
|---|---|---|
| JP | 2006-190718 | 7/2006 |
| JP | 2006-278782 | 10/2006 |
| JP | 2007-169541 | 7/2007 |
| JP | 2008-074831 | 4/2008 |
| JP | 2011-119576 A | 6/2011 |
| KR | 10-2009-0111779 | 10/2009 |
| KR | 10-2011-0131200 | 12/2011 |

OTHER PUBLICATIONS

Kwong et al., High Operational Stability of Electrosphorescent Devices, Applied Physics Letters, Jul. 1, 2002, vol. 81, No. 1, pp. 161-164.
Baldo et al., Highly Efficient Phosphorescent Emission From Organic Electroluminescent Devices, Nature, Sep. 10, 1998, vol. 395, pp. 151-154.
Lamansky et al., Highly Phosphorescent Bis-Cyclometalated Iridium Comples: Synthesis, Photophysical Characterization, and Use in Organic Light Emitting Diodes, J. Am. Chem. Soc., 2001, vol. 123, No. 8, pp. 4304-4312.
Lamansky, et al., Synthesis and Characterization of Phosphorescent Cyclometalated Iridium Complexes, Inorg. Chem., 2001, vol. 40, No. 7, pp. 1704-1711.
Kohler et al., Fluorescence and Phosphorescence in Organic Materials, Advanced Engineering Materials, 2002, 4, No. 7, pp. 453-459.
Liu, Yuqi; Effects of N-Substitution on Phosphorescence Efficiency and Color Tuning of a Series of Ir(III) Complexes with a Phosphite Tripod Ligand: A DFT/TDDFT Study; Journal (online computer file); 2012, pp. 2, American Chemical Society; China.
"Ethyl pyrimidine-4-carboxylate—Reaxys printout" (1978), XP055212394.
"I03-0325 Ethyl 4-pyrimidinecarboxylate 62846-82-6" Product catalog (2011), XP055212395.
"Ethyl 4-Pyrimidinecarboxylate" Heterocycles (2011), XP055212396.
"Pyrimidine Compounds Using Ethyl Pyrimidine-4-carboxylate—Reaxys printout" (2011), XP055212399.
European Office Action dated Sep. 16, 2015 in Corresponding European Patent Application No. 13183277.6.

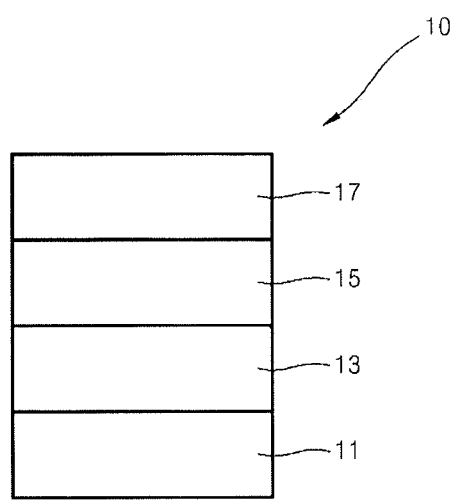

ORGANOMETALLIC COMPOUND AND ORGANIC LIGHT-EMITTING DEVICE INCLUDING THE SAME

CROSS-REFERENCE TO RELATED APPLICATION

The present application claims priority under 35 U.S.C. §119 to Korean Patent Application No. 10-2012-0099543, filed on Sep. 7, 2012, in the Korean Intellectual Property Office, and entitled: "Organometallic Compound and Organic Light Emitting Device Including the Same," which hereby incorporated by reference in its entirety.

BACKGROUND OF THE INVENTION

1. Field

Embodiments relate to a compound for organic light-emitting devices, and an organic light-emitting device including the compound.

2. Description of the Related Art

Organic light-emitting devices (OLEDs) may be light emitting devices (e.g., self-emitting devices) and may have advantages such as wide viewing angles, excellent contrast, quick response, high brightness, excellent driving voltage characteristics, and the ability to provide multicolored images.

SUMMARY

Embodiments are directed to an organometallic compound represented by Formula 1:

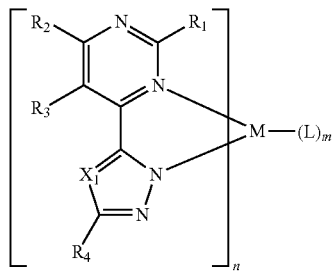

<Formula 1> wherein, in Formula 1: M may be a transition metal; $X_1$ may be N or $C(R_5)$; $R_1$ to $R_5$ each independently may be selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —N($Q_1$)($Q_2$), —Si($Q_3$)($Q_4$)($Q_5$), —C(=O)($Q_6$), and a binding site with an adjacent ligand via a single bond or a divalent linking group; two substituents of $R_1$ to $R_5$ may be optionally linked together to form one selected from the group of a substituted or unsubstituted $C_4$-$C_{20}$ alicyclic ring, a substituted or unsubstituted $C_2$-$C_{20}$ hetero alicyclic ring, a substituted or unsubstituted $C_6$-$C_{20}$ aromatic ring, and a substituted or unsubstituted $C_2$-$C_{20}$ heteroaromatic ring; $Q_1$ to $Q_6$ each independently may be selected from the group of a hydrogen atom, a substituted or unsubstituted $C_1$-$C_{60}$ alkyl group, a substituted or unsubstituted $C_6$-$C_{60}$ aryl group, and a substituted or unsubstituted $C_2$-$C_{60}$ heteroaryl group; n may be an integer from 1 to 3; L may be a monodentate, bidentate, tridentate, or tetradentate organic ligand; and m may be an integer from 0 to 4.

M may be selected from the group of ruthenium (Ru), rhodium (Rh), palladium (Pd), tungsten (W), rhenium (Re), osmium (Os), iridium (Ir), and platinum (Pt).

$X_1$ may be $C(R_5)$.

$X_1$ may be N.

$X_1$ may be $C(R_5)$; $R_1$ to $R_5$ each independently may be one selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, an n-propyl group, an i-propyl group, an n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, a pentoxy group, and a substituted group that is substituted with at least one selected from the group of a deuterium atom, a fluorine atom, a hydroxyl group, a cyano group, a nitro group, and an amino group; and the substituted group may be selected from the group of a substituted methyl group, a substituted ethyl group, a substituted n-propyl group, a substituted i-propyl group, a substituted n-butyl group, a substituted i-butyl group, a substituted t-butyl group, a substituted pentyl group, a substituted hexyl group, a substituted heptyl group, a substituted octyl group, a substituted nonyl group, a substituted decyl group, a substituted methoxy group, a substituted ethoxy group, a substituted propoxy group, a substituted butoxy group, and a substituted pentoxy group.

$X_1$ may be N; $R_1$ to $R_4$ each independently may be one selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, an n-propyl group, an i-propyl group, an n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and pentoxy group, and a substituted group that is substituted with at least one selected from the group of a deuterium atom, a fluorine atom, a hydroxyl group, a cyano group, a nitro group, and an amino group; and the substituted group may be selected from the group of a substituted methyl group, a substituted ethyl group, a substituted n-propyl group, a substituted i-propyl group, a substituted n-butyl group, a substituted i-butyl group, a substituted t-butyl group, a substituted pentyl group, a substituted hexyl group, a substituted heptyl group, a substituted octyl group, a substituted nonyl group, a substituted decyl group, a substituted methoxy group, a substituted propoxy group, a substituted butoxy group, and a substituted pentoxy group.

i) $R_2$ and $R_3$ may be linked together so that the organometallic compound is represented by Formula 1A; ii) $X_1$ may be $C(R_5)$, and $R_4$ and $R_5$ may be linked together so that the organometallic compound is represented by Formula 1B; or iii) $R_2$ and $R_3$ may be linked together, $X_1$ may be $C(R_5)$, and $R_4$ and $R_5$ may be linked together so that the organometallic compound is represented by Formula 1C:

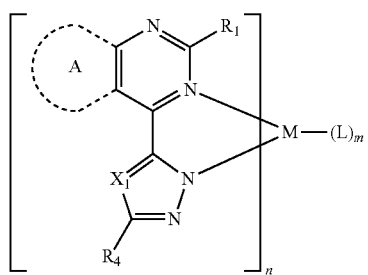

<Formula 1A>

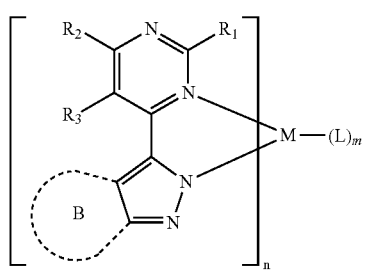

<Formula 1B>

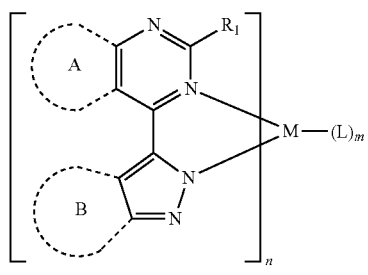

<Formula 1C> wherein, in Formulae 1A, 1B, and 1C: M, $X_1$, $R_1$ to $R_5$, n, L, and m may be as in Formula 1; and the A ring and the B ring each independently may be selected from the group of a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, and a substituted or unsubstituted $C_2$-$C_{20}$ heteroaromatic ring.

The organometallic compound may be represented by Formula 1A or Formula 1C; the A ring may be at least one selected from the group of benzene, pentalene, indene, naphtalene, azulene, heptalene, indacene, acenaphthylene, fluorene, spiro-fluorene, phenalene, phenanthrene, anthracene, fluoranthene, triphenylene, pyrene, chrysene, and a substituted group that is substituted with at least one selected from the group of: a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, $-N(Q_{11})(Q_{12})$, and $-Si(Q_{13})(Q_{14})(Q_{15})$; $Q_{11}$ to $Q_{15}$ each independently may be selected from the group of a hydrogen atom, a $C_1$-$C_{10}$ alkyl group, a $C_6$-$C_{20}$ aryl group, and a $C_2$-$C_{20}$ heteroaryl group; and the substituted group may be selected from the group of a substituted benzene, a substituted pentalene, a substituted indene, a substituted naphtalene, a substituted azulene, a substituted heptalene, a substituted indacene, a substituted acenaphthylene, a substituted fluorene, a substituted spiro-fluorene, a substituted phenalene, a substituted phenanthrene, a substituted anthracene, a substituted fluoranthene, a substituted triphenylene, a substituted pyrene, and a substituted chrysene.

The organometallic compound may be represented by Formula 1B or Formula 1C; the B ring may be at least one selected from the group of cyclopropane, cyclobutane, cyclopentane, cyclohexane, cycloheptane, cyclooctane, cyclopentene, cyclopentadiene, cyclohexadiene, cycloheptadiene, bicyclo-heptane, bicyclo-octane, benzene, pentalene, indene, naphtalene, azulene, heptalene, indacene, acenaphthylene, fluorene, spiro-fluorene, phenalene, phenanthrene, anthracene, fluoranthene, triphenylene, pyrene, chrysene, and a substituted group that is substituted with at least one selected from the group of: a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, $-N(Q_{11})(Q_{12})$, and $-Si(Q_{13})(Q_{14})(Q_{15})$; $Q_{11}$ to $Q_{15}$ each independently may be selected from the group of a hydrogen atom, a $C_1$-$C_{10}$ alkyl group, a $C_6$-$C_{20}$ aryl group, and a $C_2$-$C_{20}$ heteroaryl group; the substituted group may be selected from the group of a substituted cyclopropane, a substituted cyclobutane, a substituted cyclopentane, a substituted cyclohexane, a substituted cycloheptane, a substituted cyclooctane, a substituted cyclopentene, a substituted cyclopentadiene, a substituted cyclohexadiene, a substituted cycloheptadiene, a substituted bicyclo-heptane, a substituted bicyclo-octane, a substituted benzene, a substituted pentalene, a substituted indene, a substituted naphtalene, a substituted azulene, a substituted heptalene, a substituted indacene, a substituted acenaphthylene, a substituted fluorene, a substituted spiro-fluorene, a substituted phenalene, a substituted phenanthrene, a substituted anthracene, a substituted fluoranthene, a substituted triphenylene, a substituted pyrene, and a substituted chrysene.

The organometallic compound may be represented by one selected from the group of Formulae 1A-(1), 1B-(1), 1B-(2), 1B-(3), 1C-(1), 1C-(2), 1C-(3), and 1D-(1):

<Formula 1A-(1)>

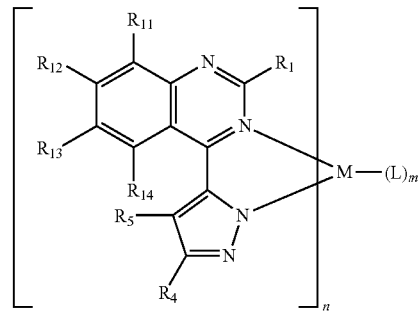

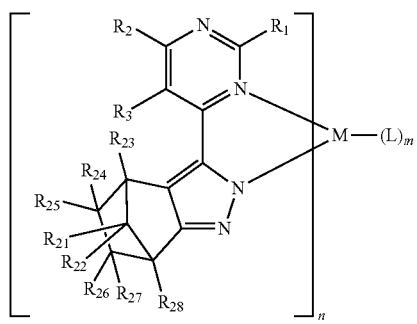

<Formula 1B-(1)>


<Formula 1B-(2)>

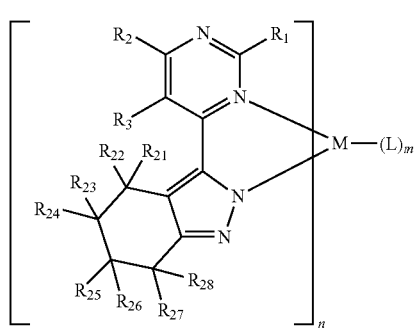

<Formula 1B-(3)>

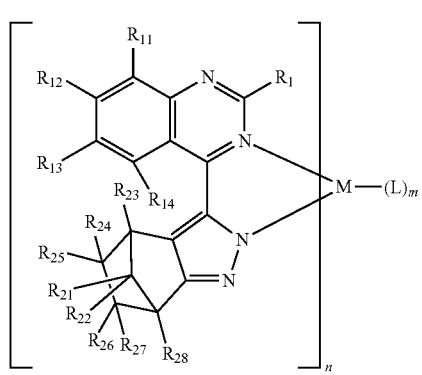

<Formula 1C-(1)>

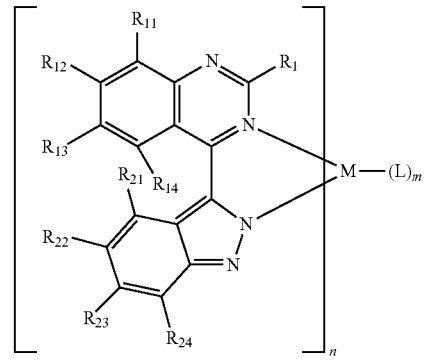

<Formula 1C-(2)>

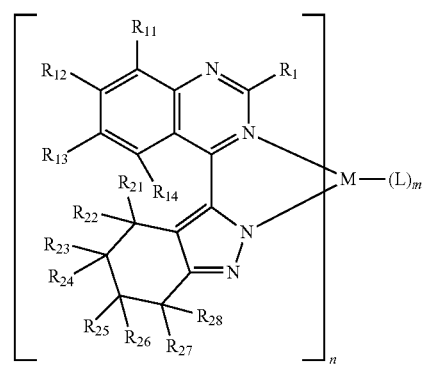

<Formula 1C-(3)>

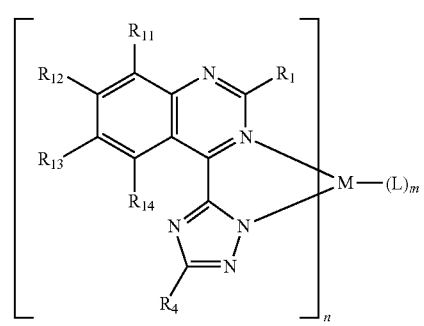

<Formula 1D-(1)> wherein, in Formulae 1A-(1), 1B-(1), 1B-(2), 1B-(3), 1C-(1), 1C-(2), 1C-(3), and 1D-(1): $R_1$ to $R_5$, $R_{11}$ to $R_{14}$, and $R_{21}$ to $R_{28}$ each independently may be selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a substituted $C_1$-$C_{20}$ alkyl group, a substituted $C_1$-$C_{20}$ alkoxy group, a phenyl group, a naphthyl group, an anthryl group, a fluorenyl group, a carbazolyl group, a pyridinyl group, a pyrimidinyl group, a triazinyl group, and a substituted cyclic group that is substituted with at least one selected from the group of: a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group; the substituted $C_1$-$C_{20}$ alkyl group and the substituted $C_1$-$C_{20}$ alkoxy group each may be substituted with at least one selected from the group of a deuterium atom, a halogen atom, a hydroxyl group, a cyano group, a nitro group, and an amino group; the substituted cyclic group may be selected from the group of a substituted phenyl group, a substituted naphthyl group, a substituted anthryl group, a substituted fluorenyl group, a substituted carbazolyl group, a substituted pyridinyl group, a substituted pyrimidinyl group, and a substituted triazinyl group; n may be an integer from 1 to 3; L may be an organic ligand; and m may be an integer from 0 to 4.

m may be 1, 2, 3, or 4; at least one of $L_m$ may be represented by one selected from the group of Formulae 2A to 2F:

Formula 2A

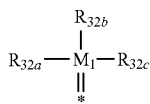

Formula 2B

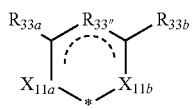

Formula 2C

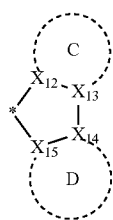

Formula 2D

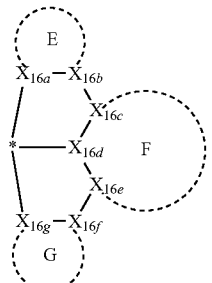

Formula 2E

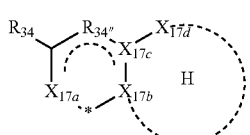

Formula 2F wherein, in Formulae 2A to 2F: $M_1$ may be P or As; $X_{11a}$, $X_{11b}$, $X_{12}$, $X_{13}$, $X_{14}$, $X_{15}$, $X_{16a}$, $X_{16b}$, $X_{16c}$, $X_{16d}$, $X_{16e}$, $X_{16f}$, $X_{16g}$, $X_{17a}$, $X_{17b}$, $X_{17c}$, and $X_{17d}$ each independently may be selected from the group of $C(R_{40})_x$, N, O, $N(R_{35})$, $P(R_{36})(R_{37})$, and $As(R_{38})(R_{39})$; $R_{33''}$ and $R_{34''}$ each independently may be selected from the group of a single bond, a substituted or unsubstituted $C_1$-$C_5$ alkylene group, and a substituted or unsubstituted $C_2$-$C_5$ alkenylene group; $R_{31}$, $R_{32a}$, $R_{32b}$, $R_{32c}$, $R_{33a}$, $R_{33b}$, $R_{34}$, $R_{35}$, $R_{36}$, $R_{37}$, $R_{38}$, $R_{39}$, and $R_{40}$ each independently may be selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, and a substituted or unsubstituted $C_2$-$C_{60}$ heteroaryl group; the C ring, the D ring, the E ring, the F ring, the G ring, and the H ring each independently may be selected from the group of a 5-membered to 20-membered saturated ring, and a 5-membered to 20-membered unsaturated ring; x may be an integer from 0 to 2; and * may be a binding site with M in Formula 1.

$R_{31}$, $R_{32a}$, $R_{32b}$, $R_{32c}$, $R_{33a}$, $R_{33b}$, $R_{34}$, $R_{35}$, $R_{36}$, $R_{37}$, $R_{38}$, and $R_{39}$ each independently may be selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a substituted $C_1$-$C_{20}$ alkyl group, a substituted $C_1$-$C_{20}$ alkoxy group, a phenyl group, a naphthyl group, an anthryl group, a fluorenyl group, a carbazolyl group, a pyridinyl group, a pyrimidinyl group, and a triazinyl group, and a substituted cyclic group that is substituted with at least one selected from the group of: a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group; the substituted $C_1$-$C_{20}$ alkyl group and the substituted $C_1$-$C_{20}$ alkoxy group each may be substituted with at least one selected from the group of a deuterium atom, a halogen atom, a hydroxyl group, a cyano group, a nitro group, and an amino group; and the substituted cyclic group may be selected from the group of a substituted phenyl group, a substituted naphthyl group, a substituted anthryl group, a substituted fluorenyl group, a substituted carbazolyl group, a substituted pyridinyl group, a substituted pyrimidinyl group, and a substituted triazinyl.

The at least one of $L_m$ may be represented by Formula 2C; and $X_{11a}$ and $X_{11b}$ in Formula 2C each independently may be selected from the group of O, $P(R_{36})(R_{37})$, and $As(R_{38})(R_{39})$.

The at least one of $L_m$ may be represented by one selected from the group of Formulae 2D, 2E, and 2F; the C ring, the D ring, the E ring, the F ring, the G ring, and the H ring in Formulae 2D, 2E, and 2F each independently may be a substituted or unsubstituted benzene, a substituted or unsubstituted pentalene, a substituted or unsubstituted indene, a substituted or unsubstituted naphtalene, a substituted or unsubstituted azulene, a substituted or unsubstituted heptalene, a substituted or unsubstituted indacene, a substituted or unsubstituted acenaphthylene, a substituted or unsubstituted fluorene, a substituted or unsubstituted spiro-fluorene, a substituted or unsubstituted phenalene, a substituted or unsubstituted phenanthrene, a substituted or unsubstituted anthracene, a substituted or unsubstituted fluoranthene, a substituted or unsubstituted triphenylene, a substituted or unsubstituted pyrene, a substituted or unsubstituted chrysene, a substituted or unsubstituted pyrrole, a substituted or unsubstituted imidazole, a substituted or unsubstituted pyrazole, a substituted or unsubstituted isothiazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted isoindole, a substituted or unsubstituted indole, a substituted or unsubstituted indazole, a substituted or unsubstituted purine, a substituted or unsubstituted isoquinoline, a substituted or unsubstituted quinoline, a substituted or unsubstituted phthalazine, a substituted or unsubstituted quinoxaline, a substituted or unsubstituted quinazoline, or a substituted or unsubstituted cinnoline; when the C ring is substituted with at least two substituents, adjacent two of the at least two substituents may be optionally linked together to form one selected from the group of a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, and a substituted or unsubstituted $C_2$-$C_{20}$ heteroaromatic ring; when the D ring is substituted with at least two substituents, adjacent two of the at least two substituents may be optionally linked together to form one selected from the group of a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, and a substituted or unsubstituted $C_2$-$C_{20}$ heteroaromatic ring; when the E ring is substituted with at least two substituents, adjacent two of the at least two substituents may be optionally linked together to form one selected from the group of a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, and a substituted or unsubstituted $C_2$-$C_{20}$ heteroaromatic ring; when the F ring is substituted with at least two substituents, adjacent two of the at least two substituents may be optionally linked together to form one selected from the group of a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, and a substituted or unsubstituted $C_2$-$C_{20}$ heteroaromatic ring; when the G ring is substituted with at least two substituents, adjacent two of the at least two substituents may be optionally linked together to form one selected from the group of a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, and a substituted or unsubstituted $C_2$-$C_{20}$ heteroaromatic ring; and when the H ring is substituted with at least two substituents, adjacent two of the at least two substituents may be optionally linked together to form one selected from the group of a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, and a substituted or unsubstituted $C_2$-$C_{20}$ heteroaromatic ring.

The organometallic compound may be represented by one selected from the group of Formulae 3 and 4:

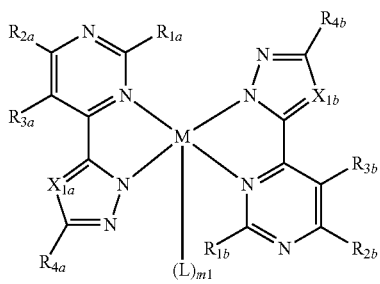

<Formula 3>

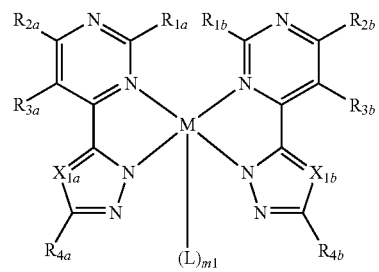

<Formula 4> wherein, in Formulae 3 and 4: M may be a transition metal; $X_{1a}$ may be N or $C(R_{5a})$; $X_{1b}$ may be N or $C(R_{5b})$; $R_{1a}$ to $R_{5a}$ and $R_{1b}$ to $R_{5b}$ each independently may be a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, $-N(Q_1)(Q_2)$, $-Si(Q_3)(Q_4)(Q_5)$, $-C(=O)(Q_6)$, and a binding site with an adjacent ligand via a single bond or a divalent linking group; two substituents of $R_{1a}$ to $R_{5a}$ may be optionally linked together to form one selected from the group of a substituted or unsubstituted $C_4$-$C_{20}$ alicyclic ring, a substituted or unsubstituted $C_2$-$C_{20}$ hetero alicyclic ring, a substituted or unsubstituted $C_6$-$C_{20}$ aromatic ring, and a substituted or unsubstituted $C_2$-$C_{20}$ heteroaromatic ring; two substituents of $R_{1b}$ to $R_{5b}$ may be optionally linked together to form one selected from the group of a substituted or unsubstituted $C_4$-$C_{20}$ alicyclic ring, a substituted or unsubstituted $C_2$-$C_{20}$ hetero alicyclic ring, a substituted or unsubstituted $C_6$-$C_{20}$ aromatic ring, and a substituted or unsubstituted $C_2$-$C_{20}$ heteroaromatic ring; $Q_1$ to $Q_6$ each independently may be a hydrogen atom, a substituted or unsubstituted $C_1$-$C_{60}$ alkyl group, a substituted or unsubstituted $C_6$-$C_{60}$ aryl group, and a substituted or unsubstituted $C_2$-$C_{60}$ heteroaryl group; L may be an organic ligand; and m may be 0, 1, or 2.

The organometallic compound may be represented by Formula 3, and $R_{1a}=R_{1b}$, $R_{2a}=R_{2b}$, $R_{3a}=R_{3b}$, $R_{4a}=R_{4b}$, $X_{1a}=X_{1b}$, M=Pt, and m1=0.

The organometallic compound may be represented by Formula 4; and $R_{1a}=R_{1b}$, $R_{2a}=R_{2b}$, $R_{3a}=R_{3b}$, $R_{4a}=R_{4b}$, $X_{1a}=X_{1b}$, M=Pt, and m1=0.

The organometallic compound may be represented by one selected from the group of Formulae 3A-(1), 3A-(2), 3A-(3), 3A-(4), 3A-(5), 3A-(6), 3A-(7), 3A-(8), and 3A-(9).

<Formula 3A-(1)>
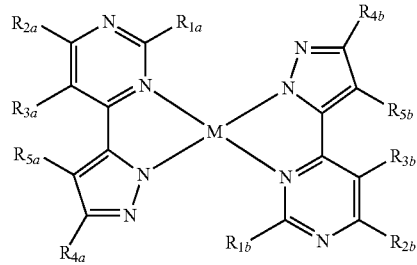
<Formula 3A-(2)>
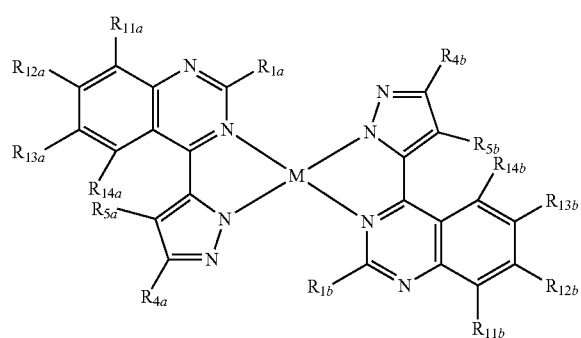
<Formula 3A-(3)>
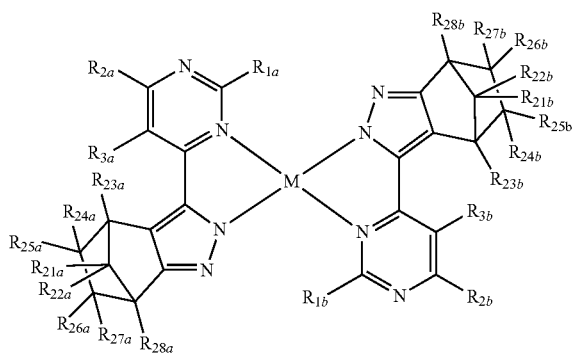
<Formula 3A-(4)>
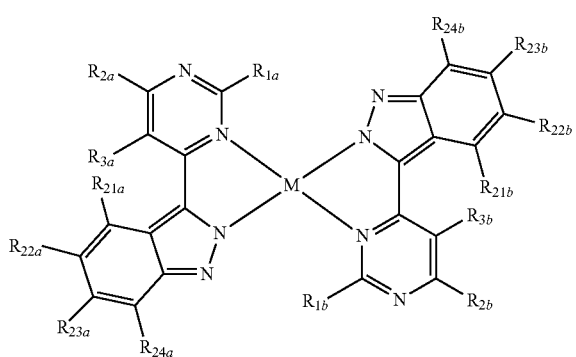
<Formula 3A-(5)>
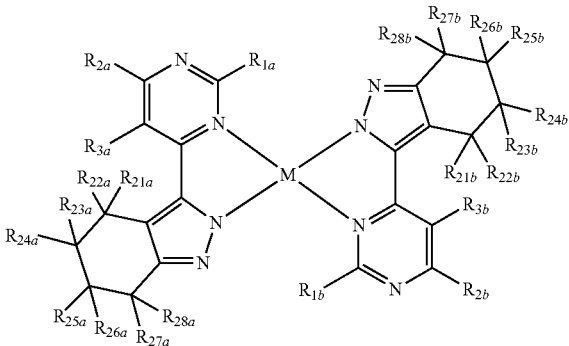
<Formula 3A-(6)>
<Formula 3A-(7)>
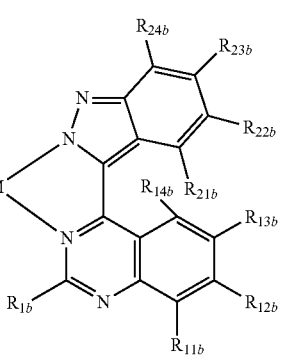
<Formula 3A-(8)>
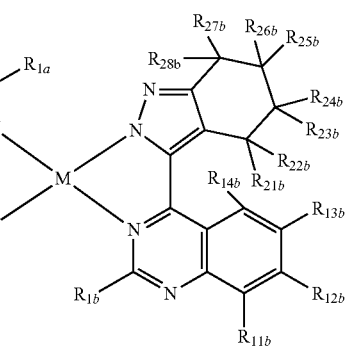

-continued

<Formula 3A-(9)>

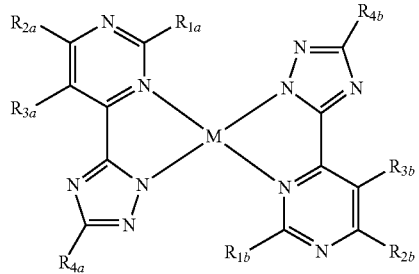

wherein, in Formulae 3A-(1), 3A-(2), 3A-(3), 3A-(4), 3A-(5), 3A-(6), 3A-(7), 3A-(8), and 3A-(9): M may be platinum (Pt); and $R_{1a}$ to $R_{5a}$, $R_{1b}$ to $R_{5b}$, $R_{11a}$ to $R_{14a}$, $R_{11b}$ to $R_{14b}$, $R_{21a}$ to $R_{28a}$, and $R_{21b}$ to $R_{28b}$ each independently may be selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group, a substituted $C_1$-$C_{20}$ alkyl group, a substituted $C_1$-$C_{20}$ alkoxy group, a phenyl group, a naphthyl group, an anthryl group, a fluorenyl group, a carbazolyl group, a pyridinyl group, a pyrimidinyl group, a triazinyl group, and a substituted cyclic group that is substituted with at least one selected from the group of: a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group; the substituted $C_1$-$C_{20}$ alkyl group and the substituted $C_1$-$C_{20}$ alkoxy group each may be substituted with at least one selected from the group of a deuterium atom, a halogen atom, a hydroxyl group, a cyano group, a nitro group, and an amino group; the substituted cyclic group may be selected from the group of a substituted phenyl group, a substituted naphthyl group, a substituted anthryl group, a substituted fluorenyl group, a substituted carbazolyl group, a substituted pyridinyl group, a substituted pyrimidinyl group, and a substituted triazinyl group.

The organometallic compound may be represented by one selected from the group of Formulae 3A-(1), 3A-(2), 3A-(4), 3A-(6), 3A-(8), and 3A-(9); and $R_{1a}$=$R_{1b}$, $R_{2a}$=$R_{2b}$, $R_{3a}$=$R_{3b}$, $R_{4a}$=$R_{4b}$, $R_{5a}$=$R_{5b}$, $R_{11a}$=$R_{11b}$, $R_{12a}$=$R_{12b}$, $R_{13a}$=$R_{13b}$, $R_{14a}$=$R_{14b}$, $R_{21a}$=$R_{21b}$, $R_{22a}$=$R_{22b}$, $R_{23a}$=$R_{23b}$, $R_{24a}$=$R_{24b}$, $R_{25a}$=$R_{25b}$, $R_{26a}$=$R_{26b}$, $R_{27a}$=$R_{27b}$, and $R_{28a}$=$R_{28b}$.

The organometallic compound may be represented by Formula 4-(a):

<Formula 4-(a)>

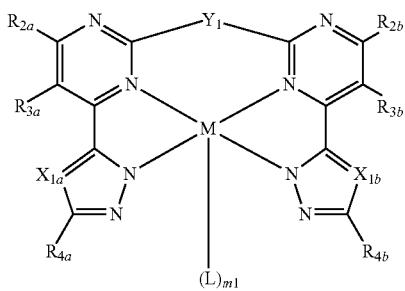

wherein, in Formula 4-(a): M may be a transition metal; $X_{1a}$ may be N or $C(R_{5a})$; $X_{1b}$ may be N or $C(R_{5b})$; $R_{2a}$ to $R_{5a}$ and $R_{2b}$ to $R_{5b}$ each independently may be selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —$N(Q_1)(Q_2)$, —$Si(Q_3)(Q_4)(Q_5)$, —$C(=O)(Q_6)$, and a binding site with an adjacent ligand via a single bond or a divalent linking group; two substituents of $R_{2a}$ to $R_{5a}$ may be optionally linked together to form at least one selected from the group of a substituted or unsubstituted $C_4$-$C_{20}$ alicyclic ring, a substituted or unsubstituted $C_2$-$C_{20}$ hetero alicyclic ring, a substituted or unsubstituted $C_6$-$C_{20}$ aromatic ring, and a substituted or unsubstituted $C_2$-$C_{20}$ heteroaromatic ring; two substituents of $R_{2b}$ to $R_{5b}$ may be optionally linked together to form at least one selected from the group of a substituted or unsubstituted $C_4$-$C_{20}$ alicyclic ring, a substituted or unsubstituted $C_2$-$C_{20}$ hetero alicyclic ring, a substituted or unsubstituted $C_6$-$C_{20}$ aromatic ring, and a substituted or unsubstituted $C_2$-$C_{20}$ heteroaromatic ring; $Q_1$ to $Q_6$ each independently may be selected from the group of a hydrogen atom, a substituted or unsubstituted $C_1$-$C_{60}$ alkyl group, a substituted or unsubstituted $C_6$-$C_{60}$ aryl group, and a substituted or unsubstituted $C_2$-$C_{60}$ heteroaryl group; L may be an organic ligand; m1 may be 0, 1, or 2; $Y_1$ may be a single bond or a divalent linking group including at least one selected from the group of —O—, —S—, —$N(Z_1)$—, —$[C(Z_2)(Z_3)]_a$—, and —$[Si(Z_4)(Z_5)]_b$—; $Z_1$ to $Z_5$ each independently may be a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, or a $C_2$-$C_{60}$ heteroaryl group, and a and b are each independently an integer from 1 to 4.

$Y_1$ may be —$N(Z_1)$—; $Z_1$ may be at least one selected from the group of a phenyl group, a naphthyl group, an anthryl group, a fluorenyl group, a carbazolyl group, a pyridinyl group, a pyrimidinyl group, a triazinyl group, and a substituted cyclic group that is substituted with at least one selected from the group of: a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group; and the substituted cyclic group may be selected from the group of a substituted phenyl group, a substituted naphthyl group, a substituted anthryl group, a substituted fluorenyl group, a substituted carbazolyl group, a substituted pyridinyl group, a substituted pyrimidinyl group, and a substituted triazinyl group.

n may be 3, and m may be 0.

n may be 1, and m may be an integer from 1 to 4.

The organometallic compound may be represented by one selected from the group of Formulae 5 to 8:

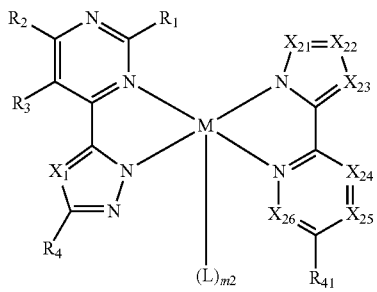
<Formula 5>

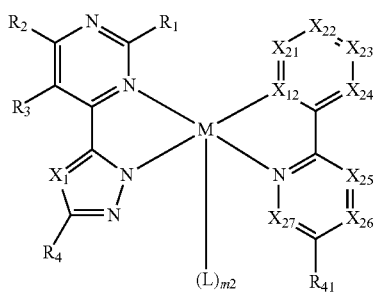
<Formula 6>

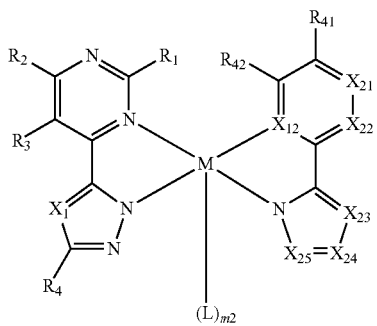
<Formula 7>

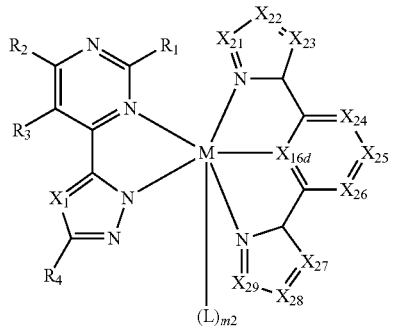
<Formula 8> wherein, in Formulae 5 to 8: M, $X_1$, $R_1$ to $R_5$, and L may be as above in Formula 1; m2 may be 0, 1, or 2; $X_{12}$ and $X_{16d}$ each independently may be N or C; $X_{21}$ may be N or C($R_{51}$), $X_{22}$ may be N or C($R_{52}$), $X_{23}$ may be N or C($R_{53}$), $X_{24}$ may be N or C($R_{54}$), $X_{25}$ may be N or C($R_{55}$), $X_{26}$ may be N or C($R_{56}$), $X_{27}$ may be N or C($R_{57}$), $X_{28}$ may be N or C($R_{58}$), and $X_{29}$ may be N or C($R_{59}$); $R_{41}$, $R_{42}$, and $R_{51}$ to $R_{59}$ each independently may be selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —N($Q_{11}$)($Q_{12}$), —Si($Q_{13}$)($Q_{14}$)($Q_{15}$), and a binding site with an adjacent ligand via a single bond or a divalent linking group; two adjacent substituents of $R_{41}$, $R_{42}$, and $R_{51}$ to $R_{59}$ may be optionally linked together to form one selected from the group of a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, and a substituted or unsubstituted $C_2$-$C_{20}$ heteroaromatic ring; and $Q_{11}$ to $Q_{15}$ each independently may be selected from the group of a hydrogen atom, a $C_1$-$C_{10}$ alkyl group, a $C_6$-$C_{20}$ aryl group, and a $C_2$-$C_{20}$ heteroaryl group.

The organometallic compound may be represented by one selected from the group of Formulae 5-(1), 5-(2), 5-(3), and 5-(4):

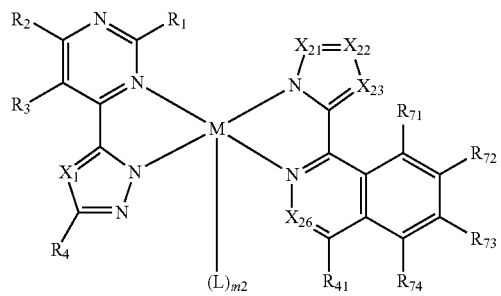
<Formula 5-(1)>

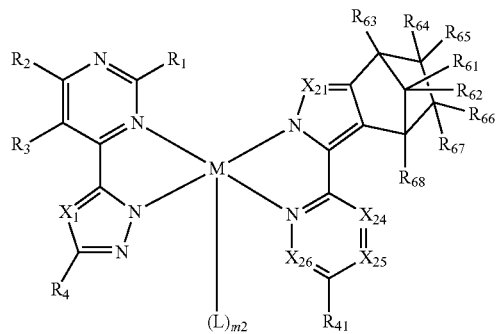
<Formula 5-(2)>

<Formula 5-(3)>

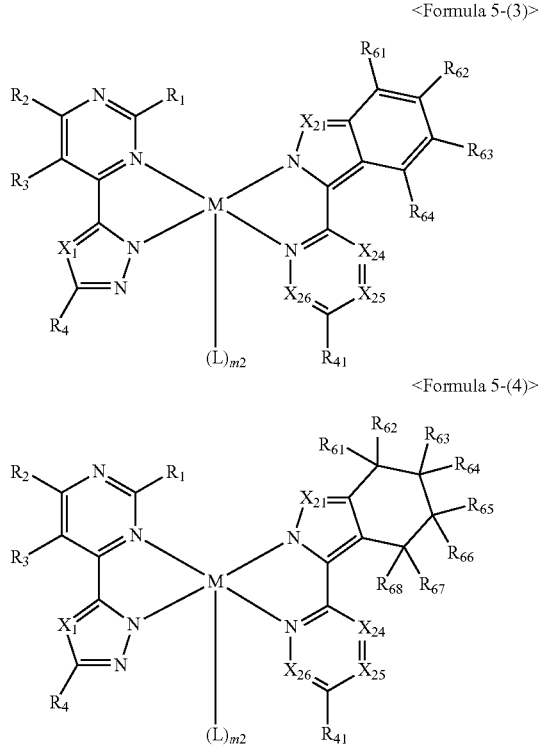

<Formula 5-(4)>

<Formula 5-(a)>

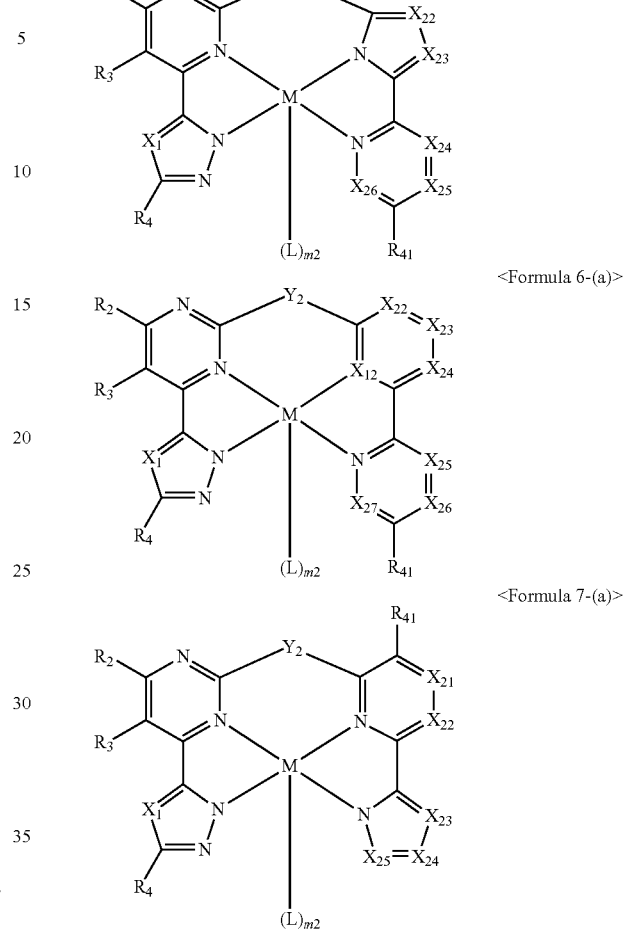

<Formula 6-(a)>

<Formula 7-(a)> wherein, in Formulae 5-(1) to 5-(4): M, $X_1$, $R_1$ to $R_5$, and L may be as in Formula 1; m2 may be 0, 1, or 2; $X_{21}$ may be N or $C(R_{51})$, $X_{22}$ may be N or $C(R_{52})$, $X_{23}$ may be N or $C(R_{53})$, $X_{24}$ may be N or $C(R_{54})$, $X_{25}$ may be N or $C(R_{55})$, and $X_{26}$ may be N or $C(R_{56})$; and $R_{41}$, $R_{51}$ to $R_{56}$, $R_{61}$ to $R_{68}$, and $R_{71}$ to $R_{74}$ each independently may be selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a substituted $C_1$-$C_{20}$ alkyl group, a substituted $C_1$-$C_{20}$ alkoxy group, a phenyl group, a naphthyl group, an anthryl group, a fluorenyl group, a carbazolyl group, a pyridinyl group, a pyrimidinyl group, a triazinyl group, and a substituted cyclic group that is substituted with at least one selected from the group of: a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group; the substituted $C_1$-$C_{20}$ alkyl group and the substituted $C_1$-$C_{20}$ alkoxy group each may be substituted with at least one selected from the group of a deuterium atom, a halogen atom, a hydroxyl group, a cyano group, a nitro group, and an amino group; and the substituted cyclic group may be selected from the group of a substituted phenyl group, a substituted naphthyl group, a substituted anthryl group, a substituted fluorenyl group, a substituted carbazolyl group, a substituted pyridinyl group, a substituted pyrimidinyl group, and a substituted triazinyl group.

The organometallic compound may be represented by one selected from the group of Formulae 5-(a), 6-(a), and 7-(a):

wherein, in Formulae 5-(a), 6-(a), and 7-(a): M, $X_1$, $R_2$ to $R_5$, and L may be as in Formula 1; m2 may be 0, 1, or 2; $X_{12}$ may be C or N; $X_{21}$ may be N or $C(R_{51})$, $X_{22}$ may be N or $C(R_{52})$, $X_{23}$ may be N or $C(R_{53})$, $X_{24}$ may be N or $C(R_{54})$, $X_{25}$ may be N or $C(R_{55})$, $X_{26}$ may be N or $C(R_{56})$, and $X_{27}$ may be N or $C(R_{57})$; $R_{41}$ and $R_{51}$ to $R_{57}$ each independently may be selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkyl group substituted with at least one fluorine atom, a $C_1$-$C_{20}$ alkoxy group, a phenyl group, a naphthyl group, and an anthryl group;

$Y_2$ may be a single bond or a divalent linking group including at least one selected from the group of —O—, —S—, —N($Z_{11}$)—, —[C($Z_{12}$)($Z_{13}$)]$_c$—, and —[Si($Z_{14}$)($Z_{15}$)]$_d$—;

$Z_{11}$ to $Z_{15}$ each independently may be selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, or a $C_2$-$C_{60}$ heteroaryl group; and c and d each independently may be an integer from 1 to 4.
The organometallic compound may be one selected from the group of compounds 1 to 68:
1
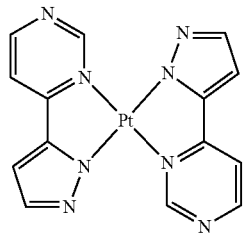
2
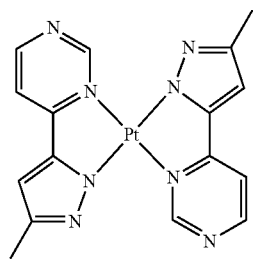
3
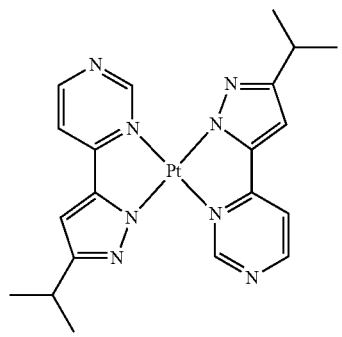
4
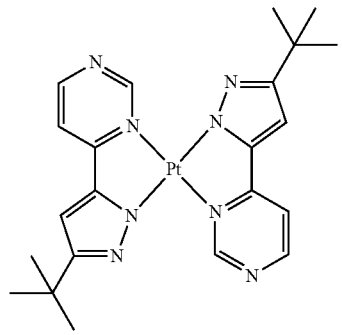
5
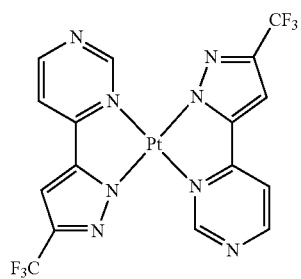
6
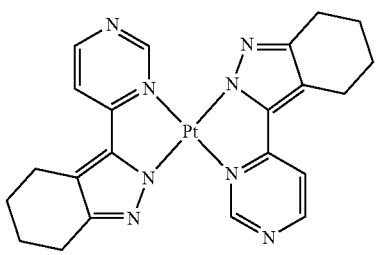
7
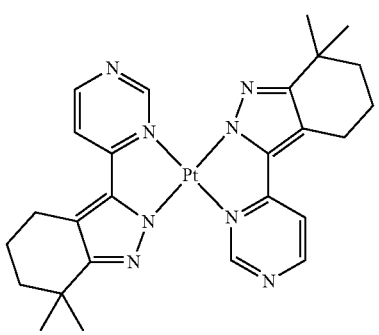
8
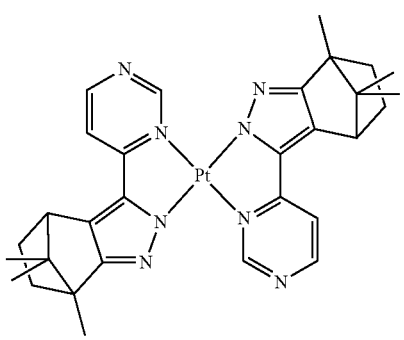
9
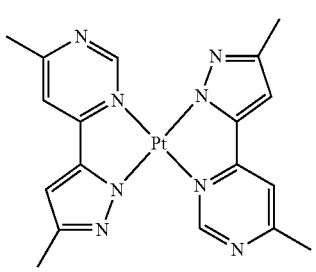
10
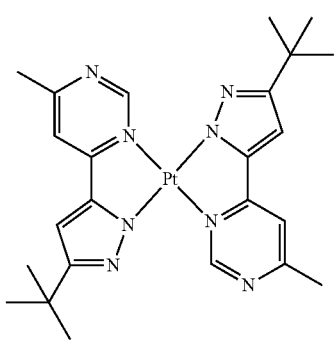

11
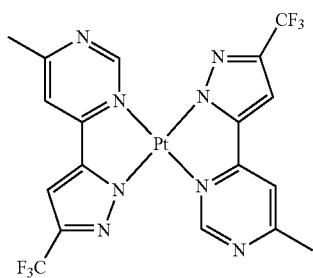
12
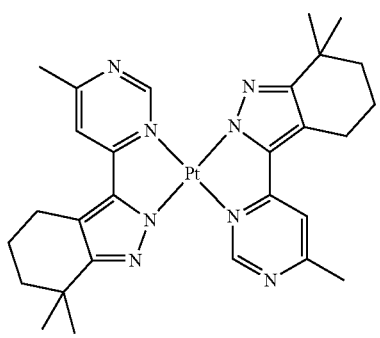
13
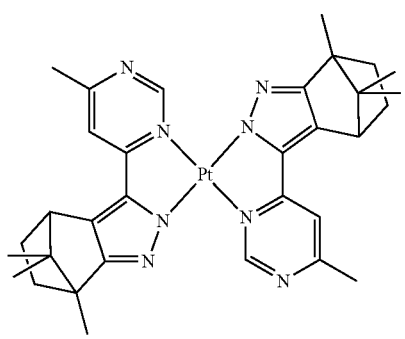
14
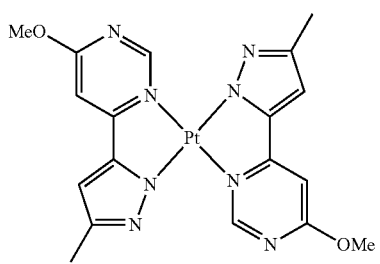
15
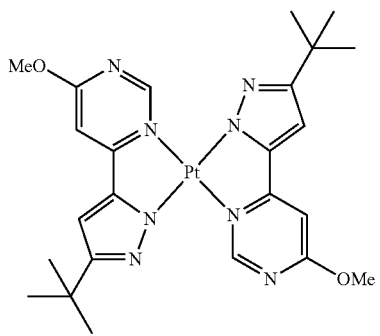
16
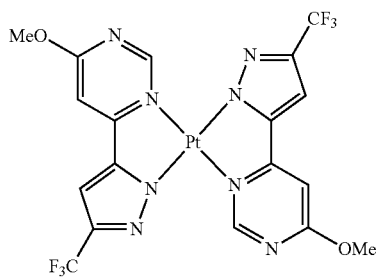
17
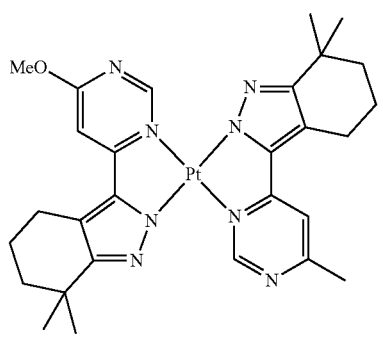
18
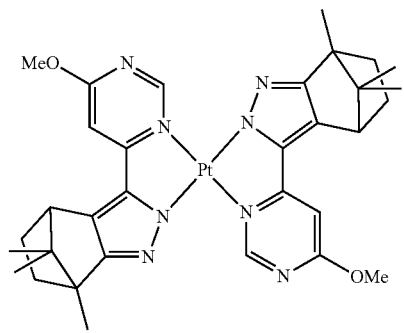
19
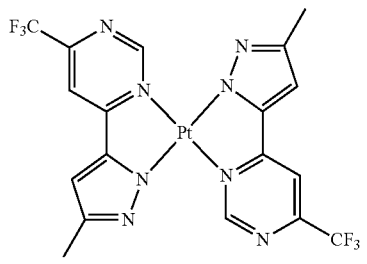
20
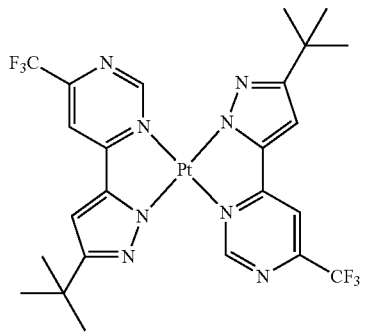

21
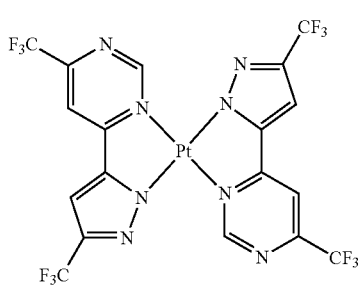
22
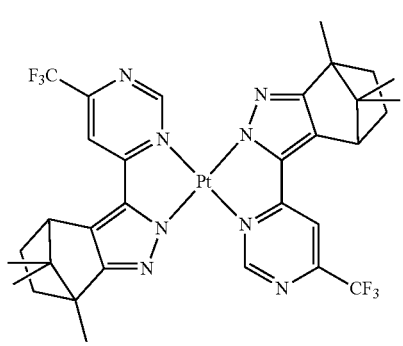
23
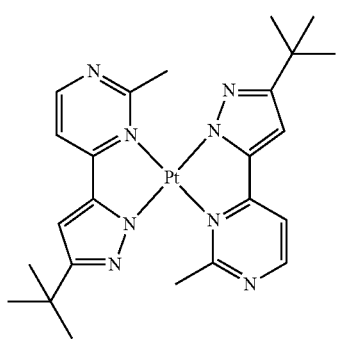
24
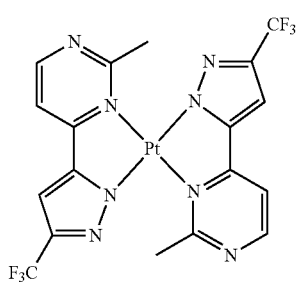
25
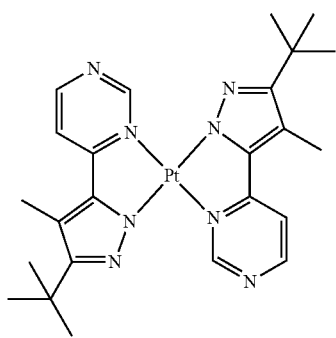
26
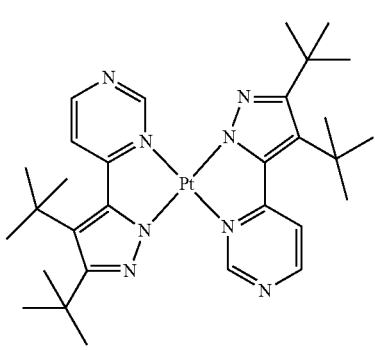
27
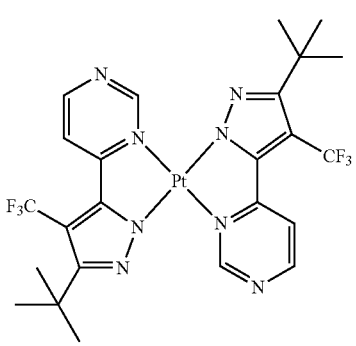
28
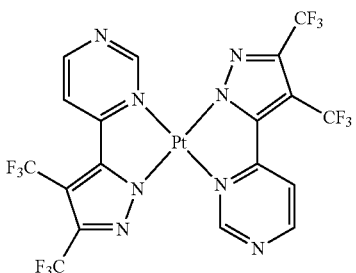
29
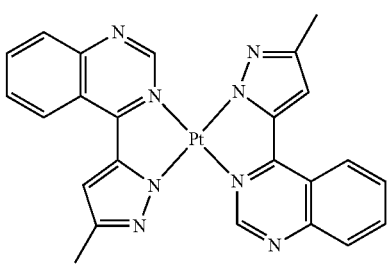
30
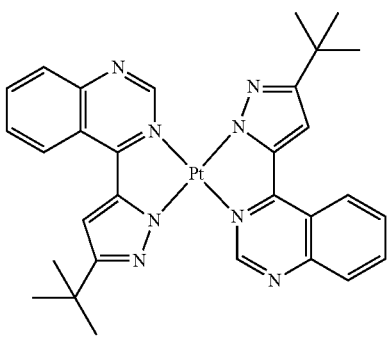

31
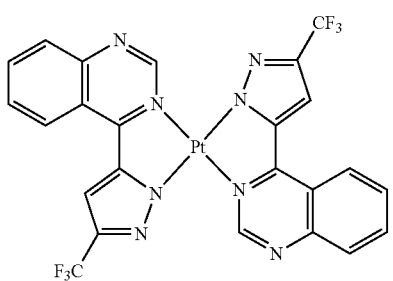
32
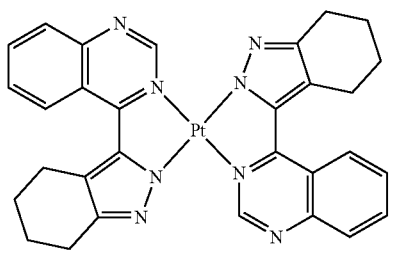
33
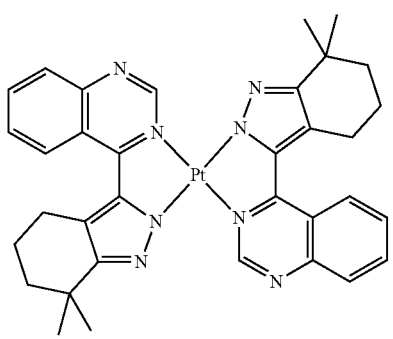
34
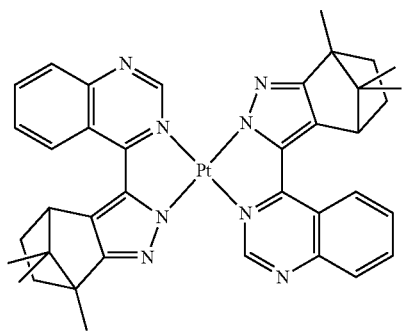
35
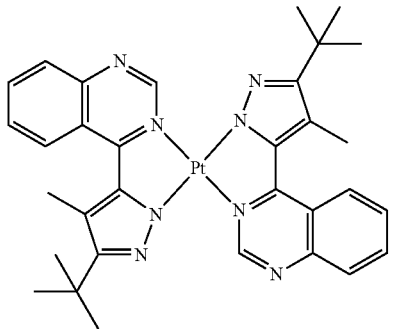
36
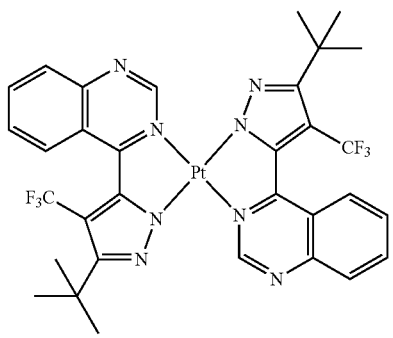
37
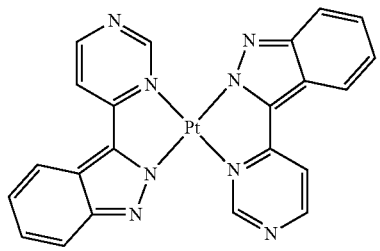
38
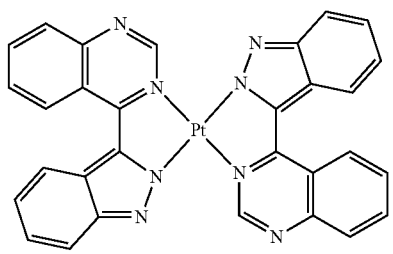
39
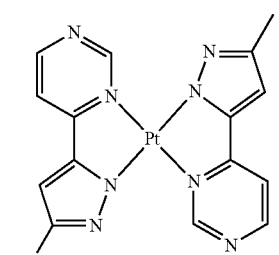
40
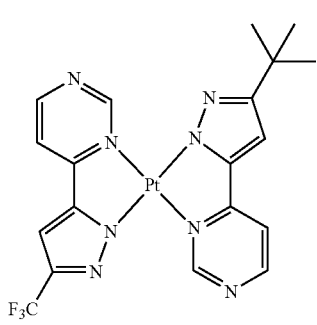

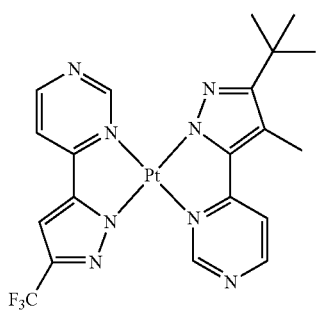
41
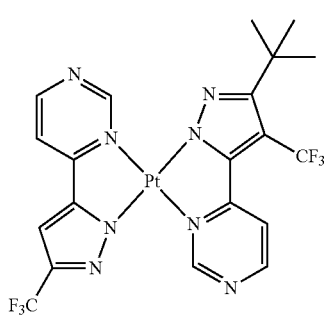
42
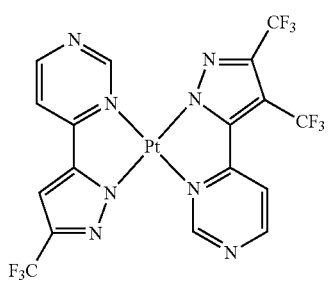
43
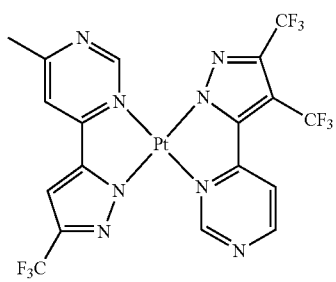
44
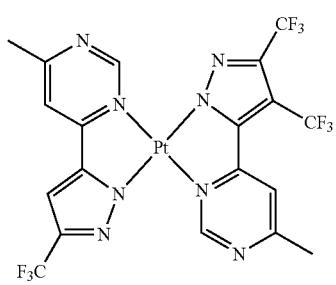
45
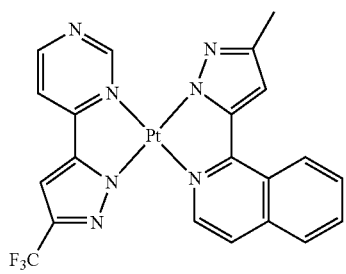
46
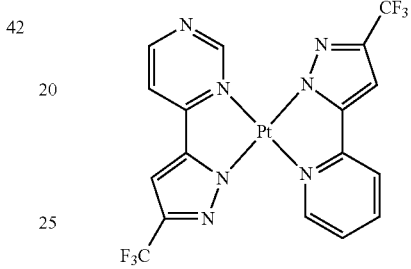
47
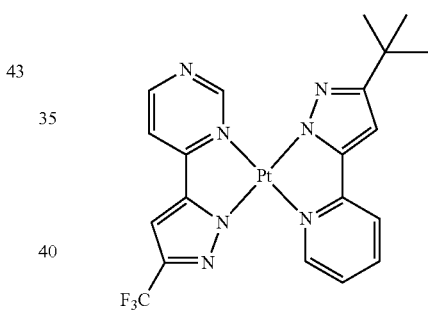
48
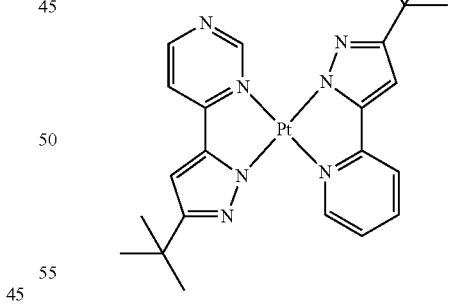
49
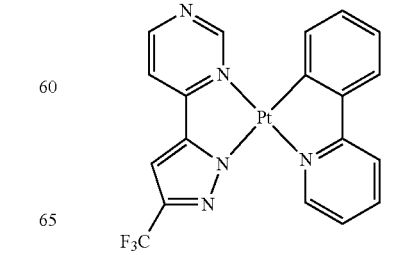
50

-continued
51 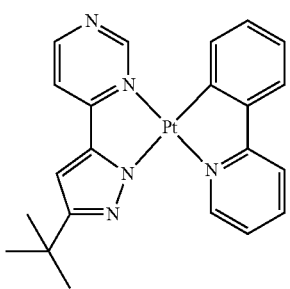
52 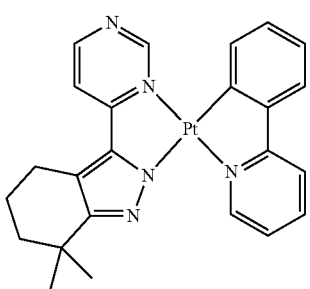
53 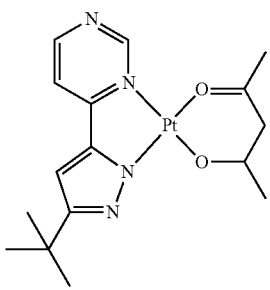
54 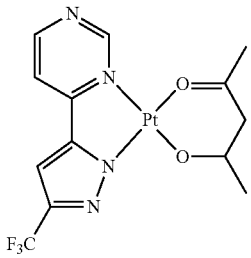
55 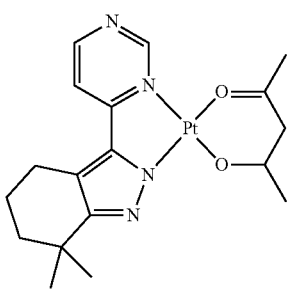
56 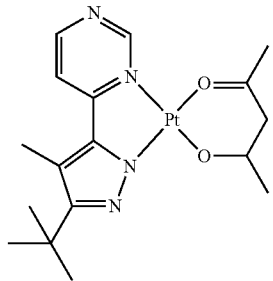
57 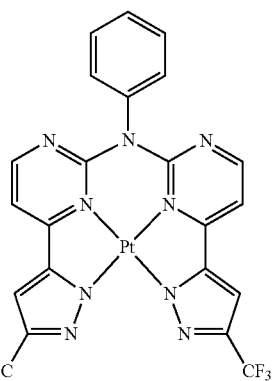
58 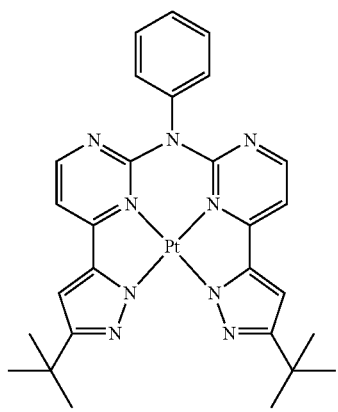
59 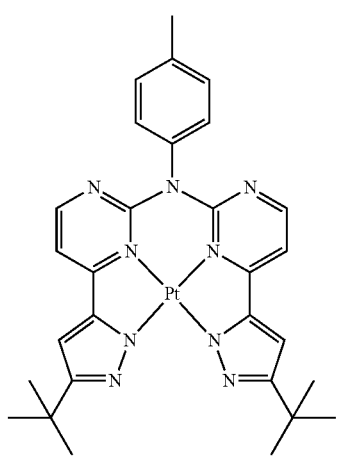

-continued
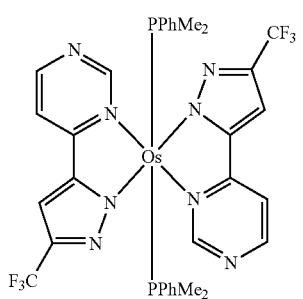
60
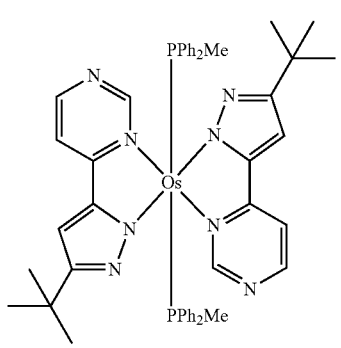
61
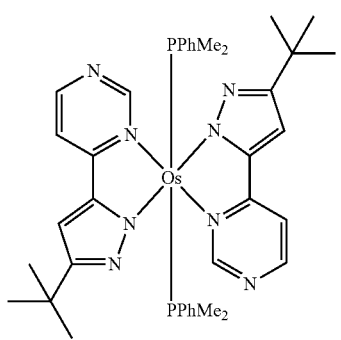
62
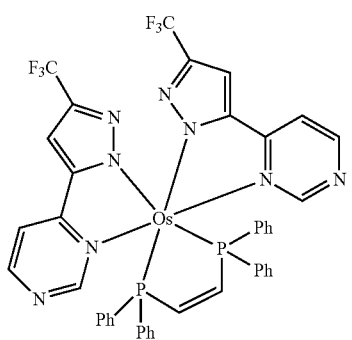
63
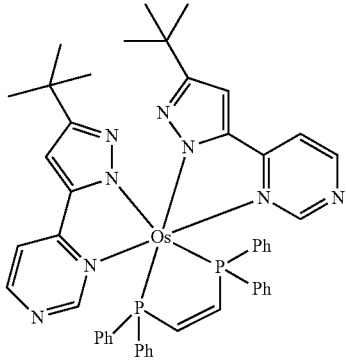
64
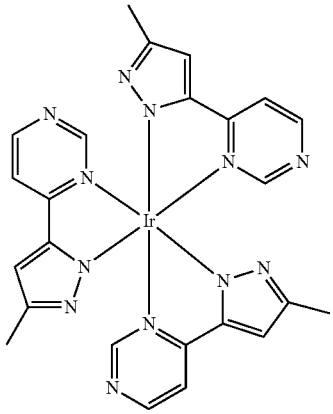
65
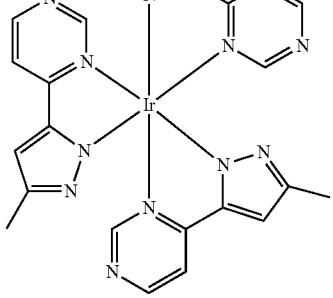
66
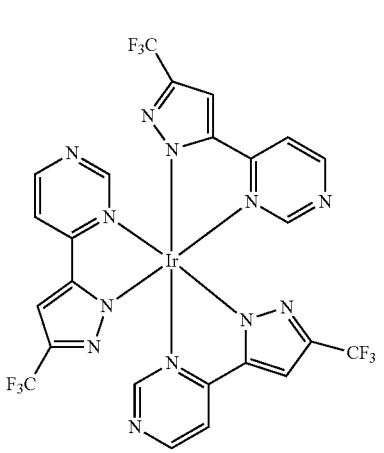
67
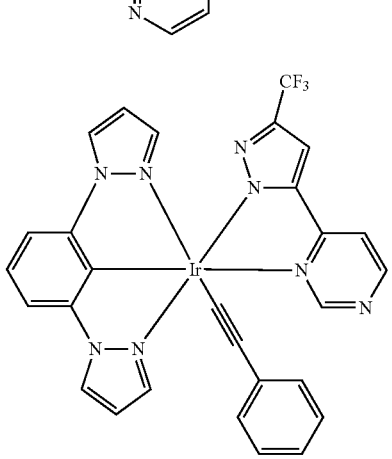

-continued

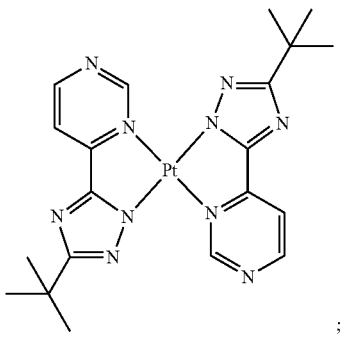

68

;

wherein, in compounds 60-62, Ph may be a phenyl group and Me may be a methyl group.

Embodiments are also directed to an organic light-emitting device, including: a substrate; a first electrode; a second electrode opposite the first electrode; and an organic layer between the first electrode and the second electrode, the organic layer including the organometallic compound.

The organic layer may include at least one selected from the group of a hole injection layer, a hole transport layer, a functional layer having both hole injection and hole transport capabilities, a buffer layer, an electron blocking layer, an emission layer, a hole blocking layer, an electron transport layer, an electron injection layer, and a functional layer having both electron injection and electron transport capabilities.

The organic layer may include an emission layer; the organometallic compound may be in the emission layer; and light may be emitted from the emission layer based on a phosphorescence mechanism.

The organometallic compound in the emission layer may serve as a dopant; and the emission layer may include a carbazole-based compound as a host.

The carbazole-based compound may be represented by Formula 10:

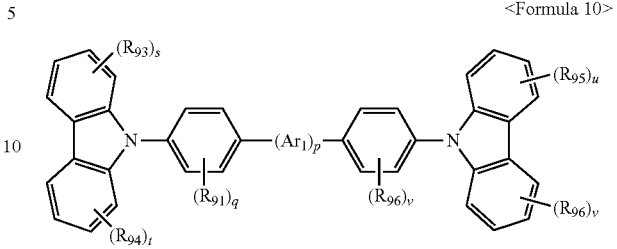

<Formula 10> wherein, in Formula 10: $Ar_1$ may be selected from the group of a substituted or unsubstituted $C_1$-$C_{60}$ alkylene group, a substituted or unsubstituted $C_2$-$C_{60}$ alkenylene group, —C(=O)—, —N($R_{100}$)—, a substituted or unsubstituted $C_6$-$C_{60}$ arylene group, and a substituted or unsubstituted $C_2$-$C_{60}$ heteroarylene group; $R_{100}$ may be selected from the group of a substituted or unsubstituted $C_6$-$C_{60}$ aryl group, and a substituted or unsubstituted $C_2$-$C_{60}$ heteroaryl group; p may be an integer from 0 to 10; $R_{91}$ to $R_{96}$ each independently may be selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, and a substituted or unsubstituted $C_2$-$C_{60}$ heteroaryl group;

two adjacent substituents of $R_{91}$ to $R_{96}$ optionally may be linked together to form one selected from the group of a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic ring, and a substituted or unsubstituted $C_2$-$C_{20}$ heteroaromatic ring; and q, r, s, t, u, and v each independently may be an integer from 1 to 4.

The carbazole-based compound may be one selected from the group of compounds H1 to H30:

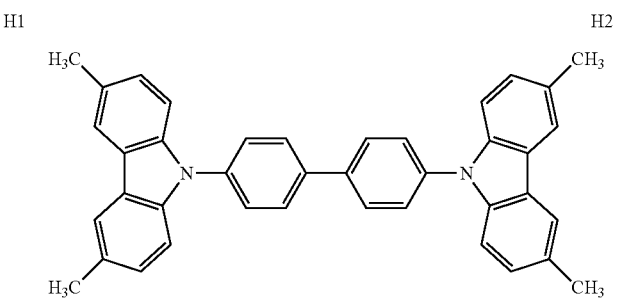

-continued
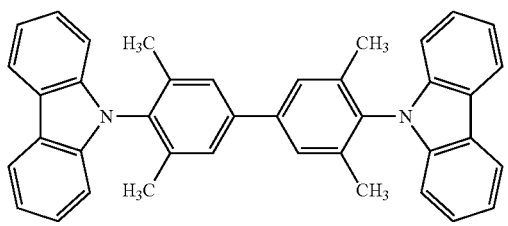 H3
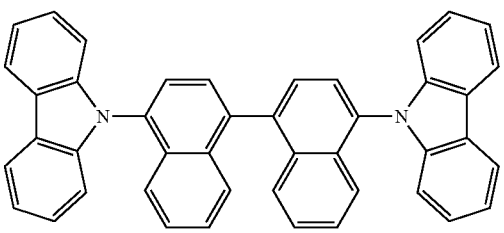 H4
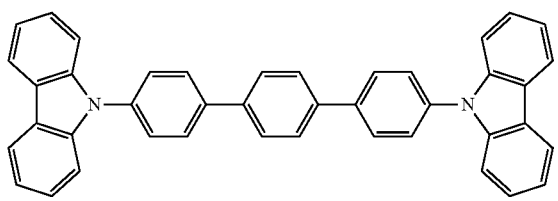 H5
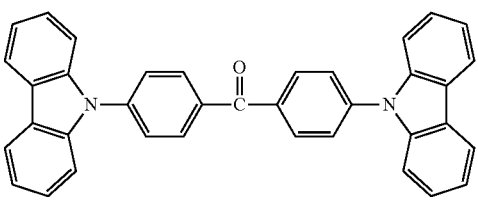 H6
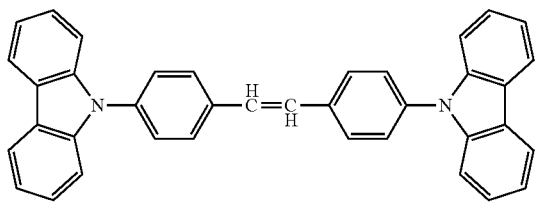 H7
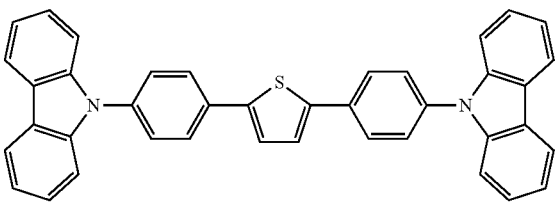 H8
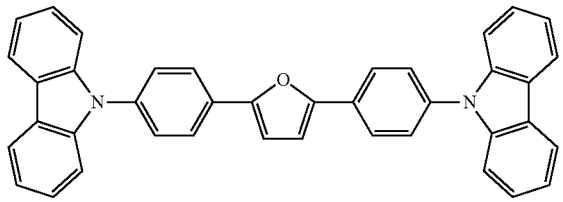 H9
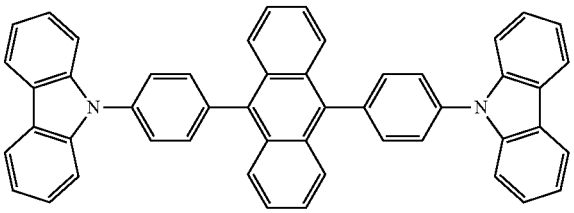 H10
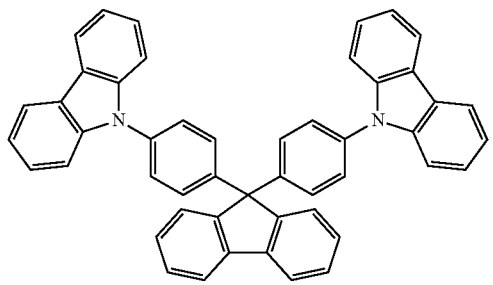 H11
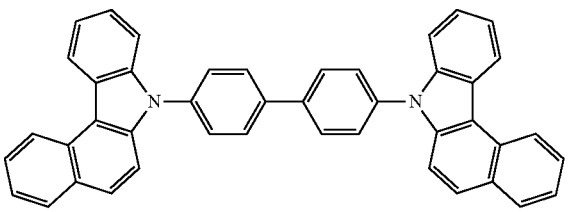 H12

-continued
H13
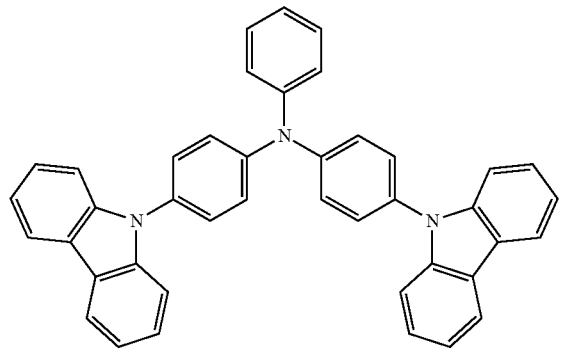
H14
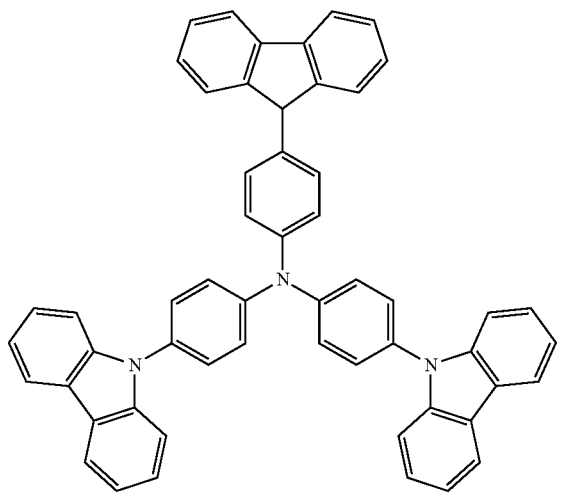
H15
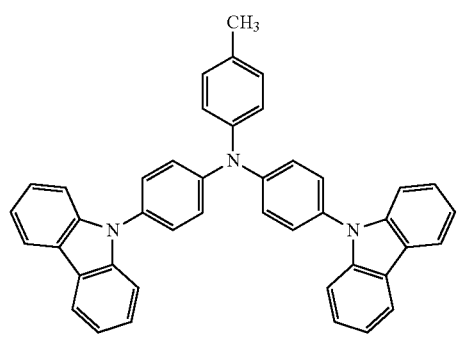
H16
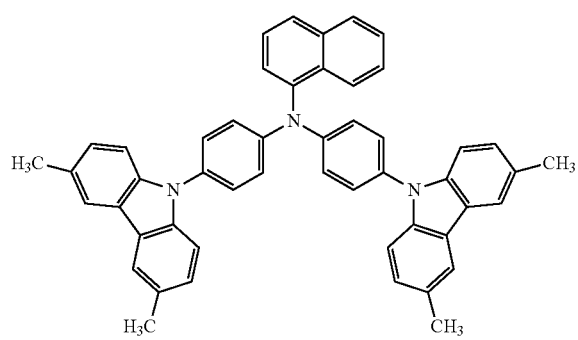
H17
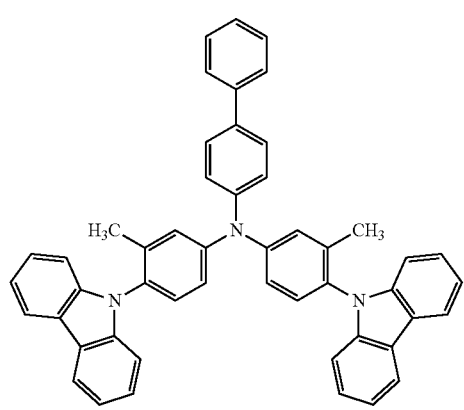
H18
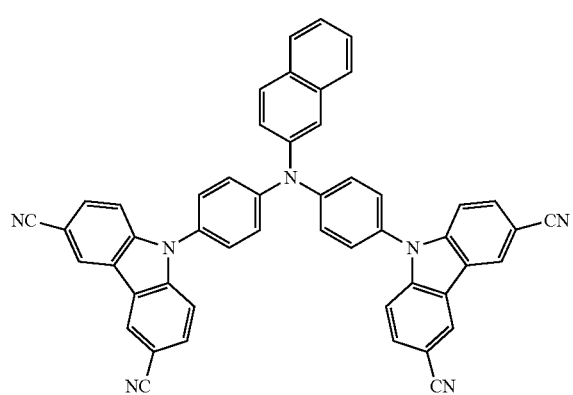

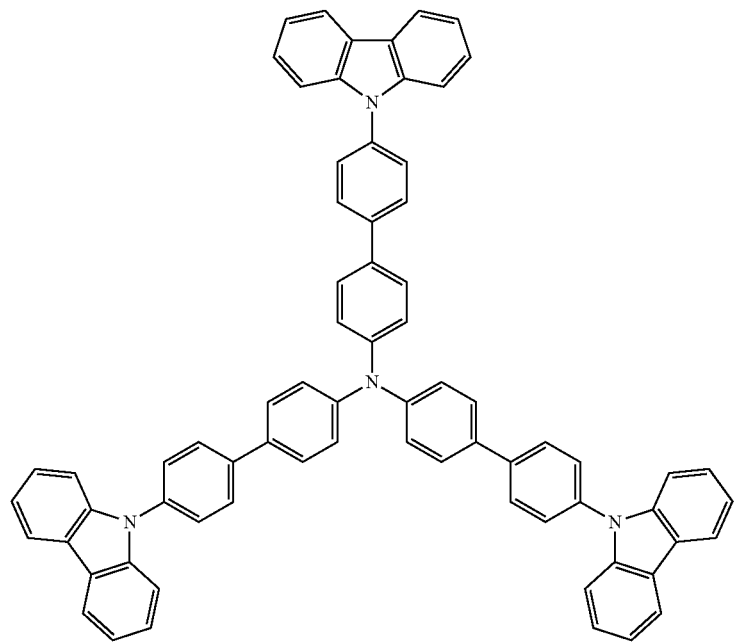
H19
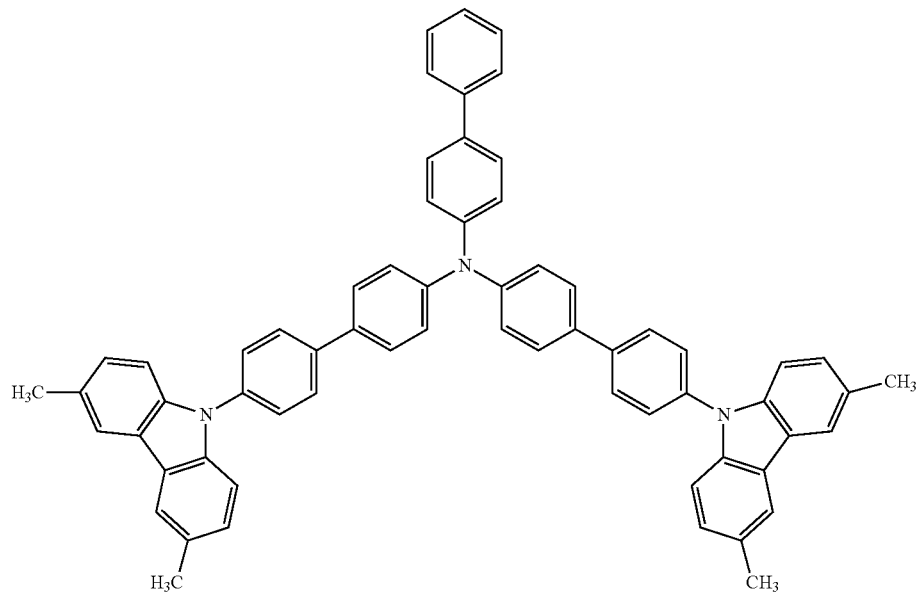
H20

-continued
H21
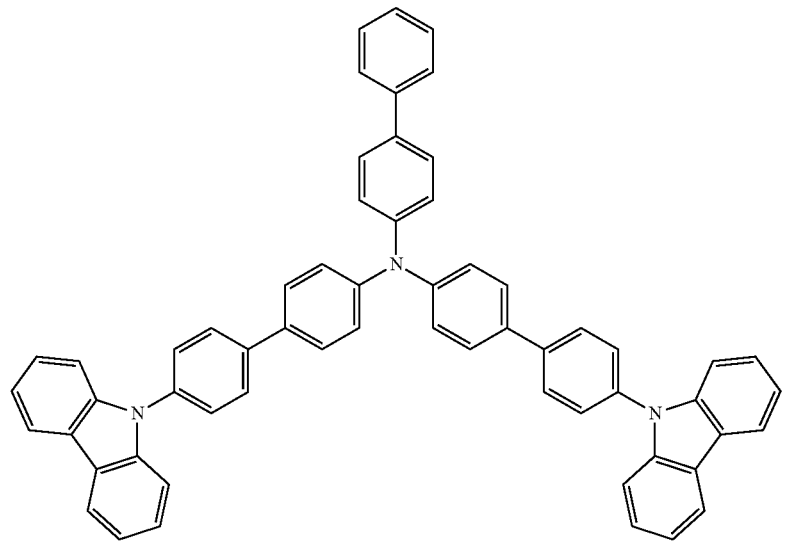
H22
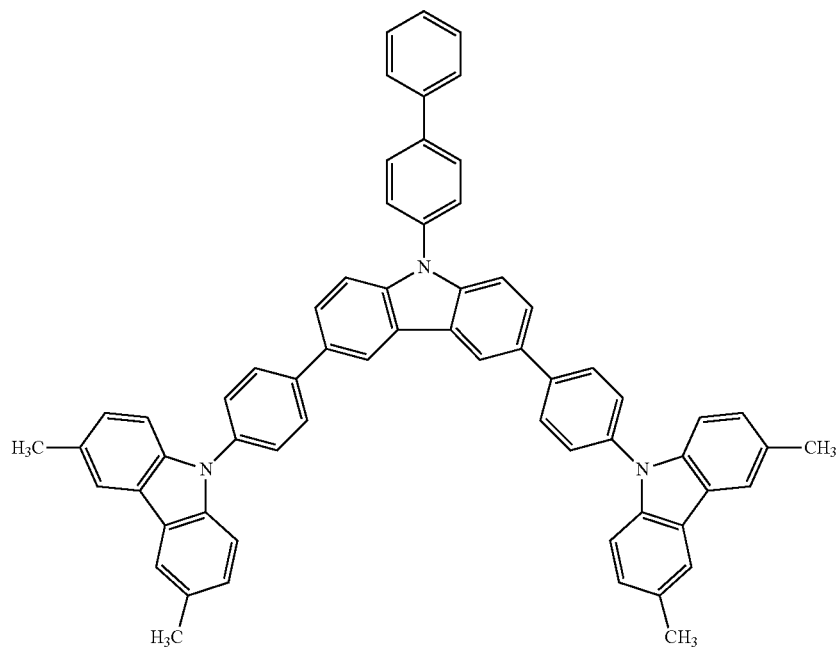
H23
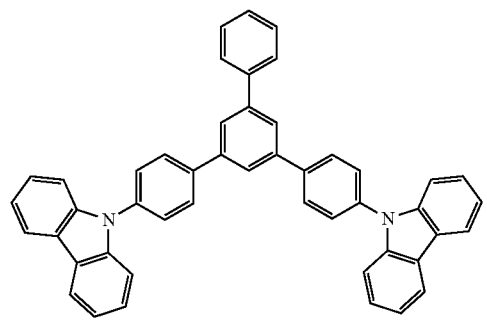
H24
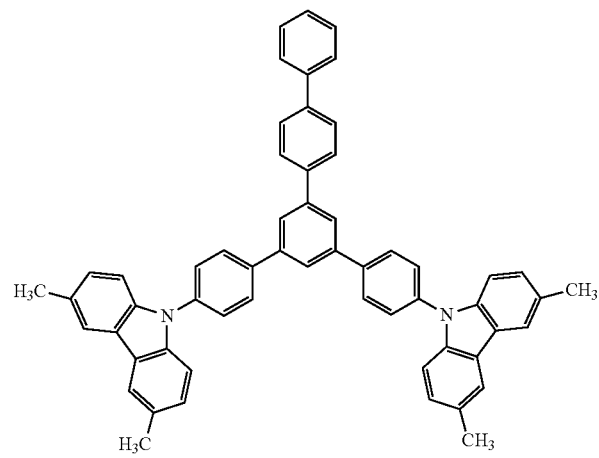

-continued
H25
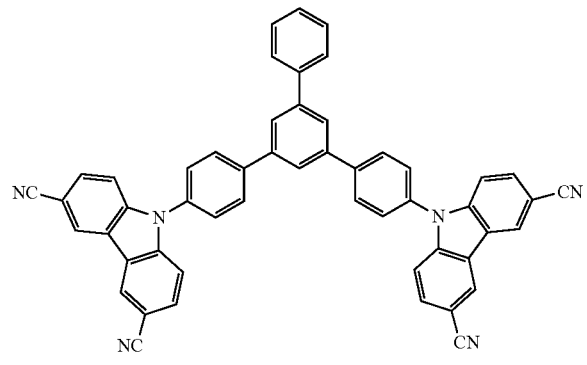
H26
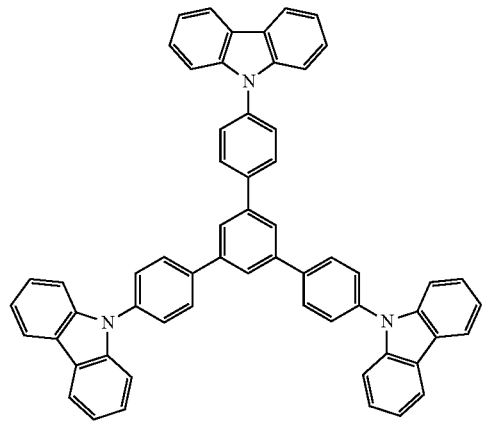
H27
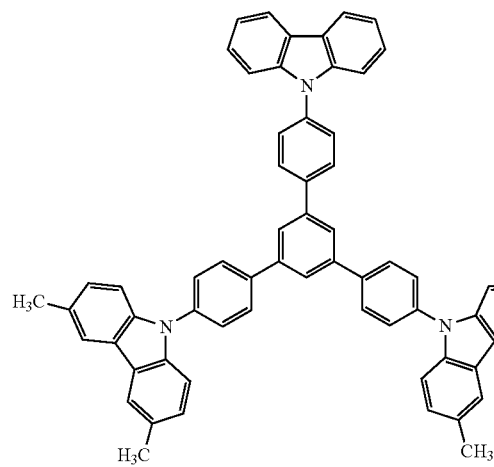
H28
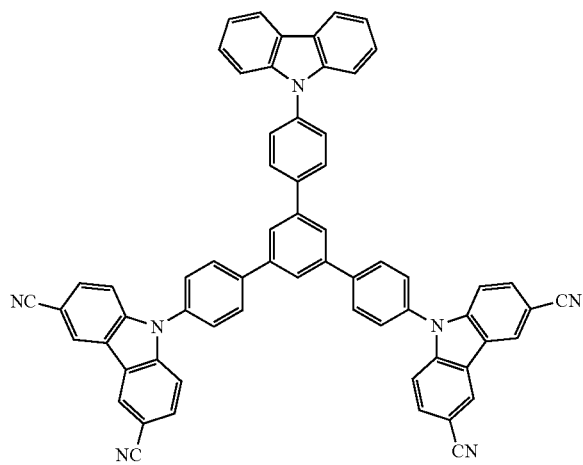
H30
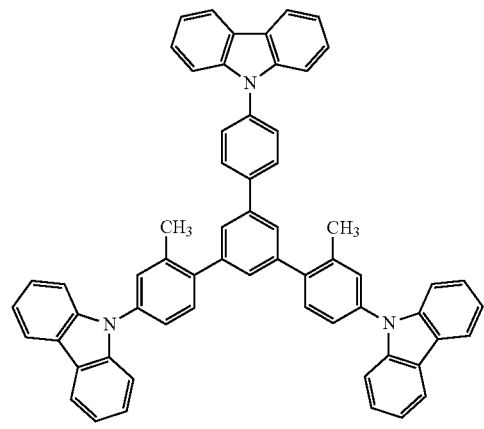
H29
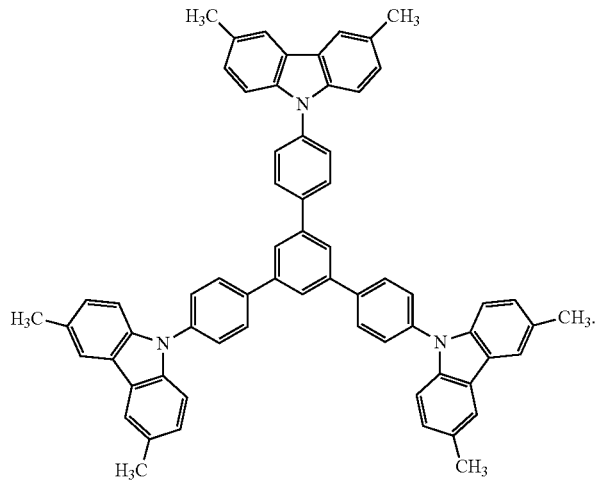

The organic layer may include at least one selected from the group of a hole injection layer, a hole transport layer, and a functional layer having both hole injection and hole transport capabilities; and the at least one of the hole injection layer, the hole transport layer, and the functional layer having both hole injection and hole transport capabilities may include a charge-generating material.

The organic layer may include an electron transport layer, and the electron transport layer may include a metal-containing material.

BRIEF DESCRIPTION OF THE DRAWING

Features will become apparent to those of ordinary skill in the art by describing in detail exemplary embodiments with reference to the attached drawing in which FIG. 1 schematically illustrates the structure of an organic light-emitting device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer is referred to as being "between" two layers, it can be the only layer between the two layers, or one or more intervening layers may also be present. Like reference numerals refer to like elements throughout.

As used herein, the term "and/or" includes any and all combinations of one or more of the associated listed items. Expressions such as "at least one of," and "selected from the group of," when preceding a list of elements, modify the entire list of elements and do not modify the individual elements of the list.

According to an embodiment, there is provided an organometallic compound represented by Formula 1:

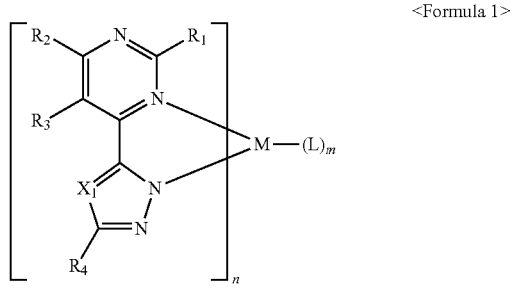

<Formula 1>

In Formula 1 above, M may be a transition metal.

For example, M may be a Group VI metal, a Group VII metal, a Group VIII metal, a Group IX metal, or a Group X metal, a Group XI metal, or the like. In an embodiment, M in Formula 1 may be ruthenium (Ru), rhodium (Rh), palladium (Pd), tungsten (W), rhenium (Re), osmium (Os), iridium (Ir), platinum (Pt), and the like.

In Formula 1, $X_1$ may be N or $C(R_5)$.

In Formula 1, $R_1$ to $R_5$ each independently may be a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —$N(Q_1)(Q_2)$, —Si$(Q_3)(Q_4)(Q_5)$, —$C(=O)(Q_6)$ (where $Q_1$ to $Q_6$ each independently may be a hydrogen atom, a substituted or unsubstituted $C_1$-$C_{60}$ alkyl group, a substituted or unsubstituted $C_6$-$C_{60}$ aryl group, or a substituted or unsubstituted $C_2$-$C_{60}$ heteroaryl group), or a binding site with an adjacent ligand via a single bond or a divalent linking group.

In Formula 1, $R_1$ to $R_5$ each independently may be one selected from the group of:

a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof;

a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group;

a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group that may be substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, —$N(Q_{11})(Q_{12})$, and —Si$(Q_{13})(Q_{14})(Q_{15})$ (where $Q_{11}$ to $Q_{15}$ are each independently a hydrogen atom, a $C_1$-$C_{10}$ alkyl group, a $C_6$-$C_{20}$ aryl group, or a $C_2$-$C_{20}$ heteroaryl group);

—$N(Q_1)(Q_2)$, —Si$(Q_3)(Q_4)(Q_5)$, and —$C(=O)(Q_6)$ (where $Q_1$ to $Q_6$ each independently may be a hydrogen atom, a $C_1$-$C_{60}$ alkyl group, a $C_6$-$C_{60}$ aryl group, or a $C_2$-$C_{60}$ heteroaryl group); and a binding site with an adjacent ligand via a single bond or a divalent linking group.

In an embodiment, in Formula 1, $R_1$ to $R_5$ each independently may be, for example, one selected from the group of:

a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof;

a $C_1$-$C_{20}$ alkyl group, a $C_1$-$C_{20}$ alkoxy group, a cyclopropyl group, a cyclobutyl group, a cyclopentyl group, a cyclohexyl group, a cycloheptyl group, a cyclopentenyl group, a cyclohexenyl group, a cyclopentadienyl group, a cyclohexadienyl group, a phenyl group, a naphthyl group, an anthryl group, a fluorenyl group, a chrysenyl group, a pyrenyl group, a phenanthrenyl group, a pyrrolyl group, a pyridinyl group, a pyrimidinyl group, a pyrazinyl group, a triazinyl group, a carbazolyl group, an indolyl group, a benzoimidazolyl group, a quinolinyl group, an isoquinolinyl group;

a $C_1$-$C_{20}$ alkyl group, a $C_1$-$C_{20}$ alkoxy group, a cyclopropyl group, a cyclobutyl group, a cyclopentyl group, a cyclohexyl group, a cycloheptyl group, a cyclopentenyl group, a cyclohexenyl group, a cyclopentadienyl group, a cyclohexadienyl group, a phenyl group, a naphthyl group, an anthryl group, a fluorenyl group, a chrysenyl group, a pyrenyl group, a phenanthrenyl group, a pyrrolyl group, a pyridinyl group, a pyrimidinyl group, a pyrazinyl group, a triazinyl group, a carbazolyl group, an indolyl group, a benzoimidazolyl group, a quinolinyl group, and an isoquinolinyl group that may be substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a dimethyl-fluorenyl group, and a phenyl-carbazolyl group;

—$N(Q_1)(Q_2)$, —$Si(Q_3)(Q_4)(Q_5)$, —$C(=O)(Q_6)$ (where $Q_1$ to $Q_6$ are each independently a hydrogen atom, a $C_1$-$C_{20}$ alkyl group, a phenyl group, a naphthyl group, or an anthryl group); and a binding site with an adjacent ligand via a single bond or a divalent linking group.

In an embodiment, $X_1$ in Formula 1 may be $C(R_5)$; and $R_1$ to $R_5$ each independently may be one of, e.g., a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof; a methyl group, an ethyl group, an n-propyl group, an i-propyl group, an n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and pentoxy group; and a methyl group, an ethyl group, an n-propyl group, an i-propyl group, an n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group that may be substituted with at least one of a deuterium atom, —F, a hydroxyl group, a cyano group, a nitro group, and an amino group.

In an embodiment, $X_1$ in Formula 1 may be N; and $R_1$ to $R_4$ each independently may be one of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof; a methyl group, an ethyl group, an n-propyl group, an i-propyl group, an n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, a hexyl group, a heptyl group, an octyl group, a nonyl group, a decyl group, a methoxy group, an ethoxy group, a propoxy group, a butoxy group, and a pentoxy group that may be substituted with at least one of a deuterium atom, —F, a hydroxyl group, a cyano group, a nitro group, and an amino group.

In an embodiment, in Formula 1, $X_1$ may be $C(R_5)$; and $R_1$ to $R_5$ each independently may be a hydrogen atom, a methyl group, an ethyl group, an n-propyl group, a i-propyl group, an n-butyl group, an i-butyl group, a t-butyl group, a methoxy group, an ethoxy group, a propoxy group, a butoxy group, a pentoxyl group, or —$CF_3$. In some other embodiments, in Formula 1, $X_1$ may be N; and $R_1$ to $R_4$ each independently may be a hydrogen atom, a methyl group, an ethyl group, an n-propyl group, a i-propyl group, an n-butyl group, an i-butyl group, a t-butyl group, a methoxy group, an ethoxy group, a propoxy group, a butoxy group, a pentoxyl group, or —$CF_3$.

In Formula 1, two substituents of $R_1$ to $R_5$ may be optionally linked together to form a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, or a substituted or unsubstituted $C_2$-$C_{20}$ heteroaromatic ring.

In an embodiment, i) $R_2$ and $R_3$ may be linked together so that the organometallic compound may be represented by Formula 1A below; ii) $X_1$ may be $C(R_5)$, and $R_5$ and $R_4$ may be linked together so that the organometallic compound may be represented by Formula 1B below; or iii) $R_2$ and $R_3$ may be linked together, $X_1$ may be $C(R_5)$, and $R_5$ and $R_4$ may be linked together so that the organometallic compound may be represented by Formula 1C below:

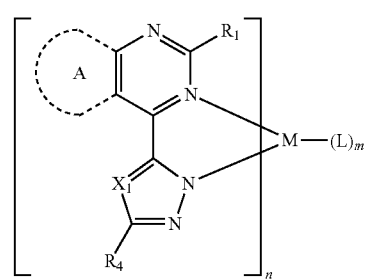

<Formula 1A>

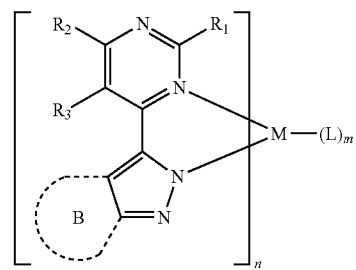

<Formula 1B>

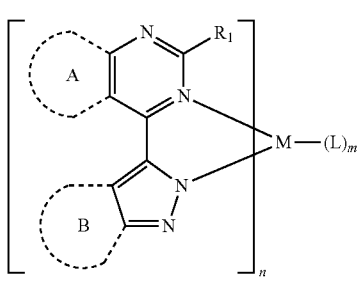

<Formula 1C>

In Formulae 1A, 1B, and 1C, M, $X_1$, and $R_1$ to $R_5$ may be the same as set forth above, and n, L, and m may be as set forth below.

In Formulae 1A, 1B, and 1C above, the A ring and the B ring each independently may be a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, or a substituted or unsubstituted $C_2$-$C_{20}$ heteroaromatic ring.

For example, in Formulae 1A and 1C, the A ring may be at least one of benzene, pentalene, indene, naphtalene, azulene, heptalene, indacene, acenaphthylene, fluorene, spiro-fluorene, phenalene, phenanthrene, anthracene, fluoranthene, triphenylene, pyrene, and chrysene; and benzene, pentalene, indene, naphtalene, azulene, heptalene, indacene, acenaphthylene, fluorene, spiro-fluorene, phenalene, phenanthrene, anthracene, fluoranthene, triphenylene, pyrene, and chrysene that may be substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, —N($Q_{11}$)($Q_{12}$), and —Si($Q_{13}$)($Q_{14}$)($Q_{15}$) (where $Q_{11}$ to $Q_{15}$ are each independently a hydrogen atom, a C1-C10 alkyl group, a $C_6$-$C_{20}$ aryl group or a $C_2$-$C_{20}$ heteroaryl group).

For example, in Formulae 1B and 1C, the B ring may be at least one of, e.g., cyclopropane, cyclobutane, cyclopentane, cyclohexane, cycloheptane, cyclooctane, cyclopentene, cyclopentadiene, cyclohexadiene, cycloheptadiene, bicyclo-heptane, bicyclo-octane, benzene, pentalene, indene, naphtalene, azulene, heptalene, indacene, acenaphthylene, fluorene, spiro-fluorene, phenalene, phenanthrene, anthracene, fluoranthene, triphenylene, pyrene, and chrysene; and cyclopropane, cyclobutane, cyclopentane, cyclohexane, cycloheptane, cyclooctane, cyclopentene, cyclopentadiene, cyclohexadiene, cycloheptadiene, bicyclo-heptane, bicyclo-octane, benzene, pentalene, indene, naphtalene, azulene, heptalene, indacene, acenaphthylene, fluorene, spiro-fluorene, phenalene, phenanthrene, anthracene, fluoranthene, triphenylene, pyrene, and chrysene that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, —N($Q_{11}$)($Q_{12}$), and —Si($Q_{13}$)($Q_{14}$)($Q_{15}$) (where $Q_{11}$ to $Q_{15}$ each independently may be a hydrogen atom, a $C_1$-$C_{10}$ alkyl group, a $C_6$-$C_{20}$ aryl group, or a $C_2$-$C_{20}$ heteroaryl group).

In an embodiment, the organometallic compound may be represented by Formula 1A-(1), 1B-(1), 1B-(2), 1B-(3), 1C-(1), 1C-(2), 1C-(3), or 1D-(1) below:

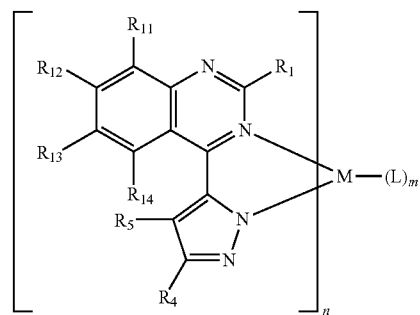

<Formula 1A-(1)>

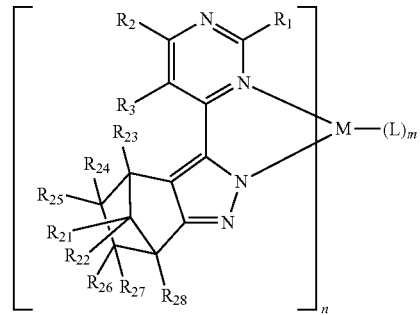

<Formula 1B-(1)>

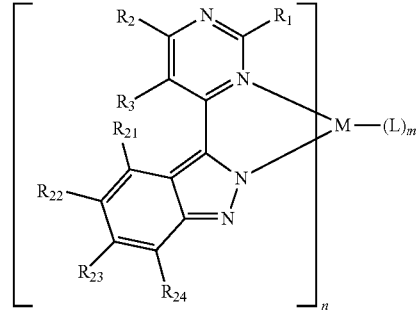

<Formula 1B-(2)>

<Formula 1B-(3)>

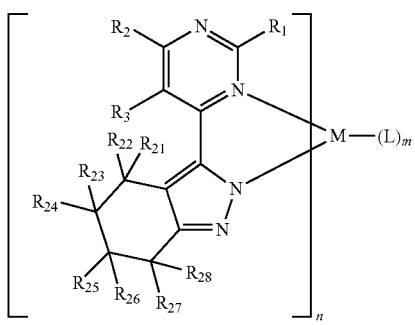

<Formula 1C-(1)>

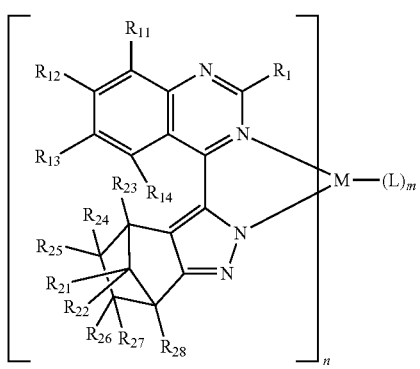

<Formula 1C-(2)>

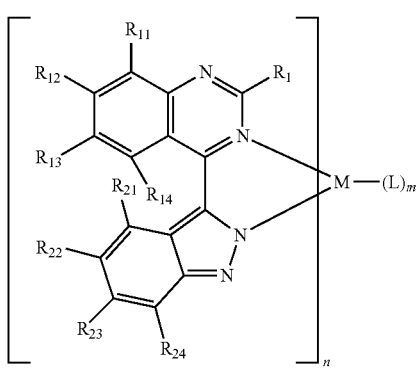

<Formula 1C-(3)>

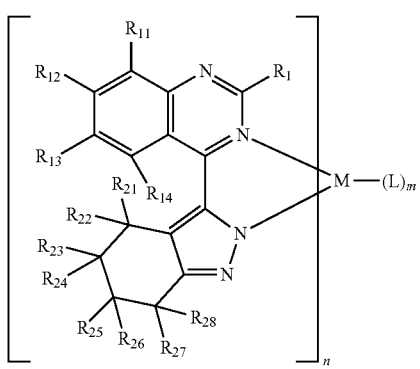

<Formula 1D-(1)>

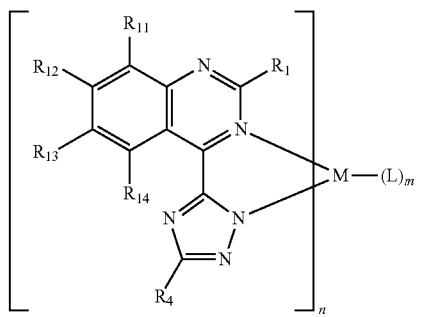

In Formulae 1A-(1), 1B-(1), 1B-(2), 1B-(3), 1C-(1), 1C-(2), 1C-(3), and 1D-(1), M, and $R_1$ to $R_5$ may be the same as set forth above; n, L and m may be the same as set forth below; and $R_{11}$ to $R_{14}$, and $R_{21}$ to $R_{28}$ may be the same as $R_1$ to $R_5$ set forth above.

For example, in Formulae 1A-(1), 1B-(1), 1B-(2), 1B-(3), 1C-(1), 1C-(2), 1C-(3), and 1D-(1) above, M may be a transition metal (for example, osmium (Os), iridium (Ir), or platinum (Pt)); $R_1$ to $R_5$, $R_{11}$ to $R_{14}$, and $R_{21}$ to $R_{28}$ each independently may be a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group; a $C_1$-$C_{20}$ alkyl group and a $C_1$-$C_{20}$ alkoxy group that are substituted with at least one of a deuterium atom, a halogen atom, a hydroxyl group, a cyano group, a nitro group, and an amino group; a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group that are substituted with at least one of a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group; n may be an integer from 1 to 3; L may be an organic ligand; and m may be an integer from 0 to 4.

In Formula 1 above, n may be an integer from 1 to 3. That is, Formula 1 above may include one, two, or three ligands represented by Formula 1':

<Formula 1'>

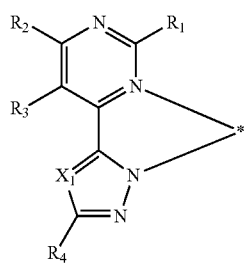

In Formula 1', * indicates a binding site with M in Formula 1.

Accordingly, the organometallic compound may include the ligand represented by Formula 1'.

If n is 2 or greater, at least two ligands represented by Formula 1' may be the same or different.

In Formula 1, L may be an organic ligand, and m may indicate the number of L's, and may be an integer from 0 to 4. L may be a monodentate ligand, bidentate ligand, a tridentate ligand, or a tetradentate ligand. When m is 0, the organometallic compound may include only the ligand represented by Formula 1'. If m is 2 or greater, at least two L may be the same or different.

L may be a suitable organic ligand, e.g., a ligand that does not undesirably change chemical and physical characteristics of the organometallic compound.

For example, L in Formula 1 may include at least one of the ligands represented by Formulae 2A to 2F below.

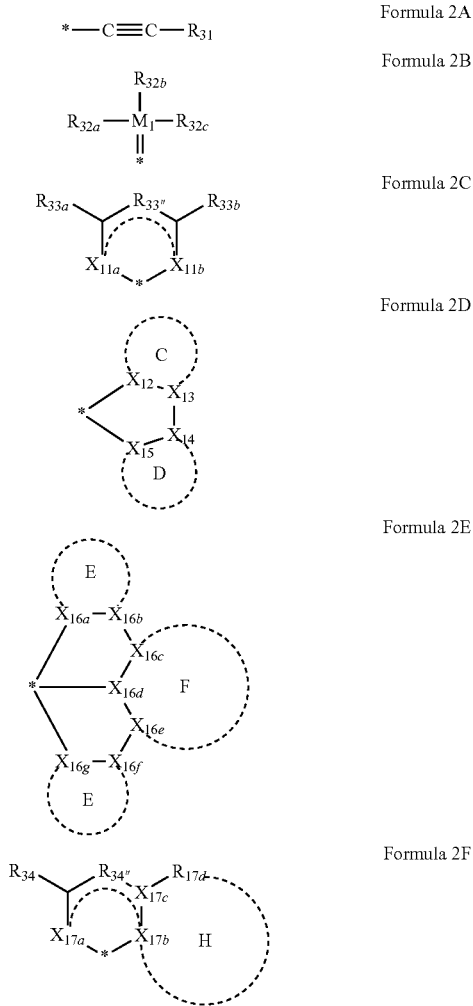

In Formula 2B, $M_1$ may be P or As.

In Formulae 2A to 2F, $X_{11a}$, $X_{11b}$, $X_{12}$, $X_{13}$, $X_{14}$, $X_{15}$, $X_{16a}$, $X_{16b}$, $X_{16c}$, $X_{16d}$, $X_{16e}$, $X_{16f}$, $X_{16g}$, $X_{17a}$, $X_{17b}$, $X_{17c}$ and $X_{17d}$ each independently may be C, N, O, $N(R_{35})$, $P(R_{36})(R_{37})$, or $As(R_{38})(R_{39})$; $R_{33''}$ and $R_{34''}$ each independently may be a single bond, a substituted or unsubstituted $C_1$-$C_5$ alkylene group (for example, methylene, ethylene, or the like), or a substituted or unsubstituted $C_2$-$C_5$ alkenylene group (for example, ethenylene or the like); $R_{31}$, $R_{32a}$, $R_{32b}$, $R_{32c}$, $R_{33a}$, $R_{33b}$, $R_{34}$, $R_{35}$, $R_{36}$, $R_{37}$, $R_{38}$, and $R_{39}$ each independently may be a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, or a substituted or unsubstituted $C_2$-$C_{60}$ heteroaryl group; the C ring, the D ring, the E ring, the F ring, the G ring, and the H ring each independently may be a 5-membered to 20-membered saturated ring, or a 5-membered or 20-membered unsaturated ring; and * may indicate a binding site with M in Formula 1.

In Formulae 2A to 2F, $R_{31}$, $R_{32a}$, $R_{32b}$, $R_{32c}$, $R_{33a}$, $R_{33b}$, $R_{34}$, $R_{35}$, $R_{36}$, $R_{37}$, $R_{38}$, and $R_{39}$ each independently may be one of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group; a $C_1$-$C_{20}$ alkyl group and a $C_1$-$C_{20}$ alkoxy group that are substituted with at least one of a deuterium atom, a halogen atom, a hydroxyl group, a cyano group, a nitro group, and an amino group; a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group that are substituted with at least one of a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group.

For example, if m is 1 or greater in Formula 1 above, L may include a ligand represented by Formula 2C above, wherein $X_{11a}$ and $X_{11b}$ in Formula 2C each independently may be, e.g., O, $P(R_{36})(R_{37})$, or $As(R_{38})(R_{39})$.

In some other embodiments, if m is 1 or greater in Formula 1 above, L may include at least one of the ligands represented by Formulae 2D, 2E, and 2F, wherein the C ring, the D ring, the E ring, the F ring, the G ring, and the H ring in Formulae 2D, 2E, and 2F each independently may be a substituted or unsubstituted benzene, a substituted or unsubstituted pentalene, a substituted or unsubstituted indene, a substituted or unsubstituted naphtalene, a substituted or unsubstituted azulene, a substituted or unsubstituted heptalene, a substituted or unsubstituted indacene, a substituted or unsubstituted acenaphthylene, a substituted or unsubstituted fluorene, a substituted or unsubstituted spiro-fluorene, a substituted or unsubstituted phenalene, a substituted or unsubstituted phenanthrene, a substituted or unsubstituted anthracene, a substituted or unsubstituted fluoranthene, a substituted or unsubstituted triphenylene, a substituted or unsubstituted pyrene, a substituted or unsubstituted chrysene, a substituted or unsubstituted pyrrole, a substituted or unsubstituted imidazole, a substituted or unsubstituted pyrazole, a substituted or unsubstituted isothiazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted isoindole, a substituted or unsubstituted indole, a substituted or unsubstituted indazole, a substituted or unsubstituted purine, a substituted or unsubstituted isoquinoline, a substituted or unsubstituted quinoline, a substituted or unsubstituted phthalazine, a substituted or unsubstituted quinoxaline, a substituted or unsubstituted quinazoline, or a substituted or unsubstituted cinnoline.

In this regard, i) when the C ring includes at least two substituents (i.e., is substituted with at least two substituents), adjacent two of the at least two substituents may be optionally linked together to form a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, or a substituted or unsubstituted $C_2$-$C_{20}$ heteroaromatic ring; ii) when the D ring includes at least two substituents (i.e., is substituted with at least two substituents), adjacent two of the at least two substituents my be optionally linked together to form a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, or a substituted or unsubstituted $C_2$-$C_{20}$ heteroaromatic ring; iii) when the E ring includes at least two substituents (i.e., is substituted with at least two substituents), adjacent two of the at least two substituents may be optionally linked together to form a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, or a substituted or unsubstituted $C_2$-$C_{20}$ heteroaromatic ring; iv) when the F ring includes at least two substituents (i.e., is substituted with at least two substituents), adjacent two of the at least two substituents may be optionally linked together to form a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, or a substituted or unsubstituted $C_2$-$C_{20}$ heteroaromatic ring; v) when the G ring includes at least two substituents (i.e., is substituted with at least two substituents), adjacent two of the at least two substituents may be optionally linked together to form a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, or a substituted or unsubstituted $C_2$-$C_{20}$ heteroaromatic ring; vi) when the H ring includes at least two substituents (i.e., is substituted with at least two substituents), adjacent two of the at least two substituents may be optionally linked together to form a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, or a substituted or unsubstituted $C_2$-$C_{20}$ heteroaromatic ring;

The above description of the B ring (in Formulae 1B and 1C) may be used to describe "the substituted or unsubstituted $C_4$-$C_{20}$ alicyclic ring, the substituted or unsubstituted $C_2$-$C_{20}$ heteroalicyclic ring, the substituted or unsubstituted $C_6$-$C_{20}$ aromatic ring, or the substituted or unsubstituted $C_2$-$C_{20}$ heteroaromatic ring," set forth above.

In an embodiment, if m is 1 or greater in Formula 1 above, L may include at least one of the ligands represented by, e.g., Formulae 2A(1), 2B(1), 2C(1), and 2C(2):

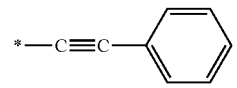

Formula 2A(1)

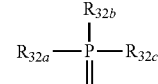

Formula 2B(1)

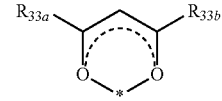

Formula 2C(1)

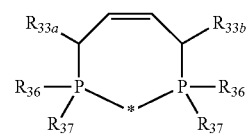

Formula 2C(2)

In Formulae 2A(1), 2B(1), 2C(1), and 2C(2), $R_{32a}$, $R_{32b}$, $R_{32c}$, $R_{33a}$, $R_{33b}$, $R_{36}$, and $R_{37}$ each independently may be as set forth above.

In Formula 1, n may be 2. Thus, the organometallic compound may be represented by Formula 3 or 4 below.

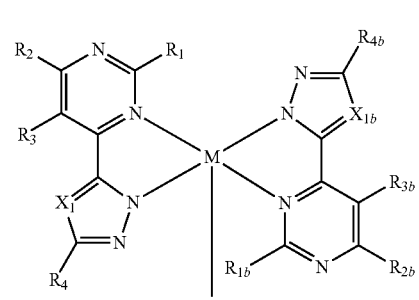

<Formula 3>

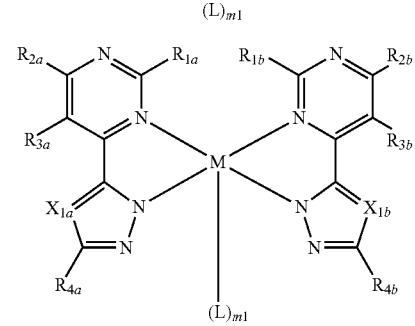

<Formula 4>

In Formulae 3 and 4, M and L may be as set forth above, and m1 may be 0, 1, or 2.

In Formulae 3 and 4, $X_{1a}$ may be N or $C(R_{5a})$; $X_{1b}$ may be N or $C(R_{5b})$; and the above-description of $R_1$ may be used to describe $R_{1a}$ to $R_{5a}$, and $R_{1b}$ to $R_{5b}$.

In an embodiment, the organometallic compound may be represented by Formula 3, wherein $R_{1a}=R_{1b}$, $R_{2a}=R_{2b}$, $R_{3a}=R_{3b}$, $R_{4a}=R_{4b}$, $X_{1a}=X_{1b}$, M=Pt, and m1=0, and may have a trans structure.

In an embodiment, the organometallic compound may be represented by Formula 4, wherein $R_{1a}=R_{1b}$, $R_{2a}=R_{2b}$, $R_{3a}=R_{3b}$, $R_{4a}=R_{4b}$, $X_{1a}=X_{1b}$, M=Pt, and m1=0, and may have a cis structure.

In an embodiment, the organometallic compound may be represented by Formula 3A-(1), 3A-(2), 3A-(3), 3A-(4), 3A-(5), 3A-(6), 3A-(7), 3A-(8), or 3A-(9) below.
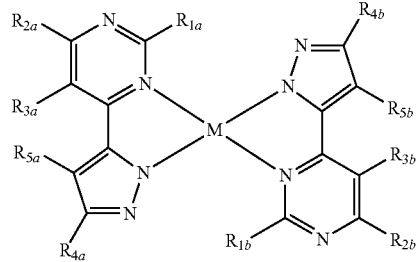
<Formula 3A-(1)>
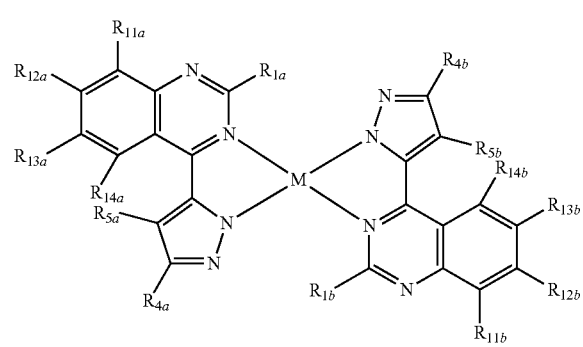
<Formula 3A-(2)>
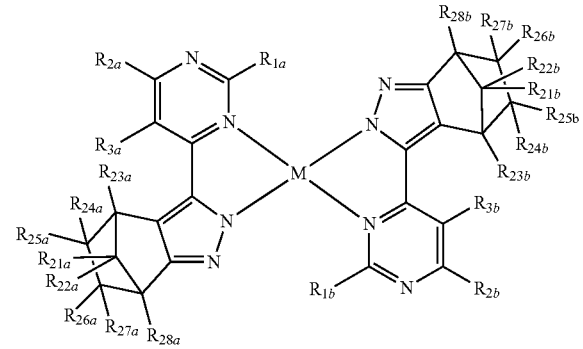
<Formula 3A-(3)>
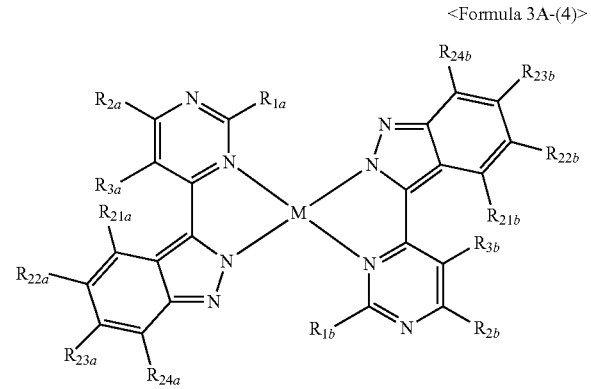
<Formula 3A-(4)>
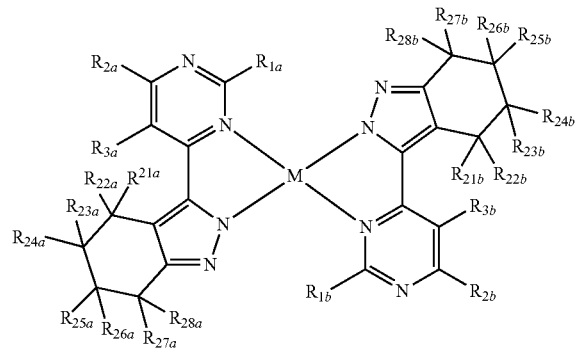
<Formula 3A-(5)>
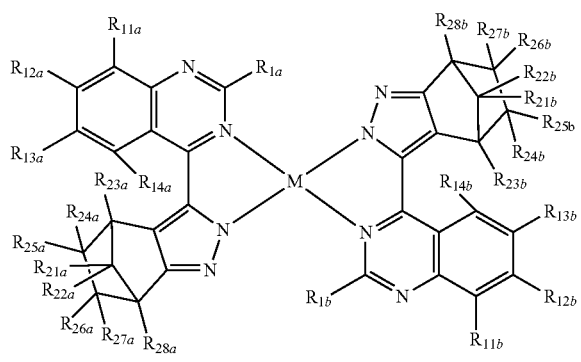
<Formula 3A-(6)>
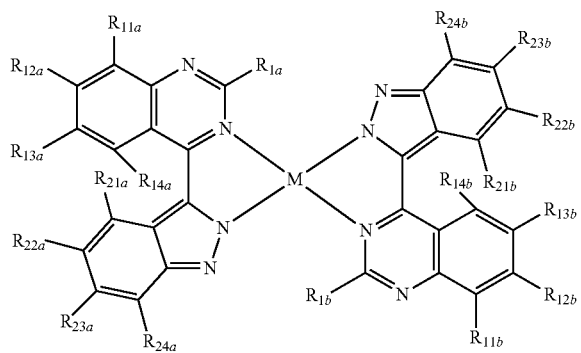
<Formula 3A-(7)>
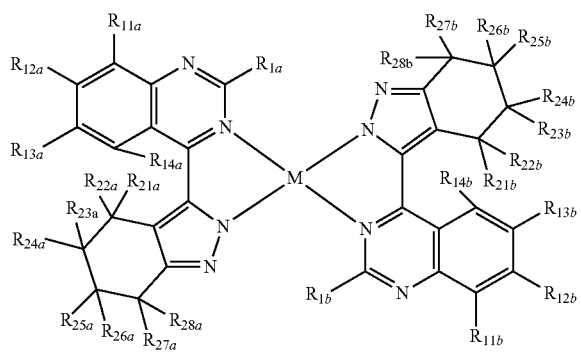
<Formula 3A-(8)>

<Formula 3A-(9)>

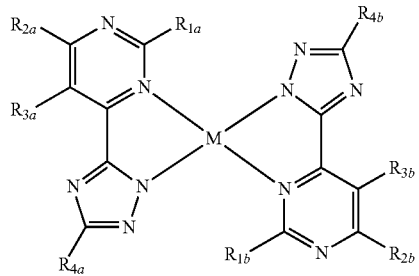

In Formulae 3A-(1), 3A-(2), 3A-(3), 3A-(4), 3A-(5), 3A-(6), 3A-(7), 3A-(8), and 3A-(9), M may be platinum (Pt); and $R_{1a}$ to $R_{5a}$, $R_{1b}$ to $R_{5b}$, $R_{11a}$ to $R_{14a}$, $R_{11b}$ to $R_{14b}$, $R_{21a}$ to $R_{28a}$, and $R_{21b}$ to $R_{28b}$ each independently may be one of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group; a $C_1$-$C_{20}$ alkyl group and a $C_1$-$C_{20}$ alkoxy group that are substituted with at least one of a deuterium atom, a halogen atom, a hydroxyl group, a cyano group, a nitro group, and an amino group; a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group that are substituted with at least one of a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group.

In an embodiment, in Formulae 3A-(1), 3A-(2), 3A-(3), 3A-(4), 3A-(5), 3A-(6), 3A-(7), 3A-(8), and 3A-(9), $R_{1a}$ to $R_{5a}$, $R_{1b}$ to $R_{5b}$, $R_{11a}$ to $R_{14a}$, $R_{11b}$ to $R_{14b}$, $R_{21a}$ to $R_{28a}$, and $R_{21b}$ to $R_{28b}$ each independently may be, e.g., a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group (for example, a methyl group, an ethyl group, an n-propyl group, a i-propyl group, an n-butyl group, a i-butyl group, a t-butyl group, a pentyl group, a hexyl group, a heptyl group, an octyl group, a nonyl group, a decyl group, or the like), a $C_1$-$C_{20}$ alkyl group substituted with at least one fluorine atom (for example, —$CF_3$), a $C_1$-$C_{20}$ alkoxy group, a phenyl group, a naphthyl group, or an anthryl group.

For example, the organometallic compound may be represented by Formula 3A-(1), 3A-(2), 3A-(4), 3A-(6), 3A-(8), or 3A-(9), wherein $R_{1a}$=$R_{1b}$, $R_{2a}$=$R_{2b}$, $R_{3a}$=$R_{3b}$, $R_{4a}$=$R_{4b}$, $R_{5a}$=$R_{5b}$, $R_{11a}$=$R_{11b}$, $R_{12a}$=$R_{12b}$, $R_{13a}$=$R_{13b}$, $R_{14a}$=$R_{14b}$, $R_{21a}$=$R_{21b}$, $R_{22a}$=$R_{22b}$, $R_{23a}$=$R_{23b}$, $R_{24a}$=$R_{24b}$, $R_{25a}$=$R_{25b}$, $R_{26a}$=$R_{26b}$, $R_{27a}$=$R_{27b}$, and $R_{28a}$=$R_{28b}$.

The organometallic compound may be represented by Formula 4-(a) below.

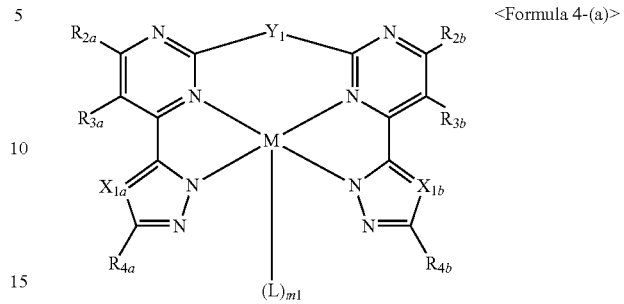

<Formula 4-(a)>

In Formula 4-(a), M and L may be as set forth above, and m1 may be 0, 1, or 2.

In Formula 4-(a), $X_{1a}$ may be N or $C(R_{5a})$; $X_{1b}$ may be N or $C(R_{5b})$; and the above-description of $R_1$ may be used to describe $R_{2a}$ to $R_{5a}$, and $R_{1b}$ to $R_{5b}$.

In Formula 4-(a), $Y_1$ may be i) a divalent linking group including at least one of —O—, —S—, —N($Z_1$)—, —[C($Z_2$)($Z_3$)]$_a$—, and —[Si($Z_4$)($Z_5$)]$_b$—, or ii) a single bond, In —N($Z_1$)—, —[C($Z_2$)($Z_3$)]$_a$—, and —[Si($Z_4$)($Z_5$)]$_b$—, $Z_1$ to $Z_5$ each independently may be a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, or a $C_2$-$C_{60}$ heteroaryl group, and a and b each independently may be an integer from 1 to 4.

In an embodiment, in —N($Z_1$)—, —[C($Z_2$)($Z_3$)]$_a$—, and —[Si($Z_4$)($Z_5$)]$_b$—, $Z_1$ to $Z_5$ each independently may be, e.g., a $C_1$-$C_{20}$ alkyl group (for example, a methyl group, an ethyl group, an n-propyl group, a i-propyl group, an n-butyl group, a i-butyl group, a t-butyl group, a pentyl group, a hexyl group, a heptyl group, an octyl group, a nonyl group, a decyl group, or the like), a $C_1$-$C_{20}$ alkyl group substituted with at least —F (for example, —$CF_3$), a phenyl group, a naphthyl group, or an anthryl group, and a and b each independently may be 1 or 2.

For example, in Formula 4-(a), $Y_1$ may be —N($Z_1$)—, wherein $Z_1$ may be at least one of, e.g., a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group that are substituted with at least one of a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group.

In some other embodiments, the organometallic compound may be an organometallic compound represented by Formula 1 with n=3 and m=0. That is, the organometallic compound may include just three ligands represented by Formula 1'. In an embodiment, in the organometallic compound represented by Formula 1 with n=3 and m=0, M may be Ir, and $X_1$ and $R_1$ to $R_4$ may be as set forth above.

In some other embodiments, the organometallic compound may be an organometallic compound represented by Formula 1 wherein n=1 and m is an integer from 1 to 4.

In an embodiment, the organometallic compound represented by Formula 1 wherein n=1 and m is an integer from 1 to 4 may be an organometallic compound represented by, e.g., one of the Formulae 5 to 8 below:

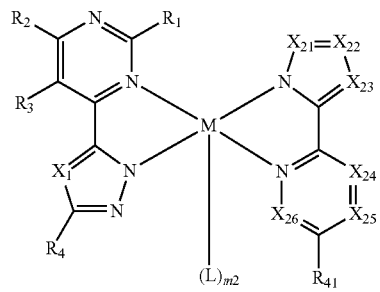
<Formula 5>

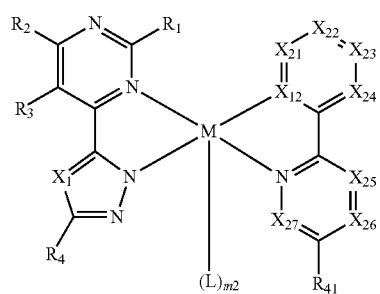
<Formula 6>

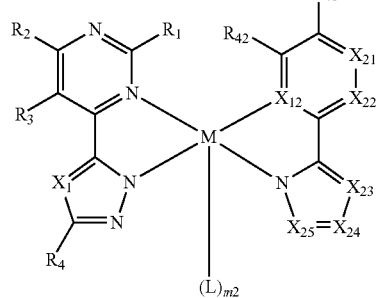
<Formula 7>

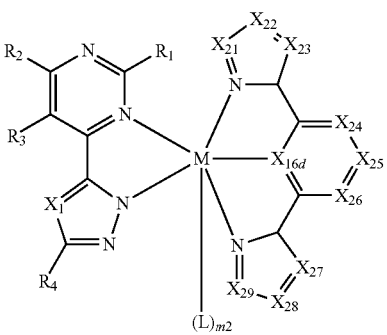
<Formula 8>

In Formulae 5 to 8, M, X1, $R_1$ to $R_5$, and L may be as set forth above, and m2 may be 0, 1, or 2.

In Formulae 5 to 8, $X_{12}$ and $X_{16d}$ each independently may be N or C; and $X_{21}$ may be N or $C(R_{51})$; $X_{22}$ may be N or $C(R_{52})$; $X_{23}$ may be N or $C(R_{53})$; $X_{24}$ may be N or $C(R_{54})$, $X_{25}$ may be N or $C(R_{55})$; $X_{26}$ may be N or $C(R_{56})$; $X_{27}$ may be N or $C(R_{57})$; $X_{28}$ may be N or $C(R_{58})$; and $X_{29}$ may be N or $C(R_{59})$; $R_{41}$, $R_{42}$, and $R_{51}$ to $R_{59}$ each independently may be a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —N($Q_{11}$)($Q_{12}$), —Si($Q_{13}$)($Q_{14}$)($Q_{15}$) (where $Q_{11}$ to $Q_{15}$ are each independently a hydrogen atom, a $C_1$-$C_{10}$ alkyl group, a $C_6$-$C_{20}$ aryl group, or a $C_2$-$C_{20}$ heteroaryl group), or a binding site with an adjacent ligand via a single bond or divalent linking group, wherein two adjacent substituents of $R_{41}$, $R_{42}$, and $R_{51}$ to $R_{59}$ are optionally linked together to form a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, or a substituted or unsubstituted $C_2$-$C_{20}$ heteroaromatic ring.

In Formulae 5 to 8, the above-description of $R_1$ may be used to describe $R_{41}$, $R_{42}$, and $R_{51}$ to $R_{59}$, and the above-description of the B ring may be used to describe "the substituted or unsubstituted $C_4$-$C_{20}$ alicyclic ring, the substituted or unsubstituted $C_2$-$C_{20}$ heteroalicyclic ring, the substituted or unsubstituted $C_6$-$C_{20}$ aromatic ring, or the substituted or unsubstituted $C_2$-$C_{20}$ heteroaromatic ring."

In an embodiment, the organometallic compound may be represented by Formula 5-(1), 5-(2), 5-(3), or 5-(4) below:

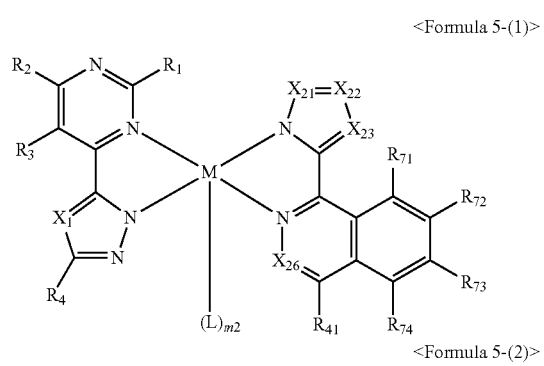
<Formula 5-(1)>

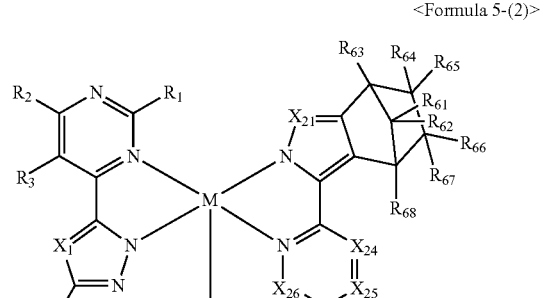
<Formula 5-(2)>

<Formula 5-(3)>

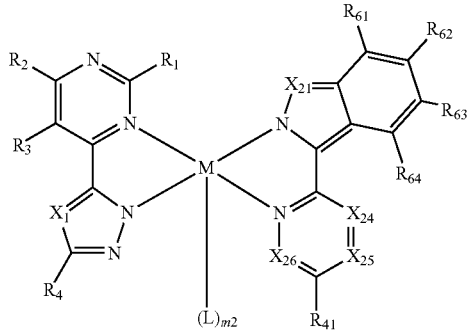

In some other embodiments, the organometallic compound may be represented by Formula 5-(a), 6-(a), or 7-(a) below:

<Formula 5-(a)>

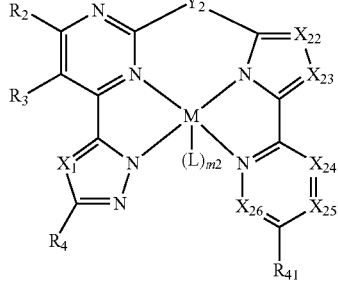

<Formula 5-(4)>

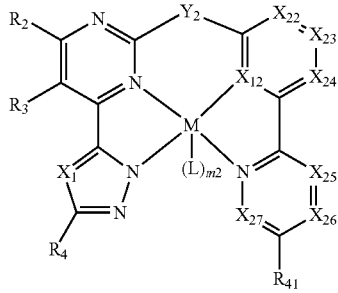

<Formula 6-(a)>

<Formula 7-(a)>

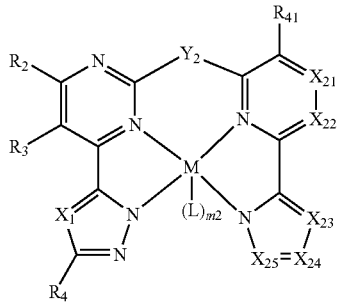

In Formulae 5-(1) to 5-(4), M, $X_1$, $R_1$ to $R_5$, L, m2, $X_{21}$ to $X_{26}$, $R_{41}$, and $R_{51}$ to $R_{59}$ may be as set forth above, and the above-description of $R_{11}$ may be used to describe $R_{61}$ to $R_{68}$, and $R_{71}$ to $R_{74}$.

In an embodiment, in Formulae 5-(1) to 5-(4), $X_{21}$ may be N or $C(R_{51})$; $X_{22}$ may be N or $C(R_{52})$; $X_{23}$ may be N or $C(R_{53})$; $X_{24}$ may be N or $C(R_{54})$; $X_{25}$ may be N or $C(R_{55})$; and $X_{26}$ may be N or $C(R_{56})$; $R_{41}$ to $R_{56}$, $R_{61}$ to $R_{68}$, and $R_{71}$ to $R_{74}$ each independently may be, e.g., a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group; a $C_1$-$C_{20}$ alkyl group and a $C_1$-$C_{20}$ alkoxy group that are substituted with at least one of a deuterium atom, a halogen atom, a hydroxyl group, a cyano group, a nitro group, and an amino group; a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group that are substituted with at least one of a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group.

In Formulae 5-(a), 6-(a), and 7-(a), M, $X_1$, $R_2$ to $R_5$, L, m2, $X_{21}$ to $X_{27}$, $R_{41}$, and $R_{51}$ to $R_{59}$ may be as set forth above. $X_{12}$ may be C or N;

In Formulae 5-(a), 6-(a), and 7-(a), $Y_2$ may be a single bond or a divalent linking group including at least one of —O—, —S—, —N($Z_{11}$)—, —[C($Z_{12}$)($Z_{13}$)]c-, and —[Si($Z_{14}$)($Z_{15}$)]d-, wherein $Z_{11}$ to $Z_{15}$ each independently may be, e.g., a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, or a $C_2$-$C_{60}$ heteroaryl group, and c and d each independently may be an integer from 1 to 4.

The organometallic compound may be, for example, one of Compounds 1 to 68 below:
1 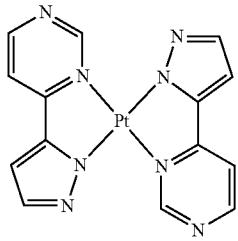
2 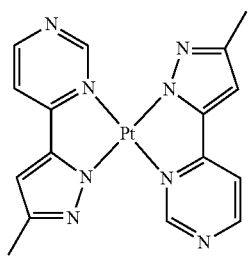
3 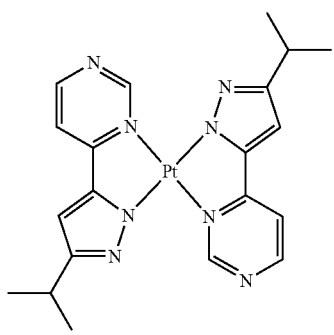
4 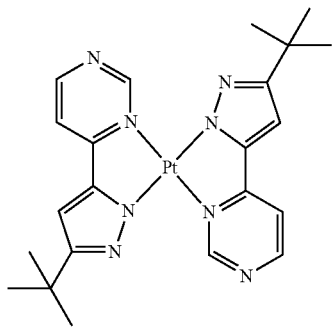
5 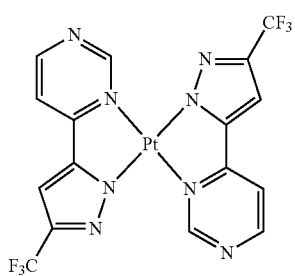
6 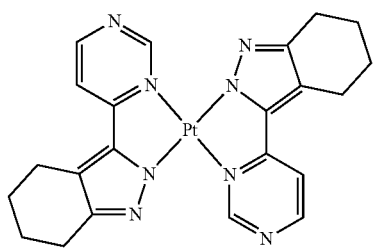
7 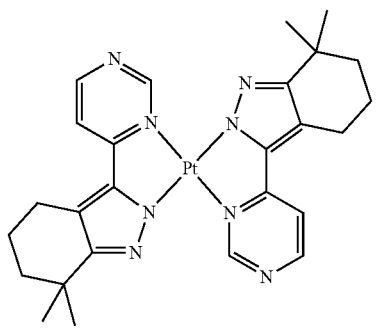
8 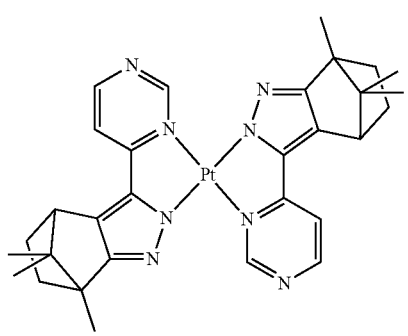
9 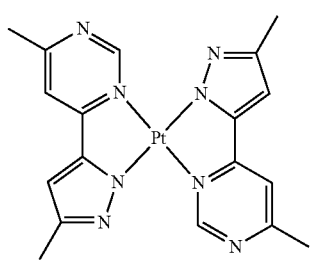
10 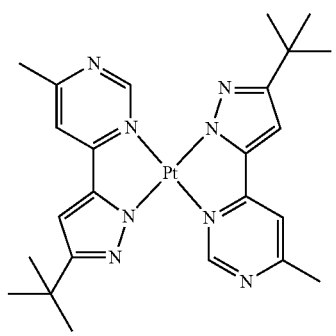

11
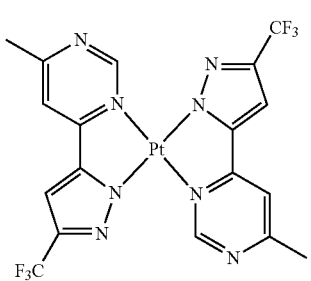
12
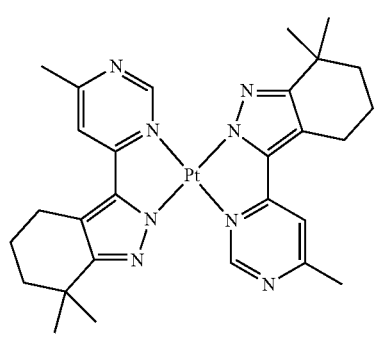
13
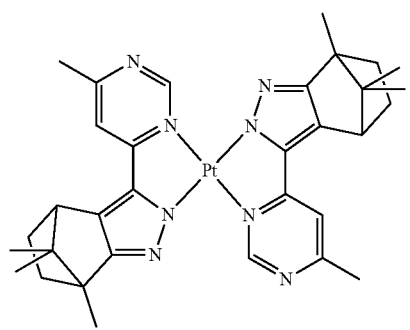
14
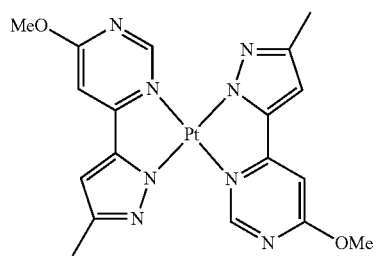
15
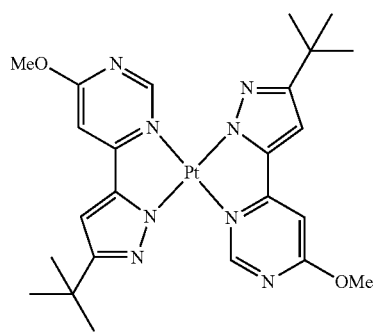
16
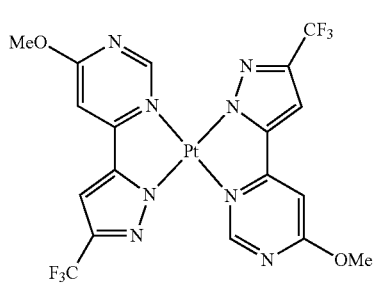
17
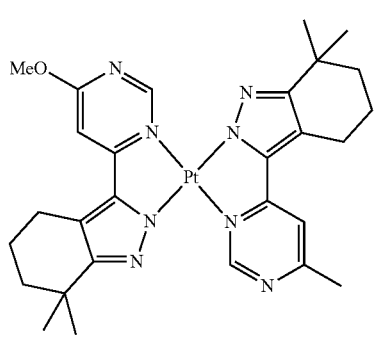
18
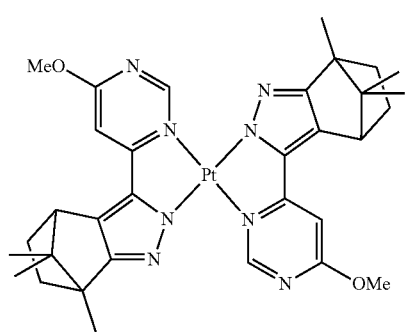
19
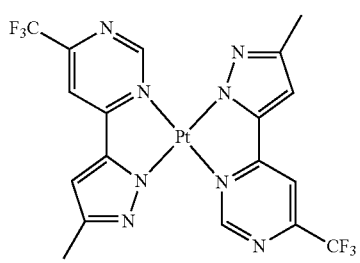
20
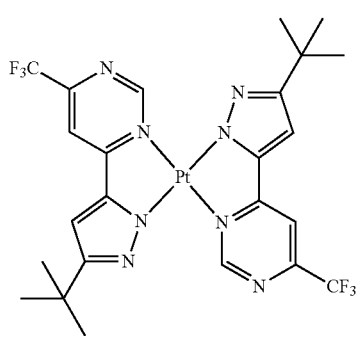

21
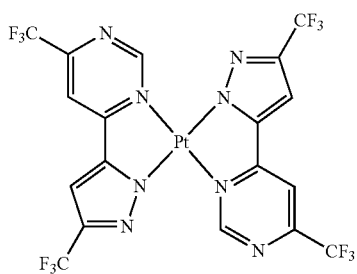
22
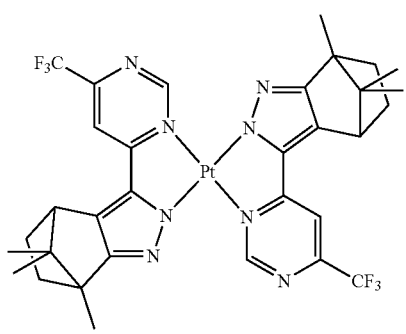
23
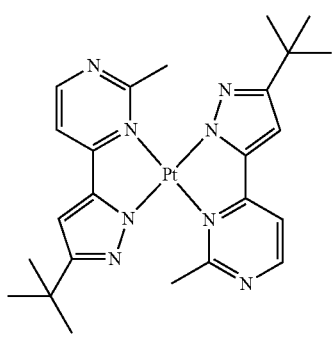
24
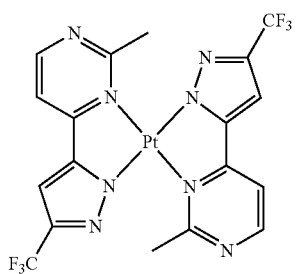
25
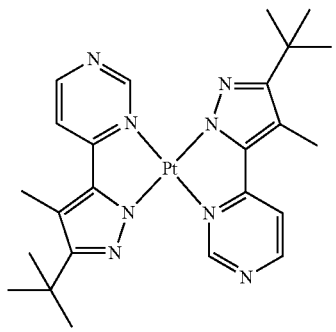
26
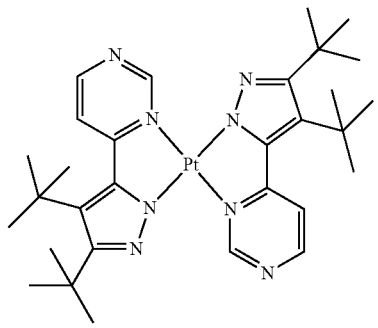
27
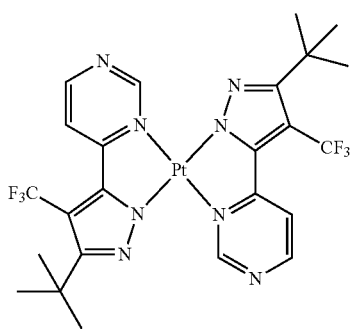
28
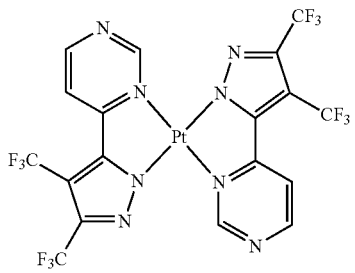
29
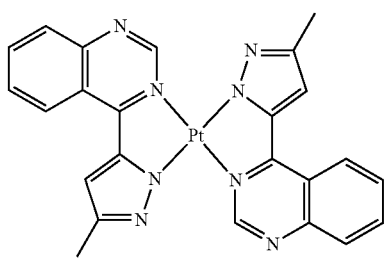
30
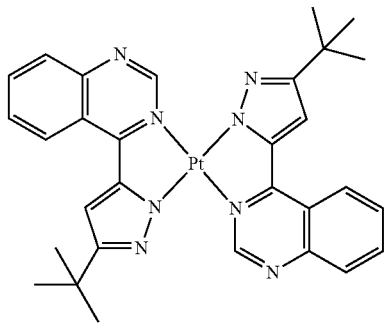

31
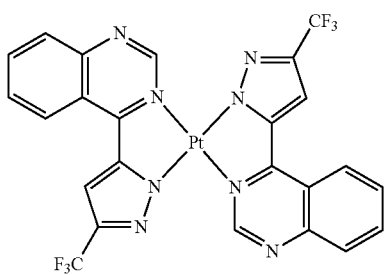
32
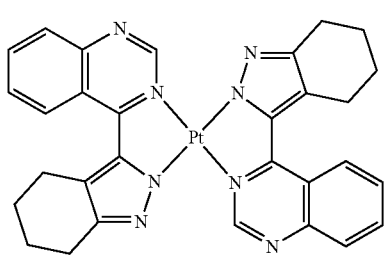
33
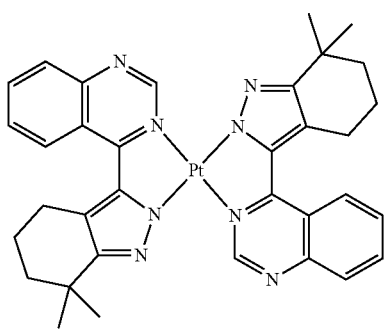
34
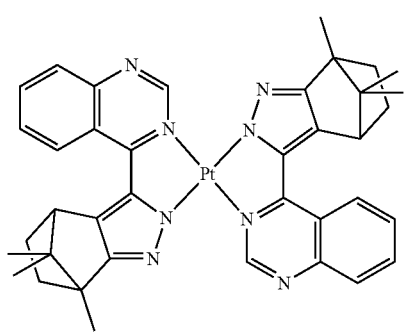
35
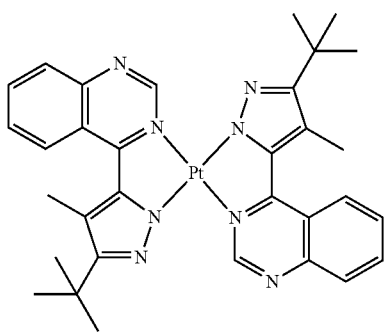
36
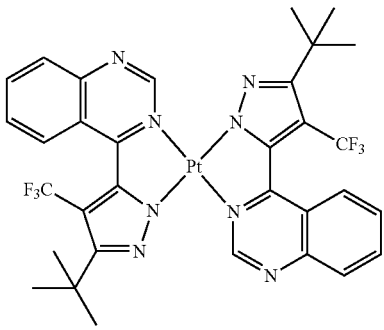
37
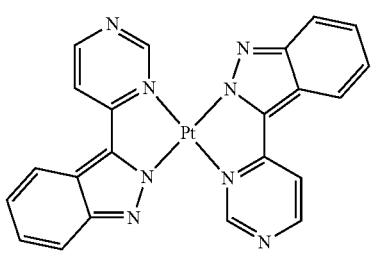
38
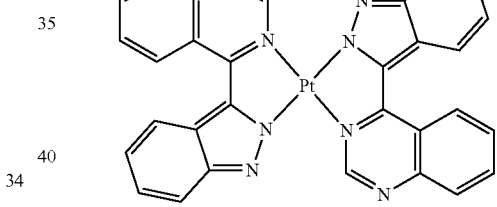
39
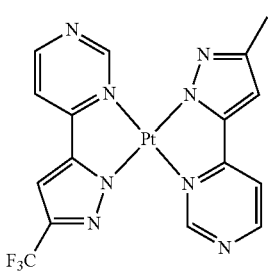
40
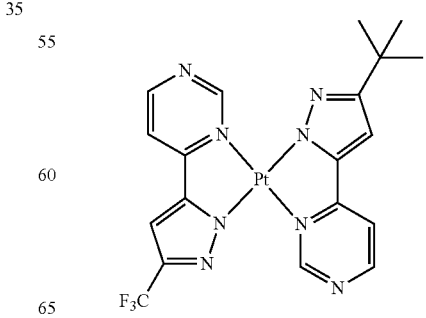

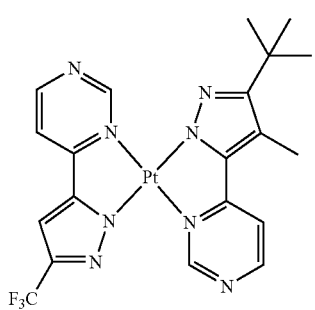
41
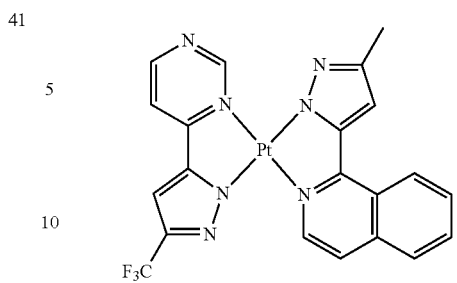
46
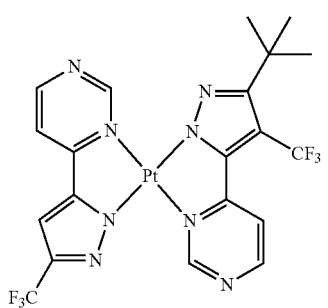
42
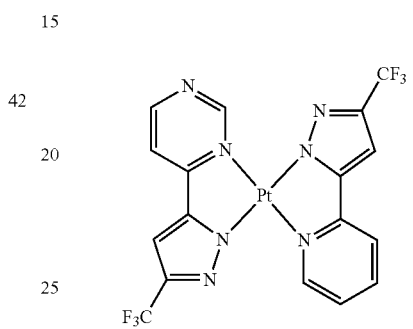
47
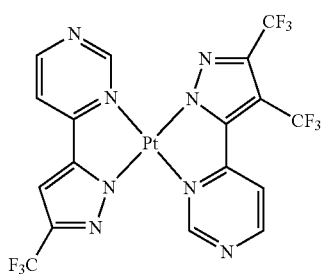
43
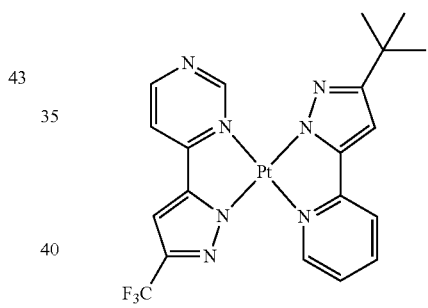
48
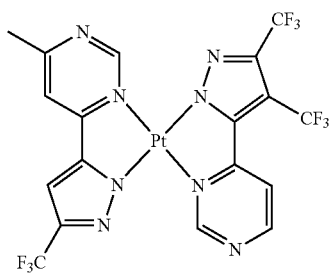
44
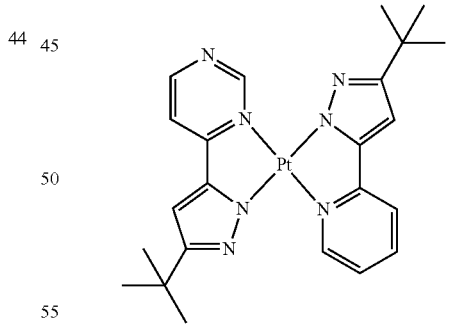
49
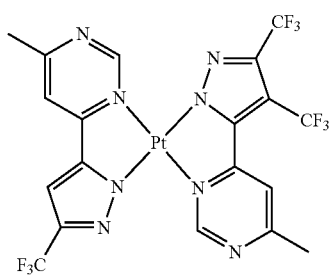
45
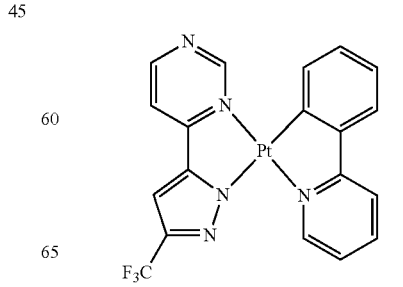
50

-continued
51 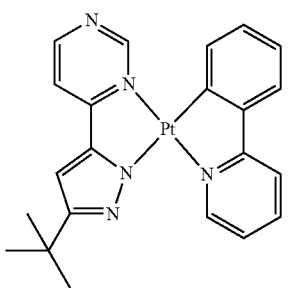
52 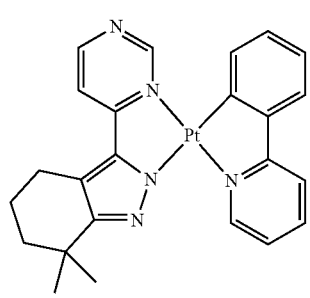
53 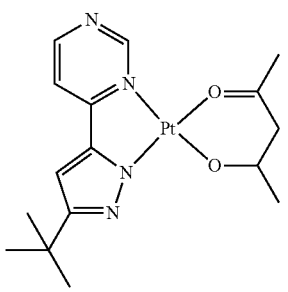
54 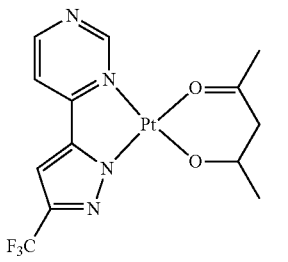
55 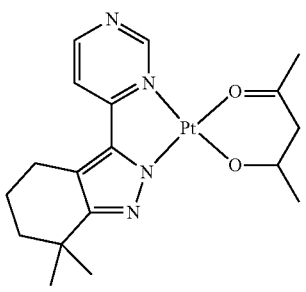
-continued
56 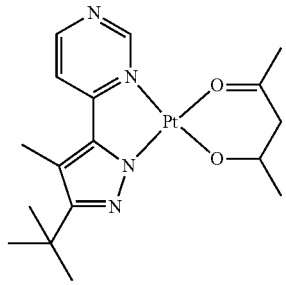
57 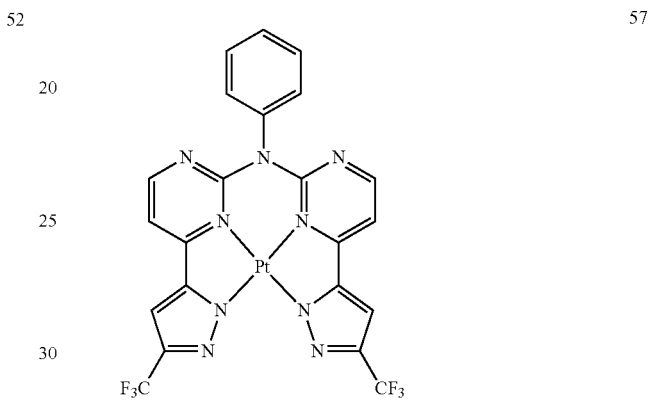
58 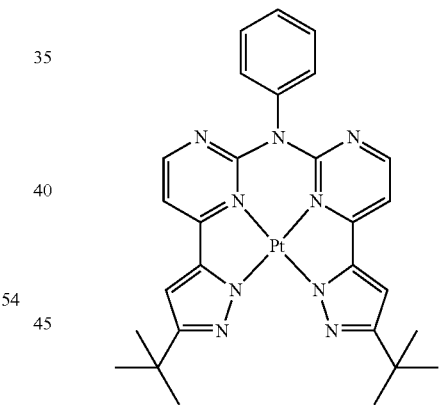
59 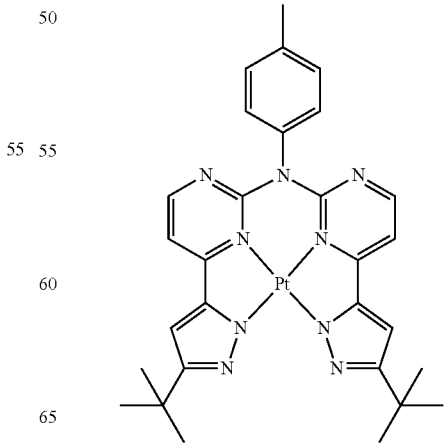

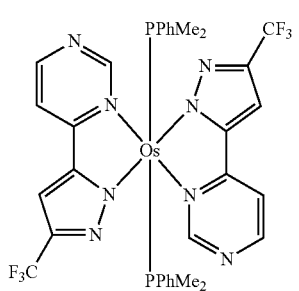
60
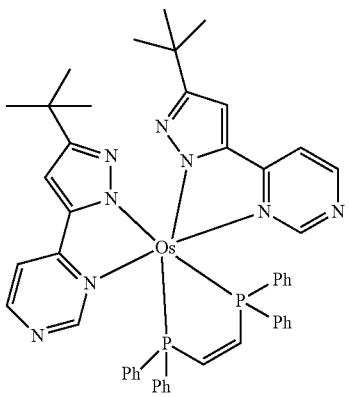
64
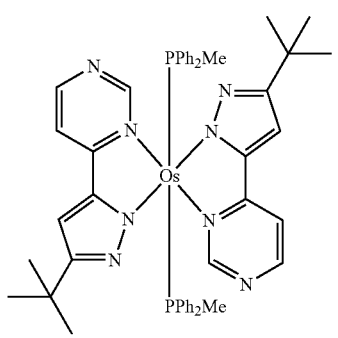
61
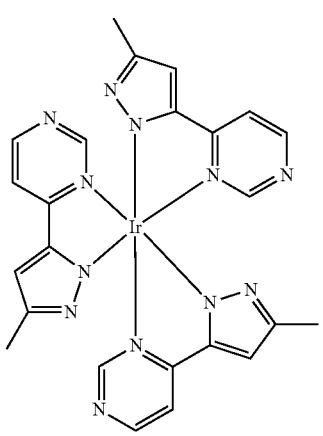
65
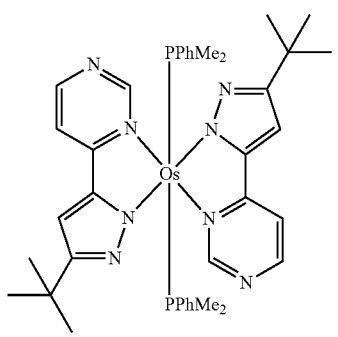
62
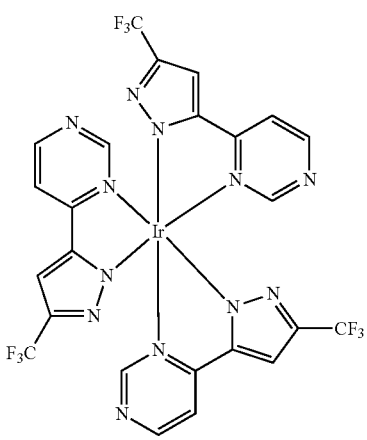
66
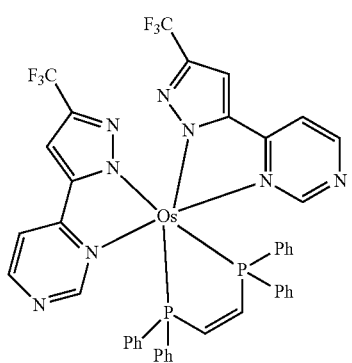
63
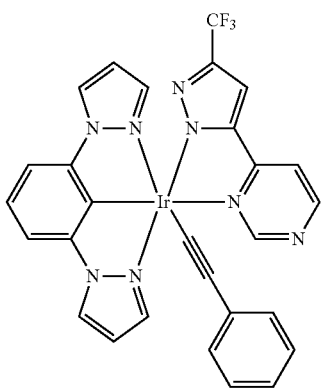
67

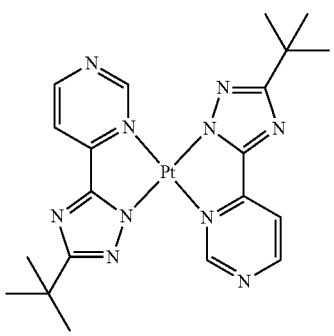

In the organometallic compound of Formula 1, $R_1$ may be located between a first nitrogen and a second nitrogen, and thus the $R_1$ may have acidic characteristics (as illustrated in Formula 1″ below), which may allow for improved thermal stability.

<Formula 1″>

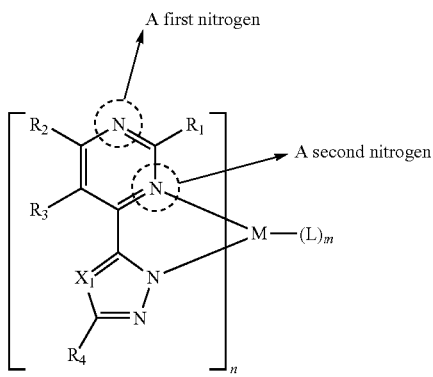

For example, in the organometallic compound represented by Formula 3, $R_{1a}$ may be located between a first nitrogen and a second nitrogen, and thus the organometallic compound may have acidic characteristics, thereby allowing for the formation of an intermolecular hydrogen bond with a third nitrogen of an adjacent ligand (as illustrated in Formula 3″ below).

<Formula 3″>

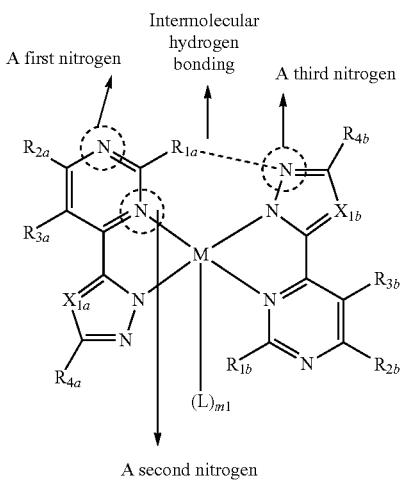

Therefore, the organometallic compounds according to one or more of the above embodiments may have improved thermal stability. Accordingly, an organic light-emitting device including the organometallic compounds according to one or more of the above embodiments may have improved properties (e.g., a low driving voltage, a high luminance, a high efficiency, a long lifetime, and the like).

The organometallic compound of Formula 1 may be synthesized using a suitable organic synthesis method. A synthesis method of the organometallic compound of Formula 1 will be understood by those skilled in the art from the examples that will be described below.

The organometallic compound of Formula 1 may be used between a pair of electrodes of an organic light-emitting device, for example, in an emission layer of the organic light-emitting device.

According to an embodiment, an organic light-emitting device may include a first electrode, a second electrode disposed opposite to the first electrode, and an organic layer disposed between the first electrode and the second electrode, wherein the organic layer may include at least one of the organometallic compounds of Formula 1 described above.

As used herein, phrases like, for example, "the organic layer includes at least one organometallic compound" mean that "the organic layer includes one of the organometallic compounds of Formula 1 above, or at least two different organometallic compounds of Formula 1 above."

The organic layer may include at least one layer selected from among a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

The term "organic layer" as used herein may refer to a single layer and/or a plurality of layers disposed between the first and second electrodes of the organic light-emitting device.

The organic layer may include an emission layer, and the emission layer may include the organometallic compound of Formula 1 described above. The emission layer including the organometallic compound may emit light generated based on the mechanism of phosphorescence.

In an embodiment, the organometallic compound in the emission layer of the organic light-emitting device may serve as a dopant, and the emission layer may further include a carbazole-based compound as a host.

An example of the carbazole-based compound available as a host is a compound represented by Formula 10 below:

<Formula 10>

In Formula 10, Ar$_1$ may be a substituted or unsubstituted C$_1$-C$_{60}$alkylene group, a substituted or unsubstituted C$_2$-C$_{60}$ alkenylene group, —C(=O)—, —N(R$_{100}$)— (where R$_{100}$ may be a substituted or unsubstituted C$_6$-C$_{60}$aryl group, or a substituted or unsubstituted C$_2$-C$_{60}$ heteroaryl group), a substituted or unsubstituted C$_6$-C$_{60}$ arylene group, or a substituted or unsubstituted C$_2$-C$_{60}$heteroarylene group; p may be an integer from 0 to 10; R$_{91}$ to R$_{96}$ each independently may be a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_3$-C$_{10}$ cycloalkenyl group, a substituted or unsubstituted C$_3$-C$_{10}$ heterocycloalkyl group, a substituted or unsubstituted C$_3$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, or a substituted or unsubstituted C$_2$-C$_{60}$ heteroaryl group, wherein adjacent two substituents of R$_{91}$ to R$_{96}$ are optionally linked together to form a substituted or unsubstituted C$_4$-C$_{20}$ alicyclic group, a substituted or unsubstituted C$_2$-C$_{20}$ heteroalicyclic group, a substituted or unsubstituted C$_6$-C$_{20}$ aromatic ring, or a substituted or unsubstituted C$_2$-C$_{20}$ heteroaromatic ring; and q, r, s, t, u, and v each independently may be an integer from 1 to 4.

In Formula 10, Ar$_1$ may be a C$_1$-C$_5$ alkylene group, a C$_2$-C$_5$ alkenylene group, —C(=O)—, or —N(R$_{100}$)—, wherein R$_{100}$ may be at least one of a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group that are substituted with at least one of a deuterium atom, a halogen atom, a hydroxyl group, a cyano group, a nitro group, an amino group, a C$_1$-C$_{20}$ alkyl group, a C$_1$-C$_{20}$ alkoxy group, a phenyl group, a naphthyl group, an anthryl group, a fluorenyl group, a carbazolyl group, a pyridinyl group, a pyrimidinyl group, and a triazinyl group.

In Formula 10, R$_{91}$ to R$_{96}$ each independently may be one of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a C$_1$-C$_{20}$ alkyl group, and a C$_1$-C$_{20}$ alkoxy group; and a C$_1$-C$_{20}$ alkyl group and a C$_1$-C$_{20}$ alkoxy group that are substituted with at least one of a deuterium atom, a halogen atom, a hydroxyl group, a cyano group, a nitro group, and an amino group.

The carbazole-based compound may be, e.g., one of the following compounds H1-H30:

H1
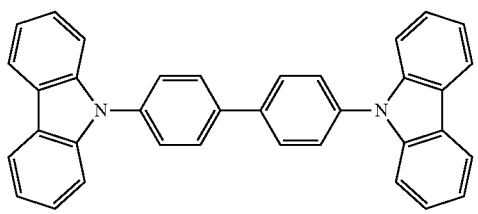

H2
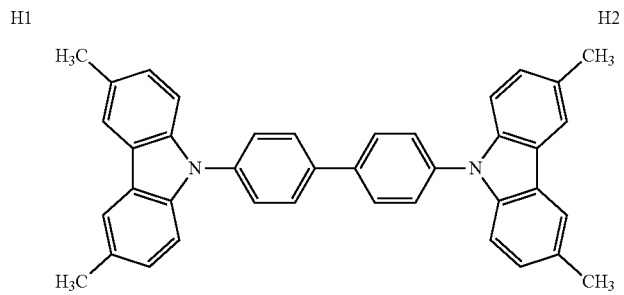

H3
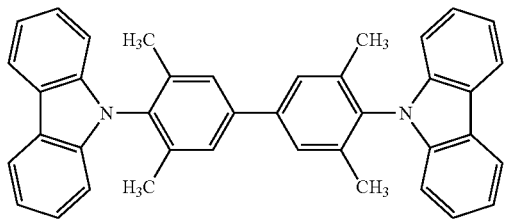

H4
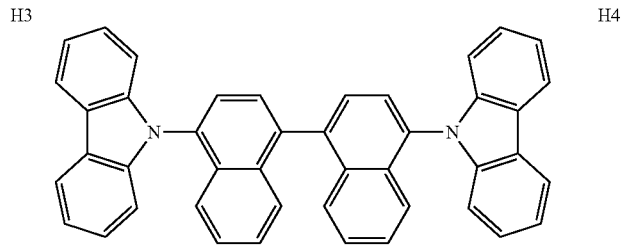

H5
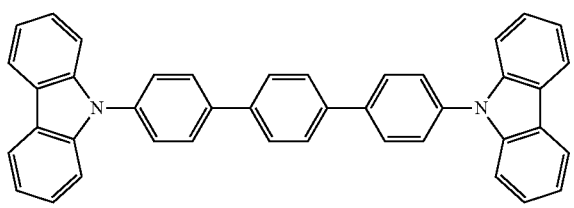

H6
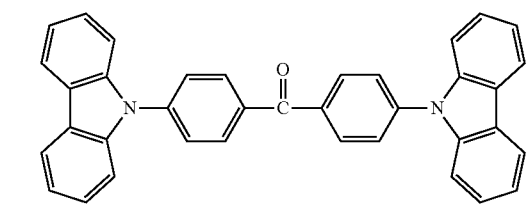

-continued
H7
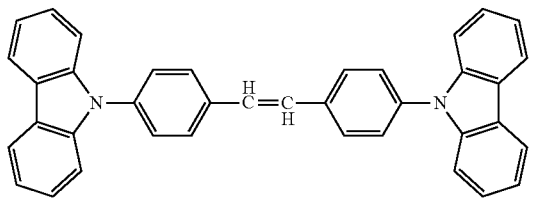
H8
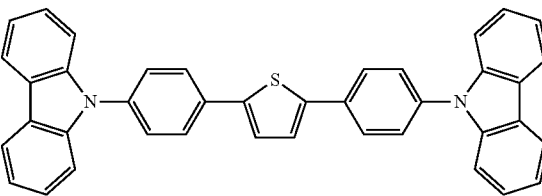
H9
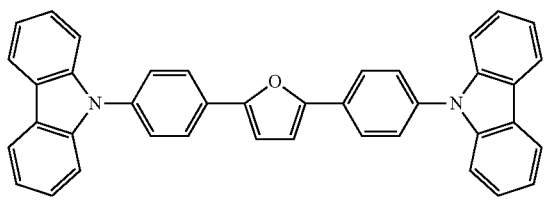
H10
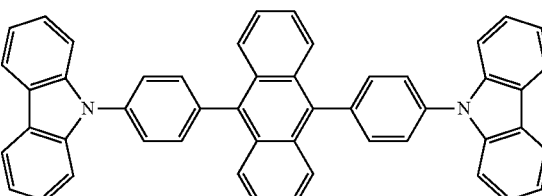
H11
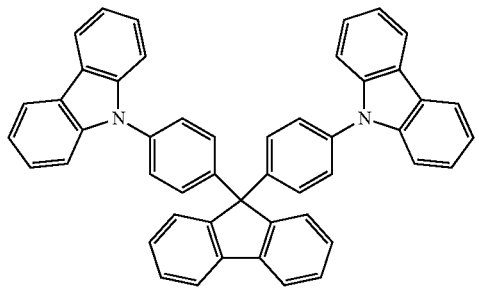
H12
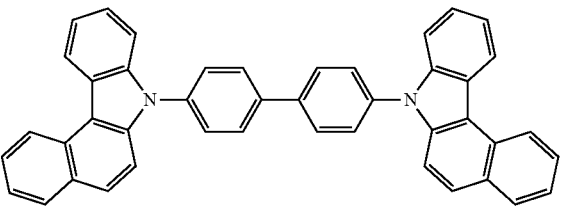
H13
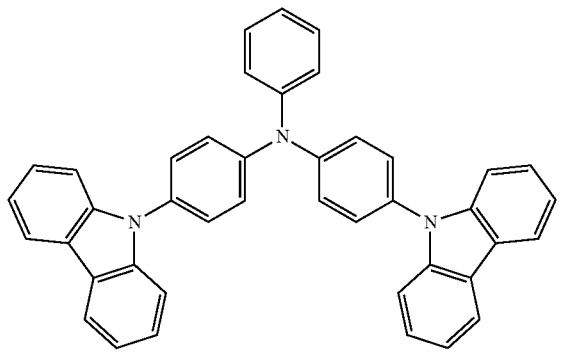
H14
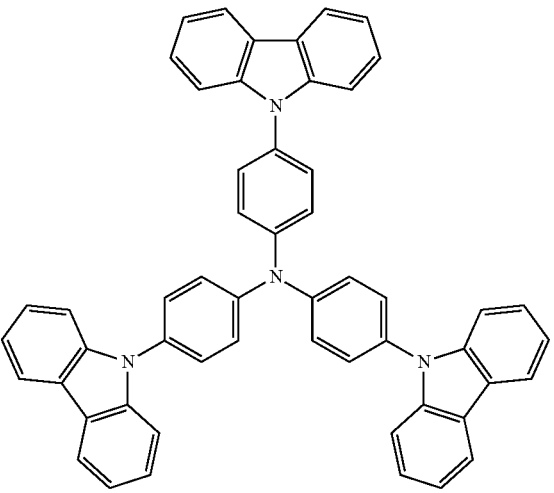
H15
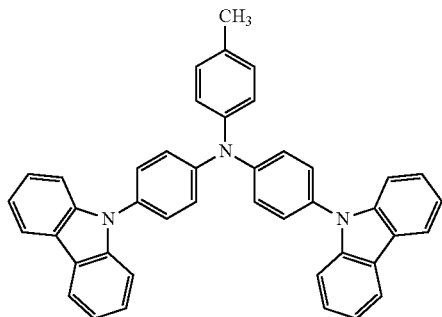
H16
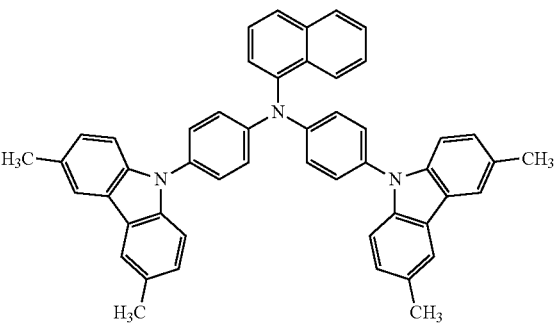

H17
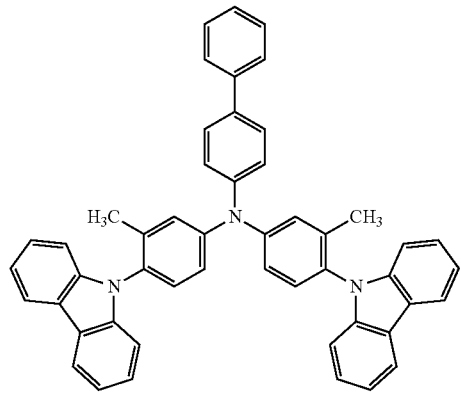
H18
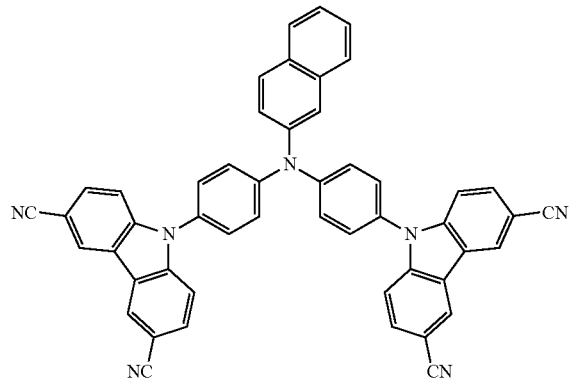
H19
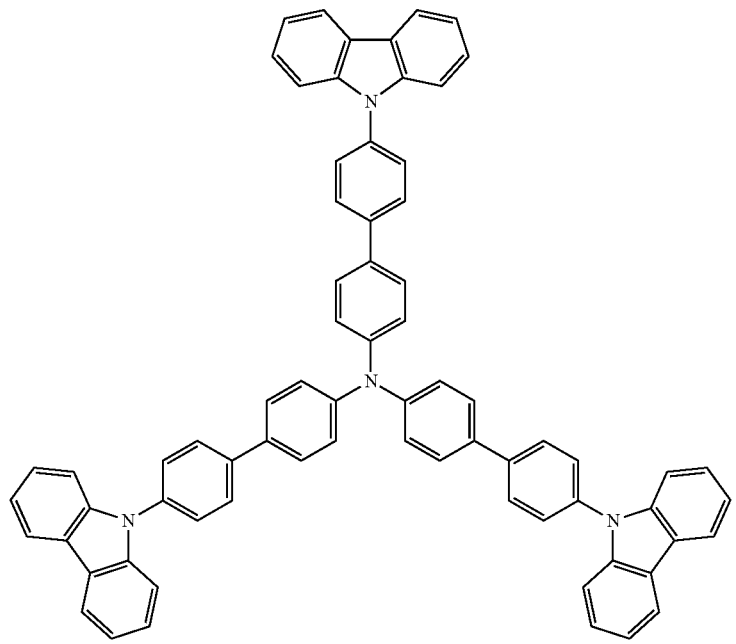
H20
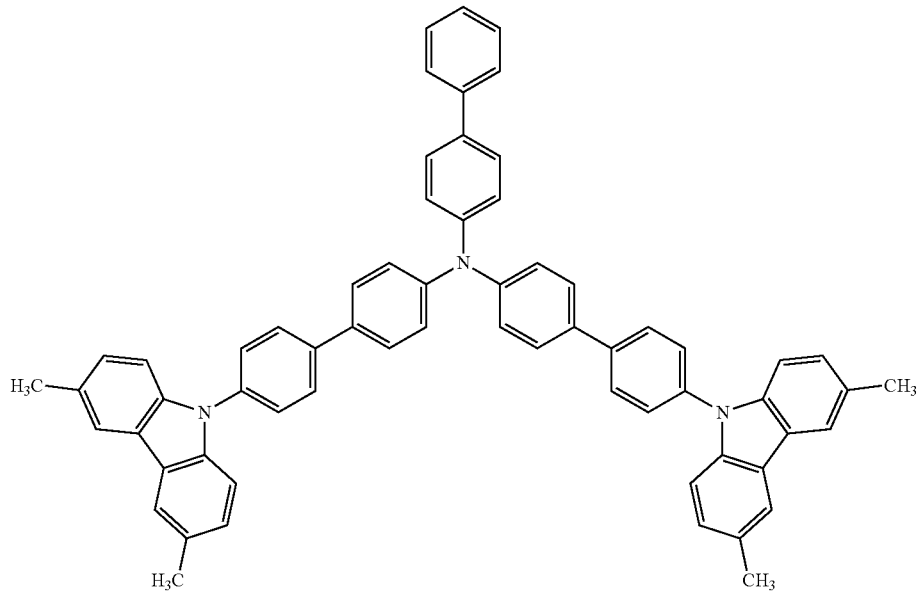

H21
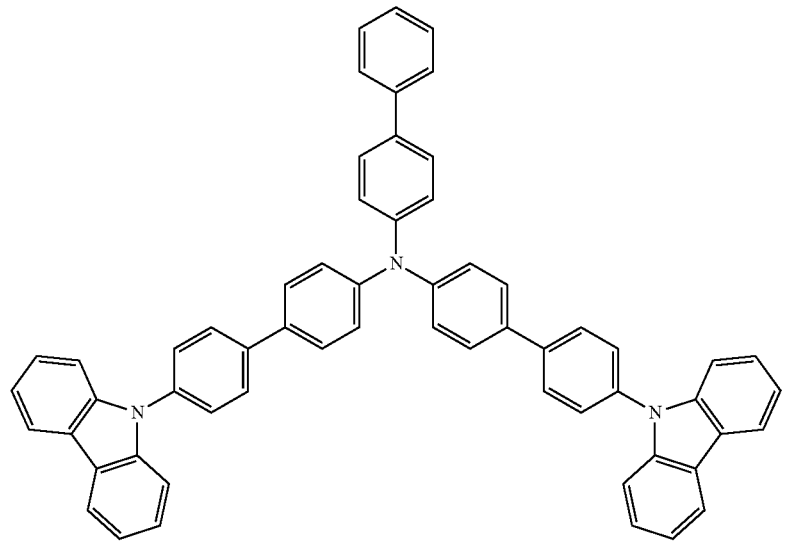
H22
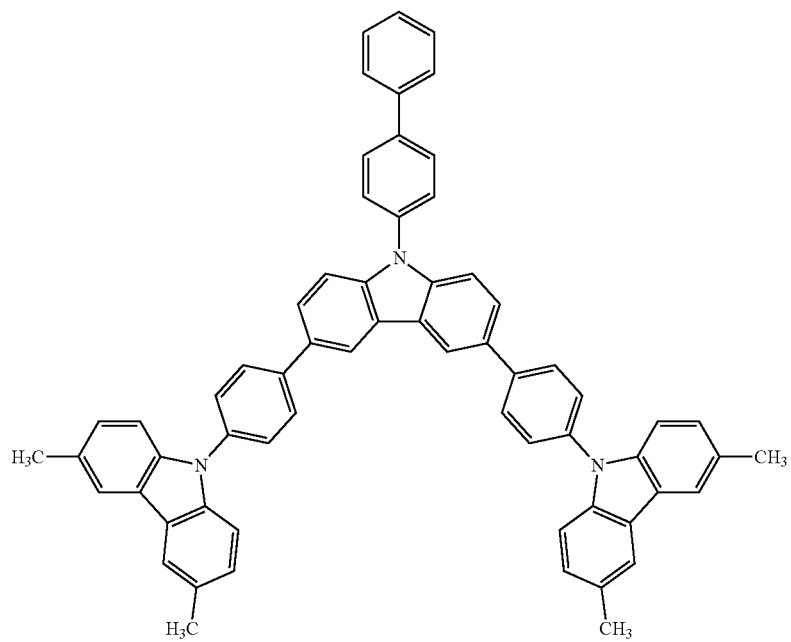
H23
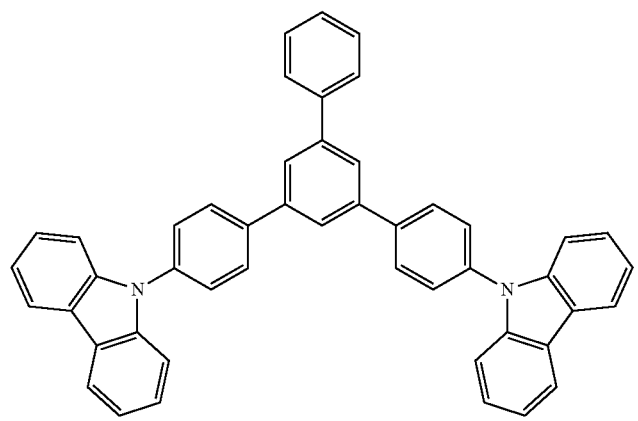

-continued
H24
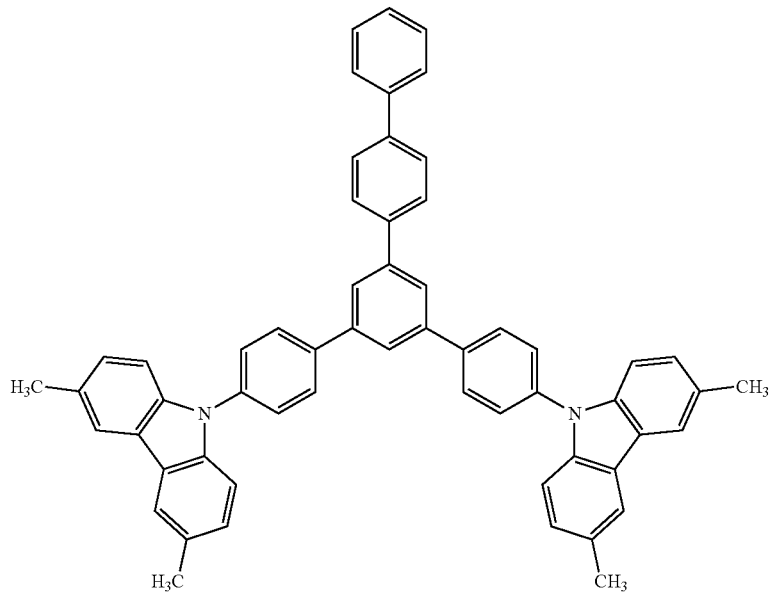
H25
H26
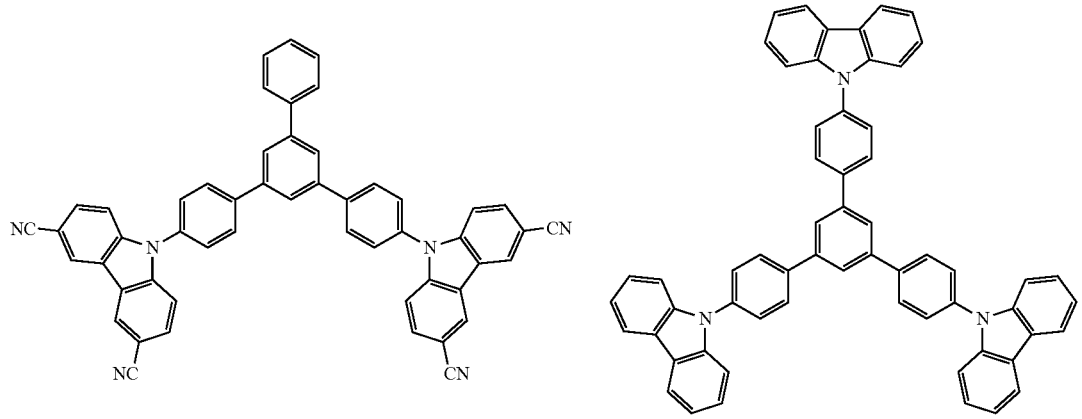
H27
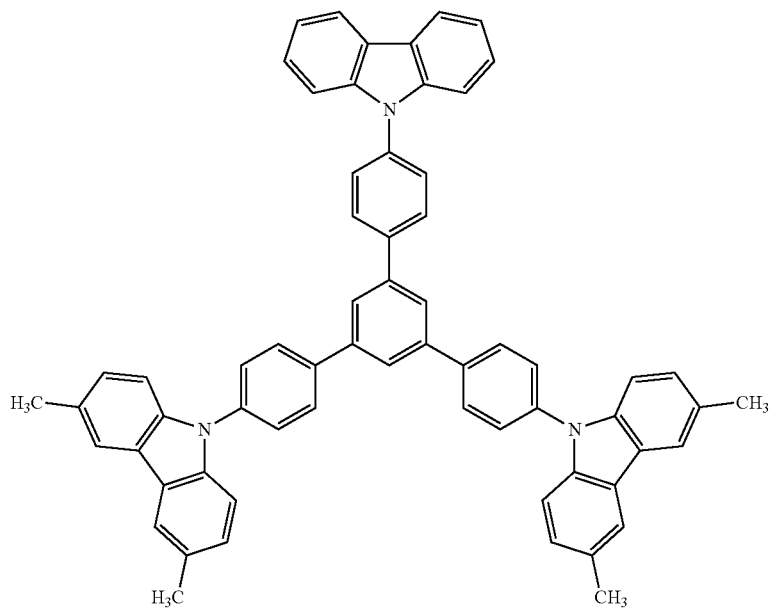

-continued

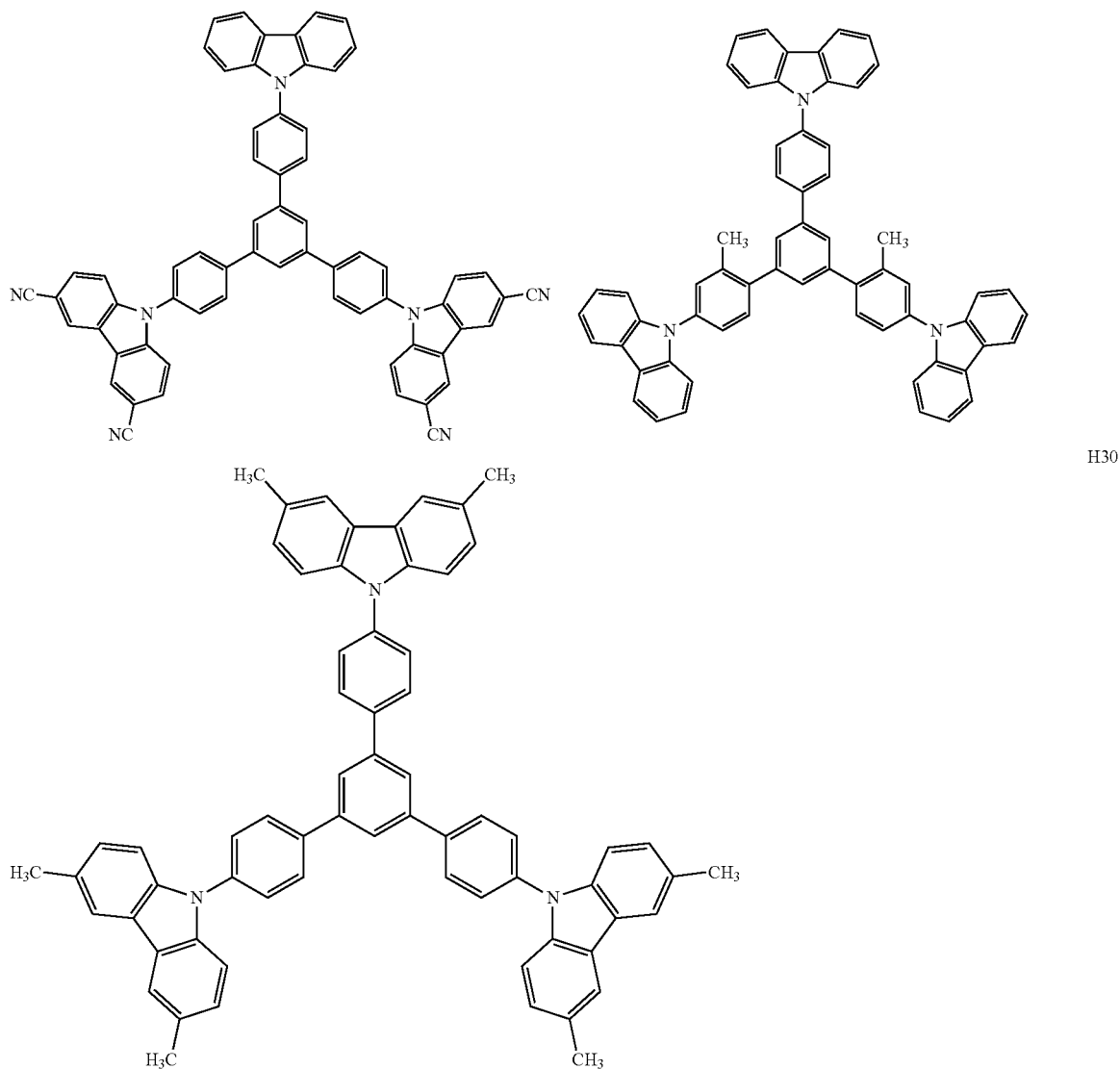

FIG. 1 illustrates a schematic sectional view of an organic light-emitting device 10 according to an embodiment. Hereinafter, a structure of an organic light-emitting device according to an embodiment and a method of manufacturing the same will be described with reference to FIG. 1.

The substrate 11 may be a suitable substrate for use in an organic light-emitting device. In an embodiment, the substrate 11 may be a glass substrate or a transparent plastic substrate with strong mechanical strength, thermal stability, transparency, surface smoothness, ease of handling, and water resistance.

A first electrode 13 may be formed by depositing or sputtering a first electrode-forming material on a surface of the substrate 11. When the first electrode 13 is an anode, a material having a high work function may be used as the first electrode-forming material to facilitate hole injection. The first electrode 13 may be a reflective electrode or a transmission electrode. Suitable first electrode-forming materials may be transparent and conductive materials such as ITO, IZO, $SnO_2$, and ZnO. The first electrode 13 may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode 13 may have a single-layer structure or a multi-layer structure including at least two layers. For example, the first electrode 13 may have a three-layered structure of ITO/Ag/ITO.

The organic layer 15 may be disposed on the first electrode 13.

The organic layer 15 may include a hole injection layer (HIL), a hole transport layer (HTL), a buffer layer, an emission layer (EML), an electron transport layer (ETL), and an electron injection layer (EIL).

The HIL may be formed on the first electrode 13 by vacuum deposition, spin coating, casting, Langmuir-Blodgett (LB) deposition, or the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about 10-8 torr to about 10-3 torr, and a deposition rate of about 0.01 to about 100 Å/sec.

When the HIL is formed using spin coating, the coating conditions may vary according to the compound that is used to form the HIL, and the desired structure and thermal properties of the HIL to be formed. For example, the coating rate may be in the range of about 2000 rpm to about 5000 rpm, and a temperature at which heat treatment may be performed to remove a solvent after coating may be in the range of about 80° C. to about 200° C.

The HIL may be formed of a suitable material for a HIL. For example, the material that can be used to form the HIL are N,N'-diphenyl-N,N'-bis-[4-(phenyl-m-tolyl-amino)-phenyl]-biphenyl-4,4'-diamine, (DNTPD), a phthalocyanine compound such as copper phthalocyanine, 4,4',4"-tris(3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly (4-styrenesulfonate) (PEDOT/PSS), polyaniline/camphor sulfonic acid (Pani/CSA), and polyaniline)/poly(4-styrenesulfonate (PANI/PSS).

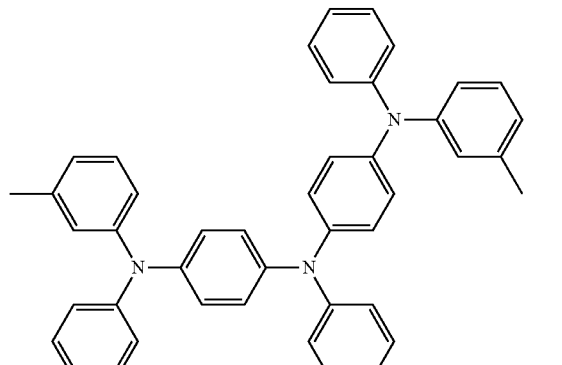

m-MTDATA

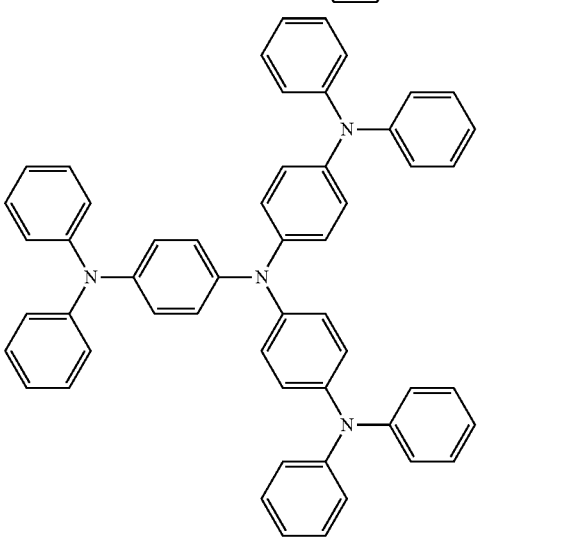

TDATA

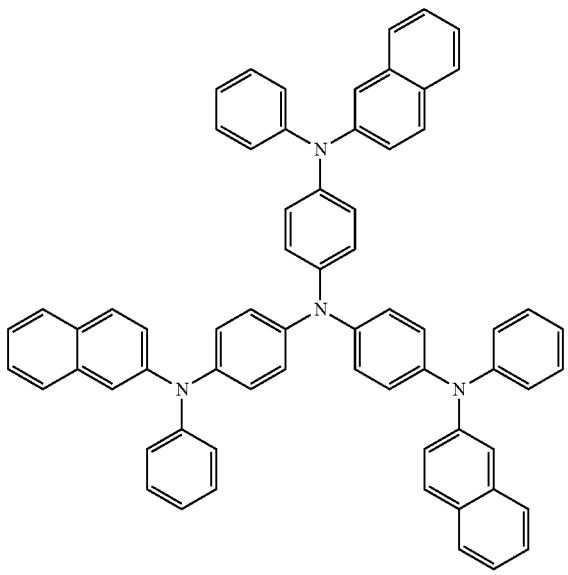

2-TNATA

The thickness of the HIL may be about 100 Å to about 10000 Å, and in an embodiment, may be from about 100 Å to about 1000 Å. When the thickness of the HIL is within these ranges, the HIL may have good hole injecting ability without a substantial increase in driving voltage.

Then, a HTL may be formed on the HIL by using vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary according to the material that is used to form the HTL.

Examples of suitable HTL forming materials are carbazole derivatives, such as N-phenylcarbazole or polyvinylcarbazole, N,N-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine) (NPB).

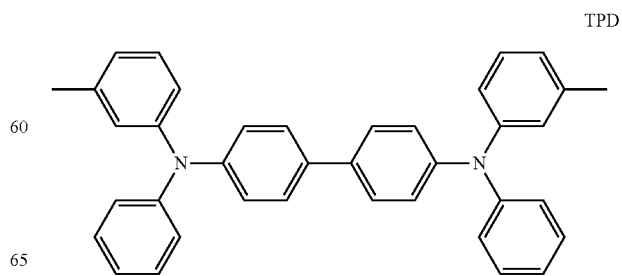

TPD

NPB

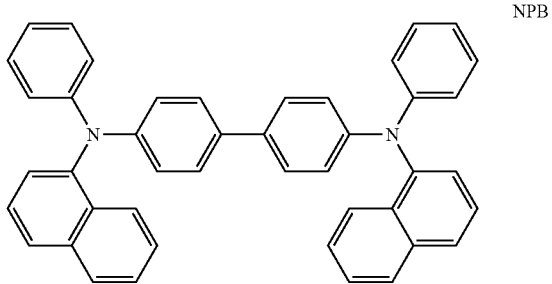

The thickness of the HTL may be about 50 Å to about 2000 Å, and for example, about 100 Å to about 1500 Å. When the thickness of the HTL is within these ranges, the HTL may have good hole transporting ability without a substantial increase in driving voltage.

The H-functional layer (having both hole injection and hole transport capabilities) may contain at least one material from each group of the hole injection layer materials and hole transport layer materials. The thickness of the H-functional layer may be from about 500 Å to about 10,000 Å, and in an embodiment, may be from about 100 Å to about 1,000 Å. When the thickness of the H-functional layer is within these ranges, the H-functional layer may have good hole injection and transport capabilities without a substantial increase in driving voltage.

In an embodiment, at least one of the HIL, HTL, and H-functional layer may include at least one of a compound of Formula 300 below and a compound of Formula 301 below:

Formula 300

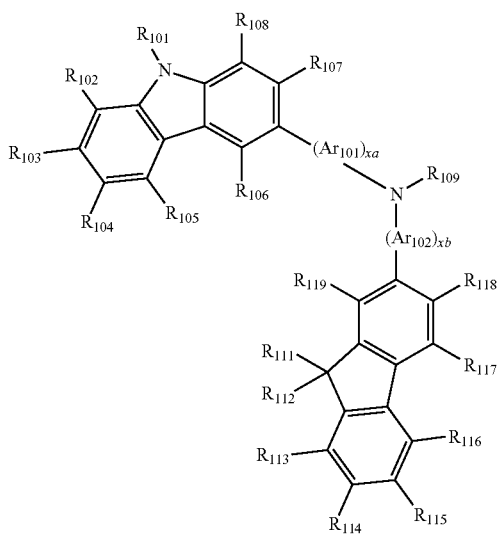

Formula 301

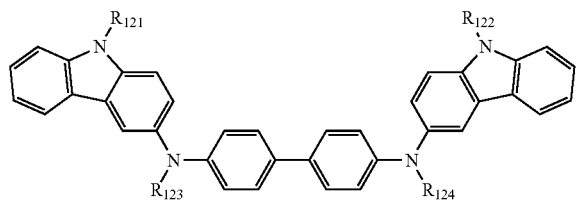

In Formula 300, $Ar_{101}$ and $Ar_{102}$ each independently may be a substituted or unsubstituted $C_6$-$C_{60}$ arylene group. In an embodiment, $Ar_{101}$ and $Ar_{102}$ each independently may be one of a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylenylene group, a chrysenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylenylene group, a chrysenylene group, a naphthacenylene group, a picenylene group, a perylenylene group, and a pentacenylene group that are substituted with at least one of a deuterium atom, a halogen atom, a hydroxyl group, a nitro group, a cyano group, an amino group, an amidino group, hydrazine, hydrazone, a carboxyl group or salt thereof, a sulfuric acid group or salt thereof, a phosphoric acid group or salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group.

In Formula 300, $x_a$ and $x_b$ each independently may be an integer from 0 to 5, for example, may be 0, 1, or 2. For example, $x_a$ may be 1, and $x_b$ may be 0.

In Formulae 300 and 301, $R_{101}$ to $R_{108}$, $R_{111}$ to $R_{119}$, and $R_{121}$ to $R_{124}$ each independently may be a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a $C_5$-$C_{60}$ arylthio group.

In an embodiment, $R_{101}$ to $R_{108}$, $R_{111}$ to $R_{119}$, and $R_{121}$ to $R_{124}$ each independently may be one of a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a phenyl group; a naphthyl group; an anthryl group; a fluorenyl group;

a pyrenyl group; and a phenyl group, a naphthyl group, an anthryl group, a fluorenyl group, and a pyrenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 300, $R_{109}$ may be one of a phenyl group, a naphthyl group, an anthryl group, a biphenyl group, and a pyridyl group; and a phenyl group, a naphthyl group, an anthryl group, a biphenyl group, and a pyridyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In an embodiment, the compound of Formula 300 may be a compound represented by Formula 300A below:

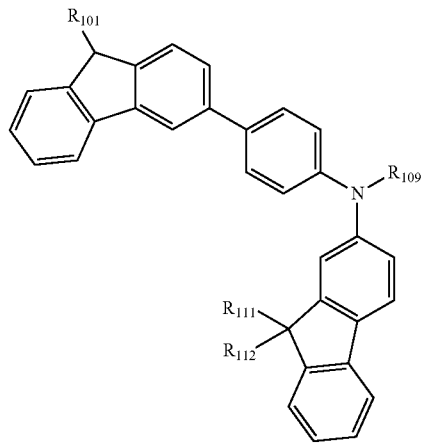

<Formula 300A>

In Formula 300A, $R_{101}$, $R_{110}$, $R_{121}$, and $R_{109}$ may be as set forth above.

In an embodiment, at least one of the HIL, HTL, and H-functional layer may include, e.g., at least one of compounds represented by Formulae 301 to 320 below:

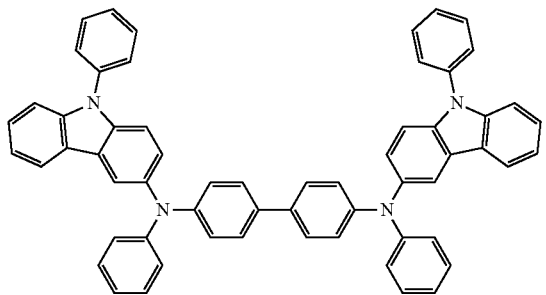

301

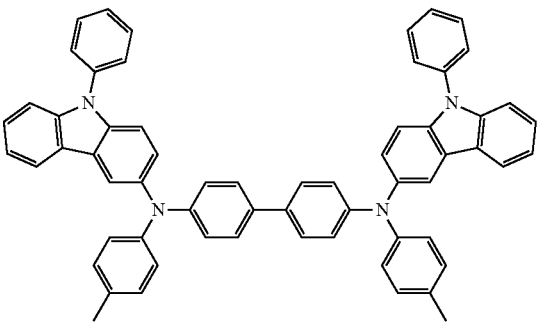

302

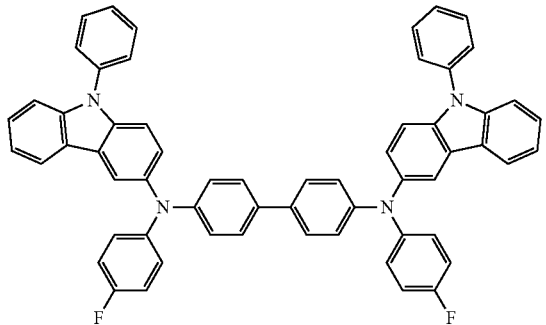

303

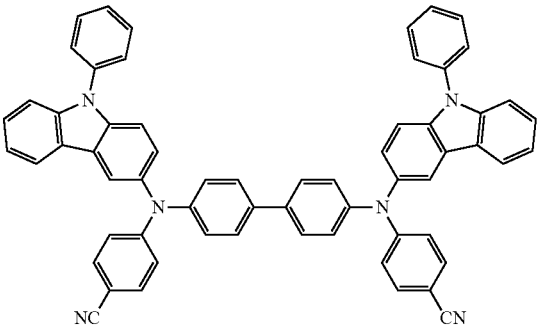

304

-continued
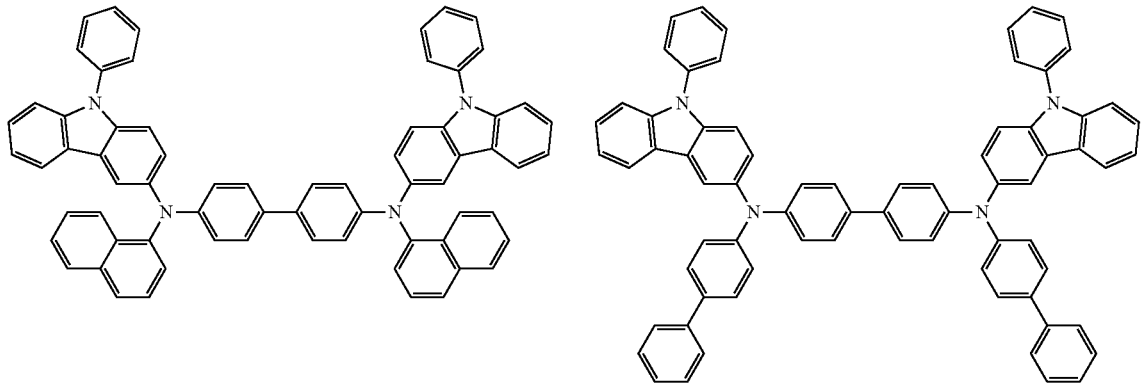
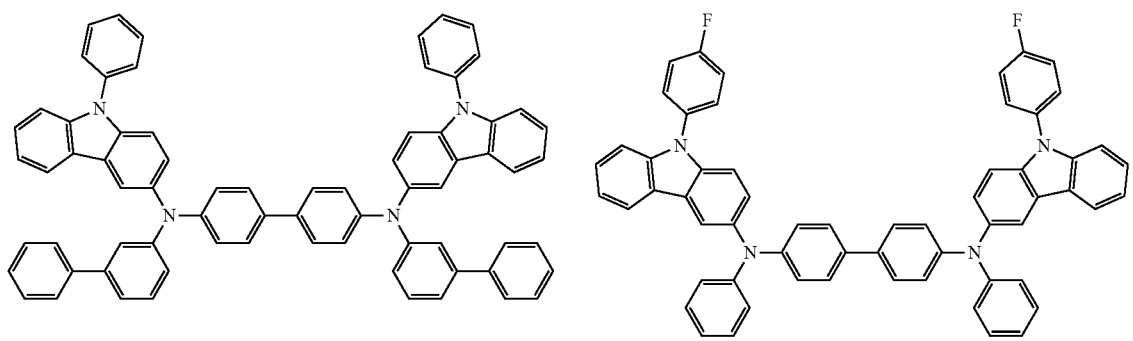
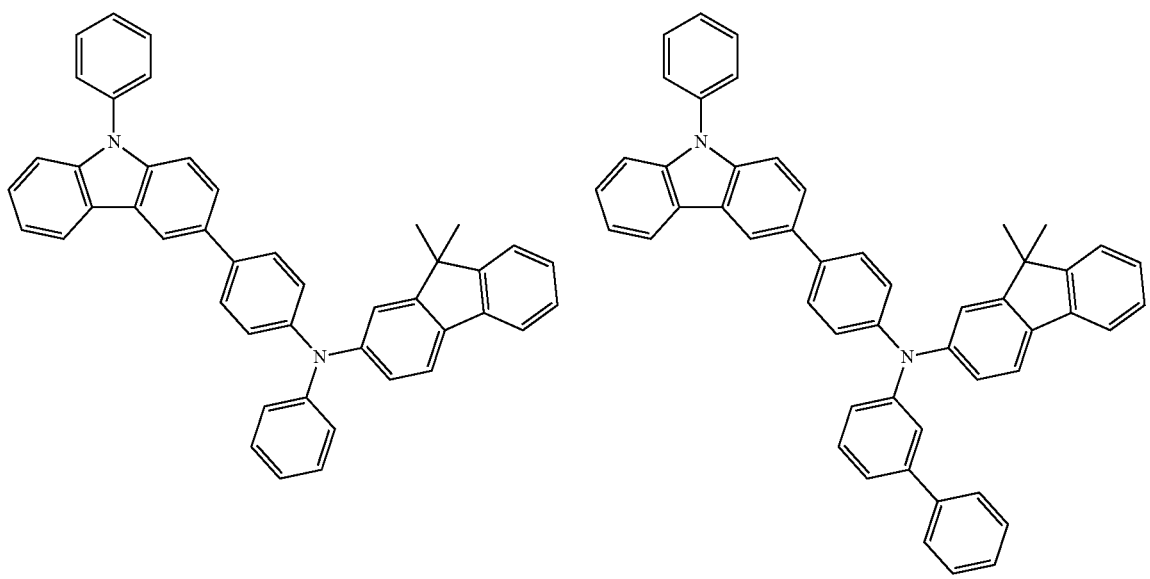

-continued
311
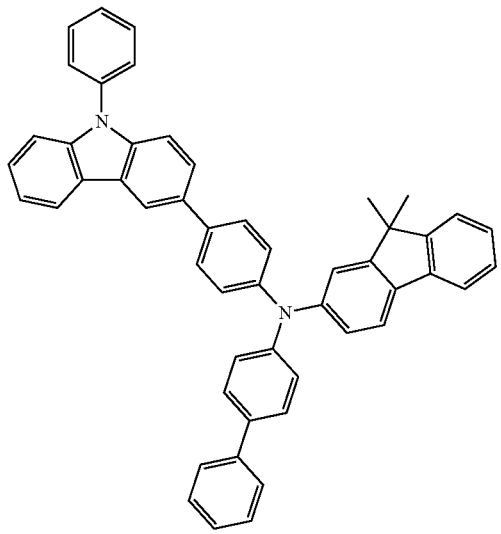
312
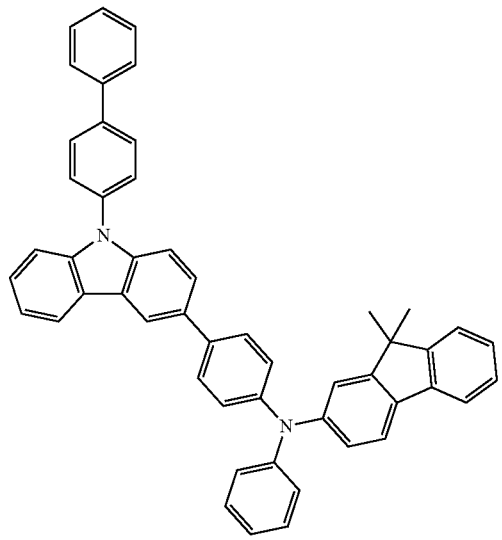
313
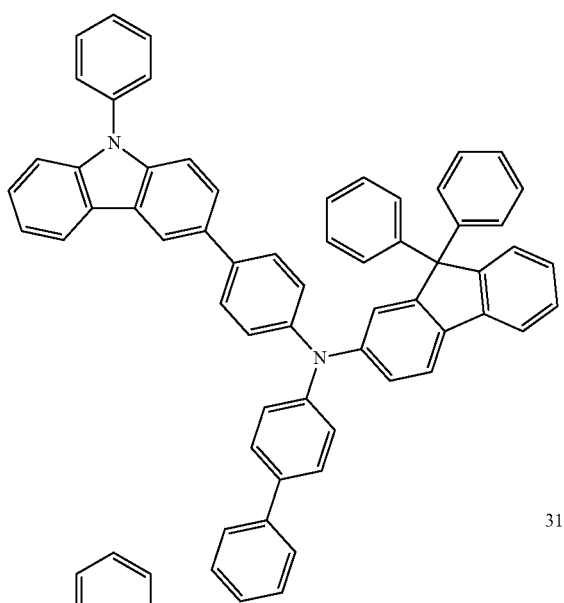
314
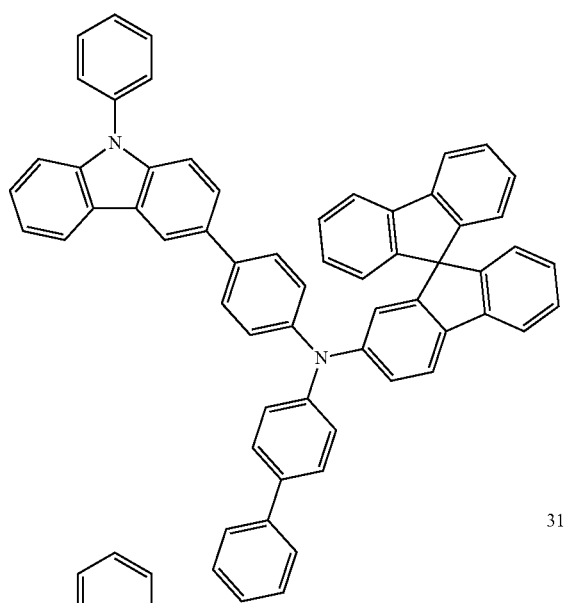
315
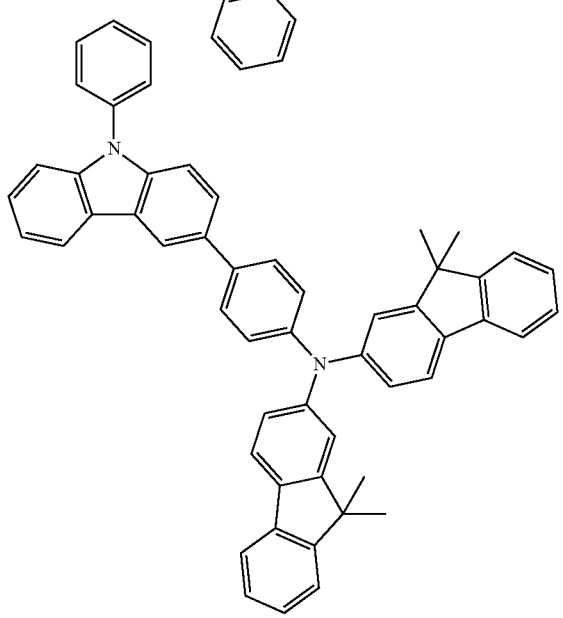
316
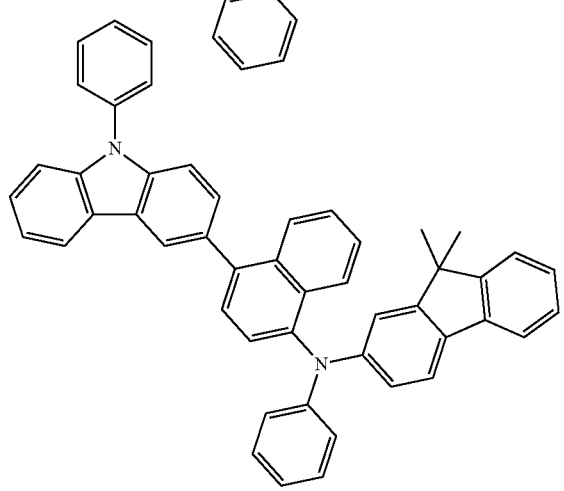

317

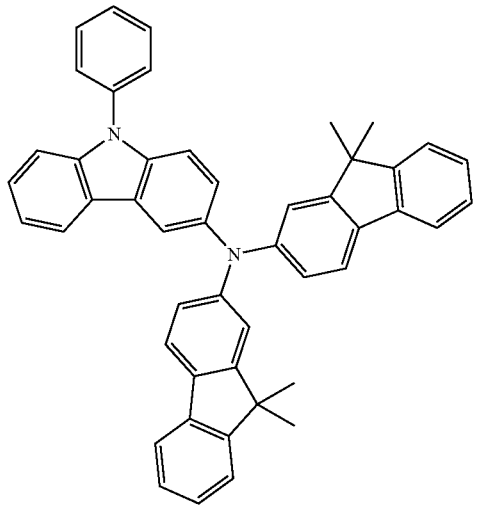

318

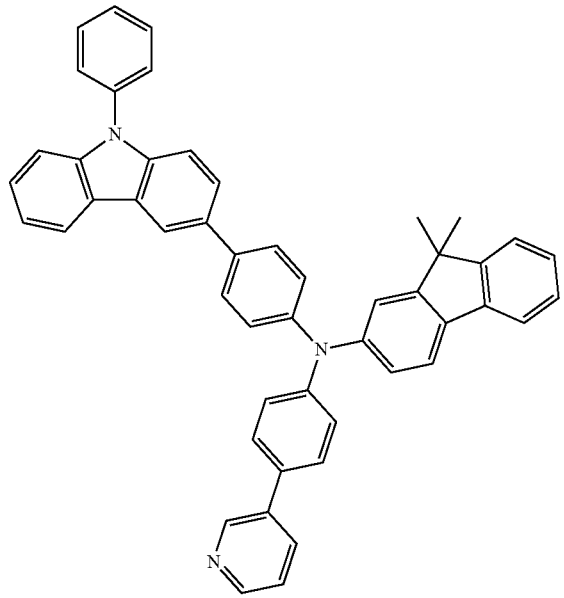

319

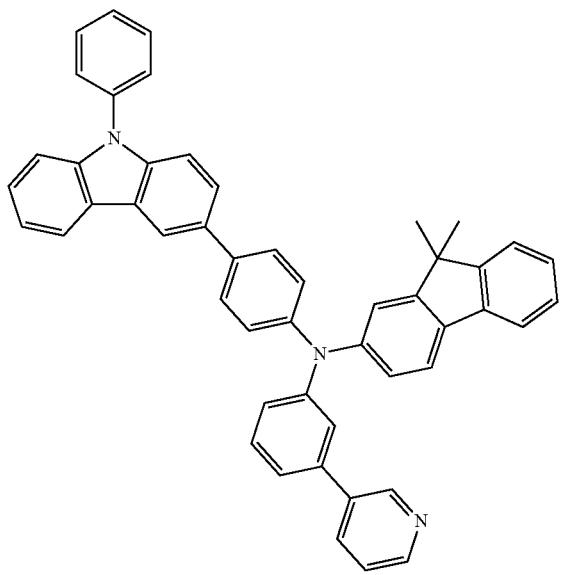

320

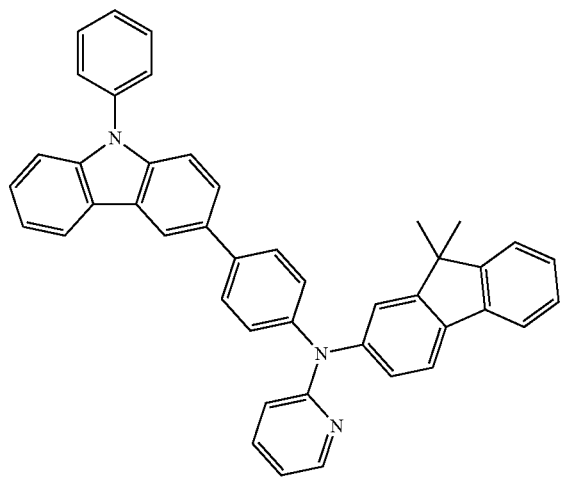

At least one of the HIL, HTL, and H-functional layer may further include a charge-generating material for improved layer conductivity, in addition to a suitable hole injecting material, hole transport material, and/or material having both hole injection and hole transport capabilities as described above.

The charge-generating material may be, for example, a p-dopant. The p-dopant may be, for example, one of quinine derivatives, metal oxides, and compounds with a cyano group. Examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200 below.

<Compound 200>

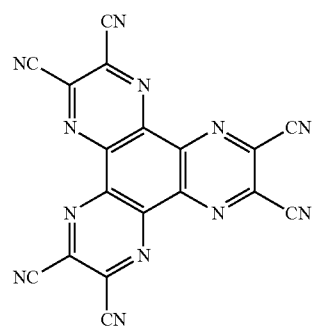

<F4-TCNQ>

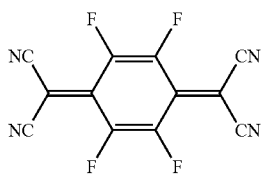

When the hole injection layer, hole transport layer, or H-functional layer further includes a charge-generating material, the charge-generating material may be homogeneously dispersed or unhomogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The buffer layer may include a suitable hole injecting material or hole transporting material. In some other embodiments, the buffer layer may include the same material as one of the materials included in the HIL, HTL, and H-functional layer that underlie the buffer layer.

Then, an EML may be formed on the HTL, H-functional layer, or buffer layer by vacuum deposition, spin coating, casting, Langmuir-Blodget (LB) deposition, or the like. When the EML is formed using vacuum deposition or spin coating, the deposition and coating conditions may be similar to those for the formation of the HIL, though the conditions for deposition and coating may vary according to the material that is used to form the EML.

The EML may include the organometallic compound (as a dopant) represented by Formula 1 above, and a host.

An amount of the dopant (i.e., the organometallic compound of Formula 1) in the EML may be selected from a range of, e.g., about 0.01 to about 15 parts by weight based on 100 parts by weight of the host.

The thickness of the EML may be from about 100 Å to about 1000 Å, and in an embodiment, may be from about 200 Å to about 600 Å. When the thickness of the EML is within these ranges, the EML may have good light emitting ability without a substantial increase in driving voltage.

A hole blocking layer (HBL) may be formed on the EML to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. A suitable hole-blocking material may be used. Examples of hole-blocking materials are oxadiazole derivatives, triazole derivatives, and phenanthroline derivatives. For example, bathocuproine (BCP) represented by the following formula may be used as a material for forming the HBL.

BCP

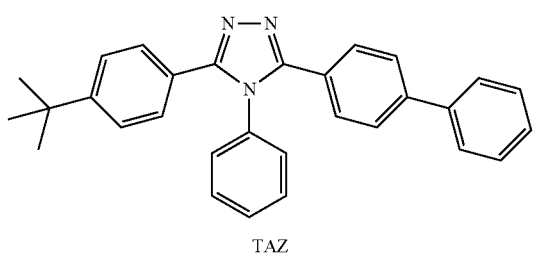

The thickness of the HBL may be from about 200 Å to about 1000 Å, and in an embodiment, may be from about 30 Å to about 300 Å. When the thickness of the HBL is within these ranges, the HBL may have improved hole blocking ability without a substantial increase in driving voltage.

Then, an ETL may be formed on the HBL by a suitable method, for example, vacuum deposition, spin coating, or casting. When the ETL is formed using vacuum deposition or spin coating, the deposition and coating conditions may be similar to those for the formation of the HIL, though the deposition and coating conditions may vary according to a compound that is used to form the ETL. A material for forming the ETL may be a suitable material that can stably transport electrons injected from an electron injecting electrode (cathode). Examples of materials for forming the ETL are a quinoline derivative, such as tris(8-quinolinorate)aluminum (Alq3), TAZ, BAlq, beryllium bis(benzoquinolin-10-olate) (Bebq2), 9,10-di(naphthalene-2-yl)anthracene (ADN), Compound 201, and Compound 202.

TAZ

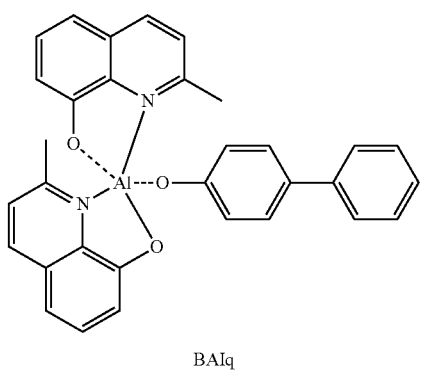

BAlq

<Compound 201>

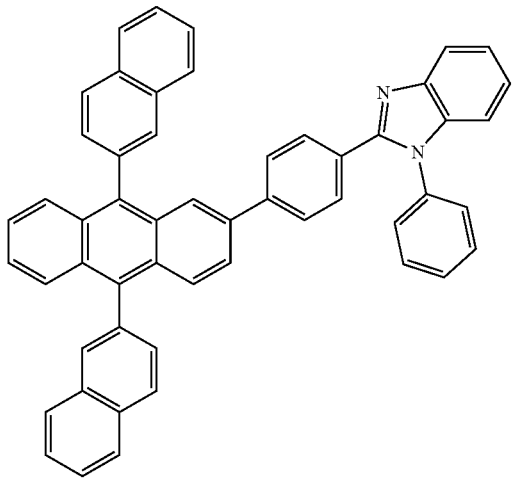

<Compound 202>

<Compound 203>

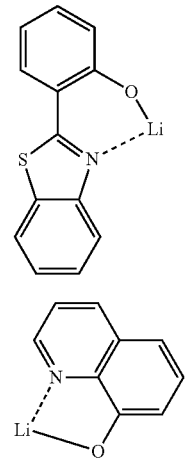

<LiQ>

The thickness of the ETL may be from about 100 Å to about 1000 Å, and in an embodiment, may be from about 150 Å to about 500 Å. When the thickness of the ETL is within these ranges, the ETL may have satisfactory electron transporting ability without a substantial increase in driving voltage.

In an embodiment the ETL may further include a metal-containing material, in addition to a suitable electron-transporting organic compound.

The metal-containing material may include a lithium (Li) compound. Examples of the Li compound are lithium quinolate (LiQ) and Compound 203 below:

Then, an EIL, which may facilitate injection of electrons from the cathode, may be formed on the ETL. A suitable electron-injecting material may be used to form the EIL.

Examples of materials for forming the EIL are LiF, NaCl, CsF, $Li_2O$, and BaO. The deposition and coating conditions for forming the EIL may be similar to those for the formation of the HIL, though the deposition and coating conditions may vary according to the material that is used to form the EIL. The thickness of the EIL may be from about 1 Å to about 100 Å, and in an embodiment, may be from about 3 Å to about 90 Å. When the thickness of the EIL is within these ranges, the EIL may have satisfactory electron injection ability without a substantial increase in driving voltage.

A second electrode 17 may be disposed on the organic layer 15. The second electrode 17 may be a cathode that is an electron injection electrode. A material for forming the second electrode 17 may be a metal, an alloy, an electro-conductive compound, which may have a low work function, or a mixture thereof. In an embodiment, the second electrode 17 may be a transmission (e.g., transparent) electrode and may be formed using a thin film of Li, Mg, Al, Al—Li, Ca, Mg—In, Mg—Ag, or the like. In an embodiment, to manufacture a top-emission light-emitting device, the transmission electrode may be formed of indium tin oxide (ITO) or indium zinc oxide (IZO).

The above description of the organic light-emitting device illustrated in FIG. 1 is given by way of example.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Examples of the unsubstituted $C_1$-$C_{60}$ alkyl group used herein are linear or branched $C_1$-$C_{60}$ alkyl groups, such as methyl group, ethyl group, propyl group, isobutyl group, sec-butyl group, pentyl group, iso-amyl group, hexyl group, or the like. In the substituted $C_1$-$C_{60}$ alkyl group, at least one hydrogen atom of the unsubstituted $C_1$-$C_{60}$ alkyl group described above may be substituted with a deuterium atom, a halogen atom, a hydroxyl group, a nitro group, a cyano group, an amino group, an amidino group, a hydrazine, a hydrazone, a carboxyl group or salts thereof, a sulfonic acid group or salts thereof, a phosphoric acid group or salts thereof, a $C_1$-$C_{60}$ alkyl group, a $C_2$-$C_{60}$ alkenyl group, a $C_2$-$C_{60}$ alkynyl group, a $C_6$-$C_{60}$ aryl group, a $C_2$-$C_{60}$ heteroaryl group, —N($Q_{11}$)($Q_{12}$), or —Si($Q_{13}$)($Q_{14}$)($Q_{15}$), wherein $Q_1$ to $Q_{15}$ each independently may be selected from the group of a hydrogen atom, a $C_1$-$C_{60}$ alkyl group, a $C_2$-$C_{60}$ alkenyl group, a $C_2$-$C_{60}$ alkynyl group, a $C_5$-$C_{60}$ aryl group, and a $C_2$-$C_{60}$ heteroaryl group. The unsubstituted $C_1$-$C_{60}$ alkoxy group may be a group represented by —OA, wherein A is an unsubstituted $C_1$-$C_{60}$ alkyl group described above.

Examples of the unsubstituted $C_1$-$C_{60}$ alkoxy group are a methoxy group, an ethoxy group, and an isopropyloxy group. At least one of the hydrogen atoms in the alkoxy group may be substituted with the substituents described above in conjunction with the substituted $C_1$-$C_{60}$ alkyl group.

As used herein, the unsubstituted $C_2$-$C_{60}$ alkenyl group may be a hydrocarbon chain having a carbon-carbon double bond in the center or at a terminal of the unsubstituted $C_2$-$C_{60}$ alkyl group. Examples of the unsubstituted $C_2$-$C_{60}$ alkenyl group are ethenyl group, propenyl group, and butenyl groups. At least one hydrogen atom in the unsubstituted $C_2$-$C_{60}$ alkenyl group may be substituted with the substituents described in conjunction with the substituted $C_1$-$C_{60}$ alkyl group.

The unsubstituted $C_2$-$C_{60}$ alkynyl group may be a hydrocarbon chain having at least one carbon-carbon triple bond in the center or at a terminal thereof. Examples of the unsubstituted $C_2$-$C_{60}$ alkynyl group are an ethenyl group, a propenyl group, a butenyl group, and the like. At least one hydrogen atom in the alkynyl group may be substituted with the substituents described above in conjunction with the $C_1$-$C_{60}$ alkyl group.

The unsubstituted $C_6$-$C_{60}$ aryl group may be a monovalent group having a carbocyclic aromatic system having 6 to 60 carbon atoms including at least one aromatic ring. The unsubstituted $C_6$-$C_{60}$ arylene group may be a bivalent group having a carbocyclic aromatic system having 6 to 60 carbon atoms including at least one aromatic ring. When the aryl group and the arylene group have at least two rings, they may be fused to each other via a single bond. At least one hydrogen atom in the aryl group and the arylene group may be substituted with the substituents described above in conjunction with the $C_1$-$C_{60}$ alkyl group.

Examples of the substituted or unsubstituted $C_6$-$C_{60}$ aryl group are a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m-, or p-fluorophenyl group and a dichlorophenyl group), a dicyanophenyl group, a trifluoromethoxyphenyl group, an o-, m-, or p-tolyl group, an o-, m- or p-cumenyl group, a mesityl group, a phenoxyphenyl group, a (α,α-dimethylbenzene) phenyl group, a (N,N'-dimethyl)aminophenyl group, a (N,N'-diphenyeaminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, hexacenyl group, a rubicenyl group, a coronenyl group, a trinaphthylenyl group, a heptaphenyl group, a heptacenyl group, a pyranthrenyl group, and an ovalenyl group. Examples of the substituted $C_5$-$C_{60}$ aryl group may be inferred based on those of the unsubstituted $C_5$-$C_{60}$ aryl group and the substituted $C_1$-$C_{60}$ alkyl group described above. Examples of the substituted or unsubstituted $C_5$-$C_{60}$ arylene group may be inferred based on those examples of the substituted or unsubstituted $C_5$-$C_{60}$ aryl group described above.

The unsubstituted $C_2$-$C_{60}$ heteroaryl group may be a monovalent group having at least one aromatic ring having at least one of the heteroatoms selected from the group of N, O, P, and S. The unsubstituted $C_2$-$C_{60}$ heteroarylene group may be a divalent group having at least one aromatic ring having at least one of the heteroatoms selected from the group of N, O, P, and S. In this regard, when the heteroaryl group and the heteroarylene group have at least two rings, they may be fused to each other via a single bond. At least one hydrogen atom in the heteroaryl group and the heteroarylene group may be substituted with those substituents described above in conjunction with the $C_1$-$C_{60}$ alkyl group.

Examples of the unsubstituted $C_2$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group and an imidazopyrimidinyl group. Examples of the substituted $C_2$-$C_{60}$ heteroarylene group may be inferred based on those examples of the substituted or unsubstituted $C_2$-$C_{60}$ arylene group described above.

The substituted or unsubstituted $C_6$-$C_{60}$ aryloxy group may be —OA$_2$ (wherein A$_2$ may be a substituted or unsubstituted $C_6$-$C_{60}$ aryl group described above). The substituted or unsubstituted $C_5$-$C_{60}$ arylthio group may be —SA$_3$ (wherein A$_3$ may be a substituted or unsubstituted $C_6$-$C_{60}$ aryl group described above).

SYNTHESIS EXAMPLES

Ligand 1(L1) to Ligand 43(L43)

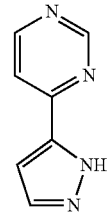

L1

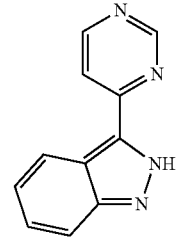

L2

111
-continued
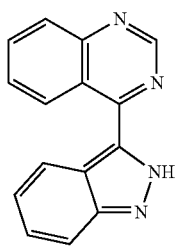
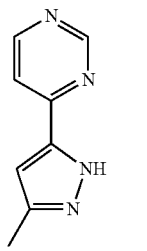
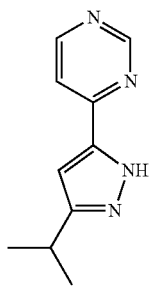
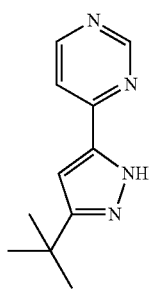
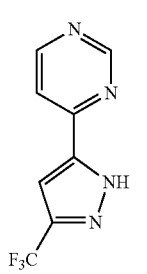
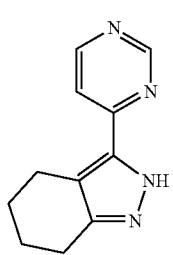
112
-continued
L3
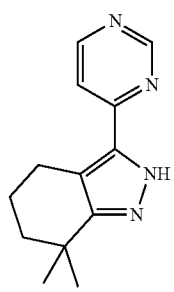   L9
L4
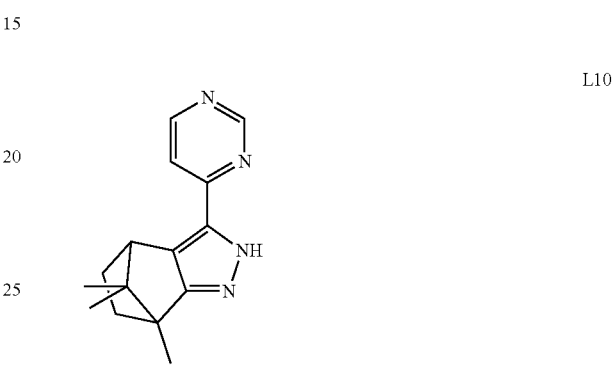   L10
L5
L6   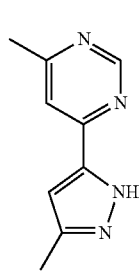   L11
L7   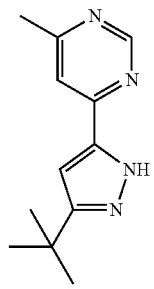   L12
L8   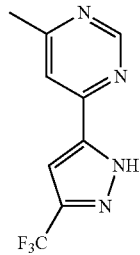   L13

-continued
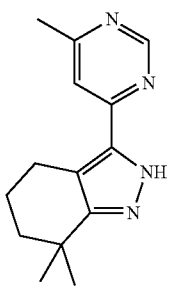 L14
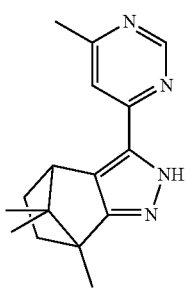 L15
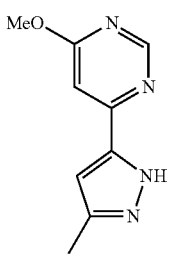 L16
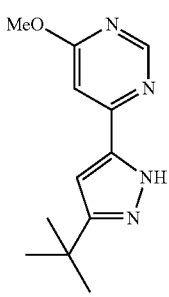 L17
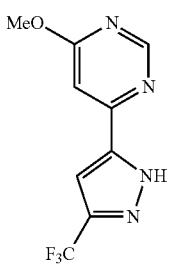 L18
-continued
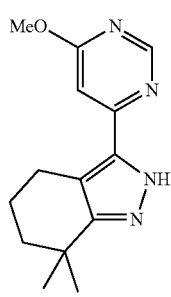 L19
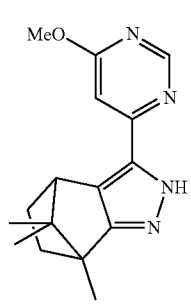 L20
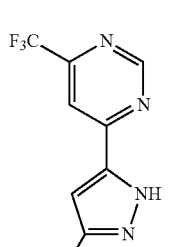 L21
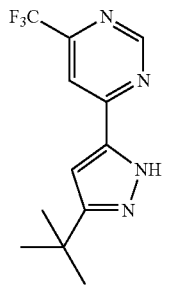 L22
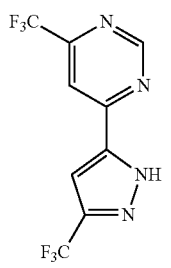 L23

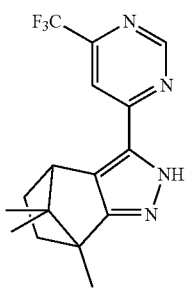
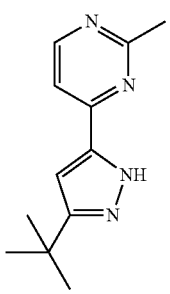
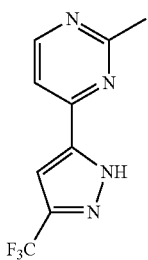
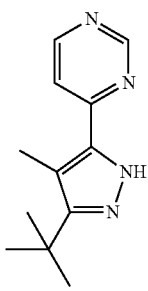
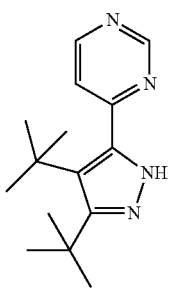
L24
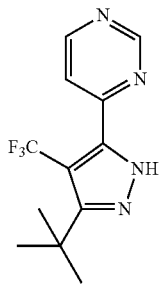
L25
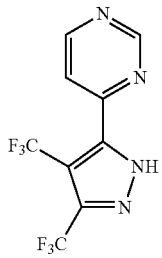
L26
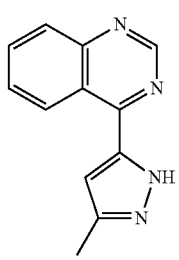
L27
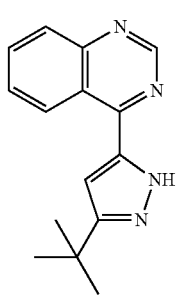
L28
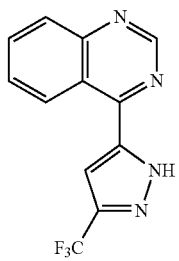
L29
L30
L31
L32
L33
L34
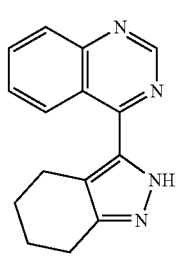

117
-continued
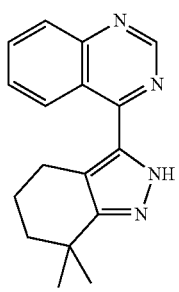
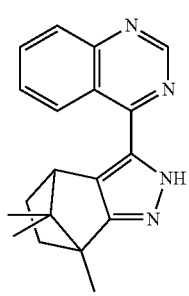
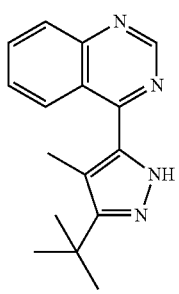
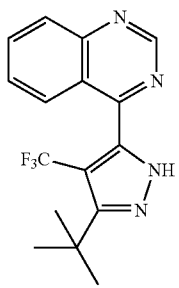
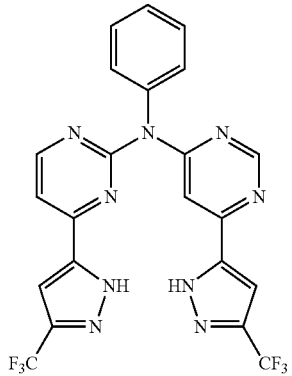
118
-continued
L35
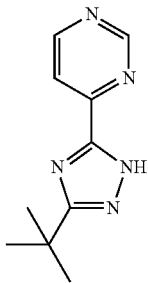
L40
L36
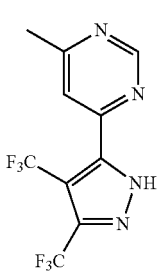
L41
L37
L38
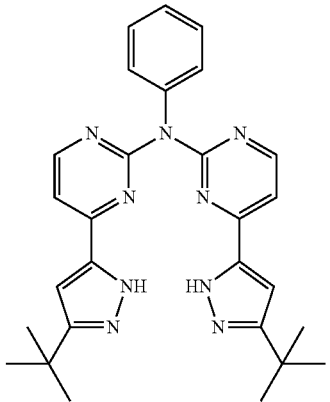
L42
L39
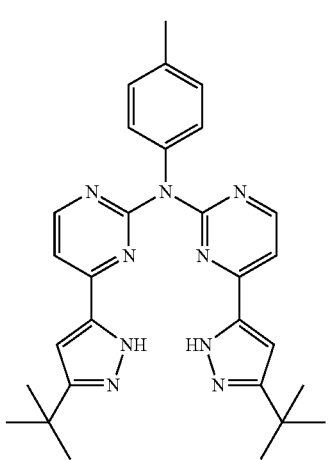
L43

Ligand Synthesis 1

Synthesis of Ligand 1 L1)

Ligand 1(L1) was synthesized according to Reaction Scheme 1 below:

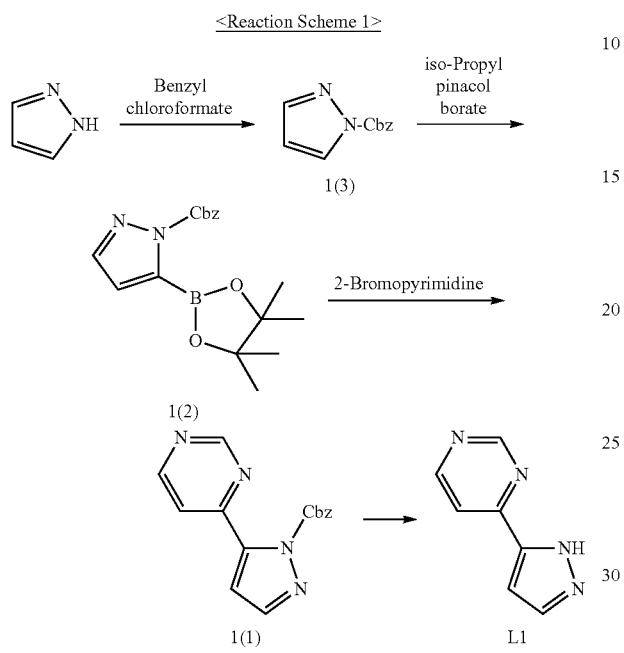

Synthesis of Intermediate 1(3)

Following adding 1.9 g (80.8 mmol) of NaH to 80 ml of dichlormethane, 5.0 g (73.5 mmol) of pyrazole was added thereto at 0° C. and then stirred for about 30 minutes. Afterward, 11.5 ml (80.8 mmol) of benzyl chloroformate dissolved in 30 ml of dichloromethane was dropwise added thereto at 0° C., and stirred for about 1 hour, then further at room temperature for about 3 hours. After completion of the reaction, 100 ml of saturated sodium hydrocarbonate was added thereto, followed by extraction with 50 ml of methylene chloride three times to obtain an organic layer, which was then dried using magnesium sulfate, followed by distillation under reduced pressure. The resulting product was separated and purified using column chromatography to obtain 12.6 g (62.4 mmol, Yield: 85%) of Intermediate 1(3). This compound was identified using liquid chromatography-mass spectroscopy (LC-MS).

LC-MS m/z=203 (M+H)+

Synthesis of Intermediate 1(2)

After dissolving 10.0 g (49.5 mmol) of Intermediate 1(3) in 80 ml of anhydrous tetrahydrofuran, 25 ml (2.2M in THF, 54.5 mmol) of n-BuLi was slowly added thereto at 0° C., and stirred at room temperature for about 1 hour. After 1 hour, the temperature was lowered to about −78° C., 12.0 ml (59.4 mmol) of isopropyl pinacol borate was slowly added to the reaction mixture, and stirred at −78° C. for about 15 minutes. Afterward, the temperature was slowly increased to 0° C., and the reaction mixture was further stirred for about 1 hour. After completion of the reaction, 100 ml of a saturated chloroammonium solution as added thereto, and extracted with 100 ml of dichloromethane to obtain an organic layer, which was then washed with 100 mL of distilled water twice and dried using magnesium sulfate, followed by distillation under reduced pressure to obtain 9.7 g (29.7 mmol, Yield: 60%) of Intermediate 1(2).

LC-MS m/z=329(M+H)+

Synthesis of Intermediate 1(1)

After dissolving 1.9 g (12.2 mmol) of 4-bromopyrimidine in 120 ml of a mixed solvent of dioxolane and water (5:1) in a seal-tube, 5.0 g (36.6 mmol) of potassium carbonate, 1.4 g (1.2 mmol) of Tetrakistriphenylphosphine Pd(0), and 8.0 g (24.4 mmol) of Intermediate 1(2) were added thereto. The resulting reaction mixture was stirred at 90° C. for a day. After completion of the reaction, 100 ml of distilled water was added to the reaction product, followed by extraction with 100 ml of dichloromethane to obtain an organic layer, which was then dried using magnesium sulfate, and distilled under reduced pressure to obtain 2.0 g (7.3 mmol, Yield: 60%) of Intermediate 1(1).

LC-MS m/z=280(M+H)+

Synthesis of Ligand 1 (L1)

After dissolving 2.0 g (7.3 mmol) of Intermediate 1(1) in 60 ml of methanol at room temperature, 0.2 g of Pd/C (10% w/w) was added thereto and stirred at room temperature for about 12 hours with hydrogen purging After completion of the reaction, Pd/C was removed using CELITE to obtain an organic layer, which was then concentrated under reduced pressure. The resulting product was separated and purified using column chromatography to obtain 1.0 g (6.9 mmol, Yield: 95%) of ligand 1 (L1). This compound was identified using LC-MS.

LC-MS m/z=203(M+H)+

Ligand Synthesis 2

Synthesis of Ligand 2 (L2)

Ligand 2 (L2) was synthesized according to Reaction Scheme 2 below:

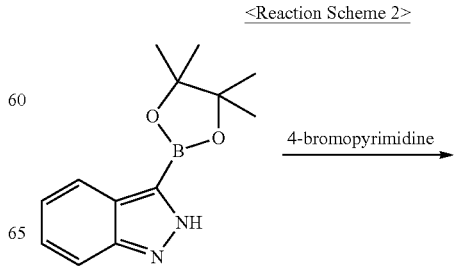

-continued

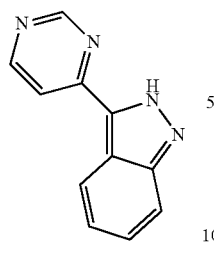

L2

Synthesis of Ligand 2 (L2)

After dissolving 2.0 g (12.6 mmol) of 4-bromopyrimidine in 80 ml of 1,2-dimethoxyethane at room temperature, 1.4 g (1.2 mmol) of tetrakistriphenylphosphine Pd(0), and 4.6 g (18.9 mmol) of 1H-indazol-3-ylboronic acid pinacol ester were added thereto. The resulting reaction mixture was heated at about 90° C. for about 18 hours under reflux. After completion of the reaction, 100 ml of distilled water was added to the reaction product, followed by extraction with 100 ml of dichloromethane to obtain an organic layer, which was then dried using magnesium sulfate, distilled under reduced pressure, and then separated and purified using column chromatography to obtain 1.1 g (5.7 mmol, Yield: 45%) of ligand 2 (L2).

LC-MS m/z=197(M+H)+

Ligand Synthesis 3

Synthesis of Ligand 3 (L3)

Ligand 3 (L3) was synthesized according to Reaction Scheme 3 below:

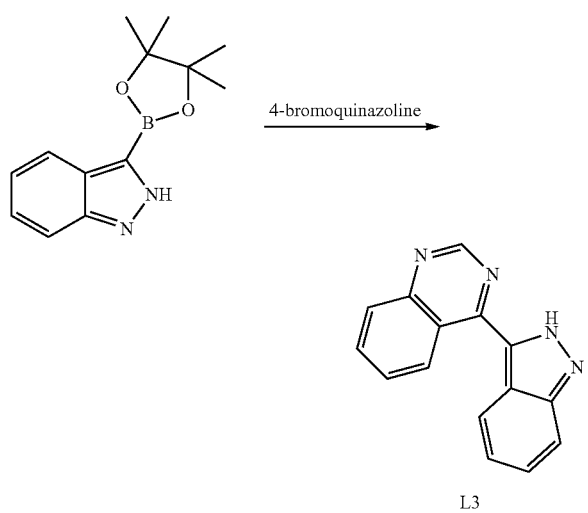

0.8 g (3.2 mmol, Yield: 25%) of ligand 3 (L3) was synthesized in the same manner as in the synthesis of ligand 2 (L2) (Ligand Synthesis 2), except that 4-bromoquinazoline, instead of 4-bromopyrimidine, was used in synthesizing Ligand (L3).

LC-MS m/z=197(M+H)+

Ligand Synthesis 4

Synthesis of Ligand 4 (L4)

Ligand 4 (L4) was synthesized according to Reaction Scheme 4 below:

<Reaction Scheme 4>

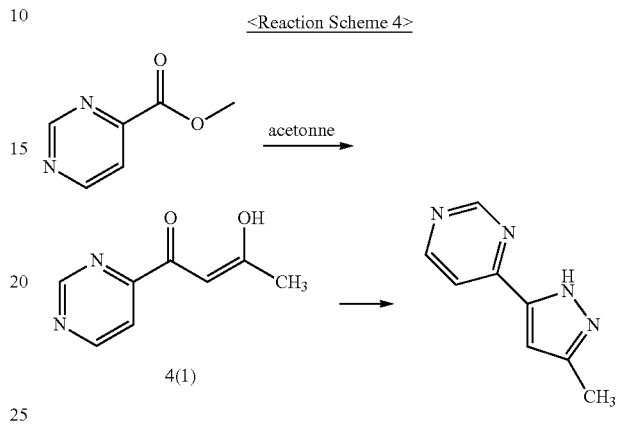

Synthesis of Intermediate 4(1)

Following adding 1.0 g (43.4 mmol) of NaH to 80 ml of anhydrous tetrahydrofuran, 2.6 ml (34.8 mmol) of acetone was slowly added thereto at 0° C. After 1 hour, 4.0 g (29.0 mmol) of pyrimidine-4-carboxylic acid methyl ester was slowly added thereto and heated under reflux at about 80° C. for about 16 hours. After completion of the reaction, 30 ml of distilled water was added thereto, 2.5 ml of acetic was then slowly added and stirred at room temperature for about 30 minutes. After 30 minutes, the resulting product was extracted with 100 ml of dichloromethane five times to obtain an organic layer, which was dried using magnesium sulfate and distilled under reduced pressure. The resulting product was separated and purified using column chromatography to obtain 1.8 g (11.0 mmol, Yield 38%) of Intermediate 4(1).

LC-MS m/z=165(M+H)+

Synthesis of Ligand 4 (L4)

After dissolving 1.8 g (11.0 mmol) of Intermediate 4(1) in 30 ml of ethanol at room temperature, 1.6 ml (55.0 mmol) of hydrazine hydrate was added thereto and heated under reflux at about 80° C. for about 18 hours. After completion of the reaction, the reaction product was concentrated under reduced pressure and extracted with 80 ml of distilled water and 100 ml of dichloromethane to obtain an organic layer, which was then dried using magnesium sulfate, distilled under reduced pressure, and then separated and purified using column chromatography to obtain 1.5 g (9.3 mmol, Yield: 88%) of ligand 4 (L4).

LC-MS m/z=161(M+H)+

Ligand Synthesis 5

Synthesis of Ligand 5 (L5)

Ligand 5 (L5) was synthesized according to Reaction Scheme 5 below:

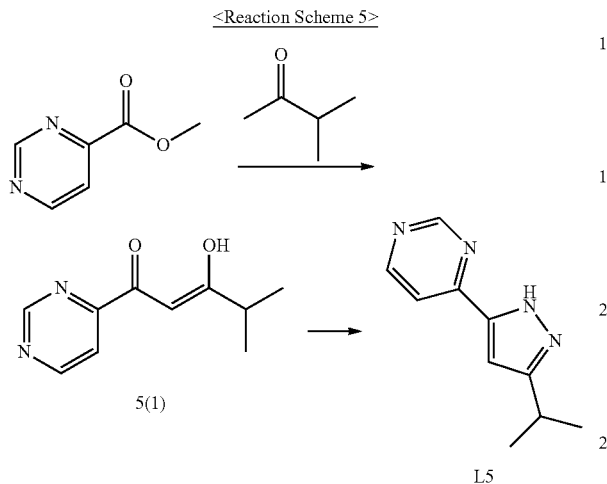

Ligand 5 (L5) was synthesized in the same manner (Yield: 25%) as in the synthesis of ligand 4 (L4) (Ligand Synthesis 4), except that 3,3-methylbutane-2-one, instead of acetone, was used in synthesizing Intermediate 4(1).
LC-MS m/z=189(M+H)+

Ligand Synthesis 6

Synthesis of Ligand 6 (L6)

Ligand 6 (L6) was synthesized according to Reaction Scheme 6 below:

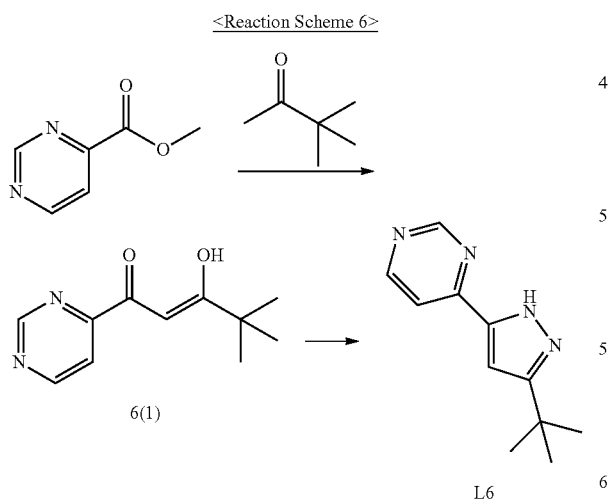

Ligand 6 (L6) was synthesized in the same manner (Yield: 21%) as in the synthesis of ligand 4 (L4) (Ligand Synthesis 4), except that 3,3-dimethylbutane-2-one, instead of acetone, was used in synthesizing Intermediate 4(1).
LC-MS m/z=203(M+H)+

Ligand Synthesis 7

Synthesis of Ligand 7 (L7)

Ligand 7 (L7) was synthesized according to Reaction Scheme 7 below:

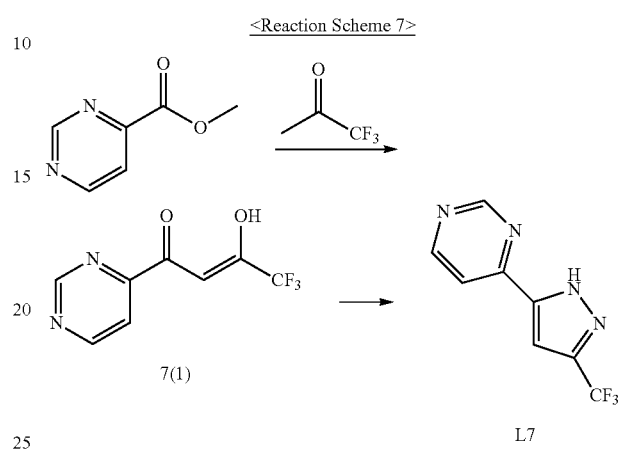

Ligand 7 (L7) was synthesized in the same manner (Yield: 63%) as in the synthesis of ligand 4 (L4) (Ligand Synthesis 4), except that 1,1,1-trifluoropropan-2-one, instead of acetone, was used in synthesizing Intermediate 4(1).
LC-MS m/z=215(M+H)+

Ligand Synthesis 8

Synthesis of Ligand 8 (L8)

Ligand 8 (L8) was synthesized according to Reaction Scheme 8 below:

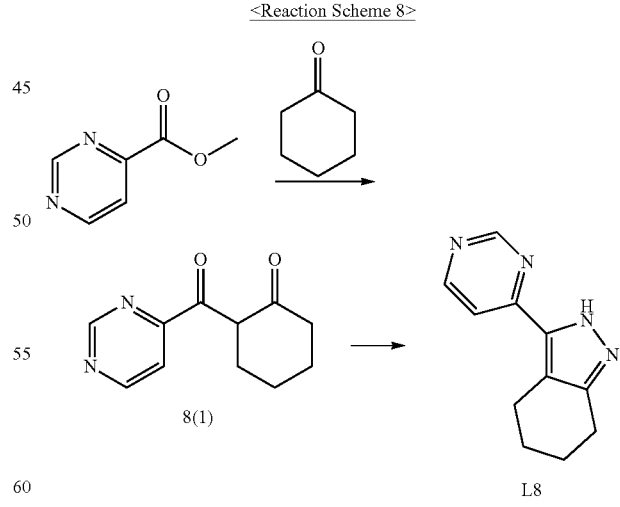

Ligand 8 (L8) was synthesized in the same manner (Yield: 35%) as in the synthesis of ligand 4 (L4) (Ligand Synthesis 4), except that cyclohexanone, instead of acetone, was used in synthesizing Intermediate 4(1).
LC-MS m/z=201(M+H)+

Ligand Synthesis 9

Synthesis of Ligand 9 (L9)

Ligand 9 (L9) was synthesized according to Reaction Scheme 9 below:

<Reaction Scheme 9>

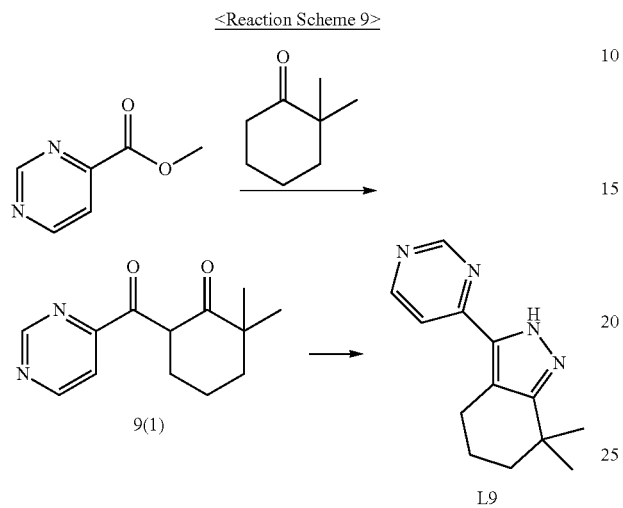

Ligand 9 (L9) was synthesized in the same manner (Yield: 43%) as in the synthesis of ligand 4 (L4) (Ligand Synthesis 4), except that 2,2-dimethylcyclohexanone, instead of acetone, was used in synthesizing Intermediate 4(1).
LC-MS m/z=229(M+H)+

Ligand Synthesis 10

Synthesis of Ligand 10 (L10)

Ligand 10 (L10) was synthesized according to Reaction Scheme 10 below:

<Reaction Scheme 10>

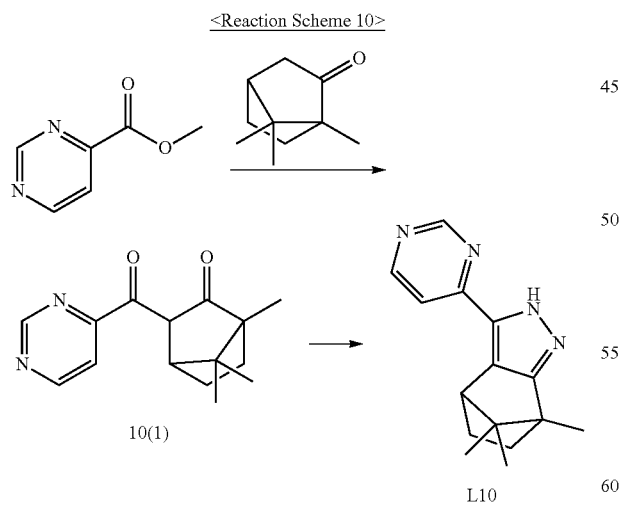

Ligand 10 (L10) was synthesized in the same manner (Yield: 65%) as in the synthesis of ligand 4 (L4) (Ligand Synthesis 4), except that camper, instead of acetone, was used in synthesizing Intermediate 4(1).
LC-MS m/z=254(M+H)+

Ligand Synthesis 11

Synthesis of Ligand 11 (L11)

Ligand 11 (L11) was synthesized according to Reaction Scheme 11 below:

<Reaction Scheme 11>

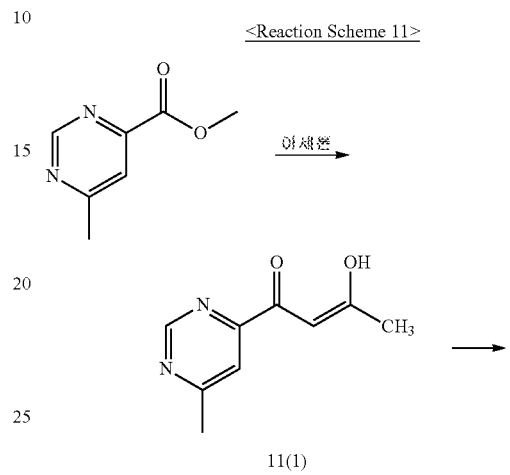

Ligand 11 (L11) was synthesized in the same manner (Yield: 17%) as in the synthesis of ligand 4 (L4) (Ligand Synthesis 4), except that methyl 6-methylpyrimidine-4-carboxylate, instead of pyrimidine-4-carboxylic acid methyl ester, was used in synthesizing Intermediate 4(1).
LC-MS m/z=175(M+H)+

Ligand Synthesis 12

Synthesis of Ligand 12 (L12)

Ligand 12 (L12) was synthesized according to Reaction Scheme 12 below:

<Reaction Scheme 12>

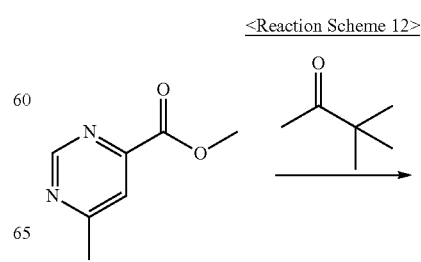

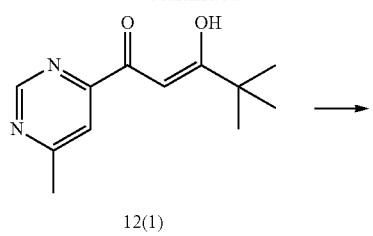

12(1)

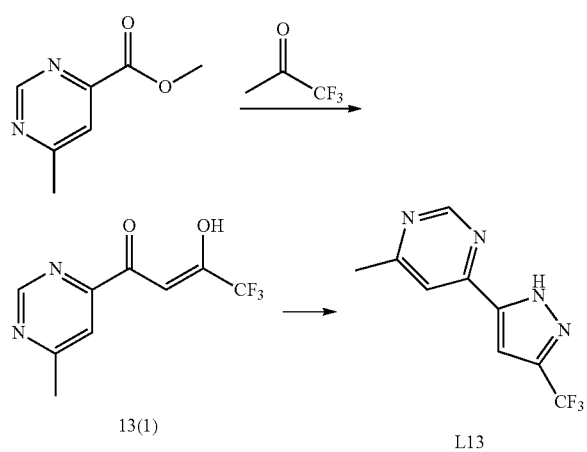

L12

Ligand 12 (L12) was synthesized in the same manner (Yield: 12%) as in the synthesis of ligand 6 (L6) (Ligand Synthesis 6), except that methyl 6-methylpyrimidine-4-carboxylate, instead of pyrimidine-4-carboxylic acid methyl ester, was used in synthesizing Intermediate 6(1).

LC-MS m/z=217(M+H)+

Ligand Synthesis 13

Synthesis of Ligand 13 (L13)

Ligand 13 (L13) was synthesized according to Reaction Scheme 13 below:

<Reaction Scheme 13>

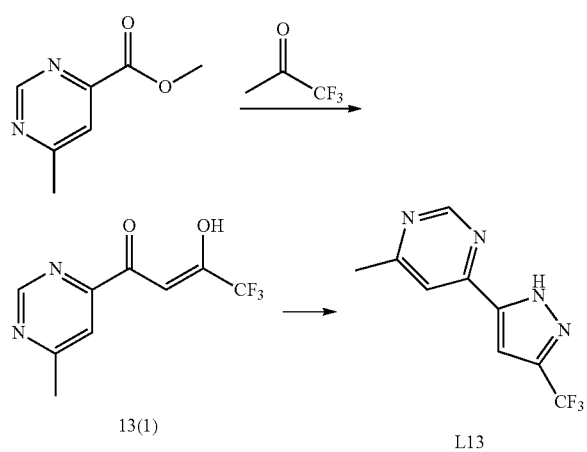

13(1)         L13

Ligand 13 (L13) was synthesized in the same manner (Yield: 35%) as in the synthesis of ligand 7 (L7) (Ligand Synthesis 7), except that methyl 6-methylpyrimidine-4-carboxylate, instead of pyrimidine-4-carboxylic acid methyl ester, was used in synthesizing Intermediate 7(1).

LC-MS m/z=229(M+H)+

Ligand Synthesis 14

Synthesis of Ligand 14 (L14)

Ligand 14 (L14) was synthesized according to Reaction Scheme 14 below:

<Reaction Scheme 14>

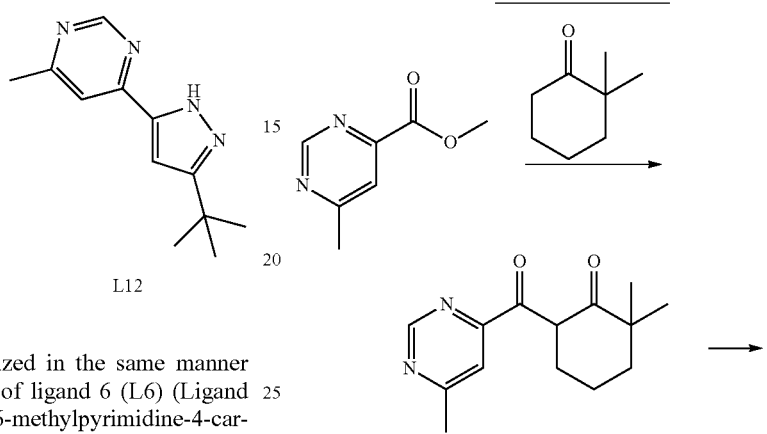

14(1)

L14

Ligand 14 (L14) was synthesized in the same manner (Yield: 26%) as in the synthesis of ligand 9 (L9) (Ligand Synthesis 9), except that methyl 6-methylpyrimidine-4-carboxylate, instead of pyrimidine-4-carboxylic acid methyl ester, was used in synthesizing Intermediate 9(1).

LC-MS m/z=243(M+H)+

Ligand Synthesis 15

Synthesis of Ligand 15 (L15)

Ligand 15 (L15) was synthesized according to Reaction Scheme 15 below:

<Reaction Scheme 15>

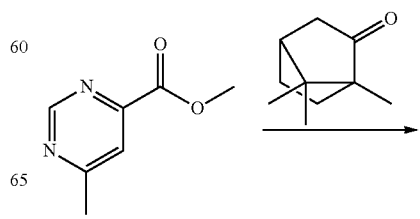

-continued

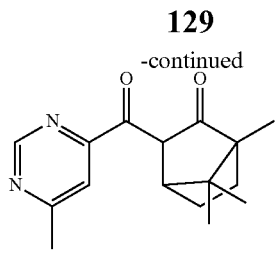

15(1)

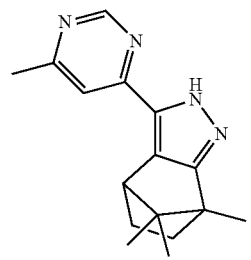

L15

Ligand 15 (L15) was synthesized in the same manner (Yield: 35%) as in the synthesis of ligand 10 (L10) (Ligand Synthesis 10), except that methyl 6-methylpyrimidine-4-carboxylate, instead of pyrimidine-4-carboxylic acid methyl ester, was used in synthesizing Intermediate 10(1).

LC-MS m/z=269(M+H)+

Ligand Synthesis 16

Synthesis of Ligand 16 (L16)

Ligand 16 (L16) was synthesized according to Reaction Scheme 16 below:

<Reaction Scheme 16>

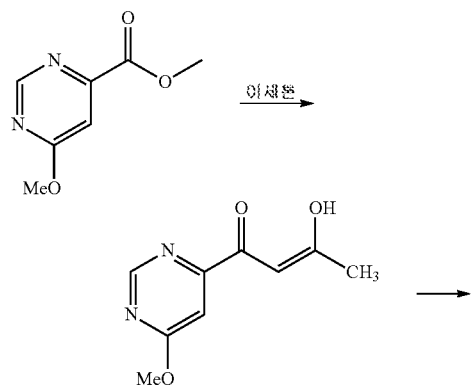

L16

Ligand 16 (L16) was synthesized in the same manner (Yield: 14%) as in the synthesis of ligand 4 (L4) (Ligand Synthesis 4), except that methyl 6-methoxypyrimidine-4-carboxylate, instead of pyrimidine-4-carboxylic acid methyl ester, was used in synthesizing Intermediate 4(1).

LC-MS m/z=191(M+H)+

Ligand Synthesis 17

Synthesis of Ligand 17 (L17)

Ligand 17 (L17) was synthesized according to Reaction Scheme 17 below:

<Reaction Scheme 17>

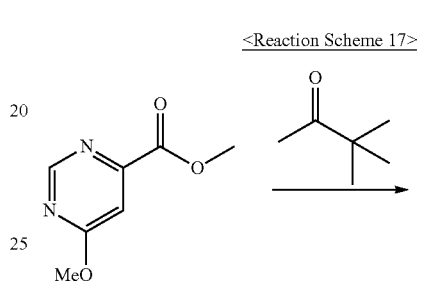

17(1)

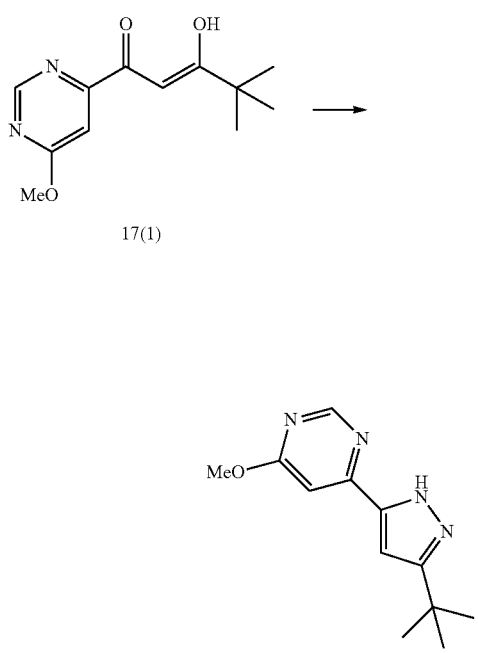

L17

Ligand 17 (L17) was synthesized in the same manner (Yield: 12%) as in the synthesis of ligand 6 (L6) (Ligand Synthesis 6), except that methyl 6-methoxypyrimidine-4-carboxylate, instead of pyrimidine-4-carboxylic acid methyl ester, was used in synthesizing Intermediate 6(1).

LC-MS m/z=233(M+H)+

Ligand Synthesis 18

Synthesis of Ligand 18 (L18)

Ligand 18 (L18) was synthesized according to Reaction Scheme 18 below:

<Reaction Scheme 18>

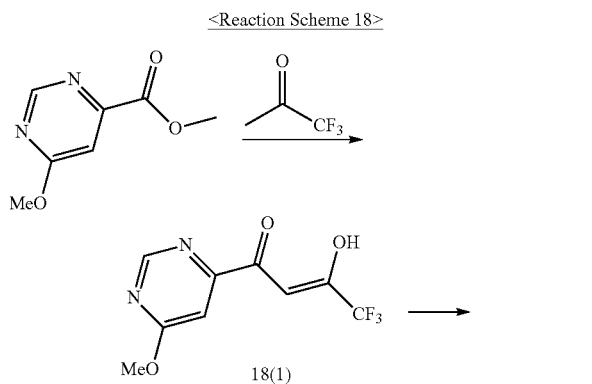

Ligand 18 (L18) was synthesized in the same manner (Yield: 25%) as in the synthesis of ligand 7 (L7) (Ligand Synthesis 7), except that methyl 6-methoxypyrimidine-4-carboxylate, instead of pyrimidine-4-carboxylic acid methyl ester, was used in synthesizing Intermediate 7(1).

LC-MS m/z=245(M+H)+

Ligand Synthesis 19

Synthesis of Ligand 19 (L19)

Ligand 19 (L19) was synthesized according to Reaction Scheme 19 below:

<Reaction Scheme 19>

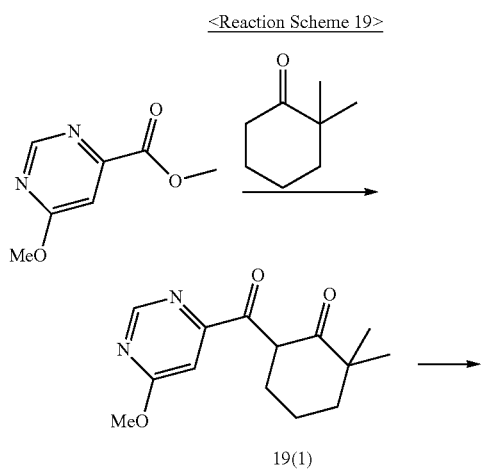

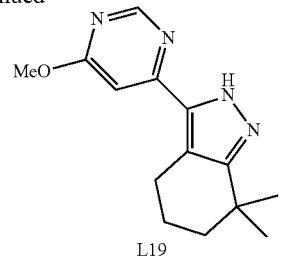

Ligand 19 (L19) was synthesized in the same manner (Yield: 22%) as in the synthesis of ligand 9 (L9) (Ligand Synthesis 9), except that methyl 6-methoxypyrimidine-4-carboxylate, instead of pyrimidine-4-carboxylic acid methyl ester, was used in synthesizing Intermediate 9(1).

LC-MS m/z=259(M+H)+

Ligand Synthesis 20

Synthesis of Ligand 20 (L20)

Ligand 20 (L20) was synthesized according to Reaction Scheme 20 below:

<Reaction Scheme 20>

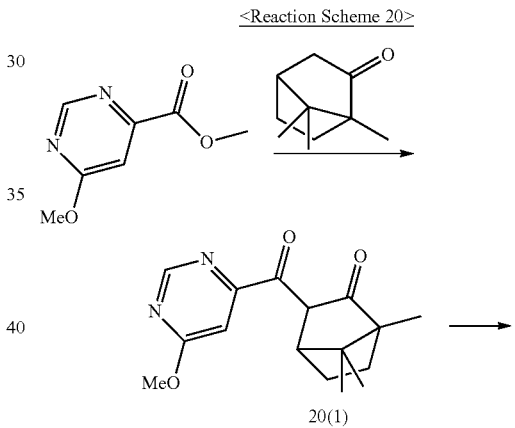

Ligand 20 (L20) was synthesized in the same manner (Yield: 30%) as in the synthesis of ligand 10 (L10) (Ligand Synthesis 10), except that methyl 6-methoxypyrimidine-4-carboxylate, instead of pyrimidine-4-carboxylic acid methyl ester, was used in synthesizing Intermediate 10(1).

LC-MS m/z=285(M+H)+

Ligand Synthesis 21

Synthesis of Ligand 21 (L21)

Ligand 21 (L21) was synthesized according to Reaction Scheme 21 below:

Reaction Scheme 21

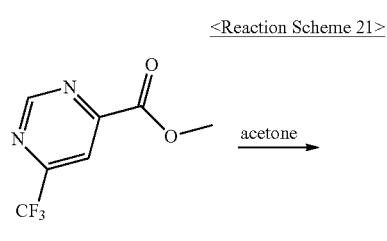

acetone

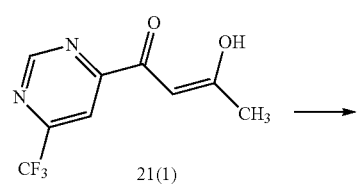

Ligand 21 (L21) was synthesized in the same manner (Yield: 26%) as in the synthesis of ligand 4 (L4) (Ligand Synthesis 4), except that methyl 6-(trifluoromethyl)pyrimidine-4-carboxylate, instead of pyrimidine-4-carboxylic acid methyl ester, was used in synthesizing Intermediate 4(1).

LC-MS m/z=229(M+H)+

Ligand Synthesis 22

Synthesis of Ligand 22 (L22)

Ligand 22 (L22) was synthesized according to Reaction Scheme 22 below:

Reaction Scheme 22

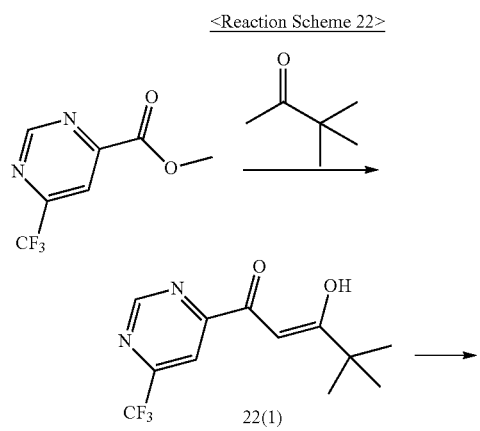

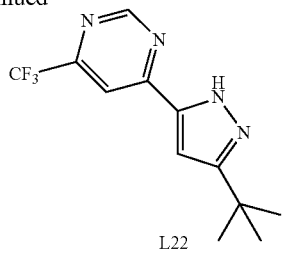

Ligand 22 (L22) was synthesized in the same manner (Yield: 24%) as in the synthesis of ligand 6 (L6) (Ligand Synthesis 6), except that methyl 6-(trifluoromethyl)pyrimidine-4-carboxylate, instead of pyrimidine-4-carboxylic acid methyl ester, was used in synthesizing Intermediate 6(1).

LC-MS m/z=271(M+H)+

Ligand Synthesis 23

Synthesis of Ligand 23 (L23)

Ligand 23 (L23) was synthesized according to Reaction Scheme 23 below:

Reaction Scheme 23

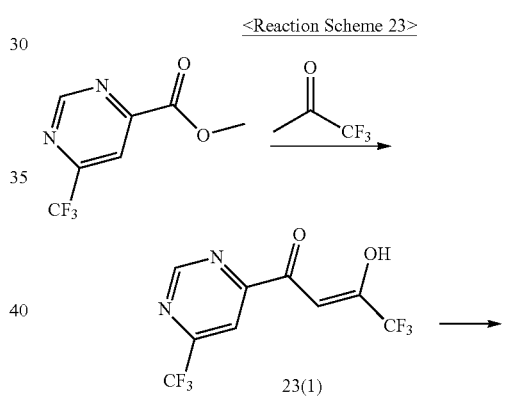

Ligand 23 (L23) was synthesized in the same manner (Yield: 37%) as in the synthesis of ligand 7 (L7) (Ligand Synthesis 7), except that methyl 6-(trifluoromethyl)pyrimidine-4-carboxylate, instead of pyrimidine-4-carboxylic acid methyl ester, was used in synthesizing Intermediate 7(1).

LC-MS m/z=283(M+H)+

Ligand Synthesis 24

Synthesis of Ligand 24 (L24)

Ligand 24 (L24) was synthesized according to Reaction Scheme 24 below:

Reaction Scheme 24

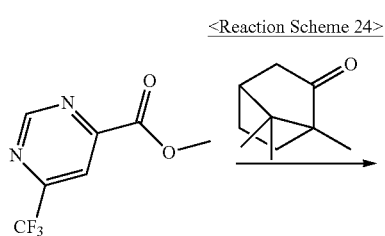

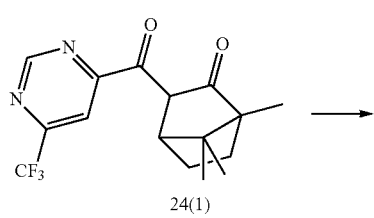

24(1)

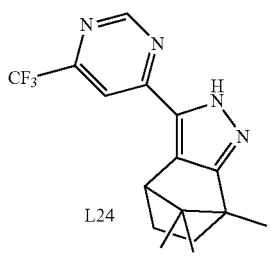

L24

Ligand 24 (L24) was synthesized in the same manner (Yield: 42%) as in the synthesis of ligand 10 (L10) (Ligand Synthesis 10), except that methyl 6-(trifluoromethyl)pyrimidine-4-carboxylate, instead of pyrimidine-4-carboxylic acid methyl ester, was used in synthesizing Intermediate 10(1).

LC-MS m/z=323(M+H)+

Ligand Synthesis 25

Synthesis of Ligand 25 (L25)

Ligand 25 (L25) was synthesized according to Reaction Scheme 25 below:

Reaction Scheme 25

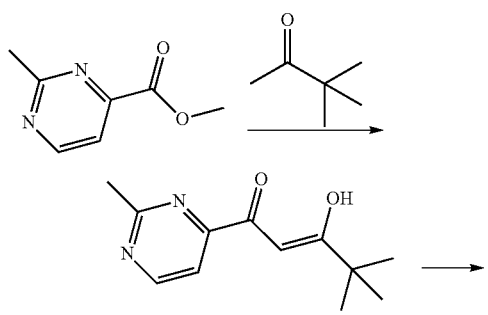

25(1)

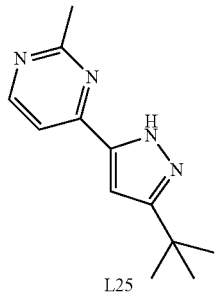

L25

Ligand 25 (L25) was synthesized in the same manner (Yield: 17%) as in the synthesis of ligand 6 (L6) (Ligand Synthesis 6), except that methyl 2-methylpyrimidine-4-carboxylate, instead of pyrimidine-4-carboxylic acid methyl ester, was used in synthesizing Intermediate 6(1).

LC-MS m/z=217(M+H)+

Ligand Synthesis 26

Synthesis of Ligand 26 (L26)

Ligand 26 (L26) was synthesized according to Reaction Scheme 26 below:

Reaction Scheme 26

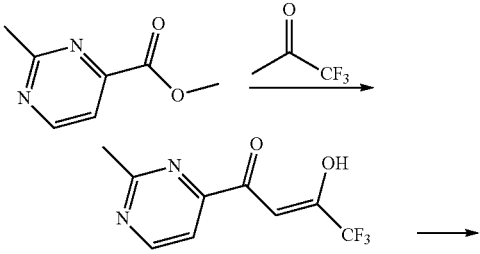

26(1)

L26

Ligand 26 (L26) was synthesized in the same manner (Yield: 22%) as in the synthesis of ligand 7 (L7) (Ligand Synthesis 7), except that methyl 2-methylpyrimidine-4-carboxylate, instead of pyrimidine-4-carboxylic acid methyl ester, was used in synthesizing Intermediate 7(1).

LC-MS m/z=229(M+H)+

Ligand Synthesis 27

Synthesis of Ligand 27 (L27)

Ligand 27 (L27) was synthesized according to Reaction Scheme 27 below:

Reaction Scheme 27

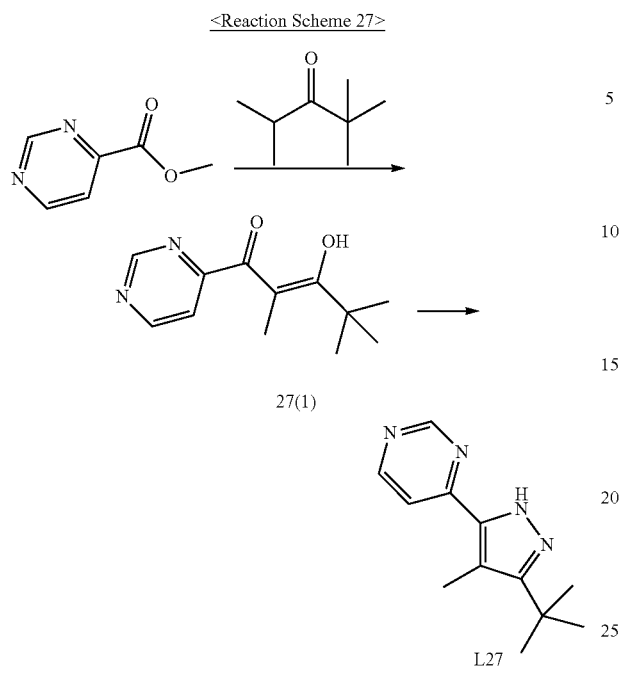

Synthesis of Intermediate 27(1)

Following adding 1.9 g (19.3 mmol) of NatOBu (sodium t-butoxide) to 50 ml of anhydrous tetrahydrofuran, 2.2 g (17.5 mmol) of 2,2-dimethyl-3-pentanone was slowly added thereto at 0° C. After heating the mixture at about 60° C. for about 2 hours, 2.2 g (15.7 mmol) of pyrimidine-4-carboxylic acid methyl ester was slowly added thereto and heated under reflux at about 80° C. for about 12 hours. After completion of the reaction, 50 ml of distilled water was added, and a 4N diluted hydrochloric acid was added for neutralization, followed by extraction with 100 ml of dichloromethane about three times to obtain an organic layer, which was then dried using magnesium sulfate, distilled under reduced pressure, and then separated and purified using column chromatography to obtain 0.6 g (2.5 mmol, Yield: 16%) of Intermediate 27(1).

LC-MS m/z=223(M+H)+

Synthesis of Ligand 27 (L17)

After dissolving 0.5 g (2.5 mmol) of Intermediate 27(1) in 10 ml of ethanol at room temperature, 0.7 ml (55.0 mmol) of hydrazine hydrate was added thereto and heated under reflux at about 80° C. for about 18 hours. After completion of the reaction, the reaction product was concentrated under reduced pressure and extracted with 30 ml of distilled water and 50 ml of dichloromethane to obtain an organic layer, which was then dried using magnesium sulfate and distilled under reduced pressure. The resulting product was separated and purified using column chromatography to obtain 0.4 g (2.1 mmol, Yield: 85%) of ligand 27 (L27).

LC-MS m/z=217(M+H)+

Ligand Synthesis 28

Synthesis of Ligand 28 (L28)

Ligand 28 (L28) was synthesized according to Reaction Scheme 28 below:

Reaction Scheme 28

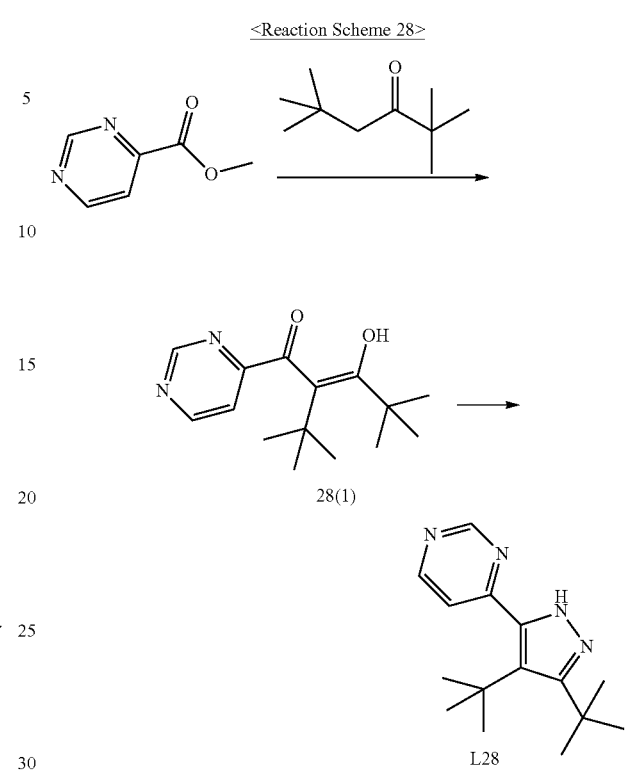

Ligand 28 (L28) was synthesized in the same manner (Yield: 12%) as in the synthesis of ligand 27 (L27) (Ligand Synthesis 27), except that 2,2,5,5-tetramethylhexan-3-one, instead of 2,2-dimethyl-3-pentanone, was used in synthesizing Intermediate 27(1).

LC-MS m/z=259(M+H)+

Ligand Synthesis 29

Synthesis of Ligand 29 (L29)

Ligand 29 (L29) was synthesized according to Reaction Scheme 29 below:

Reaction Scheme 29

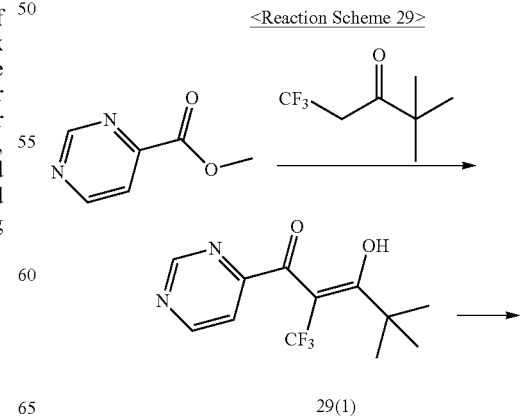

-continued

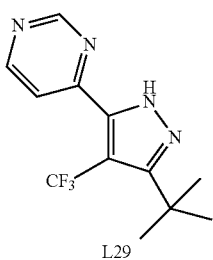

L29

Ligand 29 (L29) was synthesized in the same manner (Yield: 9%) as in the synthesis of ligand 27 (L27) (Ligand Synthesis 27), except that 2,2-dimethyl-4-(trifluoromethyl)-butanone, instead of 2,2-dimethyl-3-pentanone, was used in synthesizing Intermediate 27(1).

LC-MS m/z=271(M+H)+

Ligand Synthesis 30

Synthesis of Ligand 30 (L30)

Ligand 30 (L30) was synthesized according to Reaction Scheme 30 below:

<Reaction Scheme 30>

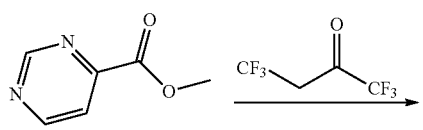

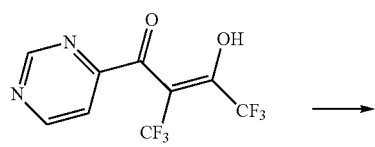

30(1)

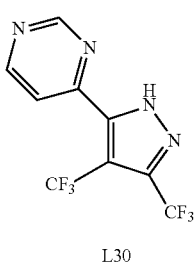

L30

Ligand 30 (L30) was synthesized in the same manner (Yield: 10%) as in the synthesis of ligand 27 (L27) (Ligand Synthesis 27), except that 1,4,-di(trifluoromethyl)-2-butanone, instead of 2,2,-dimethyl-3-pentanone, was used in synthesizing Intermediate 27(1).

LC-MS m/z=283(M+H)+

Ligand Synthesis 31

Synthesis of Ligand 31 (L31)

Ligand 31 (L31) was synthesized according to Reaction Scheme 31 below:

<Reaction Scheme 31>

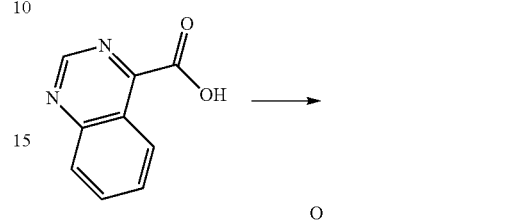

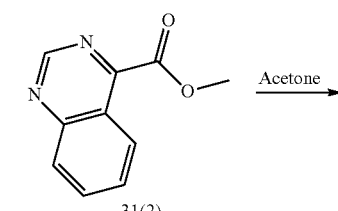

31(2)

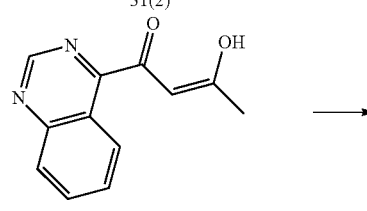

31(1)

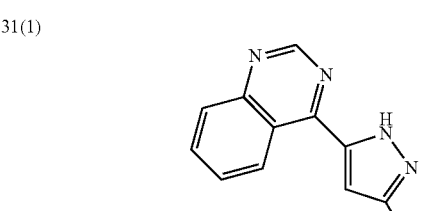

L31

Synthesis of Intermediate 31(2)

Following dissolving 25.0 g (143.6 mmol) of 4-quinazoline-carboxylic acid in 100 ml of methanol, 5 ml of sulfuric acid (conc.) was added thereto, and heated under reflux at about 80° C. for about 18 hours. After completion of the reaction, the reaction mixture was concentrated under reduced pressure, and then dissolved in 100 ml of dichloromethane. A saturated sodium hydrocarbonate solution was slowly added thereto at 0° C. for basification, followed by extraction to obtain an organic layer, which was then dried using magnesium sulfate, and distilled under reduced pressure to obtain 26.0 g (137.8 mmol, Yield: 96%) of Intermediate 31(2).

LC-MS m/z=189(M+H)+

Synthesis of Intermediate 31(1)

Following adding 1.0 g (43.4 mmol) of NaH to 80 ml of anhydrous tetrahydrofuran, 2.6 ml (34.8 mmol) of acetone was slowly added thereto at 0° C. After 1 hour, 5.5 g (29.0 mmol) of Intermediate 31(2) was slowly added thereto and heated under reflux at about 80° C. for about 16 hours. After completion of the reaction, 30 ml of distilled water was added, and a 4N diluted hydrochloric acid solution was slowly added thereto for neutralization. The resulting neutralized reaction mixture was extracted with 100 ml of dichloromethane about five times to obtain an organic layer, which was dried using magnesium sulfate and distilled under reduced pressure. The resulting product was separated and purified using column chromatography to obtain 3.3 g (15.1 mmol, Yield 52%) of Intermediate 31(1).

LC-MS m/z=215(M+H)+

Synthesis of Ligand 31 (L31)

After dissolving 3.0 g (13.9 mmol) of Intermediate 31(1) in 50 ml of ethanol at room temperature, 4.0 ml (140.0 mmol) of hydrazine hydrate was added thereto and heated under reflux at about 80° C. for about 18 hours. After completion of the reaction, the reaction product was concentrated under reduced pressure and extracted with 80 ml of distilled water and 100 ml of dichloromethane to obtain an organic layer, which was then dried using magnesium sulfate, distilled under reduced pressure, and then separated and purified using column chromatography to obtain 2.2 g (10.4 mmol, Yield: 75%) of ligand 31 (L31).

LC-MS m/z=211(M+H)+

Ligand Synthesis 32

Synthesis of Ligand 32 (L32)

Ligand 32 (L32) was synthesized according to Reaction Scheme 32 below:

<Reaction Scheme 32>

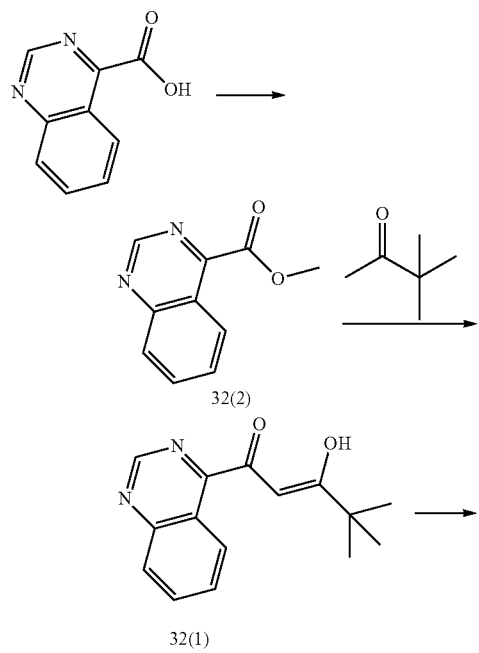

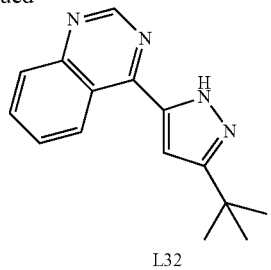

L32

Ligand 32 (L32) was synthesized in the same manner (Yield: 25%) as in the synthesis of ligand 31 (L31) (Ligand Synthesis 31), except that 3,3-dimethylbutane-2-one, instead of acetone, was used in synthesizing Intermediate 31(1).

LC-MS m/z=253(M+H)+

Ligand Synthesis 33

Synthesis of Ligand 33 (L33)

Ligand 33 (L33) was synthesized according to Reaction Scheme 33 below:

<Reaction Scheme 33>

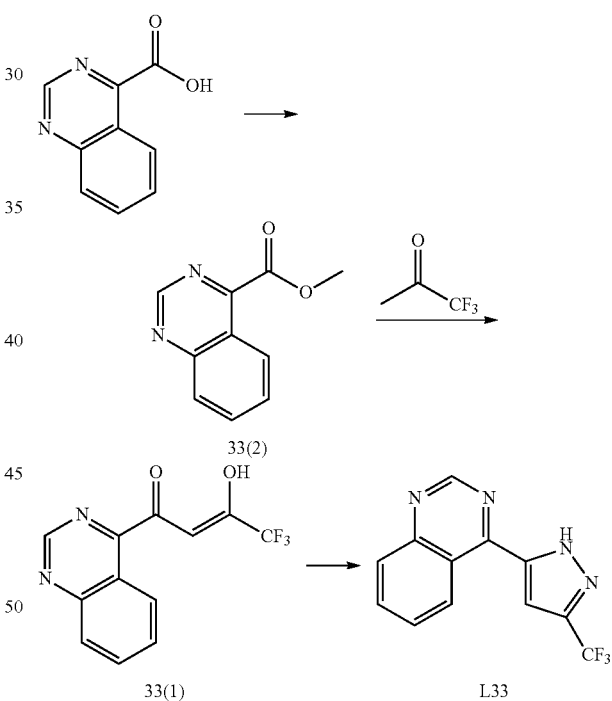

Ligand 33 (L33) was synthesized in the same manner (Yield: 22%) as in the synthesis of ligand 31 (L31) (Ligand Synthesis 31), except that 1,1,1-trifluoropropan-2-one, instead of acetone, was used in synthesizing Intermediate 31(1).

LC-MS m/z=265(M+H)+

Ligand Synthesis 34

Synthesis of Ligand 34 (L31)

Ligand 34 (L34) was synthesized according to Reaction Scheme 34 below:

<Reaction Scheme 34>

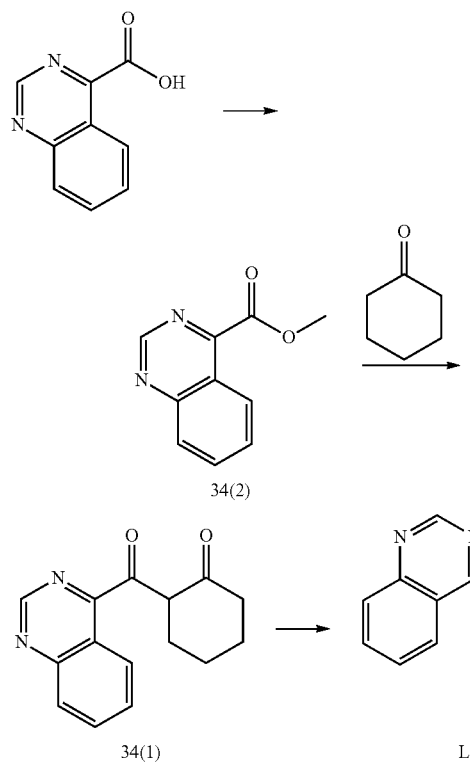

34(1) → L34

Ligand 34 (L34) was synthesized in the same manner (Yield: 20%) as in the synthesis of ligand 31 (L31) (Ligand Synthesis 31), except that cyclohexanone, instead of acetone, was used in synthesizing Intermediate 31(1).

LC-MS m/z=251(M+H)+

Ligand Synthesis 35

Synthesis of Ligand 35 (L35)

Ligand 35 (L35) was synthesized according to Reaction Scheme 35 below:

<Reaction Scheme 35>

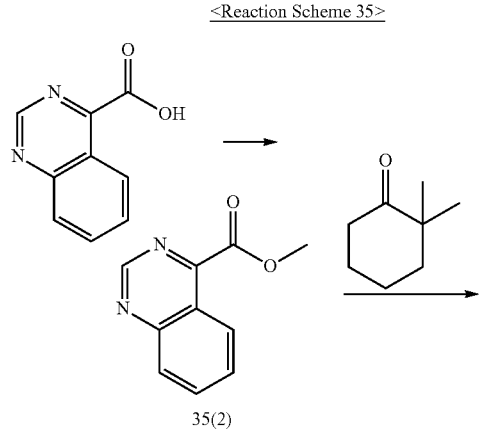

35(2)

-continued

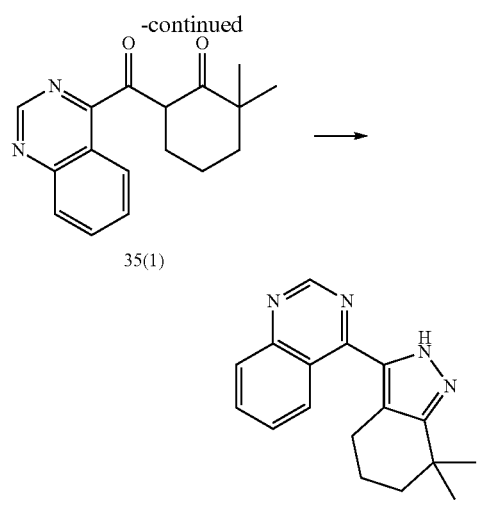

35(1) → L35

Ligand 35 (L35) was synthesized in the same manner (Yield: 22%) as in the synthesis of ligand 31 (L31) (Ligand Synthesis 31), except that 2,2-dimethylbutane-2-one, instead of acetone, was used in synthesizing Intermediate 31(1).

LC-MS m/z=279(M+H)+

Ligand Synthesis 36

Synthesis of Ligand 36 (L36)

Ligand 36 (L36) was synthesized according to Reaction Scheme 36 below:

<Reaction Scheme 36>

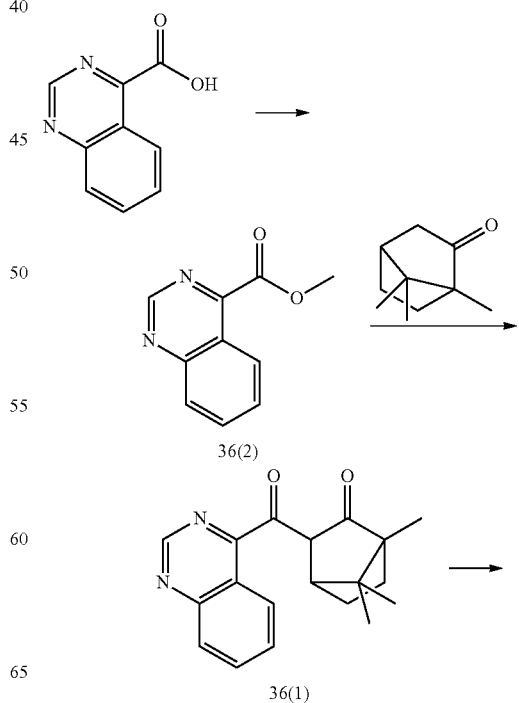

36(2)

36(1)

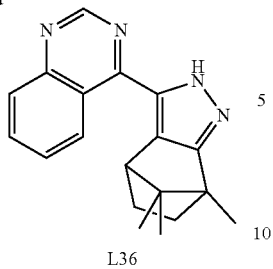

Ligand 36 (L36) was synthesized in the same manner (Yield: 22%) as in the synthesis of ligand 31 (L31) (Ligand Synthesis 31), except that camphor, instead of acetone, was used in synthesizing Intermediate 31(1).
LC-MS m/z=305(M+H)+

Ligand Synthesis 37

Synthesis of Ligand 37 (L37)

Ligand 37 (L37) was synthesized according to Reaction Scheme 37 below:

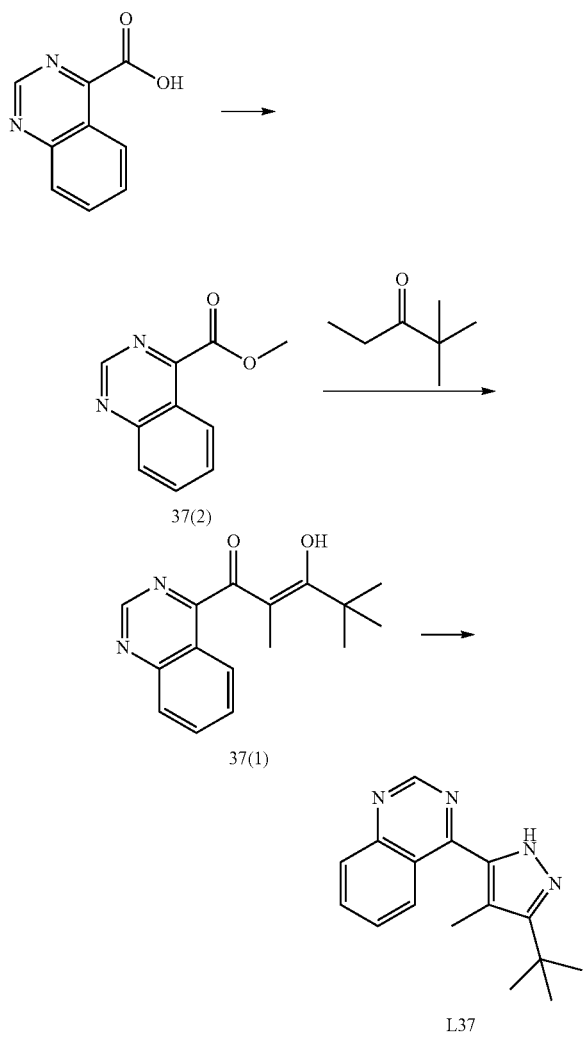

Ligand 37 (L37) was synthesized in the same manner (Yield: 18%) as in the synthesis of ligand 31 (L31) (Ligand Synthesis 31), except that 2,2-dimethylbutane-3-one, instead of acetone, was used in synthesizing Intermediate 31(1).
LC-MS m/z=267(M+H)+

Ligand Synthesis 38

Synthesis of Ligand 38 (L38)

Ligand 38 (L38) was synthesized according to Reaction Scheme 38 below:

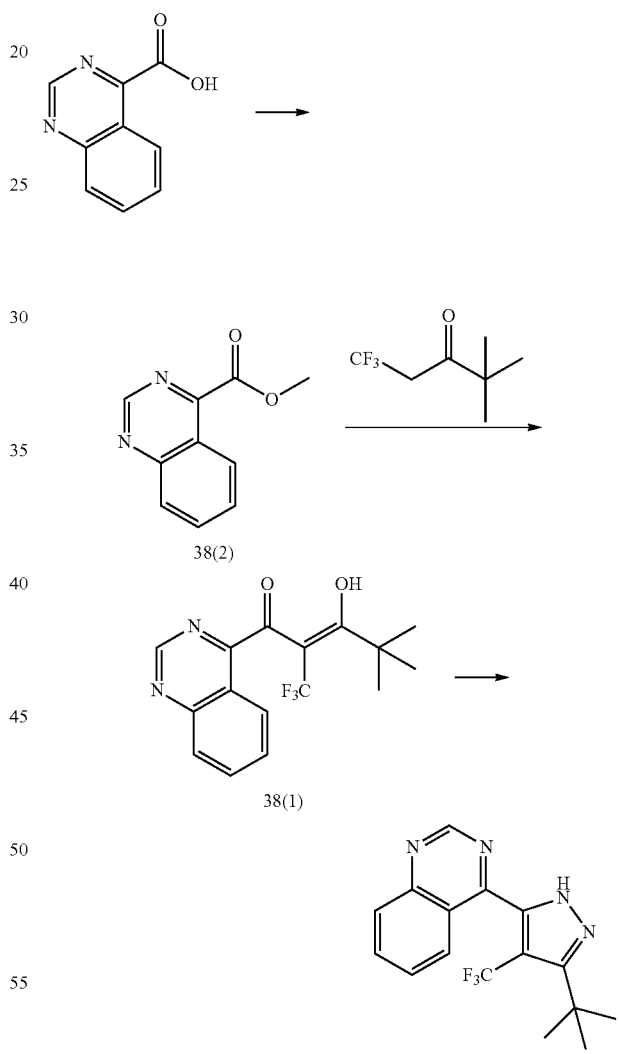

Ligand 38 (L38) was synthesized in the same manner (Yield: 20%) as in the synthesis of ligand 31 (L31) (Ligand Synthesis 31), except that 2,2-dimethyl-4-(trifluoromethyebutan-3-one, instead of acetone, was used in synthesizing Intermediate 31(1).
LC-MS m/z=321(M+H)+

Ligand Synthesis 39

Synthesis of Ligand 39 (L39)

Ligand 39 (L39) was synthesized according to Reaction Scheme 39 below:

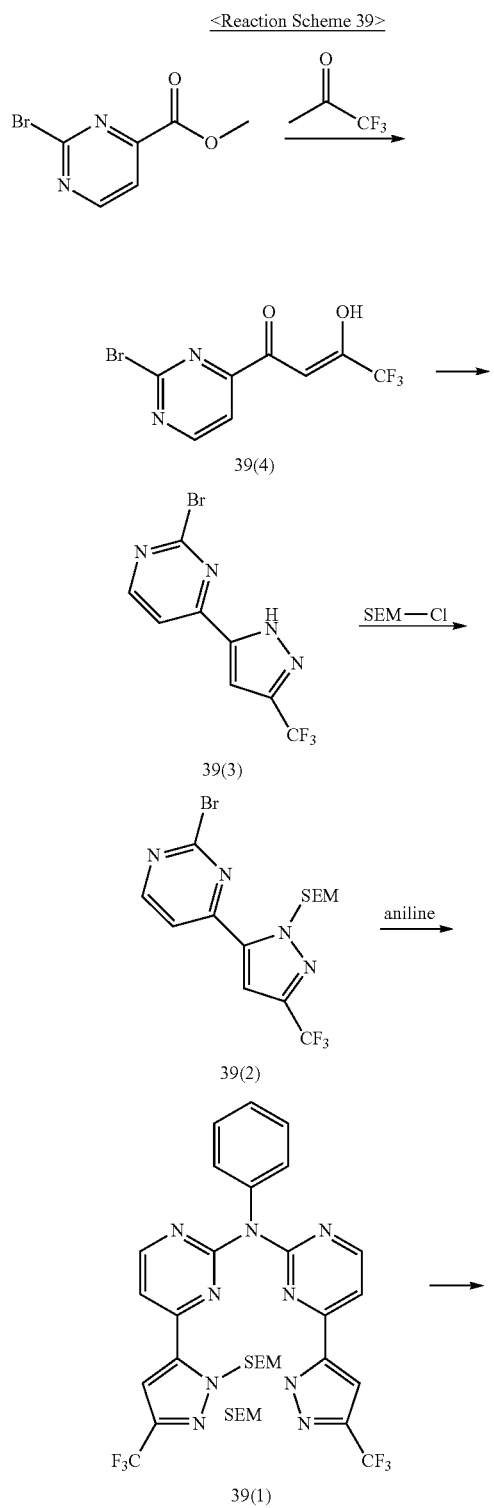

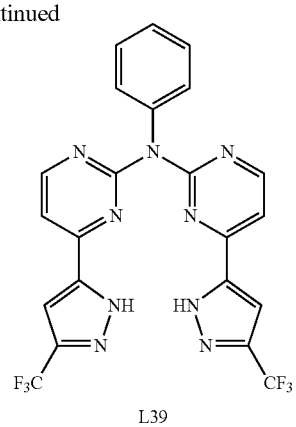

L39

Synthesis of Intermediate 39(4)

Following adding 2.1 g (86.8 mmol) of NaH to 120 ml of anhydrous tetrahydrofuran, 8.7 ml (69.6 mmol) of 1,1,1-trifluoropropan-2-one was slowly added thereto at 0° C. After 1 hour, 12.6 g (58.0 mmol) of methyl 2-bromopyrimidine-4-carboxylate was slowly added thereto and heated under reflux at about 80° C. for about 16 hours. After completion of the reaction, 100 ml of distilled water was added, and a 1N diluted hydrochloric acid solution was slowly added thereto and stirred at room temperature for about 30 minutes until the reaction mixture was neutralized. After 30 minutes, the resulting product was extracted with 100 ml of dichloromethane about five times to obtain an organic layer, which was then dried using magnesium sulfate and distilled under reduced pressure. The resulting product was separated and purified using column chromatography to obtain 5.3 g (18.6 mmol, Yield 32%) of Intermediate 39(4).

LC-MS m/z=297(M+H)+

Synthesis of Intermediate 39(3)

After dissolving 3.0 g (10.4 mmol) of Intermediate 39(4) in 30 ml of ethanol at room temperature, 2.6 ml (100.0 mmol) of hydrazine hydrate was added thereto and heated under reflux at about 80° C. for about 18 hours. After completion of the reaction, the reaction product was concentrated under reduced pressure, and then extracted with 80 ml of distilled water and 100 ml of dichloromethane to obtain an organic layer, which was then dried using magnesium sulfate and distilled under reduced pressure. The resulting product was separated and purified using column chromatography to obtain 2.1 g (7.5 mmol, Yield 72%) of Intermediate 39(3).

LC-MS m/z=293(M+H)+

Synthesis of Intermediate 39(2)

Following adding 0.2 g (9.0 mmol) of NaH to 120 ml of anhydrous tetrahydrofuran, 2.1 g (7.5 mmol) of Intermediate 39(2) was slowly added thereto at 0° C. After 30 minutes, 1.5 ml (8.3 mmol) of 2-(trimethylsilyl)ethoxymethyl chloride was slowly added thereto and stirred at room temperature for about two days. After completion of the reaction, the reaction product was extracted with 100 ml of distilled water and 100 ml of dichloromethane to obtain an organic layer, which was then dried using magnesium sulfate and distilled under reduced pressure. The resulting product was separated and purified using column chromatography to obtain 2.7 g (6.6 mmol, Yield 88%) of Intermediate 39(2).

LC-MS m/z=423(M+H)+

Synthesis of Intermediate 39(1)

Following dissolving 2.7 g (6.6 mmol) of Intermediate 39(2) in 60 ml of toluene, 0.05 g (0.05 mmol) of tris(dibenzylideneacetone)dipalladium(0), 0.2 ml (2.6 mmol) of aniline, 0.06 g (0.1 mmol) of 1,1'-bis(diphenylphospino)ferrocene, and 0.6 g (6.6 mmol) of sodium t-butoxide were added thereto, and then heated under reflux at about 120° C. for about 16 hours. After completion of the reaction, the reaction product was extracted with 100 ml of distilled water and 200 ml of ethyl acetate to obtain an organic layer, which was then dried using magnesium sulfate and distilled under reduced pressure. The resulting product was separated and purified using column chromatography to obtain 2.6 g (3.4 mmol, Yield 52%) of Intermediate 39(1).

LC-MS m/z=778(M+H)+

Synthesis of Ligand 39 (L39)

After dissolving 2.0 g (2.7 mmol) of Intermediate 39(1) in 30 ml of ethanol at room temperature, 50 ml of a 4N diluted hydrochloric acid solution was added thereto and heated under reflux at about 80° C. for about 18 hours. After completion of the reaction, the reaction product was concentrated under reduced pressure, and then extracted with 200 ml of dichloromethane to obtain an organic layer, which was then dried using magnesium sulfate and distilled under reduced pressure. The resulting product was separated and purified using column chromatography to obtain 1.1 g (2.4 mmol, Yield 90%) of ligand 39 (L39).

LC-MS m/z=518(M+H)+

Ligand Synthesis 40

Synthesis of Ligand 40 (L40)

Ligand 40 (L40) was synthesized according to Reaction Scheme 40 below:

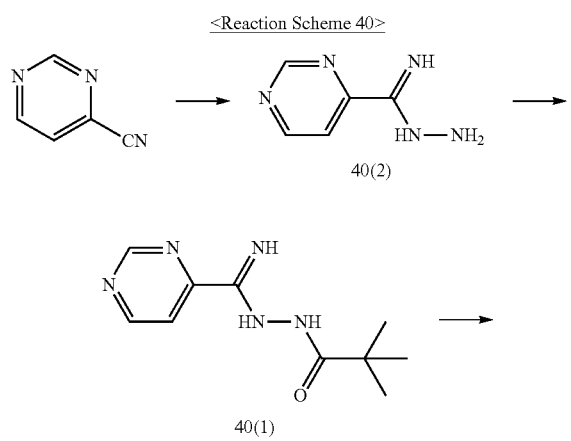

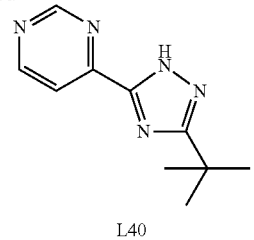

L40

Synthesis of Intermediate 40(2)

After dissolving 5.0 g (47.6 mmol) of 2-cyanopyrimidine in 100 ml of ethanol at room temperature, 20 ml (475.7 mmol) of hydrazine hydrate was added thereto and stirred at room temperature for about two days. After completion of the reaction, the reaction product was concentrated under reduced pressure, and then extracted with 100 ml of salt water and 200 ml of dichloromethane to obtain an organic layer, which was then dried using magnesium sulfate and distilled under reduced pressure. The resulting product was separated and purified using column chromatography to obtain 3.0 g (21.9 mmol, Yield 46%) of Intermediate 40(2).

LC-MS m/z=138(M+H)+

Synthesis of Intermediate 40(1)

Following dissolving 40(2) 2.9 g (21.6 mmol) of Intermediate 40(2) in 120 ml of anhydrous tetrahydrofuran and 40 ml of distilled water at room temperature, 2.7 g (32.1 mmol) of sodium hydrocarbonate was added to the reaction mixture at room temperature and stirred for about 30 minutes. After 30 minutes, 3.2 ml (25.9 mmol) of trimethyl ethylchloride was slowly added thereto at 0° C. and stirred at room temperature for about 16 hours. After completion of the reaction, the reaction product was extracted with 100 ml of distilled water and 200 ml of dichloromethane to obtain an organic layer, which was then dried using magnesium sulfate and distilled under reduced pressure. The resulting product was separated and purified using column chromatography to obtain 1.2 g (5.4 mmol, Yield 25%) of Intermediate 40(1).

LC-MS m/z=222(M+H)+

Synthesis of Ligand 40 (L40)

After dissolving 1.2 g (5.4 mmol) of Intermediate 40(1) in 30 ml of ethylene glycol at room temperature, the resulting solution was heated under reflux at about 190° C. for about 4 hours. The resulting product was dissolved in 30 ml of ethanol, and 50 ml of a 4N diluted hydrochloric acid solution was added thereto and heated under reflux at about 80° C. for about 18 hours. After completion of the reaction, the reaction product was extracted with 100 ml of distilled water and 200 ml of dichloromethane to obtain an organic layer, which was then dried using magnesium sulfate and distilled under reduced pressure. The resulting product was separated and purified using column chromatography to obtain 0.7 g (3.4 mmol, Yield 64%) of ligand 40 (L40).

LC-MS m/z=204(M+H)+

Ligand Synthesis 41

Synthesis of Ligand 41 (L41)

Ligand 41 (L41) was synthesized in the same manner (Yield: 19%) as in the synthesis of ligand 30 (L30) (Ligand Synthesis 30), except that methyl 6-methylpyrimidine-4-carboxylate, instead of methylpyrimidine-4-carboxylate, was used in synthesizing Intermediate 30(1).

LC-MS m/z=297(M+H)+

Ligand Synthesis 42

Synthesis of Ligand 42 (L42)

Ligand 42 (L42) was synthesized in the same manner (Yield: 9%) as in the synthesis of ligand 39 (L39) (Ligand Synthesis 39), except that 3,3-dimethylbutan-2-one, instead of 1,1,1-trifluoropropan-2-one, was used in synthesizing Intermediate 39(4).

LC-MS m/z=494(M+H)+

Ligand Synthesis 43

Synthesis of Ligand 43 (L43)

Ligand 43 (L43) was synthesized in the same manner (Yield: 7%) as in the synthesis of ligand 39 (L39) (Ligand Synthesis 39), except that 3,3-dimethylbutan-2-one, instead of 1,1,1-trifluoropropan-2-one, was used in synthesizing Intermediate 39(4), and p-a, instead of aniline, was used in synthesizing intermediate 39(1).

LC-MS m/z=508(M+H)+

Synthesis Example 1

Synthesis of Compound 1

Compound 1 was synthesized according to Reaction Scheme 41 below:

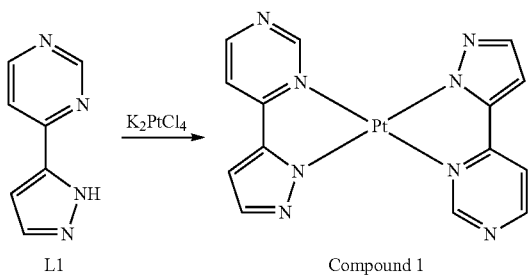

<Reaction Scheme 41>

After dissolving 1.0 g (6.8 mmol) of ligand 1 (L1) in 50 ml of an aqueous ethanol solution at room temperature, 1.4 g (3.4 mmol) of K2PtCl4 was added thereto and heated under reflux at about 100° C. for about 18 hours. After 18 hours, the reaction product was cooled to 0° C. to obtain a solid product, which was then filtered. The filtrated solid was rinsed with 80 ml of hot water and then with 50 ml of hot ethanol. The resulting product was separated and purified using column chromatography, and further purified by sublimation to obtain 0.6 g (1.2 mmol, Yield 19%) of Compound 1.

LC-MS m/z=486(M+H)+

$^1$H NMR(300 MHz, CDCl$_3$) σ=10.72(s, 1H), 8.84(d, 1H), 7.72(d, 1H), 7.53(d, 2H), 6.36(d, 1H)

Synthesis Example 2

Synthesis of Compound 2

Compound 2 (Yield 22%) was synthesized in the same manner as in Synthesis Example 1, except that ligand 4 (L4), instead of ligand 1 (L1), was used.

LC-MS m/z=514(M+H)+

$^1$H NMR(300 MHz, CDCl$_3$) σ=10.97(s, 1H), 8.68(d, 1H), 7.47(d, 1H), 6.58(s, 1H), 2.92(s, 3H)

Synthesis Example 3

Synthesis of Compound 3

Compound 3 (Yield 42%) was synthesized in the same manner as in Synthesis Example 1, except that ligand 5 (L5), instead of ligand 1 (L1), was used.

LC-MS m/z=570(M+H)+

1H NMR(300 MHz, CDCl3) σ=11.00(s, 1H), 8.71(d, 1H), 7.32(d, 1H), 6.72(s, 1H), 3.72(m, 1H), 1.28(d, 6H)

Synthesis Example 4

Synthesis of Compound 4

Compound 4 (Yield 35%) was synthesized in the same manner as in Synthesis Example 1, except that ligand 6 (L6), instead of ligand 1 (L1), was used.

LC-MS m/z=598(M+H)+

$^1$H NMR(300 MHz, CDCl$_3$) σ=11.10(s, 1H), 8.73(d, 1H), 7.56(d, 1H), 6.64(s, 1H), 1.43(s, 9H)

Synthesis Example 5

Synthesis of Compound 5

Compound 5 (Yield 32%) was synthesized in the same manner as in Synthesis Example 1, except that ligand 7 (L7), instead of ligand 1 (L1), was used.

LC-MS m/z=622(M+H)+

$^1$H NMR(300 MHz, CDCl$_3$)=11.07(s, 1H), 8.81(d, 1H), 7.61(d, 1H), 6.14(s, 1H)

Synthesis Example 6

Synthesis of Compound 6

Compound 6 (Yield 29%) was synthesized in the same manner as in Synthesis Example 1, except that ligand 8 (L8), instead of ligand 1 (L1), was used.

LC-MS m/z=594(M+H)+

$^1$H NMR(300 MHz, CDCl$_3$) σ=10.96(s, 1H), 9.17(d, 1H), 8.17(d, 1H), 2.76(br s, 2H), 2.72(br s, 2H), 1.79~1.73(br s, 4H)

Synthesis Example 7

Synthesis of Compound 7

Compound 7 (Yield 28%) was synthesized in the same manner as in Synthesis Example 1, except that ligand 9 (L9), instead of ligand 1 (L1), was used.

LC-MS m/z=650(M+H)+

$^1$H NMR(300 MHz, CDCl$_3$) σ=11.01(s, 1H), 9.26(d, 1H), 8.32(d, 1H), 2.71(br s, 2H), 1.82(br s, 2H), 1.54(br s, 2H), 1.38(s, 6H)

Synthesis Example 8

Synthesis of Compound 8

Compound 8 (Yield 17%) was synthesized in the same manner as in Synthesis Example 1, except that ligand 10 (L10), instead of ligand 1 (L1), was used.
LC-MS m/z=702(M+H)+
$^1$H NMR(300 MHz, CDCl$_3$) σ=11.03(s, 1H), 9.23(d, 1H), 8.37(d, 1H), 2.77(br s, 1H), 1.68~1.62(m, 4H), 1.47(s, 3H), 1.01(s, 6H)

Synthesis Example 9

Synthesis of Compound 9

Compound 9 (Yield 36%) was synthesized in the same manner as in Synthesis Example 1, except that ligand 11 (L11), instead of ligand 1 (L1), was used.
LC-MS m/z=542(M+H)+
$^1$H NMR(300 MHz, CDCl$_3$) σ=10.36(s, 1H), 8.48(s, 1H), 6.21(s, 1H), 2.36(s, 3H), 2.33(s, 6H)

Synthesis Example 10

Synthesis of Compound 10

Compound 10 (Yield 48%) was synthesized in the same manner as in Synthesis Example 1, except that ligand 12 (L12), instead of ligand 1 (L1), was used.
LC-MS m/z=626(M+H)+
$^1$H NMR(300 MHz, CDCl$_3$) σ=10.34(s, 1H), 8.42(s, 1H), 6.01(s, 1H), 2.32(s, 3H), 1.36(s, 9H)

Synthesis Example 11

Synthesis of Compound 11

Compound 11 (Yield 42%) was synthesized in the same manner as in Synthesis Example 1, except that ligand 13 (L13), instead of ligand 1 (L1), was used.
LC-MS m/z=650(M+H)+
$^1$H NMR(300 MHz, CDCl$_3$) σ=10.41(s, 1H), 8.19(s, 1H), 6.02(s, 1H), 2.33(s, 3H)

Synthesis Example 12

Synthesis of Compound 12

Compound 12 (Yield 49%) was synthesized in the same manner as in Synthesis Example 1, except that ligand 14 (L14), instead of ligand 1 (L1), was used.
LC-MS m/z=678(M+H)+
$^1$H NMR(300 MHz, CDCl$_3$) σ=10.34(s, 1H), 8.36(s, 1H), 2.77(br s, 2H), 2.29(s, 3H), 1.82(br s, 2H), 1.55(br s, 2H), 10.36(s, 6H)

Synthesis Example 13

Synthesis of Compound 13

Compound 13 (Yield 36%) was synthesized in the same manner as in Synthesis Example 1, except that ligand 15 (L15), instead of ligand 1 (L1), was used.
LC-MS m/z=730(M+H)+
$^1$H NMR(300 MHz, CDCl$_3$) σ=10.31(s, 1H), 8.28(s, 1H), 2.82(br s, 1H), 2.31(s, 1H), 1.66~1.62(m, 4H), 1.45(s, 3H), 0.99(s, 6H)

Synthesis Example 14

Synthesis of Compound 14

Compound 14 (Yield 28%) was synthesized in the same manner as in Synthesis Example 1, except that ligand 16 (L16), instead of ligand 1 (L1), was used.
LC-MS m/z=574(M+H)+
$^1$H NMR(300 MHz, CDCl$_3$) σ=10.06(s, 1H), 7.84(s, 1H), 6.36(s, 1H), 3.65(s, 3H), 2.21(s, 3H)

Synthesis Example 15

Synthesis of Compound 15

Compound 15 (Yield 34%) was synthesized in the same manner as in Synthesis Example 1, except that ligand 17 (L17), instead of ligand 1 (L1), was used.
LC-MS m/z=658(M+H)+
$^1$H NMR(300 MHz, CDCl$_3$) σ=10.00(s, 1H), 7.69(s, 1H), 6.12(s, 1H), 3.67(s, 3H), 1.42(s, 9H)

Synthesis Example 16

Synthesis of Compound 16

Compound 16 (Yield 27%) was synthesized in the same manner as in Synthesis Example 1, except that ligand 18 (L18), instead of ligand 1 (L1), was used.
LC-MS m/z=682(M+H)+
$^1$H NMR(300 MHz, CDCl$_3$) σ=10.13(s, 1H), 7.42(s, 1H), 6.02(s, 1H), 3.80(s, 3H)

Synthesis Example 17

Synthesis of Compound 17

Compound 17 (Yield 22%) was synthesized in the same manner as in Synthesis Example 1, except that ligand 19 (L19), instead of ligand 1 (L1), was used.
LC-MS m/z=694(M+H)+
$^1$H NMR(300 MHz, CDCl$_3$) σ=10.03(s, 1H), 7.76(s, 1H), 3.83(s, 3H), 2.76(s, 2H), 1.76(br s, 2H), 1.54(br s, 2H), 1.36(s, 6H)

Synthesis Example 18

Synthesis of Compound 18

Compound 18 (Yield 19%) was synthesized in the same manner as in Synthesis Example 1, except that ligand 20 (L20), instead of ligand 1 (L1), was used.
LC-MS m/z=762(M+H)+
$^1$H NMR(300 MHz, CDCl$_3$) σ=10.10(s, 1H), 7.81(s, 1H), 3.81(s, 3H), 2.72(br s, 1H), 1.69~1.65(m, 4H), 1.43(s, 3H), 0.99(s, 6H)

Synthesis Example 19

Synthesis of Compound 19

Compound 19 (Yield 21%) was synthesized in the same manner as in Synthesis Example 1, except that ligand 21 (L21), instead of ligand 1 (L1), was used.

LC-MS m/z=650(M+H)+
$^1$H NMR(300 MHz, CDCl$_3$) σ=11.07(s, 1H), 8.51(s, 1H), 6.41(s, 1H), 2.21(s, 3H)

Synthesis Example 20

Synthesis of Compound 20

Compound 20 (Yield 38%) was synthesized in the same manner as in Synthesis Example 1, except that ligand 22 (L22), instead of ligand 1 (L1), was used.
LC-MS m/z=734(M+H)+
$^1$H NMR(300 MHz, CDCl$_3$) σ=11.00(s, 1H), 8.38(s, 1H), 6.28(s, 1H), 1.58(s, 9H)

Synthesis Example 21

Synthesis of Compound 21

Compound 21 (Yield 42%) was synthesized in the same manner as in Synthesis Example 1, except that ligand 23 (L23), instead of ligand 1 (L1), was used.
LC-MS m/z=758(M+H)+
$^1$H NMR(300 MHz, CDCl$_3$) σ=11.02(s, 1H), 8.13(s, 1H), 6.53(s, 1H)

Synthesis Example 22

Synthesis of Compound 22

Compound 22 (Yield 37%) was synthesized in the same manner as in Synthesis Example 1, except that ligand 24 (L24), instead of ligand 1 (L1), was used.
LC-MS m/z=838(M+H)+
$^1$H NMR(300 MHz, CDCl$_3$) σ=11.12(s, 1H), 8.31(s, 1H), 2.96-2.94(m, 1H), 1.93-1.89(m, 2H), 1.69~1.65(m, 2H), 1.42(s, 3H), 0.99(s, 6H)

Synthesis Example 23

Synthesis of Compound 23

Compound 23 (Yield 35%) was synthesized in the same manner as in Synthesis Example 1, except that ligand 25 (L25), instead of ligand 1 (L1), was used.
LC-MS m/z=626(M+H)+
$^1$H NMR(300 MHz, CDCl$_3$) σ=8.87(d, 1H), 7.68(d, 1H), 6.32(s, 1H), 2.63(s, 3H), 1.33(s, 9H)

Synthesis Example 24

Synthesis of Compound 24

Compound 24 (Yield 21%) was synthesized in the same manner as in Synthesis Example 1, except that ligand 26 (L26), instead of ligand 1 (L1), was used.
LC-MS m/z=650(M+H)+
$^1$H NMR(300 MHz, CDCl$_3$) σ=8.76(d, 1H), 7.53(d, 1H), 6.48(s, 1H), 2.44(s, 3H)

Synthesis Example 25

Synthesis of Compound 25

Compound 27 (Yield 36%) was synthesized in the same manner as in Synthesis Example 1, except that ligand 27 (L27), instead of ligand 1 (L1), was used.

LC-MS m/z=626(M+H)+
$^1$H NMR(300 MHz, CDCl$_3$) σ=11.32(s, 1H), 9.21(d, 1H), 8.17(d, 1H), 2.04(s, 3H), 1.36(s, 9H)

Synthesis Example 26

Synthesis of Compound 26

Compound 26 (Yield 34%) was synthesized in the same manner as in Synthesis Example 1, except that ligand 28 (L28), instead of ligand 1 (L1), was used.
LC-MS m/z=710(M+H)+
$^1$H NMR(300 MHz, CDCl$_3$) σ=11.23(s, 1H), 8.78(d, 1H), 8.05(d, 1H), 1.41(s, 9H), 1.33(s, 9H)

Synthesis Example 27

Synthesis of Compound 27

Compound 27 (Yield 21%) was synthesized in the same manner as in Synthesis Example 1, except that ligand 29 (L29), instead of ligand 1 (L1), was used.
LC-MS m/z=734(M+H)+
$^1$H NMR(300 MHz, CDCl$_3$) σ=11.18(s, 1H), 9.13(d, 1H), 8.15(d, 1H), 1.38(s, 9H)

Synthesis Example 28

Synthesis of Compound 28

Compound 28 (Yield 35%) was synthesized in the same manner as in Synthesis Example 1, except that ligand 30 (L30), instead of ligand 1 (L1), was used.
LC-MS m/z=758(M+H)+
$^1$H NMR(300 MHz, CDCl$_3$) σ=11.13(s, 1H), 8.86(d, 1H), 7.64(d, 1H)

Synthesis Example 29

Synthesis of Compound 68

Compound 68 (Yield 27%) was synthesized in the same manner as in Synthesis Example 1, except that ligand 40 (L40), instead of ligand 1 (L1), was used.
LC-MS m/z=600(M+H)+
$^1$H NMR(300 MHz, CDCl$_3$) σ=10.86(s, 1H), 8.92(d, 1H), 7.73(d, 1H), 1.35(2, 9H)

Synthesis Example 30

Synthesis of Compound 37

Compound 37 (Yield 22%) was synthesized in the same manner as in Synthesis Example 1, except that ligand 2 (L2), instead of ligand 1 (L1), was used.
LC-MS m/z=586(M+H)+
$^1$H NMR(300 MHz, CDCl$_3$) σ=10.47(s, 1H), 9.20(d, 1H), 8.32(d, 1h), 8.17(d, 1H), 7.92(d, 1H), 7.62(m, 1H), 7.48(m, 1H)

Synthesis Example 31

Synthesis of Compound 38

Compound 38 (Yield 26%) was synthesized in the same manner as in Synthesis Example 1, except that ligand 3 (L3), instead of ligand 1 (L1), was used.

LC-MS m/z=686(M+H)+
$^1$H NMR(300 MHz, CDCl$_3$) σ=10.54(s, 1H), 8.46(m, 1H), 7.84(m, 1H), 7.58(m, 1H), 7.34(d, 1H), 6.31(d, 1H)

Synthesis Example 32

Synthesis of Compound 29

Compound 29 was synthesized according to Reaction Scheme 42 below:

<Reaction Scheme 42>

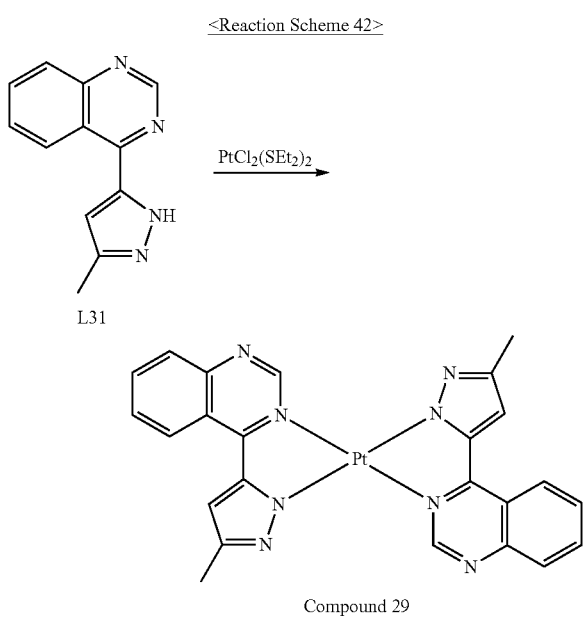

Compound 29

Following dissolving 0.1 g (4.9 mmol) of NaH in 50 ml of anhydrous tetrahydrofuran at 0° C., 1.0 g (4.8 mmol) of ligand 31 (L31) was slowly added thereto. After 30 minutes, 1.1 g (2.4 mmol) of PtCl(SEt$_2$)$_2$ was added to the mixture, stirred at room temperature for about 1 hour, and then heated under reflux at about 80° C. for about 18 hours. After 18 hours the reaction product was extracted with 80 ml of distilled water and 100 ml of dichloromethane to obtain an organic layer, which was then dried using magnesium sulfate and concentrated under reduced pressure. The resulting product was separated and purified using column chromatography, followed by further purification by sublimation to obtain 0.4 g (0.6 mmol, Yield 28%) of Compound 29.

LC-MS m/z=614(M+H)+
$^1$H NMR(300 MHz, CDCl$_3$) σ=10.32(s, 1H), 8.36(d, 1H), 7.83-7.81(m, 2H), 7.58(br s, 1H), 7.43(s, 1H), 2.04(s, 3H)

Synthesis Example 33

Synthesis of Compound 30

Compound 30 (Yield 22%) was synthesized in the same manner as in Synthesis Example 32, except that ligand 32 (L32), instead of ligand 31 (L31), was used.
$^1$H NMR(300 MHz, CDCl$_3$) σ=10.29(s, 1H), 8.16(d, 1H), 7.84-7.83(m, 2H), 7.55(br s, 1H), 6.38(s, 1H), 1.39(s, 9H)

Synthesis Example 34

Synthesis of Compound 31

Compound 31 (Yield 18%) was synthesized in the same manner as in Synthesis Example 32, except that ligand 33 (L33), instead of ligand 31 (L31), was used.
$^1$H NMR(300 MHz, CDCl$_3$) σ=10.41(s, 1H), 8.31(d, 1H), 7.85-7.81(m, 2H), 7.49(br s, 1H), 6.02(s, 1H)

Synthesis Example 35

Synthesis of Compound 32

Compound 32 (Yield 31%) was synthesized in the same manner as in Synthesis Example 32, except that ligand 34 (L34), instead of ligand 31 (L31), was used.
$^1$H NMR(300 MHz, CDCl$_3$) σ=10.29(s, 1H), 8.16(d, 1H), 7.83-7.81(m, 2H), 7.52(br s, 1H), 2.76-2.72(m, 4H), 1.83-1.76(m, 4H)

Synthesis Example 36

Synthesis of Compound 33

Compound 33 (Yield 27%) was synthesized in the same manner as in Synthesis Example 32, except that ligand 35 (L35), instead of ligand 31 (L31), was used.
$^1$H NMR(300 MHz, CDCl$_3$) σ=10.36(s, 1H), 8.21(d, 1H), 7.86-7.84(m, 2H), 7.56(br s, 1H), 2.74-2.72(m, 2H), 1.82-1.79(m, 2H), 1.58-1.54(m, 2H), 1.42(s, 6H)

Synthesis Example 37

Synthesis of Compound 34

Compound 34 (Yield 25%) was synthesized in the same manner as in Synthesis Example 32, except that ligand 36 (L36), instead of ligand 31 (L31), was used.
$^1$H NMR(300 MHz, CDCl$_3$) σ=10.28(s, 1H), 8.18(d, 1H), 7.84-7.83(m, 2H), 7.58(br s, 1H), 2.77-2.75(m, 2H), 1.93-1.90(m, 2H), 1.87-1.85(m, 2H), 1.47(s, 3H), 1.02(s, 6H)

Synthesis Example 38

Synthesis of Compound 35

Compound 35 (Yield 22%) was synthesized in the same manner as in Synthesis Example 32, except that ligand 37 (L37), instead of ligand 31 (L31), was used.
$^1$H NMR(300 MHz, CDCl$_3$) σ=10.29(s, 1H), 8.16(d, 1H), 7.86-7.84(m, 2H), 7.61(br s, 1H), 2.12(s, 3H), 1.37(s, 9H)

Synthesis Example 39

Synthesis of Compound 36

Compound 36 (Yield 21%) was synthesized in the same manner as in Synthesis Example 32, except that ligand 38 (L38), instead of ligand 31 (L31), was used.
$^1$H NMR(300 MHz, CDCl$_3$) σ=10.16(s, 1H), 8.35(d, 1H), 7.73-7.71(m, 2H), 7.55(br s, 1H), 1.35(s, 9H)

Synthesis Example 40

Synthesis of Compound 39

Compound 39 was synthesized according to Reaction Scheme 43 below:

<Reaction Scheme 43>

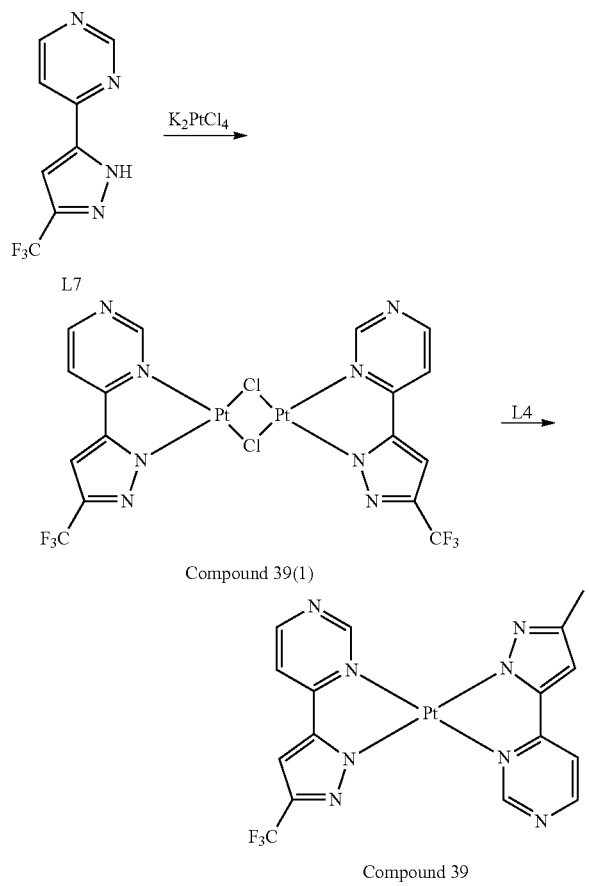

Synthesis of Compound 39(1)

Synthesis of Compound 39(1)

Following dissolving 1.0 g (4.7 mmol) of ligand 7 (L7) and 1.9 g (4.7 mmol) of K₂PtCl₄ in 100 ml of distilled water at room temperature, 3 ml of a 4N diluted hydrochloric acid was added thereto and heated under reflux at about 80° C. for about 6 hours. After 6 hours the reaction product was cooled to room temperature and filtered to obtain a solid compound, which was then rinsed with 50 ml of distilled water and dried to obtain 2.0 g (2.4 mmol, Yield: 50%) of Compound 39(1).

Synthesis of Compound 39

Following dissolving 0.1 g (4.9 mmol) of NaH in 50 ml of anhydrous tetrahydrofuran at 0° C. 0.4 g (2.4 mmol) of ligand 4 (L4) was slowly added thereto. After about 30 minutes, 2.0 g (2.4 mmol) of Compound 39(1) was added thereto and heated under reflux at about 80° C. for about 18 hours. After 18 hours, the reaction product was extracted with 80 ml of distilled water and 100 ml of dichloromethane to obtain an organic layer, which was then dried using magnesium sulfate and concentrated under reduced pressure. The resulting product was separated and purified using column chromatography, followed by further purification by sublimation to obtain 0.6 g (1.2 mmol, Yield 48%) of Compound 39.
LC-MS m/z=568(M+H)+

¹H NMR(300 MHz, CDCl₃) σ=11.32(s, 1H), 11.26(s, 1H), 8.92(d, 1H), 8.76(d, 1H), 6.75(s, 1H), 6.64(s, 1H), 2.32(s, 3H)

Synthesis Example 41

Synthesis of Compound 40

Compound 40 (Yield 9%) was synthesized in the same manner as in Synthesis Example 40, except that ligand 6 (L6) was used, instead of ligand 4 (L4) used in synthesizing Compound 39.
¹H NMR(300 MHz, CDCl₃) σ=11.29(s, 1H), 11.19(s, 1H), 8.96(d, 1H), 8.65(d, 1H), 6.81(s, 1H), 6.68(s, 1H), 1.35(s, 9H)

Synthesis Example 42

Synthesis of Compound 41

Compound 41 (Yield 12%) was synthesized in the same manner as in Synthesis Example 40, except that ligand 27 (L27) was used, instead of ligand 4 (L4) used in synthesizing Compound 39.
¹H NMR(300 MHz, CDCl₃) σ=11.30(s, 1H), 11.24(s, 1H), 8.90(d, 1H), 8.71(d, 1H), 6.72(s, 1H), 2.04(s, 314), 1.33(s, 9H)

Synthesis Example 43

Synthesis of Compound 42

Compound 42 (Yield 10%) was synthesized in the same manner as in Synthesis Example 40, except that ligand 29 (L29) was used, instead of ligand 4 (L4) used in synthesizing Compound 39.
¹H NMR(300 MHz, CDCl₃) σ=11.29(s, 1H), 11.21(s, 1H), 8.91(d, 1H), 8.56(d, 1H), 6.70(s, 1H), 1.38(s, 9H)

Synthesis Example 44

Synthesis of Compound 43

Compound 43 (Yield 11%) was synthesized in the same manner as in Synthesis Example 40, except that ligand 30 (L30) was used, instead of ligand 4 (L4) used in synthesizing Compound 39.
¹H NMR(300 MHz, CDCl₃) σ=11.32(s, 1H), 11.15(s, 1H), 8.92(d, 1H), 8.72(d, 1H), 6.72(s, 1H)

Synthesis Example 45

Synthesis of Compound 44

Compound 44 (Yield 12%) was synthesized in the same manner as in Synthesis Example 40, except that ligand 13 (L13), instead of ligand 7 (L7) used in synthesizing Compound 39(1), and ligand 30 (L30), instead of ligand 4 (L4) used in synthesizing Compound 39, were used.
¹H NMR(300 MHz, CDCl₃) σ=11.16(s, 1H), 11.26(s, 1H), 9.21(d, 1H), 8.64(d, 1H), 6.68(s, 1H), 2.36(s, 3H)

Synthesis Example 46

Synthesis of Compound 45

Compound 45 (Yield 11%) was synthesized in the same manner as in Synthesis Example 40, except that ligand 13 (L13), instead of ligand 7 (L7) used in synthesizing Compound 39(1), and ligand 41 (L41), instead of ligand 4 (L4) used in synthesizing Compound 39, were used.

$^1$H NMR(300 MHz, CDCl$_3$) σ=11.13(s, 1H), 11.10(s, 1H), 8.07(d, 1H), 8.02(d, 1H), 6.35(s, 1H)

Synthesis Example 47

Synthesis of Compound 46

Compound 46 (Yield 7%) was synthesized in the same manner as in Synthesis Example 40, except that ligand 31 (L31) was used, instead of ligand 4 (L4) used in synthesizing Compound 39.

$^1$H NMR(300 MHz, CDCl$_3$) σ=11.33(s, 1H), 11.26(s, 1H), 10.85(d, 1H), 8.63(d, 1H), 8.54(br s, 1H), 7.85-7.83(m, 2H), 7.58(br s, 1H), 6.85(s, 1H), 6.33(s, 1H), 2.33(s, 3H)

Synthesis Example 48

Synthesis of Compound 47

Compound 47 (Yield 10%) was synthesized in the same manner as in Synthesis Example 40, except that ligand 42 (L42) was used, instead of ligand 4 (L4) used in synthesizing Compound 39.

$^1$H NMR(300 MHz, CDCl$_3$) σ=11.32(s, 11-1), 9.20(d, 1H), 8.85(d, 1H), 8.57(d, 1H), 8.05-8.03(m, 1H), 7.87-7.85(m, 1H), 6.39(s, 1H), 6.32(s, 1H)

Synthesis Example 49

Synthesis of Compound 48

Compound 48 (Yield 12%) was synthesized in the same manner as in Synthesis Example 40, except that ligand 43 (L43) was used, instead of ligand 4 (L4) used in synthesizing Compound 39.

$^1$H NMR(300 MHz, CDCl$_3$) σ=11.23(s, 1H), 9.52(d, 1H), 8.55(d, 1H), 8.31(d, 1H), 8.16-8.14(m, 1H), 7.92-7.90(m, 1H), 6.35(s, 1H), 6.33(s, 1H), 1.37(s, 9H)

Synthesis Example 50

Synthesis of Compound 49

Compound 49 (Yield 11%) was synthesized in the same manner as in Synthesis Example 40, except that ligand 6 (L6), instead of ligand 7 (L7) used in synthesizing Compound 39(1), and ligand 43 (L43), instead of ligand 4 (L4) used in synthesizing Compound 39, were used.

$^1$H NMR(300 MHz, CDCl$_3$) σ=11.13(s, 1H), 9.86(d, 1H), 8.71(d, 1H), 8.46(d, 1H), 8.09-8.07(m, 1H), 7.88-7.87(m, 1H), 6.39(s, 1H), 6.30(s, 1H), 1.37(s, 9H), 1.35(s, 9H)

Synthesis Example 51

Synthesis of Compound 50

Compound 50 (Yield 16%) was synthesized in the same manner as in Synthesis Example 40, except that 2-phenylpyridine was used, instead of ligand 4 (L4) used in synthesizing Compound 39.

$^1$H NMR(300 MHz, CDCl$_3$) σ=11.21(s, 1H), 9.20(d, 1H), 8.56(d, 1H), 8.30(d, 1H), 8.17(d, 1H), 7.97(d, 1H), 7.51-7.47(m, 3H), 7.41(br s, 1H), 7.02-7.00(m, 1H), 6.32(s, 1H)

Synthesis Example 52

Synthesis of Compound 51

Compound 51 (Yield 14%) was synthesized in the same manner as in Synthesis Example 40, except that ligand 6 (L6), instead of ligand 7 (L7) used in synthesizing Compound 39(1), and 2-phenylpyridine, instead of ligand 4 (L4) used in synthesizing Compound 39, were used.

$^1$H NMR(300 MHz, CDCl$_3$) σ=11.18(s, 1H), 9.17(d, 1H), 8.48(d, 1H), 8.36(d, 1H), 8.21(d, 1H), 7.88(d, 1H), 7.55-7.51(m, 3H), 7.36(br s, 1H), 7.02-7.00(m, 1H), 6.33(s, 1H), 1.38(s, 9H)

Synthesis Example 53

Synthesis of Compound 52

Compound 52 (Yield 16%) was synthesized in the same manner as in Synthesis Example 40, except that ligand 9 (L9), instead of ligand 7 (L7) used in synthesizing Compound 39(1), and 2-phenylpyridine, instead of ligand 4 (L4) used in synthesizing Compound 39, were used.

$^1$H NMR(300 MHz, CDCl$_3$) σ=11.22(s, 1H), 9.20(d, 1H), 8.53(d, 1H), 8.31(d, 1H), 8.15(d, 1H), 8.02(d, 1H), 7.50-7.46(m, 3H), 7.43(br s, 1H), 7.05-7.03(m, 1H), 2.76-2.74(m, 2H), 1.79-1.77(m, 2H), 1.54-1.52(m, 2H), 1.38(s, 6H)

Synthesis Example 54

Synthesis of Compound 53

Compound 53 (Yield 26%) was synthesized in the same manner as in Synthesis Example 40, except that ligand 6 (L6), instead of ligand 7 (L7) used in synthesizing Compound 39(1), and sodium acetylacetate (Na(acac)), instead of ligand 4 (L4) used in synthesizing Compound 39, were used.

$^1$H NMR(300 MHz, CDCl$_3$) σ=10.89(s, 1H), 9.20(d, 1H), 8.17(d, 1H), 6.21(s, 1H), 5.31(br s, 1H), 3.52-3.50(m, 1H), 1.38(s, 9H), 1.18(s, 6H)

Synthesis Example 55

Synthesis of Compound 54

Compound 54 (Yield 22%) was synthesized in the same manner as in Synthesis Example 40, except that sodium acetylacetate (Na(acac)) was used, instead of ligand 4 (L4) used in synthesizing Compound 39.

$^1$H NMR(300 MHz, CDCl$_3$) σ=10.74(s, 1H), 9.26(d, 1H), 8.13(d, 1H), 6.36(s, 1H), 5.33(br s, 1H), 3.53-3.51(m, 1H), 1.18(s, 6H)

Synthesis Example 56

Synthesis of Compound 55

Compound 55 (Yield 26%) was synthesized in the same manner as in Synthesis Example 40, except that ligand 9 (L9), instead of ligand 7 (L7) used in synthesizing Compound 39(1), and sodium acetylacetate (Na(acac)), instead of ligand 4 (L4) used in synthesizing Compound 39, were used.

$^1$H NMR(300 MHz, CDCl$_3$) σ=11.02(s, 1H), 8.72(d, 1 h), 8.58(d, 1H), 5.31(br s, 1H), 3.52-3.50(m, 1H), 2.75-2.73(m, 2H), 1.79-1.76(m, 2H), 1.54-1.52(m, 2H), 1.40(s, 6H), 1.20(s, 6H)

Synthesis Example 57

Synthesis of Compound 56

Compound 56 (Yield 21%) was synthesized in the same manner as in Synthesis Example 40, except that ligand 27 (L27), instead of ligand 7 (L7) used in synthesizing Compound 39(1), and sodium acetylacetate (Na(acac)), instead of ligand 4 (L4) used in synthesizing Compound 39, were used.

$^1$H NMR(300 MHz, CDCl$_3$) σ=10.91(s, 1H), 8.25(d, 1 h), 7.85(d, 1H), 5.31(br s, 1H), 3.52-3.50(m, 1H), 2.75-2.73(m, 2H), 2.10(s, 3H), 1.35(s, 9H), 1.18(s, 6H)

Synthesis Example 58

Synthesis of Compound 57

Compound 57 was synthesized according to Reaction Scheme 44 below:

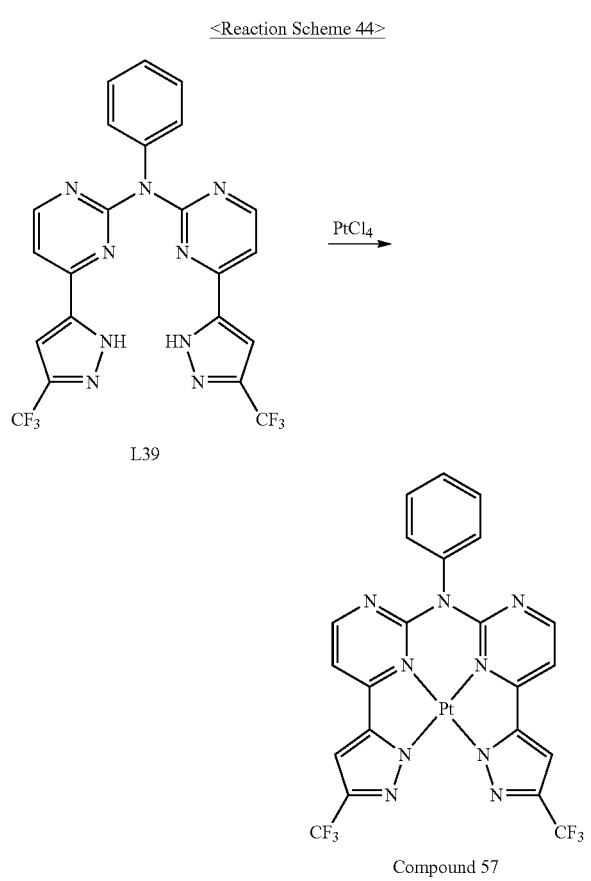

Following dissolving 2.0 mmol of ligand 39 (L39) in 30 ml of benzonitrile, 0.7 g (2.0 mmol) of PtCl4 was added thereto and stirred at about 240□ for about 36 hours. After 36 hours, the reaction product was cooled to room temperature and filtered to obtain a solid product, which was rinsed with 50 ml of ether and dried to obtain Compound 37 (Yield: less than 3%).

LC-MS m/z=711(M+H)+

Synthesis Example 59

Synthesis of Compound 58

Compound 58 (Yield 3%) was synthesized in the same manner as in Synthesis Example 58, except that ligand 44 (L44), instead of ligand 39 (L39), was used.

LC-MS m/z=701(M+H)+

Synthesis Example 60

Synthesis of Compound 59

Compound 59 (Yield 7%) was synthesized in the same manner as in Synthesis Example 58, except that ligand 45 (L45), instead of ligand 39 (L39), was used.

LC-MS m/z=701(M+H)+

$^1$H NMR(300 MHz, CDCl$_3$) σ=7.48-7.45(m, 2H), 7.25-7.23(m, 2H), 6.99-6.97(m, 2H), 6.66-6.63(m, 2H), 6.51-6.49(m, 2H), 6.32(s, 2H), 2.31(s, 3H), 1.35(s, 18H)

Synthesis Example 61

Synthesis of Compound 60

Compound 60 was synthesized according to Reaction Scheme 45 below:

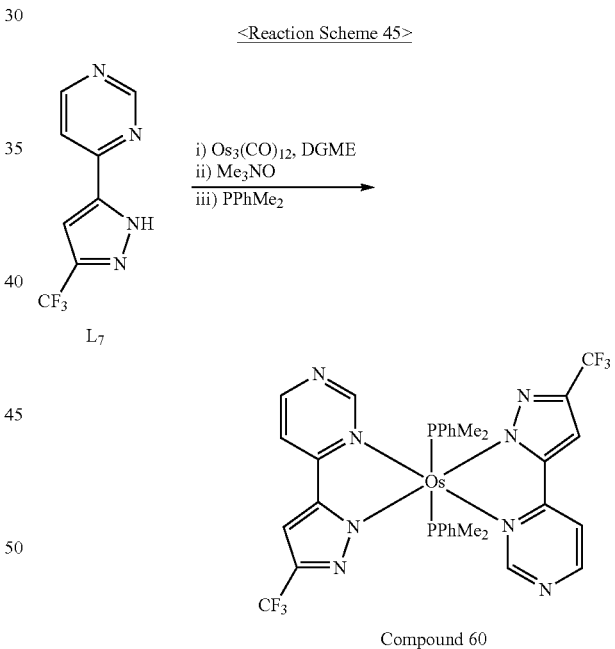

Following dissolving 6.0 mmol of ligand 7 (L7) in 40 ml of diethylene glycol monoethyl ether, 0.9 g (1.0 mmol) of Os$_3$(CO)$_{12}$ was added thereto and stirred at about 180° C. for about 24 hours. After the temperature was cooled to about 140° C., 0.4 g (5.0 mmol) of trimethylamine N-oxide was added thereto and stirred at about 180° C. for about 5 minutes. After 5 minutes, 5.0 mmol of dimethyl(phenyl)phosphine (PPhMe2) was added thereto and stirred for about 24 hours. After completion of the reaction, the reaction product was extracted with 80 ml of distilled water and 200 ml of dichloromethane to obtain an organic layer, which was then dried using magnesium sulfate and distilled under reduced pressure. The resulting product was separated and purified using column chromatography, followed by further purification by sublimation to obtain Compound 60 (Yield 65%).

$^1$H NMR(300 MHz, CDCl$_3$) σ=11.19(s, 2H), 7.62(d, 2H), 7.05(d, 2H), 6.92-6.87(m, 8H), 6.41-6.38(m, 4H), 0.81(m, 6H), 0.60(m, 6H)

Synthesis Example 62

Synthesis of Compound 61

Compound 61 (Yield 62%) was synthesized in the same manner as in Synthesis Example 61, except that ligand 6 (L6), instead of ligand 7 (L7) was used, and diphenyl(methyl)phosphine (PPh2Me), instead of PPhMe2, was used.

$^1$H NMR(300 MHz, CDCl$_3$) σ=11.20(s, 2H), 7.73(d, 2H), 7.12(d, 2H), 6.96-6.93(m, 8H), 6.46-6.43(m, 4H), 1.37(m, 18H), 0.81(m, 6H), 0.60(m, 6H)

Synthesis Example 63

Synthesis of Compound 62

Compound 62 (Yield 62%) was synthesized in the same manner as in Synthesis Example 61, except that ligand 6 (L6), instead of ligand 7 (L7), was used.

$^1$H NMR(300 MHz, CDCl$_3$) σ=11.17(s, 2H), 7.55(d, 2H), 7.32(d, 2H), 7.23-7.11(m, 4H), 7.00-6.97(m, 4H), 6395-6.92(m, 4H), 6.89-6.85(m, 4H), 6.69-6.64(m, 4H), 1.26(t, 6H)

Synthesis Example 64

Synthesis of Compound 63

Compound 63 (Yield 22%) was synthesized in the same manner as in Synthesis Example 61, except that 1,2-bis(diphenylphospino)ethanol, instead of dimethyl(phenyl)phosphine (PPhMe2), was used.

$^1$H NMR(300 MHz, CDCl$_3$) σ=9.06-9.03(m, 2H), 7.90-7.87(m, 4H), 7.78-7.75(m, 2H), 7.43-7.41(m, 2H), 7.35-7.31(m, 4H), 7.30-7.27(m, 2H), 7.17-7.15(m, 2H), 7.09-7.08(m, 2H), 6.80-6.77(m, 4H), 6.62-6.60(m, 4H), 6.41-6.38(m, 2H)

Synthesis Example 65

Synthesis of Compound 64

Compound 64 (Yield 21%) was synthesized in the same manner as in Synthesis Example 61, except that ligand 6 (L6), instead of ligand 7 (L7), and 1,2-bis(diphenylphospino)ethanol, instead of diphenyl(methyl)phosphine (PPh2Me), were used.

$^1$H NMR(300 MHz, CDCl$_3$) σ=9.03-9.01(m, 2H), 7.84-7.2(m, 4H), 7.75-7.73(m, 2H), 7.46-7.44(m, 2H), 7.43-7.40(m, 4H), 7.35-7.32(m, 2H), 7.21-7.19(m, 2H), 7.12-7.10(m, 2H), 6.76-6.73(m, 4H), 6.63-6.60(m, 4H), 6.53-6.51(m, 2H), 1.37-1.34(m, 18H)

Synthesis Example 66

Synthesis of Compound 65

Compound 65 was synthesized according to Reaction Scheme 46 below:

<Reaction Scheme 46>

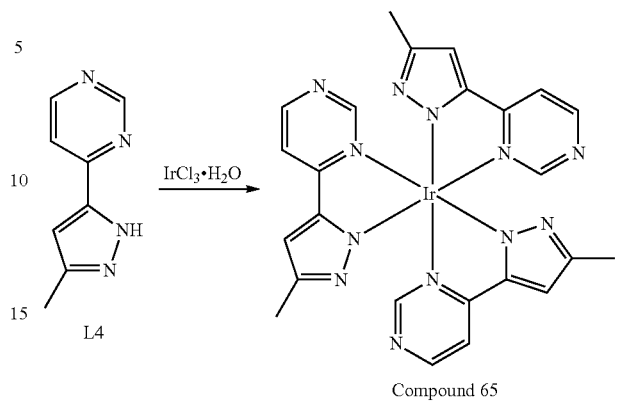

Compound 65

Following dissolving 2.0 mmol of ligand 4 (L4) in 30 ml of ethyleneglycol, 0.4 g (0.3 mmol) of IrCl$_3$.3H$_2$O was added thereto and stirred at about 220° C. for about 24 hours. After completion of the reaction, the reaction product was extracted with 50 ml of distilled water and 100 ml of methylenechloride to obtain an organic layer, which was then dried using magnesium sulfate and distilled under reduced pressure. The resulting product was separated and purified using column chromatography to obtain Compound 65 (Yield 26%).

LC-MS m/z=671(M+H)+

Synthesis Example 67

Synthesis of Compound 66

Compound 66 (Yield 22%) was synthesized in the same manner as in Synthesis Example 66, except that ligand 7 (L7), instead of ligand 4 (L4), was used.

LC-MS m/z=833(M+H)+

Synthesis Example 68

Synthesis of Compound 67

Compound 67 was synthesized according to Reaction Scheme 47 below:

<Reaction Scheme 47>

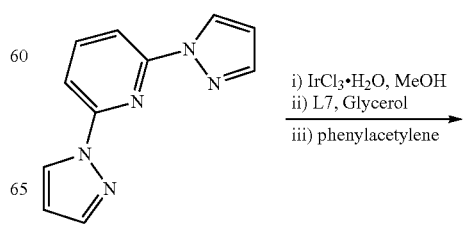

i) IrCl$_3$•H$_2$O, MeOH
ii) L7, Glycerol
iii) phenylacetylene

-continued

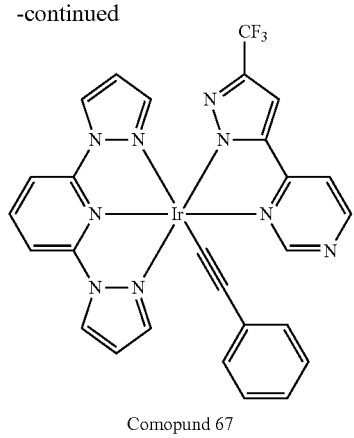

Comopund 67

1.5 g (7.1 mmol) of 2,6-dipyrazole-1-yl pyridine as a start material and 2.6 g (2.0 mmol) of $IrCl_3.3H_2O$ were dissolved in 60 ml of methanol and heated under reflux for about 15 hours. Afterward, the reaction product was cooled and filtered to obtain a solid product, which was then dried and dissolved in 120 ml of glycerol. 4.5 g (21.3 mmol) of ligand 7 (L7) was added to the reaction mixture and subjected to microwave radiation (300W) for about 3 hours for reaction. After completion of the reaction, 200 ml of a saturated salt solution was added to the reaction product and filtered to obtain a solid product, which was then dried and recrystallized using a mixed solvent of dichloromethane and hexane. The resulting solid compound was dissolved in 80 ml of glycerol, and subjected to microwave radiation (300W) for about 6 hours with an addition of potassium hydroxide. After completion of the reaction, the reaction product was extracted with 100 ml of a saturated salt solution and 300 ml of methylenechloride at room temperature to obtain an organic layer, which was then dried using magnesium sulfate and distilled under reduced pressure. The resulting product was separated and purified using column chromatography to obtain Compound 67 (Yield 2%).

LC-MS m/z=719(M+H)+

Example 1

A glass substrate with an anode (ITO/Ag/ITO deposited to a thickness of 70 Å/1000 Å/70 Å, respectively) was cut to a size of 50 mm×50 mm×0.5 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

2-TNATA was deposited on a surface of the anode to form an HIL having a thickness of 600 Å, and then 4.4'-bis[N-(1-naphthyl)-N-phenylamino]biphenyl (NPB) was deposited on the HIL to form a HTL having a thickness of 1000 Å.

CBP (host) and Compound 2 (dopant) were co-deposited in a weight ratio of 95:5 on a surface of the HTL to form an EML having a thickness of about 400 Å, followed by deposition of BCP on the EML to form a HBL having a thickness of about 50 Å. Then, $Alq_3$ was deposited on the HBL to form an ETL having a thickness of about 350 Å, and then LiF was deposited on the ETL to form an EIL having a thickness of about 10 Å. Then, Mg and Ag were deposited in a weight ratio of 90:10 on the EIL to form a cathode having a thickness of about 120 Å, thereby completing the manufacture of an organic light-emitting device.

Example 2

An organic light-emitting device was manufactured in the same manner as in Example 1, except that Compound 3, instead of Compound 2, was used to form the EML.

Example 3

An organic light-emitting device was manufactured in the same manner as in Example 1, except that Compound 4, instead of Compound 2, was used to form the EML.

Example 4

An organic light-emitting device was manufactured in the same manner as in Example 1, except that Compound 6, instead of Compound 2, was used to form the EML.

Example 5

An organic light-emitting device was manufactured in the same manner as in Example 1, except that Compound 7, instead of Compound 2, was used to form the EML.

Example 6

An organic light-emitting device was manufactured in the same manner as in Example 1, except that Compound 68, instead of Compound 2, was used to form the EML.

Example 7

An organic light-emitting device was manufactured in the same manner as in Example 1, except that the thickness of the HTL was changed to about 1350 Å, and CBP (host) and Compound 30 (dopant) were co-deposited in a weight ratio of 94:6 to form an EML having a thickness of about 400 Å.

Example 8

An organic light-emitting device was manufactured in the same manner as in Example 7, except that Compound 33, instead of Compound 30, was used to form the EML.

Example 9

An organic light-emitting device was manufactured in the same manner as in Example 7, except that Compound 34, instead of Compound 30, was used to form the EML.

Example 10

An organic light-emitting device was manufactured in the same manner as in Example 7, except that Compound 60, instead of Compound 30, was used to form the EML.

Example 11

An organic light-emitting device was manufactured in the same manner as in Example 7, except that Compound 63, instead of Compound 30, was used to form the EML.

Comparative Example 1

An organic light-emitting device was manufactured in the same manner as in Example 1, except that $Ir(ppy)_3$, instead of Compound 2, was used to form the EML.

Comparative Example 2

An organic light-emitting device was manufactured in the same manner as in Example 7, except that PtOEP, instead of Compound 30, was used to form the EML.

Comparative Example 3

An organic light-emitting device was manufactured in the same manner as in Example 1, except that Compound A below, instead of Compound 2, was used to form the EML.

Comparative Example 4

An organic light-emitting device was manufactured in the same manner as in Example 1, except that Compound B below, instead of Compound 2, was used to form the EML.

2-TNATA

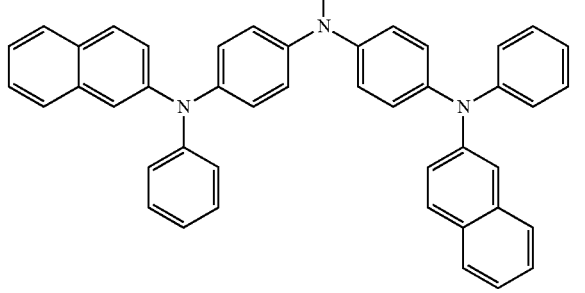

NPB

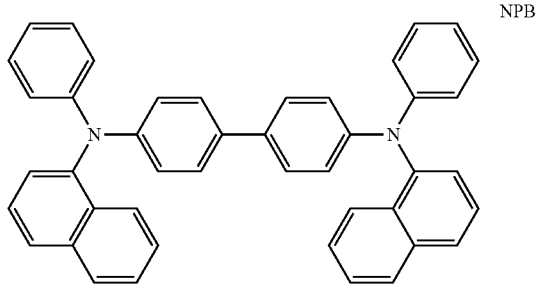

CBP

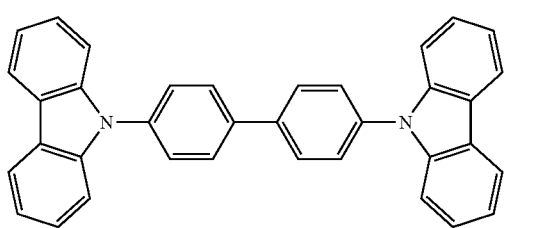

-continued

Compound A

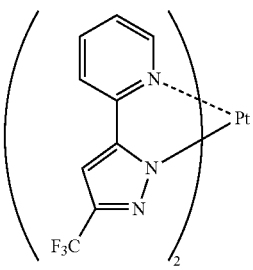

Compound B

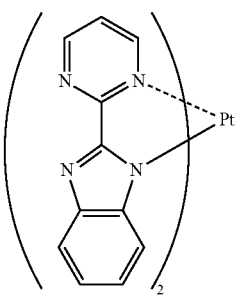

Ir(ppy)$_3$

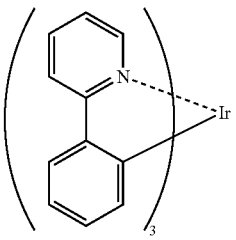

PtOEP

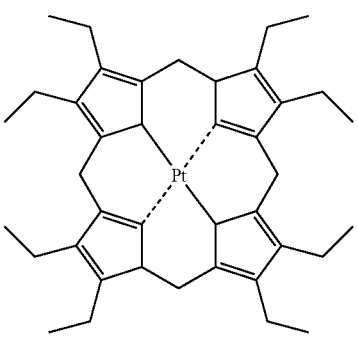

BCP

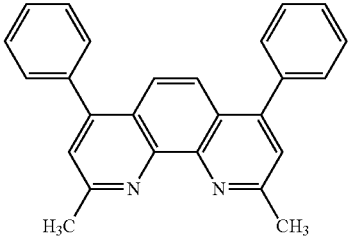

Evaluation Example 1

Driving voltages, current densities, luminescences, efficiencies, and color purities of the organic light-emitting devices of Examples 1 to 11 and Comparative Examples 1 to 4 were measured using a PR650 (Spectroscan) Source Measurement Unit. (available from Photo Research, Inc.). $LT_{97}$ is lifetime data as the time it takes for an initial luminescence (assumed as 100% at a current density of about 10 mA/cm² is reduced to 97%. The results are shown in Table 1 below, in which $V_{dr}$ is driving voltage, Cmp is compound, L is luminance, Eff is efficiency, Clr is emission color, and $Clr_{coor}$ is color coordinate.

TABLE 1

|  | Host | Dopant | $V_{dr}$ (V) | Current density (mA/cm²) | L (cd/m²) | Eff (cd/A) | Clr | $Clr_{coor}$ | $LT_{97}$ (HR) |
|---|---|---|---|---|---|---|---|---|---|
| Example 1 | CBP | Cmp 2 | 5.5 | 10 | 6,330 | 63.3 | green | 0.29, 0.70 | 97 |
| Example 2 | CBP | Cmp 3 | 5.6 | 10 | 6,521 | 65.2 | green | 0.26, 0.72 | 94 |
| Example 3 | CBP | Cmp 4 | 5.5 | 10 | 6,870 | 68.7 | green | 0.27, 0.72 | 98 |
| Example 4 | CBP | Cmp 6 | 5.6 | 10 | 6,625 | 66.2 | green | 0.25, 0.71 | 92 |
| Example 5 | CBP | Cmp 7 | 5.7 | 10 | 6,590 | 65.9 | green | 0.26, 0.71 | 93 |
| Example 6 | CBP | Cmp 68 | 5.6 | 10 | 6,228 | 62.2 | green | 0.28, 0.70 | 90 |
| Example 7 | CBP | Cmp 30 | 5.9 | 10 | 3,042 | 30.4 | red | 0.65, 0.34 | 121 |
| Example 8 | CBP | Cmp 33 | 5.3 | 10 | 3,283 | 32.8 | red | 0.66, 0.37 | 116 |
| Example 9 | CBP | Cmp 34 | 5.3 | 10 | 3,330 | 33.3 | red | 0.66, 0.35 | 110 |
| Example 10 | CBP | Cmp 60 | 5.5 | 10 | 3,570 | 35.7 | red | 0.64, 0.33 | 92 |
| Example 11 | CBP | Cmp 63 | 5.6 | 10 | 3,487 | 34.8 | red | 0.63, 0.34 | 105 |
| Comp. Example 1 | CBP | Ir(ppy)₃ | 6.8 | 10 | 4,766 | 47.7 | green | 0.25, 0.70 | 61 |
| Comp. Example 2 | CBP | PtOEP | 7.3 | 10 | 2,212 | 22.1 | red | 0.67, 0.32 | 89 |
| Comp. Example 3 | CBP | Cmp A | 5.9 | 10 | 4,856 | 48.5 | green | 0.25, 0.68 | 76 |
| Comp. Example 4 | CBP | Cmp B | 6.3 | 10 | 5,510 | 55.1 | green | 0.27, 0.70 | 55 |

Referring to Table 1 above, the organic light-emitting device of Examples 1 to 6 are found to be improved in terms of driving voltage, luminance, efficiency, and lifetime characteristics, relative to the organic light-emitting devices of Comparative Examples 1, 3, and 4. The organic light-emitting device of Examples 7 to 11 are found have improved driving voltages, luminances, efficiencies, and lifetime characteristics, as compared with the organic light-emitting device of Comparative Example 2.

By way of summary and review, an OLED may have a structure including a substrate, and an anode, a hole transport layer (HTL), an emission layer (EML), an electron transport layer (ETL), and a cathode which are sequentially stacked on the substrate. In this regard, the HTL, the EML, and the ETL may be organic thin films formed of organic compounds.

An operating principle of an OLED having the above-described structure may be as follows. When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

As described above, an organic light-emitting device including the organometallic compounds according to one or more of the above embodiments may provide an OLED with a low driving voltage, a high efficiency, and a long lifetime.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:
1. An organometallic compound represented by Formula 1:

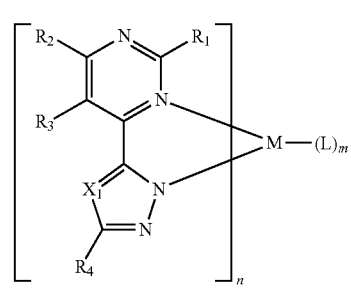

<Formula 1> wherein, in Formula 1:
M is a transition metal;
$X_1$ is N or $C(R_5)$;
$R_1$ to $R_5$ are each independently selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —N($Q_1$)($Q_2$), —Si($Q_3$)($Q_4$)($Q_5$), —C(=O)($Q_6$), and a binding site with an adjacent ligand via a single bond or a divalent linking group;

two substituents of $R_1$ to $R_5$ are optionally linked together to form one selected from the group of a substituted or unsubstituted $C_4$-$C_{20}$ alicyclic ring, a substituted or unsubstituted $C_2$-$C_{20}$ hetero alicyclic ring, a substituted or unsubstituted $C_6$-$C_{20}$ aromatic ring, and a substituted or unsubstituted $C_2$-$C_{20}$ heteroaromatic ring;

$Q_1$ to $Q_6$ are each independently selected from the group of a hydrogen atom, a substituted or unsubstituted $C_1$-$C_{60}$ alkyl group, a substituted or unsubstituted $C_6$-$C_{60}$ aryl group, and a substituted or unsubstituted $C_2$-$C_{60}$ heteroaryl group;

n is an integer from 1 to 3;

m is an integer from 0 to 4, wherein when m is 1, 2, 3, or 4, L is represented by at least one selected from the group of Formulae 2A to 2F:

Formula 2A

Formula 2B

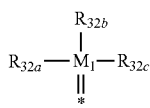

Formula 2C

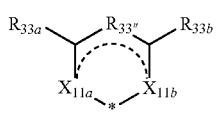

Formula 2D

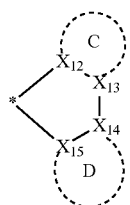

Formula 2E

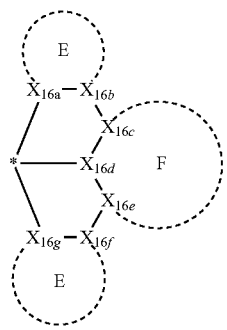

Formula 2F

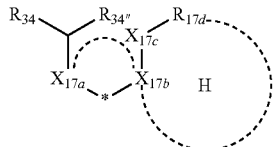

wherein, in Formulae 2A to 2F:

$M_1$ is P or As;

$X_{11a}$, $X_{11b}$, $X_{12}$, $X_{13}$, $X_{14}$, $X_{15}$, $X_{16a}$, $X_{16b}$, $X_{16c}$, $X_{16d}$, $X_{16e}$, $X_{16f}$, $X_{16g}$, $X_{17a}$, $X_{17b}$, $X_{17c}$, and $X_{17d}$ are each independently selected from the group of $C(R_{40})_x$, N, O, $N(R_{35})$, $P(R_{36})(R_{37})$, and $As(R_{38})(R_{39})$;

$R_{33''}$ and $R_{34''}$ are each independently selected from the group of a single bond, a substituted or unsubstituted $C_1$-$C_5$ alkylene group, and a substituted or unsubstituted $C_2$-$C_5$ alkenylene group;

$R_{31}$, $R_{32a}$, $R_{32b}$, $R_{32c}$, $R_{33a}$, $R_{33b}$, $R_{34}$, $R_{35}$, $R_{36}$, $R_{37}$, $R_{38}$, $R_{39}$, and $R_{40}$ are each independently selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, and a substituted or unsubstituted $C_2$-$C_{60}$ heteroaryl group;

the C ring, the D ring, the E ring, the F ring, the G ring, and the H ring are each independently selected from the group of a 5-membered to 20-membered saturated ring, and a 5-membered to 20-membered unsaturated ring;

x is an integer from 0 to 2; and

* is a binding site with M in Formula 1.

2. The organometallic compound as claimed in claim 1, wherein M is selected from the group of ruthenium (Ru), rhodium (Rh), palladium (Pd), tungsten (W), rhenium (Re), osmium (Os), iridium (Ir), and platinum (Pt).

3. The organometallic compound as claimed in claim 1, wherein $X_1$ is $C(R_5)$.

4. The organometallic compound as claimed in claim 1, wherein $X_1$ is N.

5. The organometallic compound as claimed in claim 1, wherein:

$X_1$ is $C(R_5)$;

R₁ to R₅ are each independently one selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, an n-propyl group, an i-propyl group, an n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, a pentoxy group, and a substituted group that is substituted with at least one selected from the group of a deuterium atom, a fluorine atom, a hydroxyl group, a cyano group, a nitro group, and an amino group; and the substituted group is selected from the group of a substituted methyl group, a substituted ethyl group, a substituted n-propyl group, a substituted i-propyl group, a substituted n-butyl group, a substituted i-butyl group, a substituted t-butyl group, a substituted pentyl group, a substituted hexyl group, a substituted heptyl group, a substituted octyl group, a substituted nonyl group, a substituted decyl group, a substituted methoxy group, a substituted ethoxy group, a substituted propoxy group, a substituted butoxy group, and a substituted pentoxy group.

6. The organometallic compound as claimed in claim 1, wherein:

$X_1$ is N;

$R_1$ to $R_4$ are each independently one selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, an n-propyl group, an i-propyl group, an n-butyl group, an i-butyl group, a t-butyl group, a pentyl group, a hexyl group, a heptyl group, an octyl group, a nonyl group, a decyl group, a methoxy group, an ethoxy group, a propoxy group, a butoxy group, and pentoxy group, and a substituted group that is substituted with at least one selected from the group of a deuterium atom, a fluorine atom, a hydroxyl group, a cyano group, a nitro group, and an amino group; and the substituted group is selected from the group of a substituted methyl group, a substituted ethyl group, a substituted n-propyl group, a substituted i-propyl group, a substituted n-butyl group, a substituted i-butyl group, a substituted t-butyl group, a substituted pentyl group, a substituted hexyl group, a substituted heptyl group, a substituted octyl group, a substituted nonyl group, a substituted decyl group, a substituted methoxy group, a substituted ethoxy group, a substituted propoxy group, a substituted butoxy group, and a substituted pentoxy group.

7. The organometallic compound as claimed in claim 1, wherein:

i) $R_2$ and $R_3$ are linked together so that the organometallic compound is represented by Formula 1A;

ii) $X_1$ is $C(R_5)$, and $R_4$ and $R_5$ are linked together so that the organometallic compound is represented by Formula 1B; or iii) $R_2$ and $R_3$ are linked together, $X_1$ is $C(R_5)$, and $R_4$ and $R_5$ are linked together so that the organometallic compound is represented by Formula 1C:

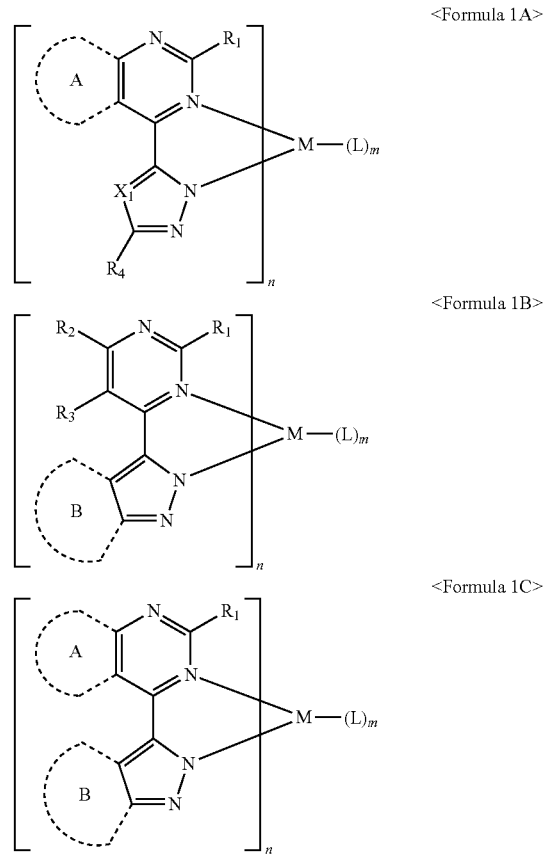

<Formula 1A>

<Formula 1B>

<Formula 1C> wherein, in Formulae 1A, 1B, and 1C:

M, $X_1$, $R_1$ to $R_5$, n, L, and m are as defined in Formula 1; and the A ring and the B ring are each independently selected from the group of a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, and a substituted or unsubstituted $C_2$-$C_{20}$ heteroaromatic ring.

8. The organometallic compound as claimed in claim 7, wherein:

the organometallic compound is represented by Formula 1A or Formula 1C;

the A ring is at least one selected from the group of benzene, pentalene, indene, naphthalene, azulene, heptalene, indacene, acenaphthylene, fluorene, spiro-fluorene, phenalene, phenanthrene, anthracene, fluoranthene, triphenylene, pyrene, chrysene, and a substituted group that is substituted with at least one selected from the group of:

a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, —$N(Q_{11})(Q_{12})$, and —$Si(Q_{13})(Q_{14})(Q_{15})$;

$Q_{11}$ to $Q_{15}$ are each independently selected from the group of a hydrogen atom, a $C_1$-$C_{10}$ alkyl group, a $C_6$-$C_{20}$ aryl group, and a $C_2$-$C_{20}$ heteroaryl group; and the substituted group is selected from the group of a substituted benzene, a substituted pentalene, a substituted indene, a substituted naphthalene, a substituted azulene, a substituted heptalene, a substituted indacene, a substituted acenaphthylene, a substituted fluorene, a substituted Spiro-fluorene, a substituted phenalene, a substituted phenanthrene, a substituted anthracene, a substituted fluoranthene, a substituted triphenylene, a substituted pyrene, and a substituted chrysene.

9. The organometallic compound as claimed in claim 7, wherein:

the organometallic compound is represented by Formula 1B or Formula 1C;

the B ring is at least one selected from the group of cyclopropane, cyclobutane, cyclopentane, cyclohexane, cycloheptane, cyclooctane, cyclopentene, cyclopentadiene, cyclohexadiene, cycloheptadiene, bicyclo-heptane, bicyclo-octane, benzene, pentalene, indene, naphthalene, azulene, heptalene, indacene, acenaphthylene, fluorene, spiro-fluorene, phenalene, phenanthrene, anthracene, fluoranthene, triphenylene, pyrene, chrysene, and a substituted group that is substituted with at least one selected from the group of:

a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, —$N(Q_{11})(Q_{12})$, and —$Si(Q_{13})(Q_{14})(Q_{15})$;

$Q_{11}$ to $Q_{15}$ are each independently selected from the group of a hydrogen atom, a $C_1$-$C_{10}$ alkyl group, a $C_6$-$C_{20}$ aryl group, and a $C_2$-$C_{20}$ heteroaryl group;

the substituted group is selectd from the group of a substituted cyclopropane, a substituted cyclobutane, a substituted cyclopentane, a substituted cyclohexane, a substituted cycloheptane, a substituted cyclooctane, a substituted cyclopentene, a substituted cyclopentadiene, a substituted cyclohexadiene, a substituted cycloheptadiene, a substituted bicyclo-heptane, a substituted bicyclo-octane, a substituted benzene, a substituted pentalene, a substituted indene, a substituted naphthalene, a substituted azulene, a substituted heptalene, a substituted indacene, a substituted acenaphthylene, a substituted fluorene, a substituted spiro-fluorene, a substituted phenalene, a substituted phenanthrene, a substituted anthracene, a substituted fluoranthene, a substituted triphenylene, a substituted pyrene, and a substituted chrysene.

10. The organometallic compound as claimed in claim 7, wherein:

the organometallic compound is represented by one selected from the group of Formulae 1A-(1), 1B-(1), 1B-(2), 1B-(3), 1C-(1), 1C-(2), 1C-(3), and 1D-(1):

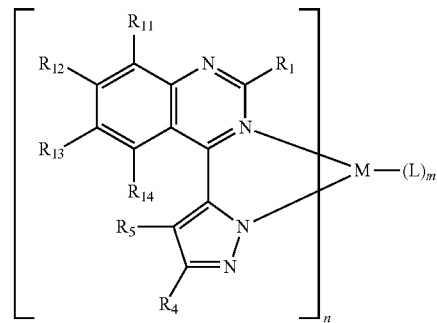

<Formula 1A-(1)>

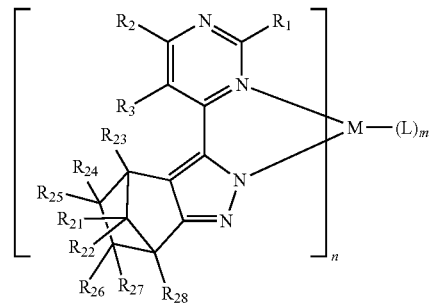

<Formula 1B-(1)>

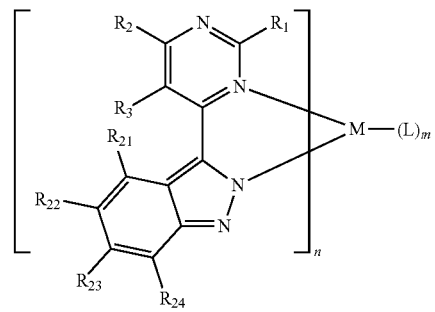

<Formula 1B-(2)>

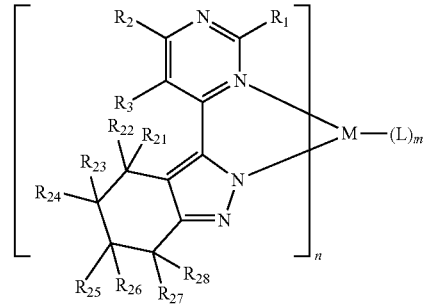

<Formula 1B-(3)>

<Formula 1C-(1)>

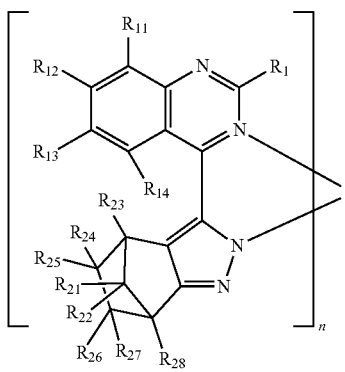

<Formula 1C-(2)>

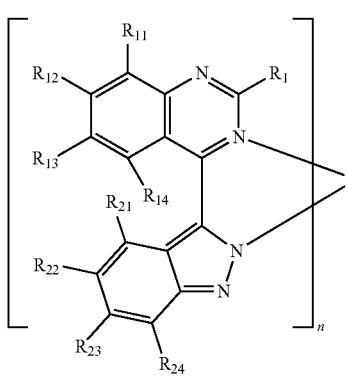

<Formula 1C-(3)>

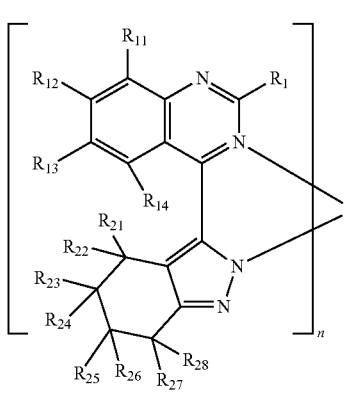

<Formula 1D-(1)>

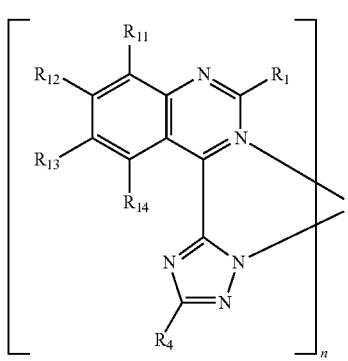

wherein, in Formulae 1A-(1), 1B-(1), 1B-(2), 1B-(3), 1C-(1), 1C-(2), 1C-(3), and 1D-(1):

$R_1$ to $R_5$, $R_{11}$ to $R_{14}$, and $R_{21}$ to $R_{28}$ are each independently selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a substituted $C_1$-$C_{20}$ alkyl group, a substituted $C_1$-$C_{20}$ alkoxy group, a phenyl group, a naphthyl group, an anthryl group, a fluorenyl group, a carbazolyl group, a pyridinyl group, a pyrimidinyl group, a triazinyl group, and a substituted cyclic group that is substituted with at least one selected from the group of:
  a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group;

the substituted $C_1$-$C_{20}$ alkyl group and the substituted $C_1$-$C_{20}$ alkoxy group are each substituted with at least one selected from the group of a deuterium atom, a halogen atom, a hydroxyl group, a cyano group, a nitro group, and an amino group;

the substituted cyclic group is selected from the group of a substituted phenyl group, a substituted naphthyl group, a substituted anthryl group, a substituted fluorenyl group, a substituted carbazolyl group, a substituted pyridinyl group, a substituted pyrimidinyl group, and a substituted triazinyl group;

n is an integer from 1 to 3; and m is an integer from 0 to 4, wherein, when m is 1, 2, 3, or 4, L is as defined in Formula 1.

11. The organometallic compound as claimed in claim 1, wherein:
m is 1, 2, 3, or 4.

12. The organometallic compound as claimed in claim 11, wherein:

$R_{31}$, $R_{32a}$, $R_{32b}$, $R_{32c}$, $R_{33a}$, $R_{33b}$, $R_{34}$, $R_{35}$, $R_{36}$, $R_{37}$, $R_{38}$, and $R_{39}$ are each independently selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a substituted $C_1$-$C_{20}$ alkyl group, a substituted $C_1$-$C_{20}$ alkoxy group, a phenyl group, a naphthyl group, an anthryl group, a fluorenyl group, a carbazolyl group, a pyridinyl group, a pyrimidinyl group, and a triazinyl group, and a substituted cyclic group that is substituted with at least one selected from the group of:
  a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group;

the substituted $C_1$-$C_{20}$ alkyl group and the substituted $C_1$-$C_{20}$ alkoxy group are each substituted with at least one selected from the group of a deuterium atom, a halogen atom, a hydroxyl group, a cyano group, a nitro group, and an amino group; and the substituted cyclic group is selected from the group of a substituted phenyl group, a substituted naphthyl group, a substituted anthryl group, a substituted fluorenyl group, a substituted carbazolyl group, a substituted pyridinyl group, a substituted pyrimidinyl group, and a substituted triazinyl.

13. The organometallic compound as claimed in claim 11, wherein:
the at least one of $L_m$ is represented by Formula 2C; and $X_{11a}$ and $X_{11b}$ in Formula 2C are each independently selected from the group of O, $P(R_{36})(R_{37})$, and $As(R_{38})(R_{39})$.

14. The organometallic compound as claimed in claim 11, wherein:
the at least one of $L_m$ is represented by one selected from the group of Formulae 2D, 2E, and 2F;
the C ring, the D ring, the E ring, the F ring, the G ring, and the H ring in Formulae 2D, 2E, and 2F are each independently a substituted or unsubstituted benzene, a substituted or unsubstituted pentalene, a substituted or unsubstituted indene, a substituted or unsubstituted naphthalene, a substituted or unsubstituted azulene, a substituted or unsubstituted heptalene, a substituted or unsubstituted indacene, a substituted or unsubstituted acenaphthylene, a substituted or unsubstituted fluorene, a substituted or unsubstituted spiro-fluorene, a substituted or unsubstituted phenalene, a substituted or unsubstituted phenanthrene, a substituted or unsubstituted anthracene, a substituted or unsubstituted fluoranthene, a substituted or unsubstituted triphenylene, a substituted or unsubstituted pyrene, a substituted or unsubstituted chrysene, a substituted or unsubstituted pyrrole, a substituted or unsubstituted imidazole, a substituted or unsubstituted pyrazole, a substituted or unsubstituted isothiazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted isoindole, a substituted or unsubstituted indole, a substituted or unsubstituted indazole, a substituted or unsubstituted purine, a substituted or unsubstituted isoquinoline, a substituted or unsubstituted quinoline, a substituted or unsubstituted phthalazine, a substituted or unsubstituted quinoxaline, a substituted or unsubstituted quinazoline, or a substituted or unsubstituted cinnoline;
when the C ring is substituted with at least two substituents, adjacent two of the at least two substituents are optionally linked together to form one selected from the group of a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, and a substituted or unsubstituted $C_2$-$C_{20}$ heteroaromatic ring;
when the D ring is substituted with at least two substituents, adjacent two of the at least two substituents are optionally linked together to form one selected from the group of a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, and a substituted or unsubstituted $C_2$-$C_{20}$ heteroaromatic ring;
when the E ring is substituted with at least two substituents, adjacent two of the at least two substituents are optionally linked together to form one selected from the group of a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, and a substituted or unsubstituted $C_2$-$C_{20}$ heteroaromatic ring;
when the F ring is substituted with at least two substituents, adjacent two of the at least two substituents are optionally linked together to form one selected from the group of a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, and a substituted or unsubstituted $C_2$-$C_{20}$ heteroaromatic ring;
when the G ring is substituted with at least two substituents, adjacent two of the at least two substituents are optionally linked together to form one selected from the group of a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, and a substituted or unsubstituted $C_2$-$C_{20}$ heteroaromatic ring; and
when the H ring is substituted with at least two substituents, adjacent two of the at least two substituents are optionally linked together to form one selected from the group of a substituted or unsubstituted $C_4$-$C_{20}$ alicyclic ring, a substituted or unsubstituted $C_2$-$C_{20}$ heteroalicyclic ring, a substituted or unsubstituted $C_6$-$C_{20}$ aromatic ring, and a substituted or unsubstituted $C_2$-$C_{20}$ heteroaromatic ring.

15. The organometallic compound as claimed in claim 1, wherein:
the organometallic compound is represented by one selected from the group of Formulae 3 and 4:

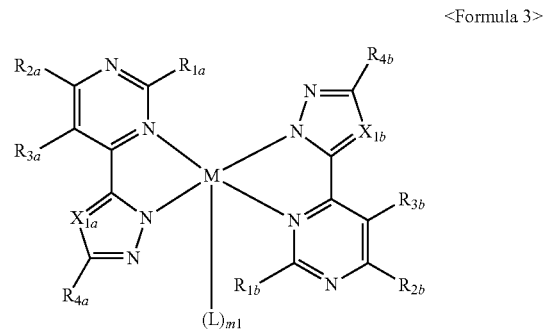

<Formula 3>

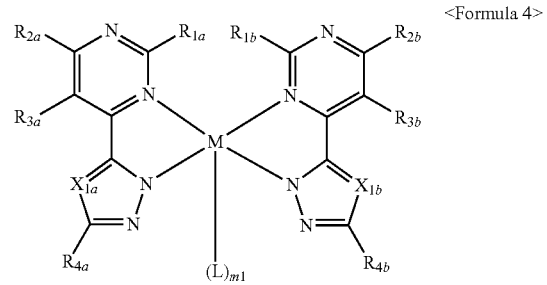

<Formula 4> wherein, in Formulae 3 and 4:
M is a transition metal;
$X_{1a}$ is N or $C(R_{5a})$;
$X_{1b}$ is N or $C(R_{5b})$;
$R_{1a}$ to $R_{5a}$ and $R_{1b}$ to $R_{5b}$ are each independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —N($Q_1$)($Q_2$),
—Si($Q_3$)($Q_4$)($Q_5$), —C(=O)($Q_6$), and a binding site with an adjacent ligand via a single bond or a divalent linking group;

two substituents of $R_{1a}$ to $R_{5a}$ are optionally linked together to form one selected from the group of a substituted or unsubstituted $C_4$-$C_{20}$ alicyclic ring, a substituted or unsubstituted $C_2$-$C_{20}$ hetero alicyclic ring, a substituted or unsubstituted $C_6$-$C_{20}$ aromatic ring, and a substituted or unsubstituted $C_2$-$C_{20}$ heteroaromatic ring;

two substituents of $R_{1b}$ to $R_{5b}$ are optionally linked together to form one selected from the group of a substituted or unsubstituted $C_4$-$C_{20}$ alicyclic ring, a substituted or unsubstituted $C_2$-$C_{20}$ hetero alicyclic ring, a substituted or unsubstituted $C_6$-$C_{20}$ aromatic ring, and a substituted or unsubstituted $C_2$-$C_{20}$ heteroaromatic ring;

$Q_1$ to $Q_6$ are each independently a hydrogen atom, a substituted or unsubstituted $C_1$-$C_{60}$ alkyl group, a substituted or unsubstituted $C_6$-$C_{60}$ aryl group, and a substituted or unsubstituted $C_2$-$C_{60}$ heteroaryl group; and m1 is 0, 1, or 2, wherein when m1 is 1 or 2, L is as defined in Formula 1.

16. The organometallic compound as claimed in claim 15, wherein:
the organometallic compound is represented by Formula 3, and
$R_{1a}$=$R_{1b}$, $R_{2a}$=$R_{2b}$, $R_{3a}$=$R_{3b}$, $R_{4a}$=$R_{4b}$, $X_{1a}$=$X_{1b}$, M=Pt, and m1=0.

17. The organometallic compound as claimed in claim 15, wherein:
the organometallic compound is represented by Formula 4; and
$R_{1a}$=$R_{1b}$, $R_{2a}$=$R_{2b}$, $R_{3a}$=$R_{3b}$, $R_{4a}$=$R_{4b}$, $X_{1a}$=$X_{1b}$, M=Pt, and m1=0.

18. The organometallic compound as claimed in claim 1, wherein
the organometallic compound is represented by one selected from the group of Formulae 3A-(1), 3A-(2), 3A-(3), 3A-(4), 3A-(5), 3A-(6), 3A-(7), 3A-(8), and 3A-(9):

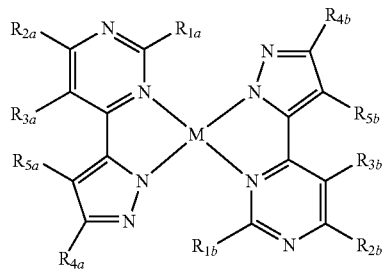
<Formula 3A-(1)>

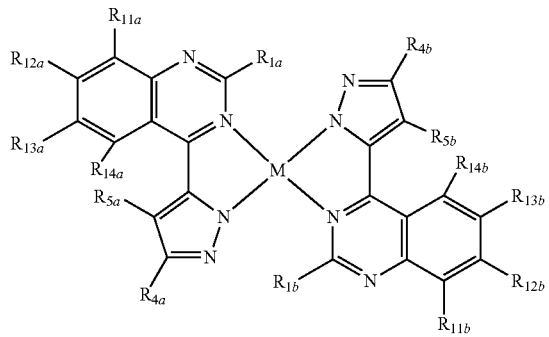
<Formula 3A-(2)>

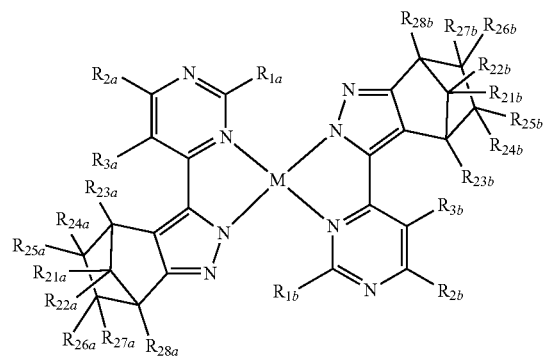
<Formula 3A-(3)>

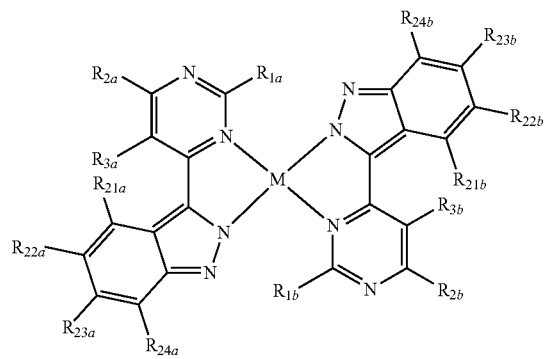
<Formula 3A-(4)>

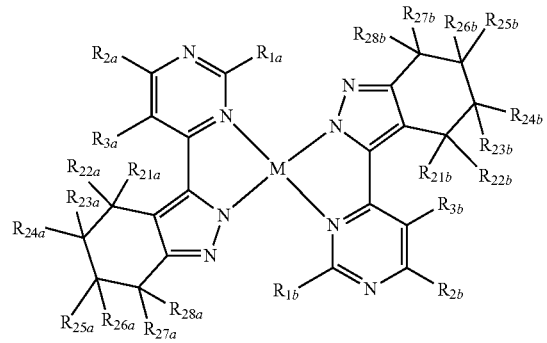
<Formula 3A-(5)>

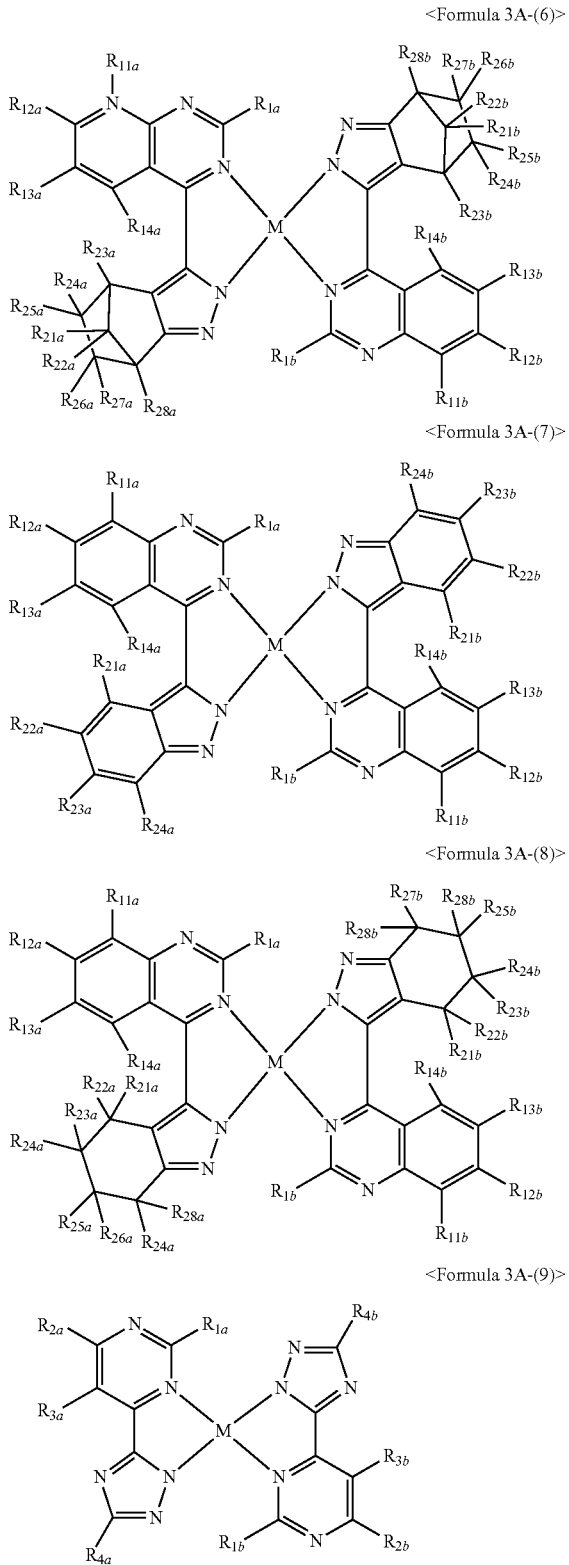

<Formula 3A-(6)>

<Formula 3A-(7)>

<Formula 3A-(8)>

<Formula 3A-(9)> wherein, in Formulae 3A-(1), 3A-(2), 3A-(3), 3A-(4), 3A-(5), 3A-(6), 3A-(7), 3A-(8), and 3A-(9):

M is platinum (Pt); and $R_{1a}$ to $R_{5a}$, $R_{1b}$ to $R_{5b}$, $R_{11a}$ to $R_{14a}$, $R_{11b}$ to $R_{14b}$, $R_{21a}$ to $R_{28a}$, and $R_{21b}$ to $R_{28b}$ are each independently selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof a phosphoric acid group or a salt thereof, a $C_1$-$C_{20}$ alkyl group, and a $C_1$-$C_{20}$ alkoxy group, a substituted $C_1$-$C_{20}$ alkyl group, a substituted $C_1$-$C_{20}$ alkoxy group, a phenyl group, a naphthyl group, an anthryl group, a fluorenyl group, a carbazolyl group, a pyridinyl group, a pyrimidinyl group, a triazinyl group, and a substituted cyclic group that is substituted with at least one selected from the group of:

a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group;

the substituted $C_1$-$C_{20}$ alkyl group and the substituted $C_1$-$C_{20}$ alkoxy group are each substituted with at least one selected from the group of a deuterium atom, a halogen atom, a hydroxyl group, a cyano group, a nitro group, and an amino group;

the substituted cyclic group is selected from the group of a substituted phenyl group, a substituted naphthyl group, a substituted anthryl group, a substituted fluorenyl group, a substituted carbazolyl group, a substituted pyridinyl group, a substituted pyrimidinyl group, and a substituted triazinyl group.

19. The organometallic compound of claim 18, wherein:

the organometallic compound is represented by one selected from the group of Formulae 3A-(1), 3A-(2), 3A-(4), 3A-(6), 3A-(8), and 3A-(9); and $R_{1a}$=$R_{1b}$, $R_{2a}$=$R_{2b}$, $R_{3a}$=$R_{3b}$, $R_{4a}$=$R_{4b}$, $R_{5a}$=$R_{5b}$, $R_{11a}$=$R_{11b}$, $R_{12a}$=$R_{12b}$, $R_{13a}$=$R_{13b}$, $R_{14a}$=$R_{14b}$, $R_{21a}$=$R_{21b}$, $R_{22a}$=$R_{22b}$, $R_{23a}$=$R_{23b}$, $R_{24a}$=$R_{24b}$, $R_{25a}$=$R_{25b}$, $R_{26a}$=$R_{26b}$, $R_{27a}$=$R_{27b}$, and $R_{28a}$=$R_{28b}$.

20. The organometallic compound as claimed in claim 1, wherein:

the organometallic compound is represented by Formula 4-(a):

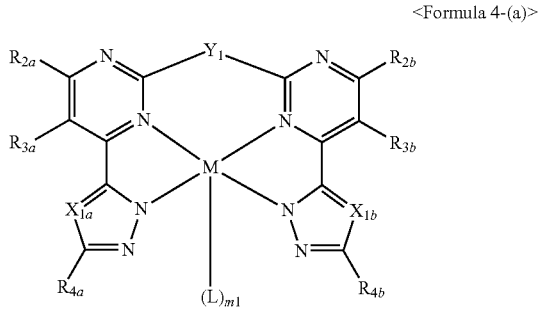

<Formula 4-(a)> wherein, in Formula 4-(a):

M is a transition metal;

$X_{1a}$ is N or C($R_{5a}$);

$X_{1b}$ is N or C($R_{5b}$);

$R_{2a}$ to $R_{5a}$ and $R_{2b}$ to $R_{5b}$ are each independently selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —N($Q_1$)($Q_2$), —Si($Q_3$)($Q_4$)($Q_5$), —C(=O)($Q_6$), and a binding site with an adjacent ligand via a single bond or a divalent linking group;

two substituents of $R_{2a}$ to $R_{5a}$ are optionally linked together to form at least one selected from the group of a substituted or unsubstituted $C_4$-$C_{20}$ alicyclic ring, a substituted or unsubstituted $C_2$-$C_{20}$ hetero alicyclic ring, a substituted or unsubstituted $C_6$-$C_{20}$ aromatic ring, and a substituted or unsubstituted $C_2$-$C_{20}$ heteroaromatic ring;

two substituents of $R_{2b}$ to $R_{5b}$ are optionally linked together to form at least one selected from the group of a substituted or unsubstituted $C_4$-$C_{20}$ alicyclic ring, a substituted or unsubstituted $C_2$-$C_{20}$ hetero alicyclic ring, a substituted or unsubstituted $C_6$-$C_{20}$ aromatic ring, and a substituted or unsubstituted $C_2$-$C_{20}$ heteroaromatic ring;

$Q_1$ to $Q_6$ are each independently selected from the group of a hydrogen atom, a substituted or unsubstituted $C_1$-$C_{60}$ alkyl group, a substituted or unsubstituted $C_6$-$C_{60}$ aryl group, and a substituted or unsubstituted $C_2$-$C_{60}$ heteroaryl group;

m1 is 0, 1, or 2, where, when m1 is 1 or 2, L is as defined in Formula 1;

$Y_1$ is a single bond or a divalent linking group including at least one selected from the group of —O—, —S—, —N($Z_1$)—, —[C($Z_2$)($Z_3$)]$_a$—, and —[Si($Z_4$)($Z_5$)]$_b$—;

$Z_1$ to $Z_5$ are each independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, or a $C_2$-$C_{60}$ heteroaryl group, and a and b are each independently an integer from 1 to 4.

21. The organometallic compound as claimed in claim 20, wherein:
$Y_1$ is —N($Z_1$)—;
$Z_1$ is at least one selected from the group of a phenyl group, a naphthyl group, an anthryl group, a fluorenyl group, a carbazolyl group, a pyridinyl group, a pyrimidinyl group, a triazinyl group, and a substituted cyclic group that is substituted with at least one selected from the group of:
a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group; and the substituted cyclic group is selected from the group of a substituted phenyl group, a substituted naphthyl group, a substituted anthryl group, a substituted fluorenyl group, a substituted carbazolyl group, a substituted pyridinyl group, a substituted pyrimidinyl group, and a substituted triazinyl group.

22. The organometallic compound as claimed in claim 1, wherein n is 3, and m is 0.

23. The organometallic compound as claimed in claim 1, wherein n is 1, and m is an integer from 1 to 4.

24. An organometallic compound selected from the group of compounds 1 to 68:

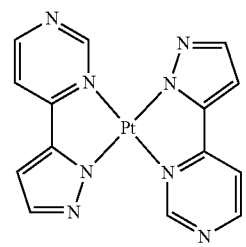

1

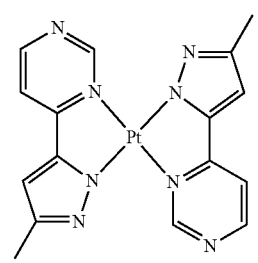

2

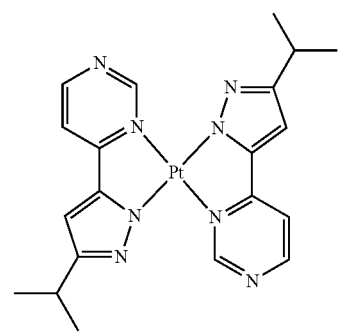

3

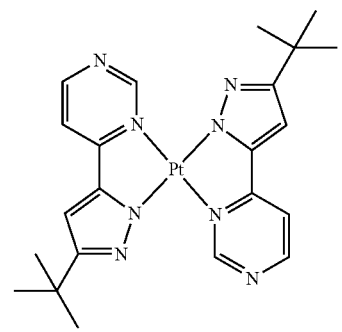

4

189
-continued
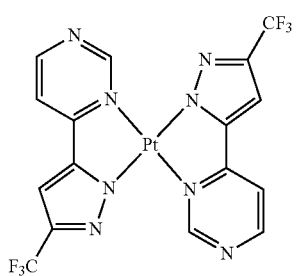
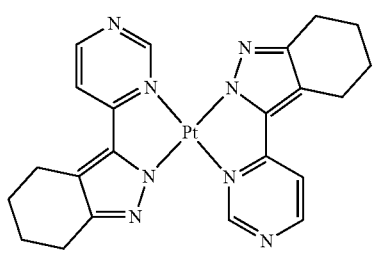
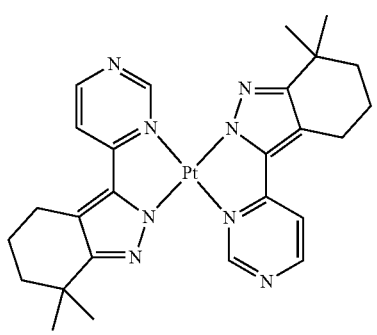
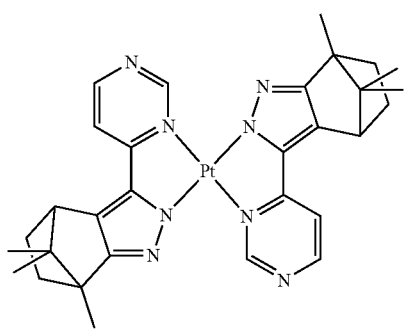
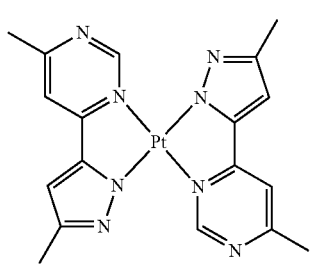
190
-continued
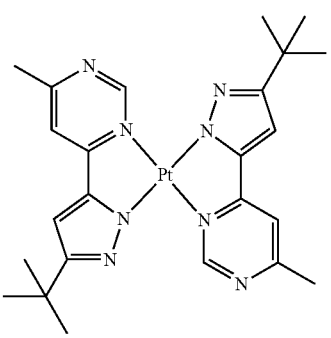
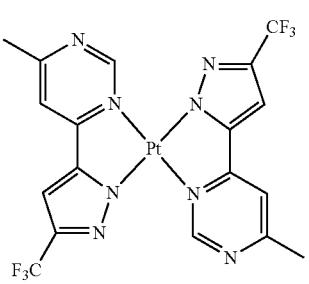
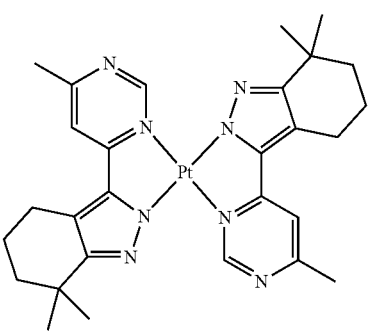
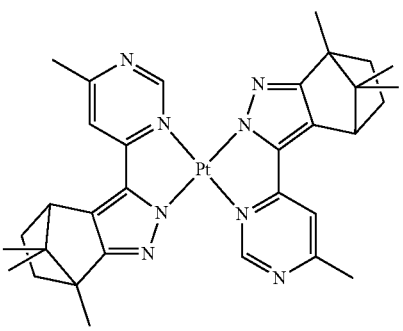
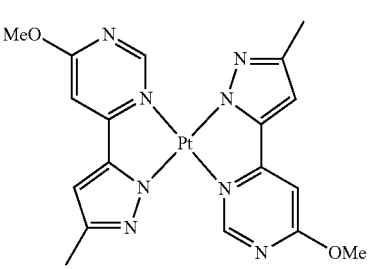

191
-continued
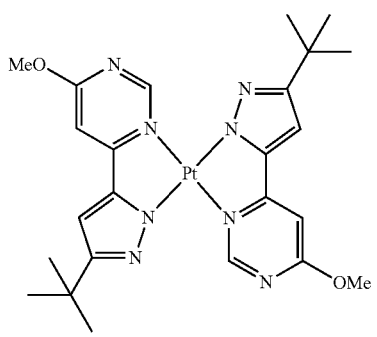
15
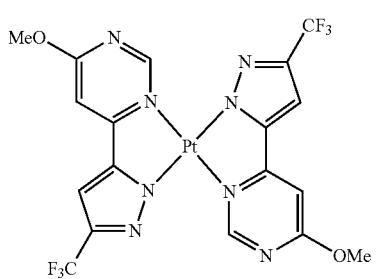
16
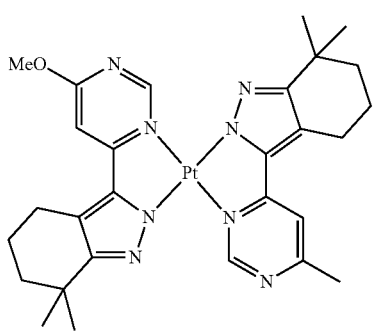
17
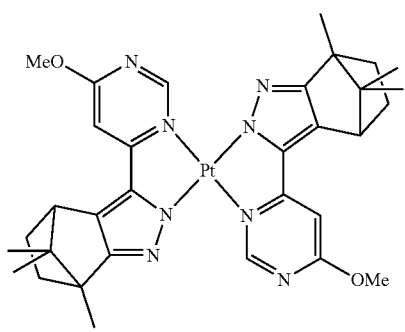
18
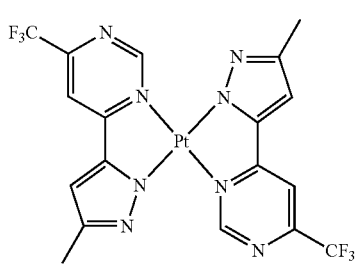
19
192
-continued
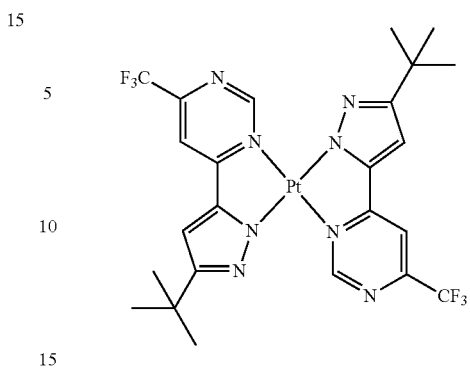
20
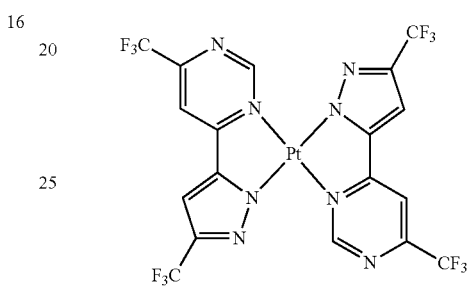
21
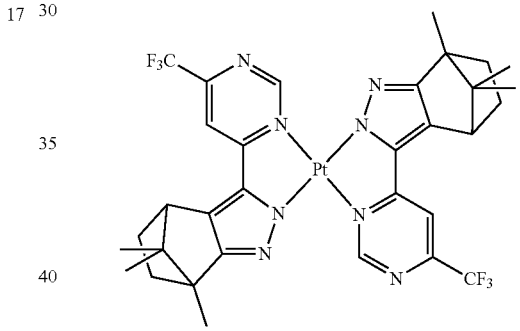
22
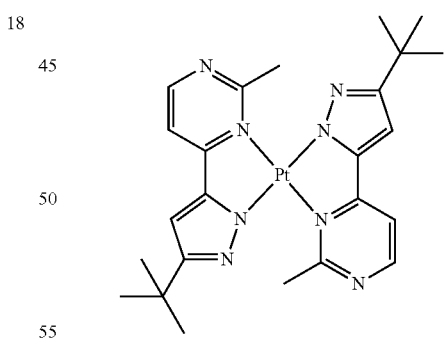
23
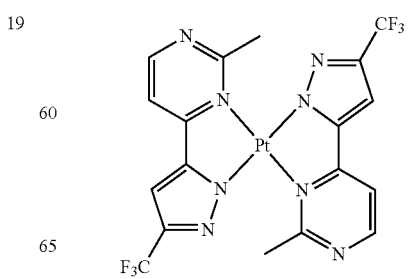
24

-continued
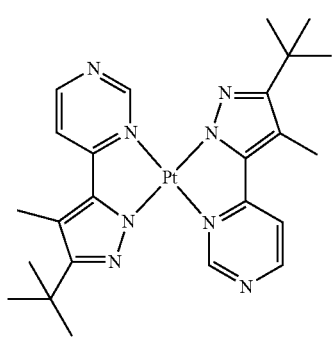
25
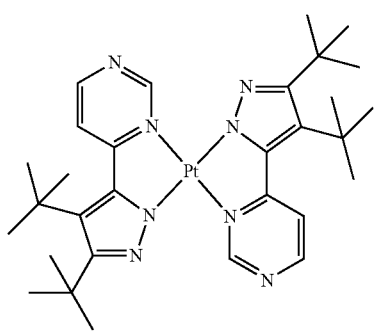
26
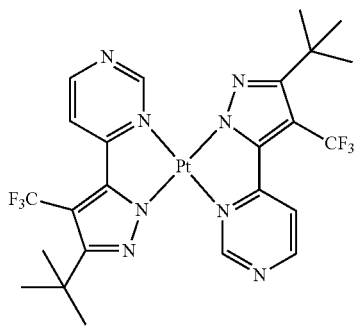
27
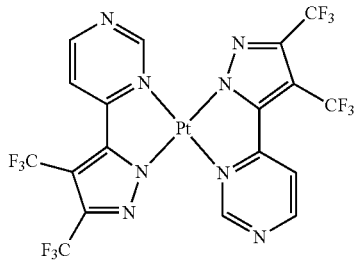
28
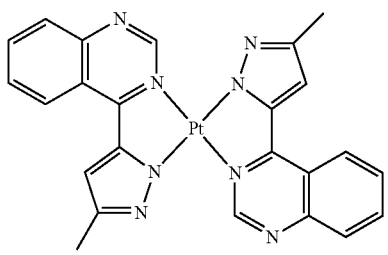
29
-continued
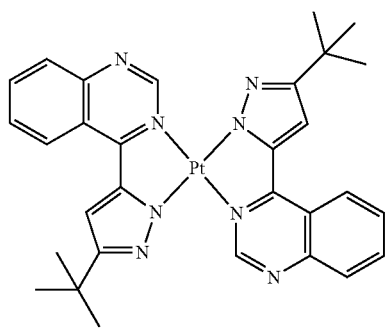
30
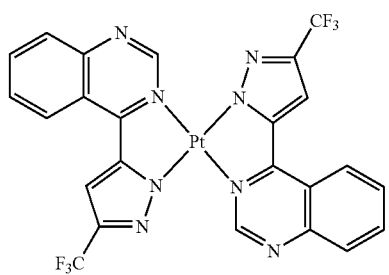
31
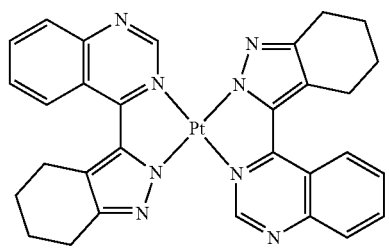
32
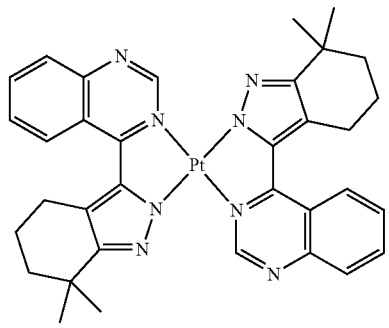
33
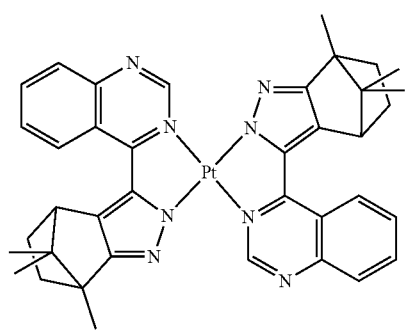
34

| 35 | 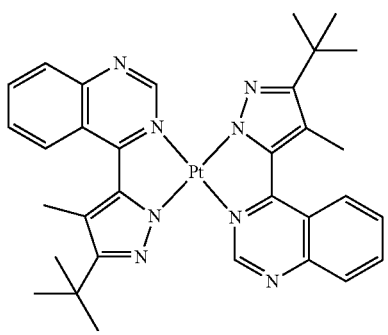 | 40 | 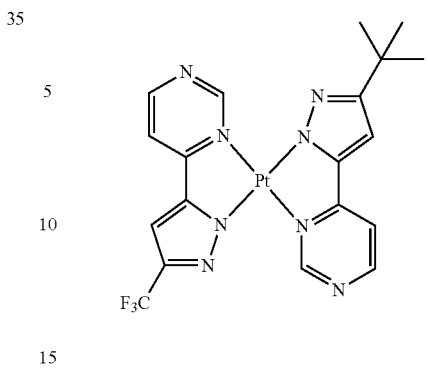 |
| 36 | 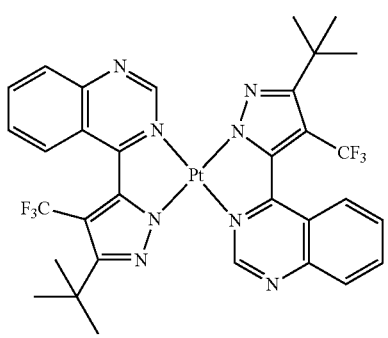 | 41 | 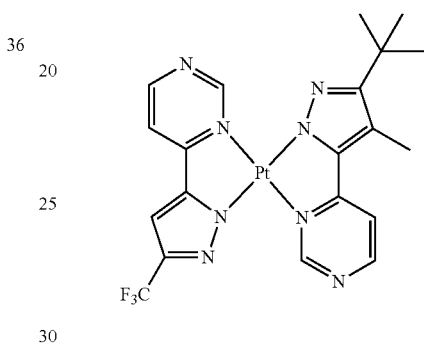 |
| 37 | 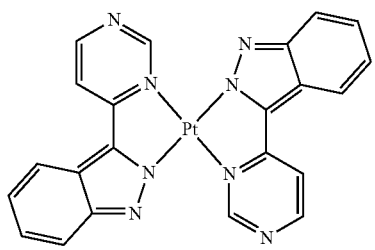 | 42 | 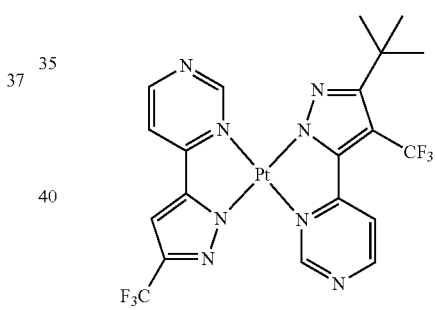 |
| 38 | 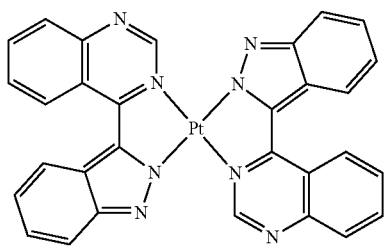 | 43 | 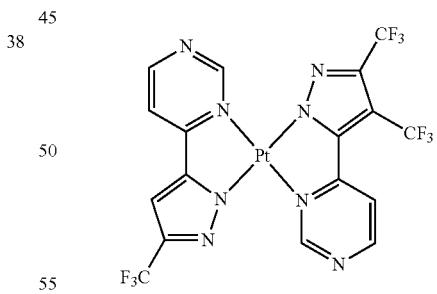 |
| 39 | 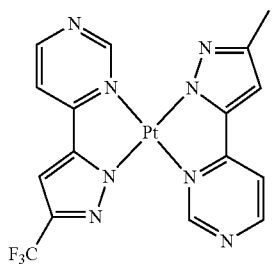 | 44 | 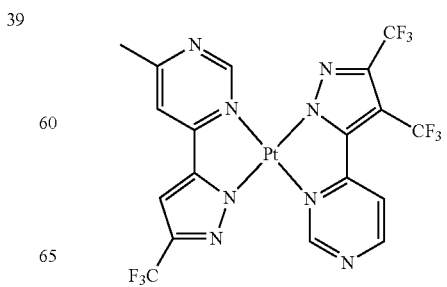 |

197
-continued
| | |
|---|---|
| 45 | 50 |
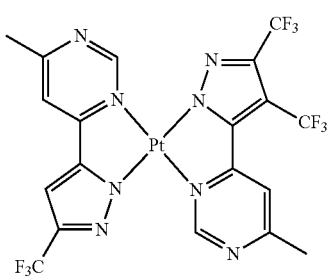
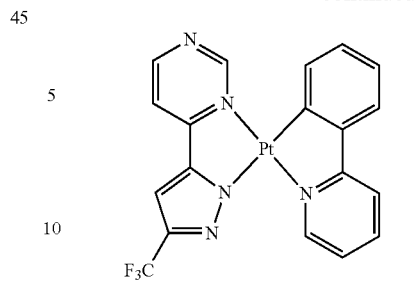
| | |
|---|---|
| 46 | 51 |
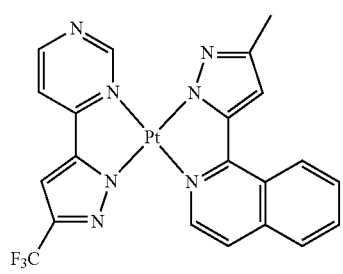
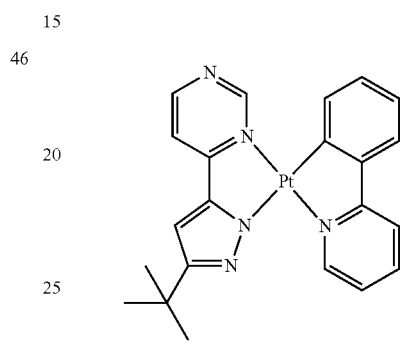
| | |
|---|---|
| 47 | 52 |
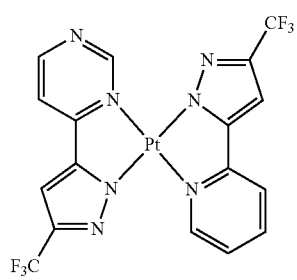
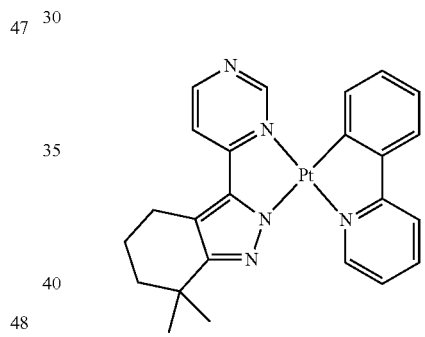
48
| | |
|---|---|
| | 53 |
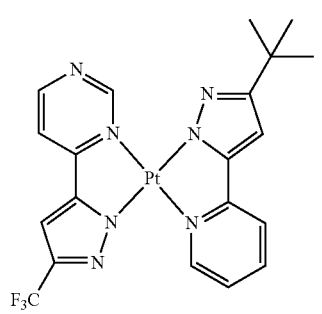
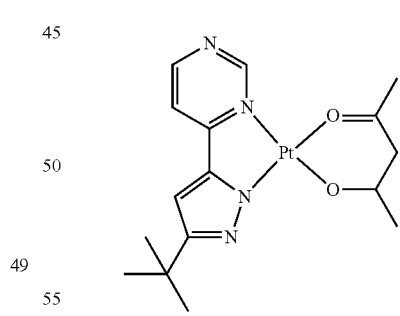
49
| | |
|---|---|
| | 54 |
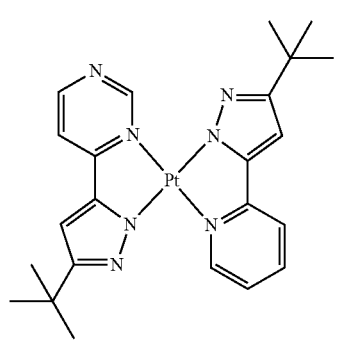
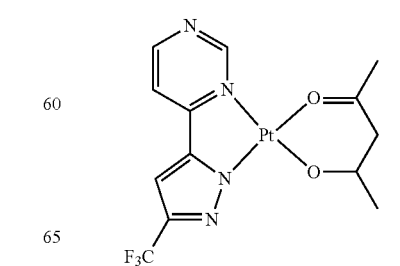
198
-continued 199
-continued
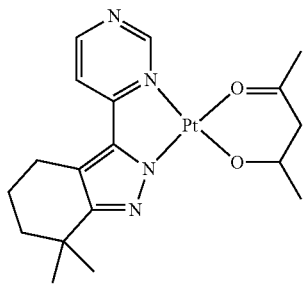
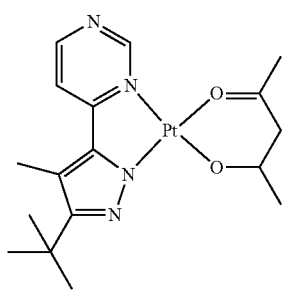
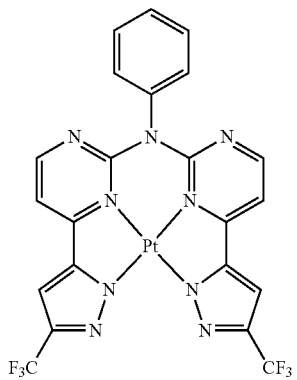
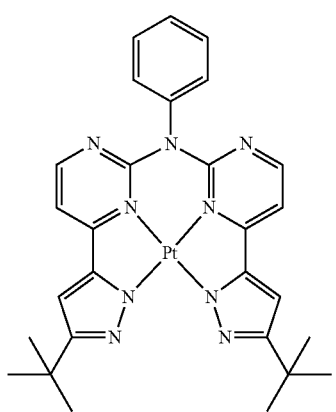
200
-continued
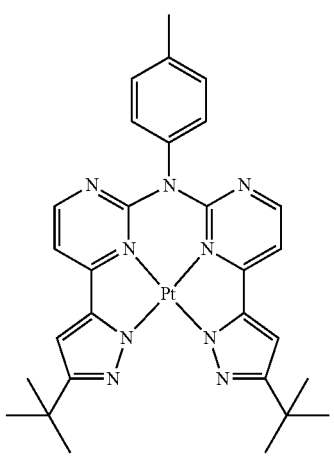
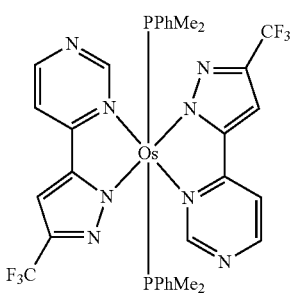
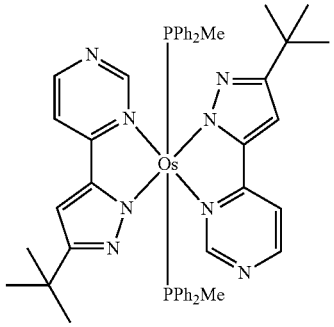
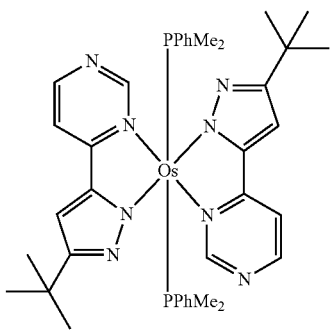

-continued

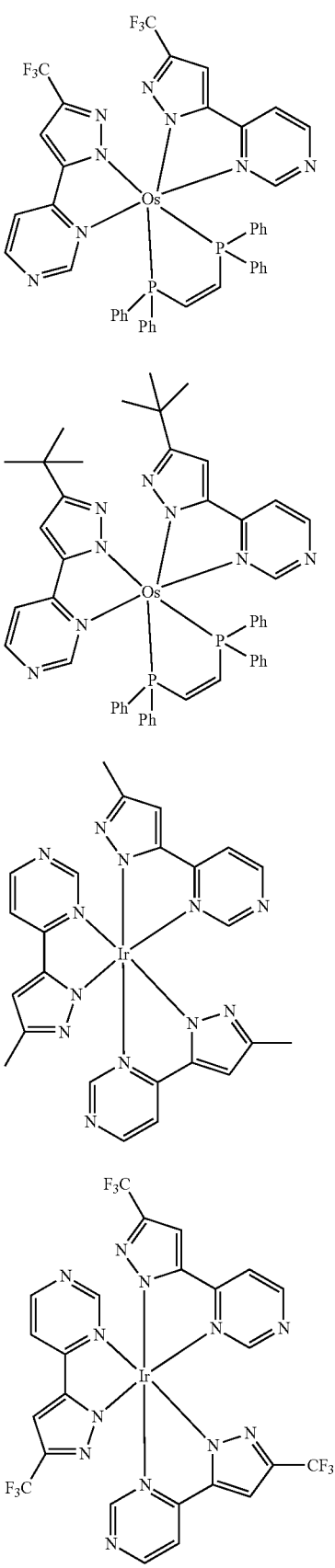

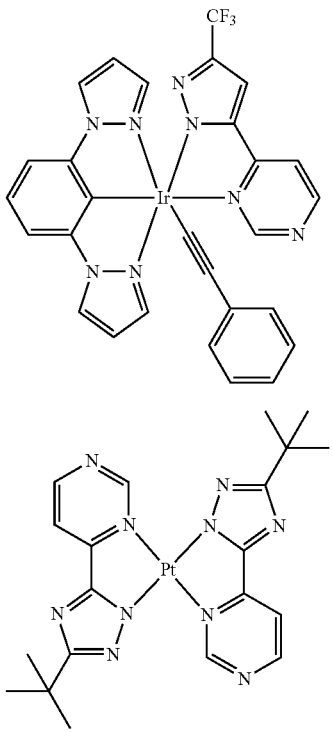

wherein, in compounds 60-62, Ph is a phenyl group and Me is a methyl group.

25. An organic light-emitting device, comprising:
a substrate;
a first electrode;
a second electrode opposite the first electrode; and
an organic layer between the first electrode and the second electrode, the organic layer including the organometallic compound as claimed in claim 1.

26. The organic light-emitting device as claimed in claim 25, wherein the organic layer includes at least one selected from the group of a hole injection layer, a hole transport layer, a functional layer having both hole injection and hole transport capabilities, a buffer layer, an electron blocking layer, an emission layer, a hole blocking layer, an electron transport layer, an electron injection layer, and a functional layer having both electron injection and electron transport capabilities.

27. The organic light-emitting device as claimed in claim 25, wherein:
the organic layer includes an emission layer;
the organometallic compound is in the emission layer; and
light is emitted from the emission layer based on a phosphorescence mechanism.

28. The organic light-emitting device as claimed in claim 27, wherein:
the organometallic compound in the emission layer serves as a dopant; and
the emission layer includes a carbazole-based compound as a host.

29. The organic light-emitting device as claimed in claim 28, wherein:
the carbazole-based compound is represented by Formula 10:

<Formula 10>

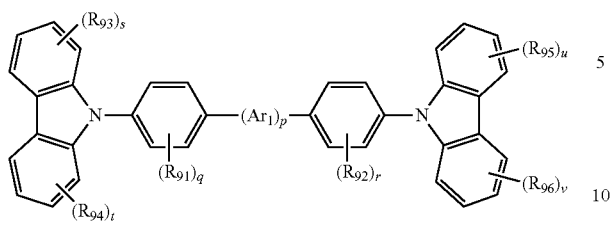

wherein, in Formula 10:
Ar₁ is selected from the group of a substituted or unsubstituted $C_1$-$C_{60}$ alkylene group, a substituted or unsubstituted $C_2$-$C_{60}$ alkenylene group, —C(═O)—, —N($R_{100}$)—, a substituted or unsubstituted $C_6$-$C_{60}$ arylene group, and a substituted or unsubstituted $C_2$-$C_{60}$ heteroarylene group;
$R_{100}$ is selected from the group of a substituted or unsubstituted $C_6$-$C_{60}$ aryl group, and a substituted or unsubstituted $C_2$-$C_{60}$ heteroaryl group;
p is an integer from 0 to 10;
$R_{91}$ to $R_{96}$ are each independently selected from the group of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, and a substituted or unsubstituted $C_2$-$C_{60}$ heteroaryl group;
two adjacent substituents of $R_{91}$ to $R_{96}$ are optionally linked together to form one selected from the group of a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic ring, and a substituted or unsubstituted $C_2$-$C_{20}$ heteroaromatic ring; and
q, r, s, t, u, and v are each independently an integer from 1 to 4.

30. The organic light-emitting device as claimed in claim 28, wherein the carbazole-based compound is one selected from the group of compounds H1 to H30:

H1

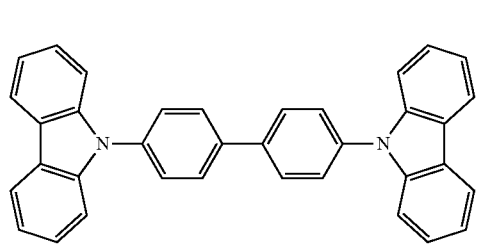

H2

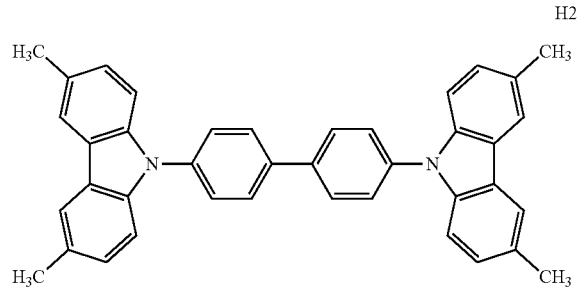

H3

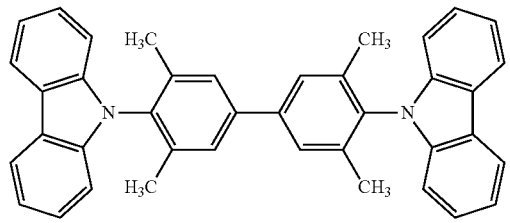

H4

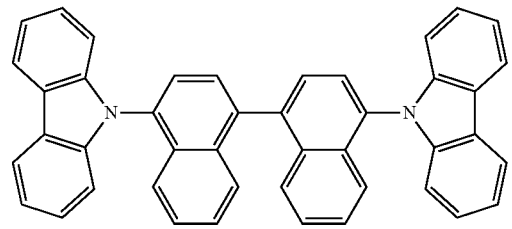

H5

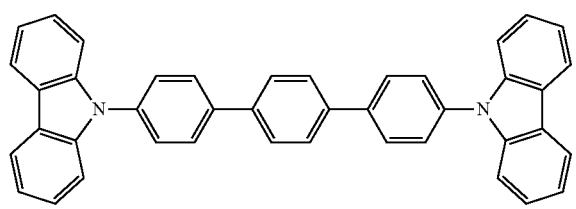

H6

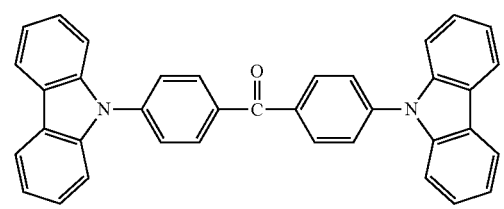

-continued
H7
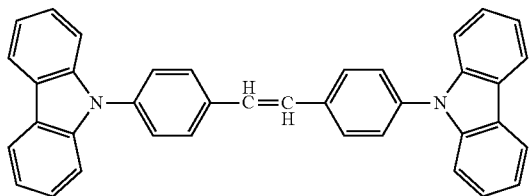
H8
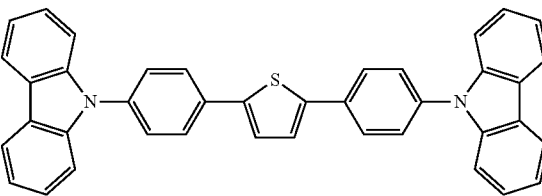
H9
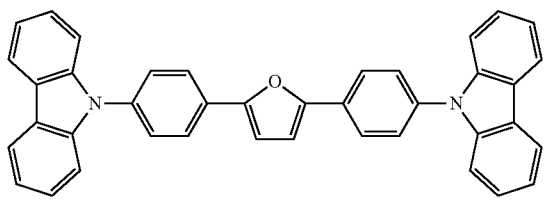
H10
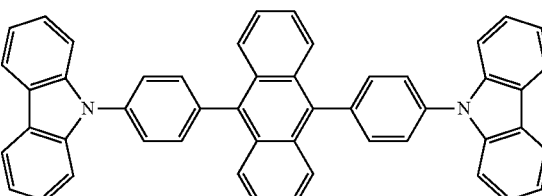
H11
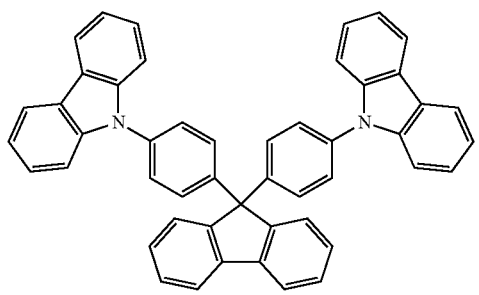
H12
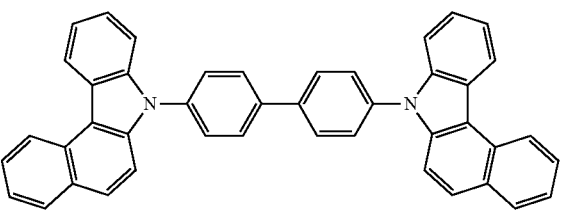
H13
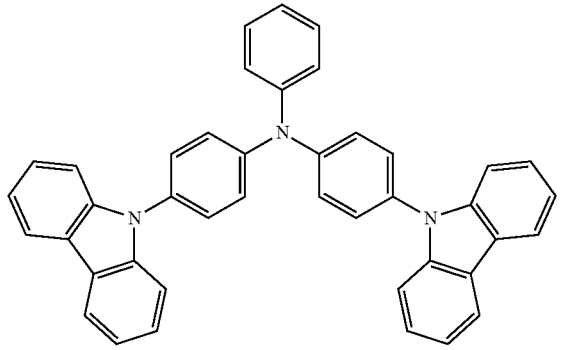
H14
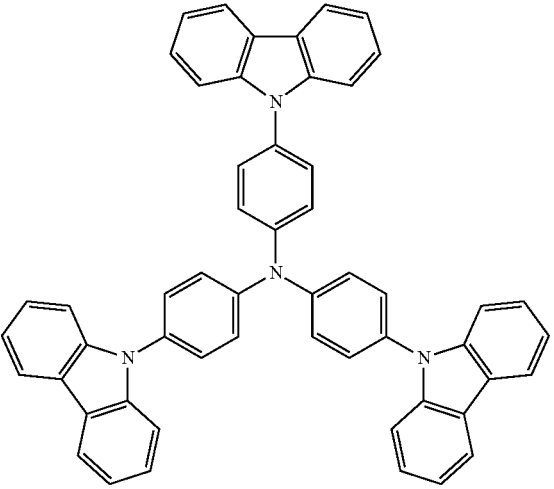
H15
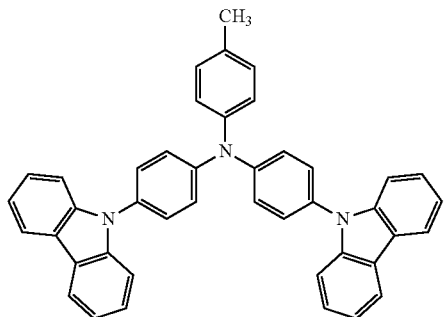
H16
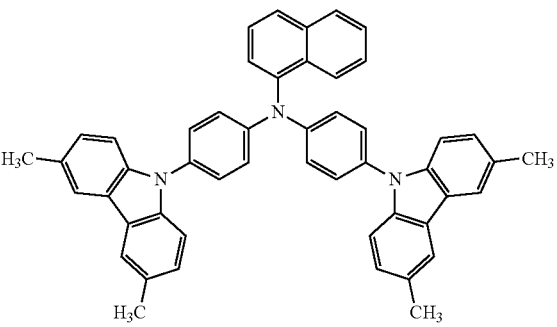

-continued
207
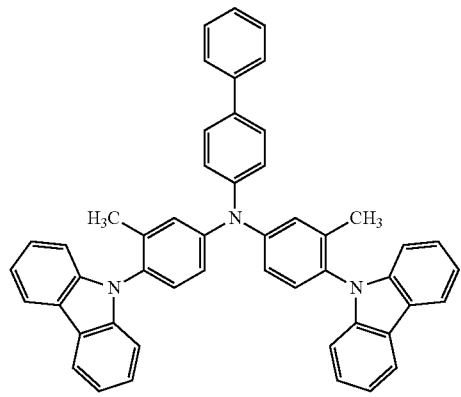
H17
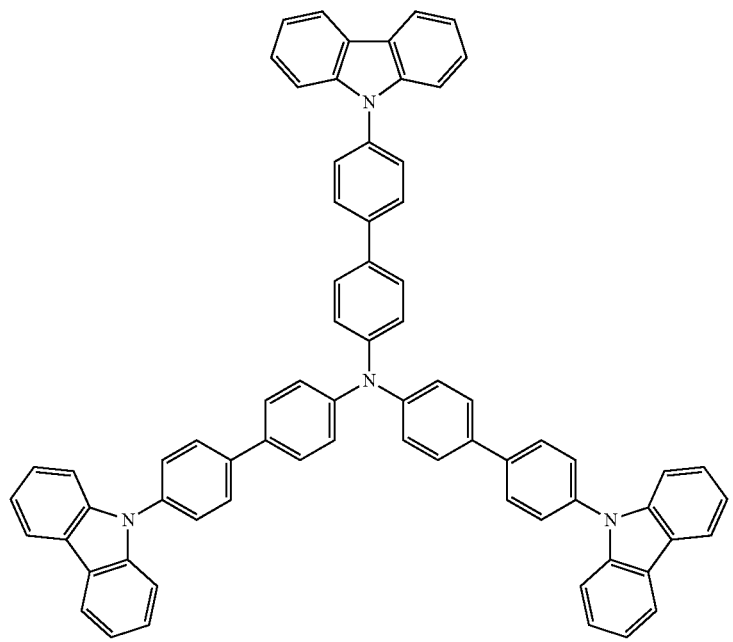
H19
208
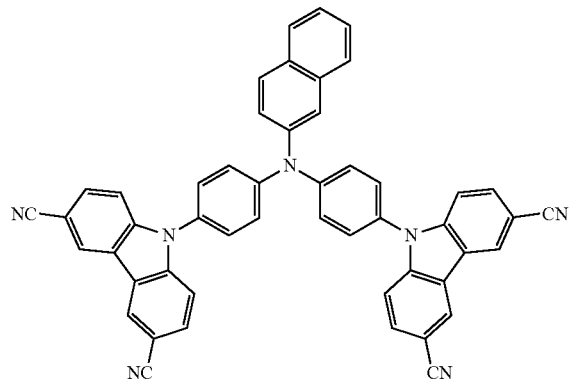
H18
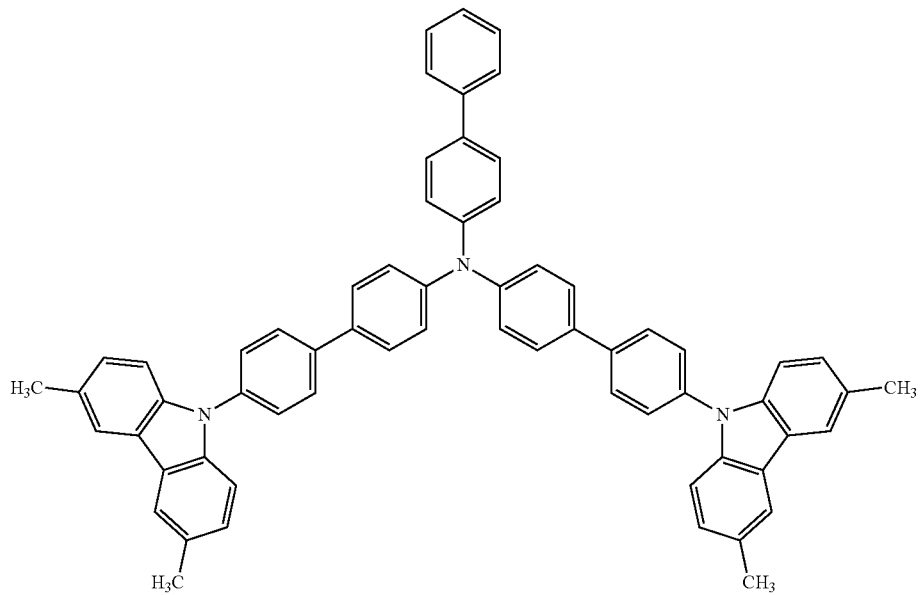
H20

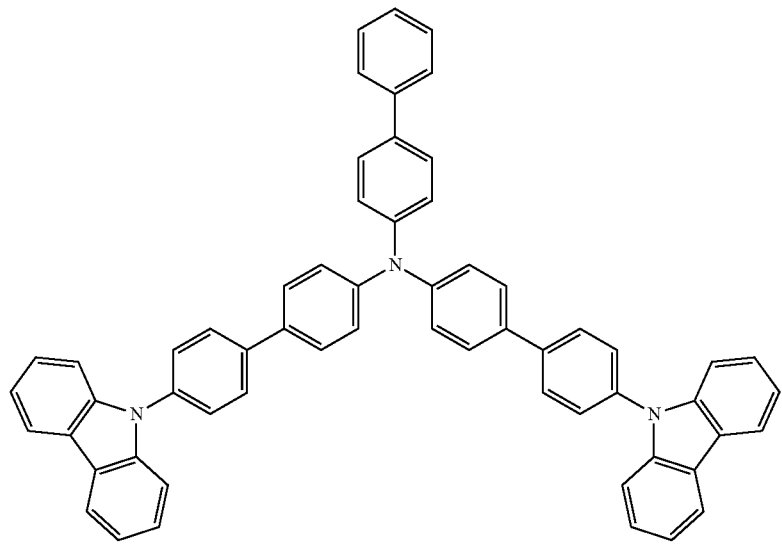
H21
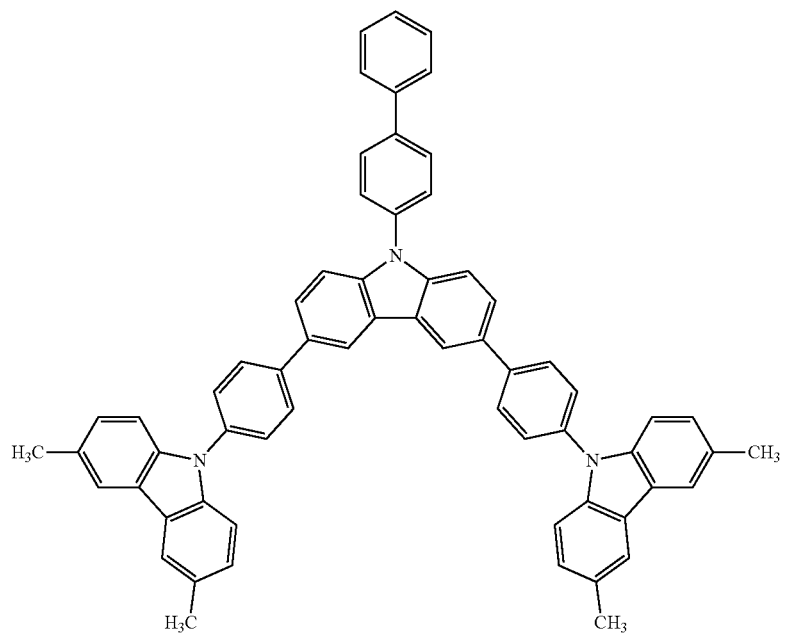
H22
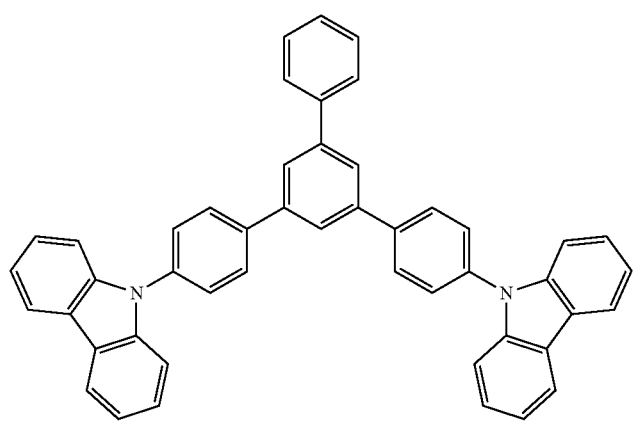
H23

-continued
H24
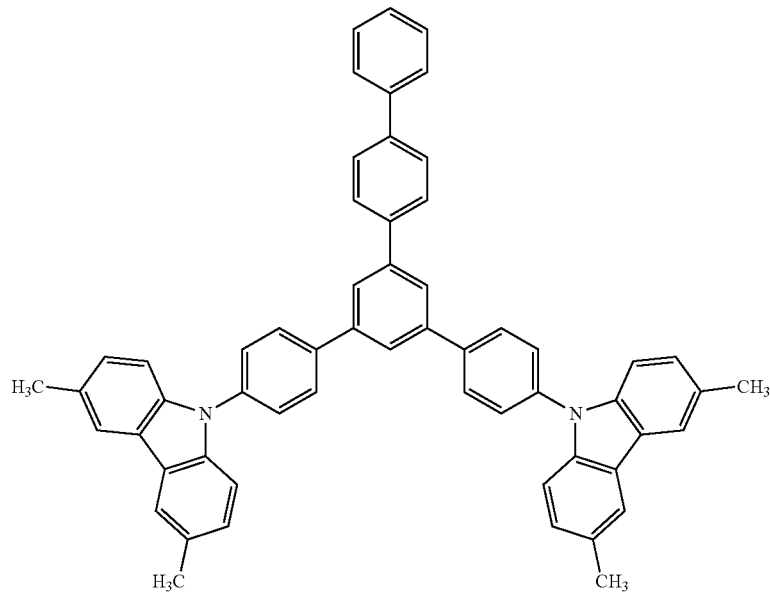
H25
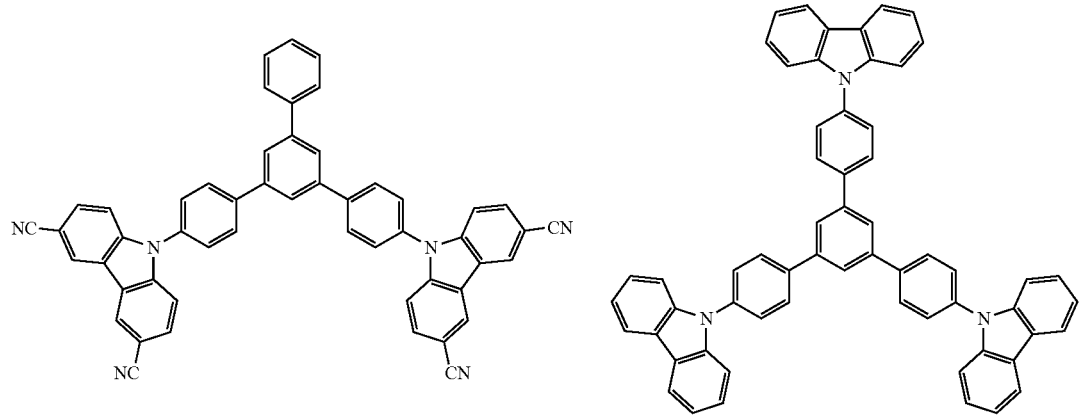
H26
H27
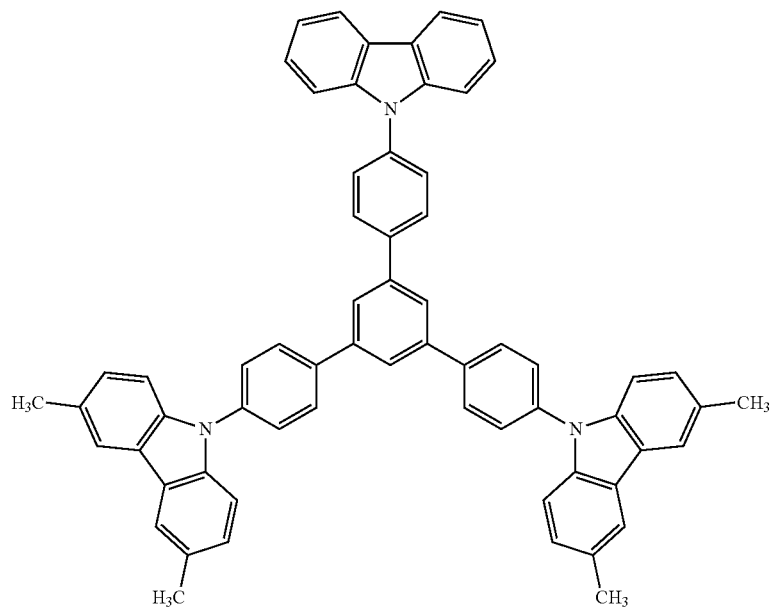

-continued

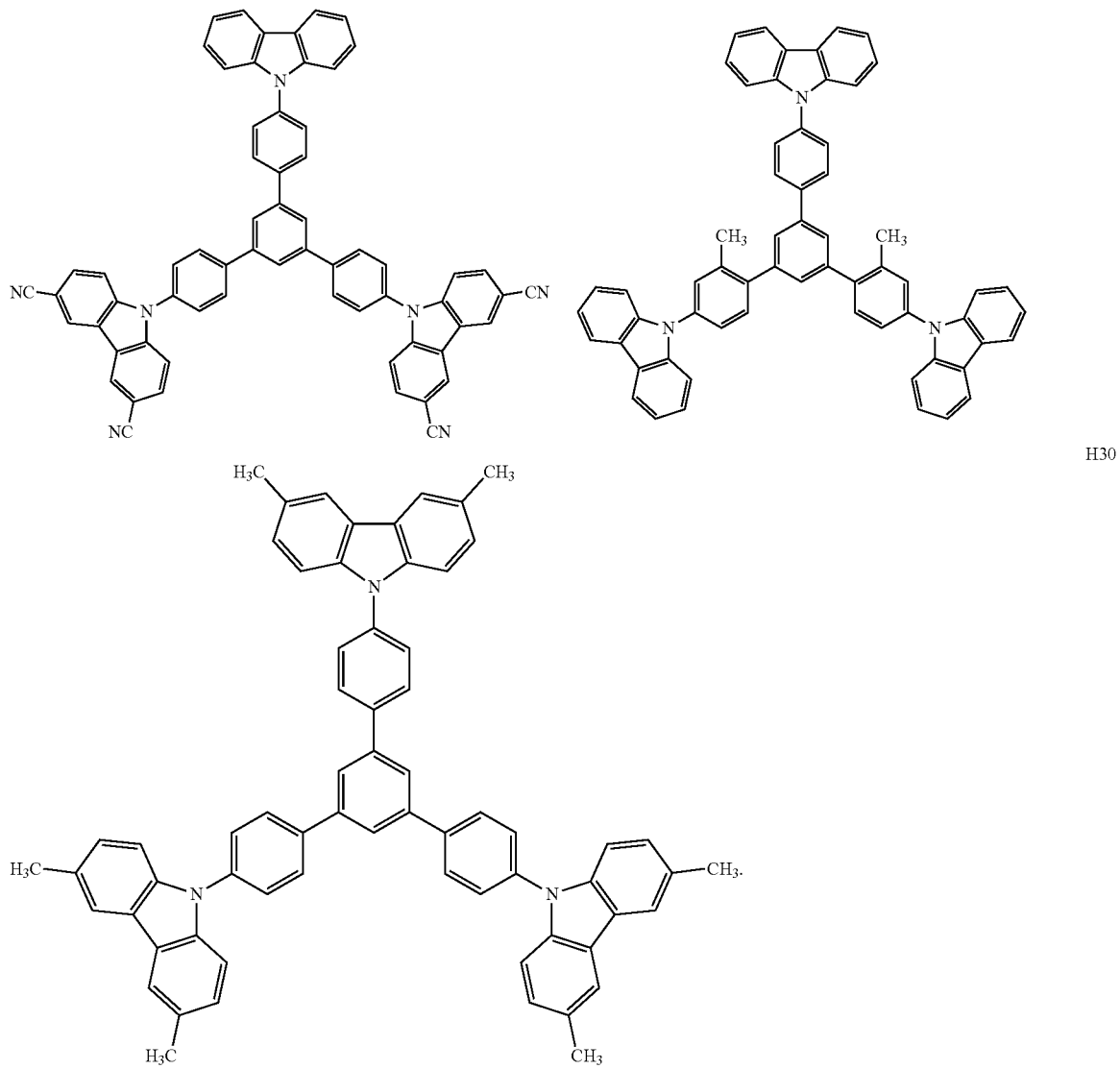

31. The organic light-emitting device as claimed in claim 25, wherein:

the organic layer includes at least one selected from the group of a hole injection layer, a hole transport layer, and a functional layer having both hole injection and hole transport capabilities; and the at least one of the hole injection layer, the hole transport layer, and the functional layer having both hole injection and hole transport capabilities includes a charge-generating material.

32. The organic light-emitting device as claimed in claim 26, wherein the organic layer includes an electron transport layer, and the electron transport layer includes a metal-containing material.

* * * * *